(12) United States Patent
Choudhary et al.

(10) Patent No.: US 12,404,348 B2
(45) Date of Patent: Sep. 2, 2025

(54) BIFUNCTIONAL CHIMERIC MOLECULES FOR LABELING OF KINASES WITH TARGET BINDING MOIETIES AND METHODS OF USE THEREOF

(71) Applicants: The Brigham and Women's Hospital, Inc., Boston, MA (US); The Broad Institute, Inc., Cambridge, MA (US)

(72) Inventors: Amit Choudhary, Boston, MA (US); Vika Anokhina, Cambridge, MA (US); Santosh Chaudhary, Cambridge, MA (US); Prashant Singh, Cambridge, MA (US); Sameek Singh, Cambridge, MA (US); Veronika Shoba, Cambridge, MA (US); Uttam Dhawa, Cambridge, MA (US); Ashley Modell, Cambridge, MA (US); Praveen Tiwari, Boston, MA (US)

(73) Assignees: The Brigham and Women's Hospital, Inc., Boston, MA (US); The Broad Institute, Inc., Cambridge, MA (US)

( * ) Notice: Subject to any disclaimer, the term of this patent is extended or adjusted under 35 U.S.C. 154(b) by 31 days.

(21) Appl. No.: 18/057,127

(22) Filed: Nov. 18, 2022

(65) Prior Publication Data
US 2023/0192904 A1 Jun. 22, 2023

Related U.S. Application Data

(60) Provisional application No. 63/281,538, filed on Nov. 19, 2021.

(51) Int. Cl.
*A61K 49/00* (2006.01)
*C07K 16/40* (2006.01)
*C07K 19/00* (2006.01)

(52) U.S. Cl.
CPC .......... *C07K 19/00* (2013.01); *A61K 49/0017* (2013.01); *C07K 16/40* (2013.01)

(58) Field of Classification Search
CPC ..... C07K 19/00; C07K 16/40; A61K 49/0017
See application file for complete search history.

(56) References Cited

U.S. PATENT DOCUMENTS

| | | | |
|---|---|---|---|
| 6,534,501 | B2 | 3/2003 | Abraham et al. |
| 7,998,474 | B2 * | 8/2011 | Kelly ............... A61P 43/00 424/93.4 |
| 8,242,080 | B2 | 8/2012 | Kuriyan et al. |
| 8,785,450 | B2 | 7/2014 | Salituro et al. |
| 9,757,369 | B2 | 9/2017 | Martinez Gil et al. |
| 2005/0038068 | A1 | 2/2005 | Iyengar et al. |
| 2005/0203155 | A1 | 9/2005 | Salassidis et al. |
| 2008/0051327 | A1 | 2/2008 | Conti et al. |
| 2009/0209022 | A1 | 8/2009 | Breed et al. |

FOREIGN PATENT DOCUMENTS

| | | |
|---|---|---|
| CN | 103649076 A | 3/2014 |
| WO | 2007/019914 A1 | 2/2007 |
| WO | 2008/006432 A1 | 1/2008 |
| WO | 2008/070016 A2 | 6/2008 |
| WO | 2009/100130 A1 | 8/2009 |
| WO | 2009/124636 A1 | 10/2009 |
| WO | 2009/135580 A1 | 11/2009 |
| WO | 2009/152909 A1 | 12/2009 |
| WO | 2010/036613 A1 | 4/2010 |
| WO | 2010/047982 A1 | 4/2010 |
| WO | 2010/051176 A1 | 5/2010 |
| WO | 2010/051206 A1 | 5/2010 |
| WO | 2011/029855 A1 | 3/2011 |
| WO | 2011/032320 A1 | 3/2011 |
| WO | 2011/033099 A1 | 3/2011 |
| WO | 2011/069298 A1 | 6/2011 |
| WO | 2011/070039 A1 | 6/2011 |
| WO | 2011/080277 A1 | 7/2011 |
| WO | 2011/106273 A1 | 9/2011 |
| WO | 2011/128251 A1 | 10/2011 |
| WO | 2011/138307 A1 | 11/2011 |
| WO | 2012/001020 A1 | 1/2012 |
| WO | 2012/033149 A1 | 3/2012 |
| WO | 2012/116145 A1 | 8/2012 |
| WO | 2012/119978 A1 | 9/2012 |
| WO | 2012/119979 A1 | 9/2012 |
| WO | 2012/158413 A2 | 11/2012 |
| WO | 2013/056153 A1 | 4/2013 |
| WO | 2014/118556 A2 | 8/2014 |
| WO | 2014/177123 A1 | 11/2014 |
| WO | 2015/075051 A1 | 5/2015 |
| WO | 2016/101885 A1 | 6/2016 |
| WO | 2019/173761 A1 | 9/2019 |
| WO | 2020/076723 A1 | 4/2020 |
| WO | 2021/142351 A1 | 7/2021 |
| WO | 2022/225728 A2 | 10/2022 |

OTHER PUBLICATIONS

The Broad Institute, Inc., "International Preliminary Report on Patentability received in PCT Application No. PCT/US2022/080175", mailed on May 30, 2024, 9 pages.

(Continued)

*Primary Examiner* — Jeanette M Lieb

(74) *Attorney, Agent, or Firm* — F. Brent Nix, Esq.; Johnson, Marcou, Isaacs & Nix, LLC; Drew P. Harding

(57) ABSTRACT

The present disclosure relates to chimeric small molecules, which find utility as modifiers of target substrates according to the formula A-$L_1$-E-B or A-$L_1$-E-$L_2$-B, wherein A is a kinase binding moiety; B is a target binding moiety; $L_1$ and $L_2$ are each a linker; and E is an electrophilic reactive group. Molecules according to the present invention find use making substrate modifications such as post-translational modifications to targets that are not the natural substrate of the kinase; accordingly, diseases or disorders may be treated or prevented with molecules of the present disclosure.

27 Claims, 9 Drawing Sheets

Specification includes a Sequence Listing.

(56) References Cited

OTHER PUBLICATIONS

The Broad Institute, Inc., "International Search Report & Written Opinion received in PCT Application No. PCT/US2022/080175", mailed on Jul. 11, 2023, 14 pages.

* cited by examiner

FIG. 4A-C

BIFUNCTIONAL CHIMERIC MOLECULES FOR LABELING OF KINASES WITH TARGET BINDING MOIETIES AND METHODS OF USE THEREOF

CROSS-REFERENCE TO RELATED APPLICATIONS

This application claims the benefit of U.S. Provisional Application No. 63/281,538 filed Nov. 19, 2021. The entire contents of the above-identified applications are hereby fully incorporated herein by reference.

STATEMENT REGARDING FEDERALLY SPONSORED RESEARCH

This invention was made with government support under Grant No. AI154099 awarded by the National Institutes of Health, and Grant No. N66001-17-2-4055 awarded by the Defense Advanced Research Projects Agency. The government has certain rights in the invention.

SEQUENCE LISTING

This application contains a sequence listing filed in electronic form as an xml file entitled BROD-5400US_ST26.xml, created on Nov. 18, 2022 and modified on Dec. 7, 2022 and having a size of 45,107 bytes. The content of the sequence listing is incorporated herein in its entirety.

TECHNICAL FIELD

The subject matter disclosed herein is generally directed to multifunctional chemical conjugation molecules utilized to induce modifications in target substrates.

BACKGROUND

An ongoing need exists in the art for effective treatments for diseases associated with enzymatic and other dysfunctions, as well as a need to make modifications such as post-translational modifications. However, obstacles such as non-specific effects remain as obstacles to the development of effective modifications and treatments. Small molecules that endow new functions to enzymes via proximity-mediated effects could be useful in the study and treatment of critical cellular functions and diseases.

Citation or identification of any document in this application is not an admission that such a document is available as prior art to the present invention.

SUMMARY

In certain example embodiments, chimeric small molecules are provided according to the formula:

$$A\text{-}L_1\text{-}E\text{-}B \text{ or } A\text{-}L_1\text{-}E\text{-}L_2\text{-}B,$$

wherein A is a kinase binding moiety; B is a target binding moiety; $L_1$ and $L_2$ are each a linker; and E is an electrophilic reactive group is selected from the group consisting of

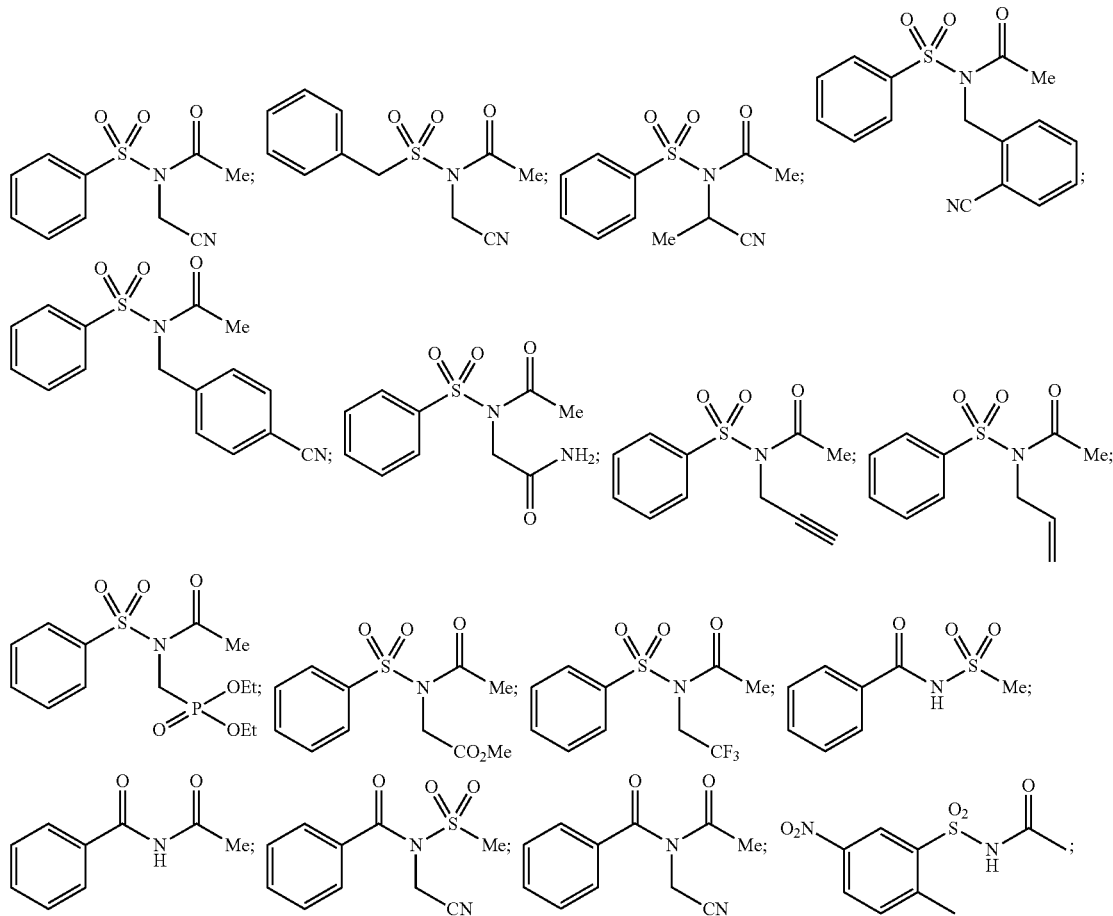

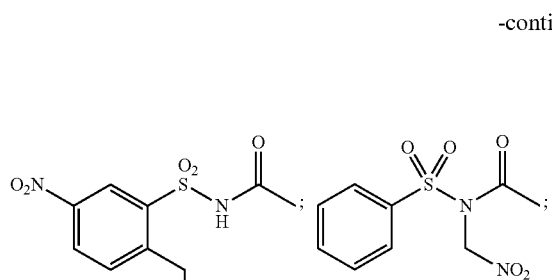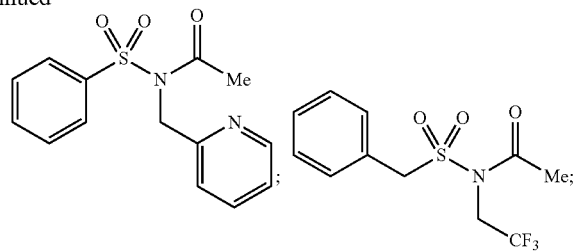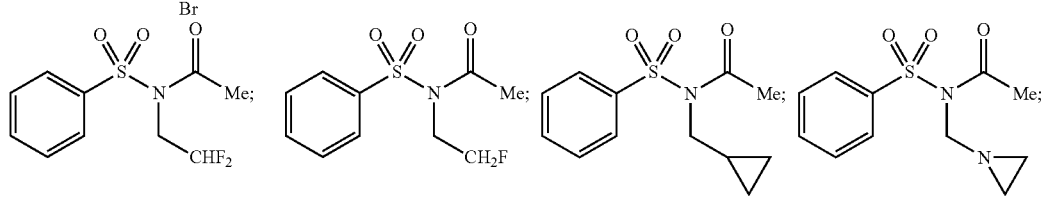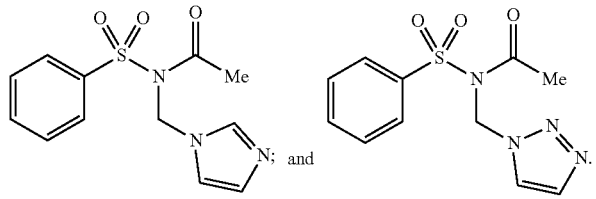 [SMILES: CC(=O)N(Cn1ccnc1)S(=O)(=O)c1ccccc1 ; CC(=O)N(Cn1ccnn1)S(=O)(=O)c1ccccc1]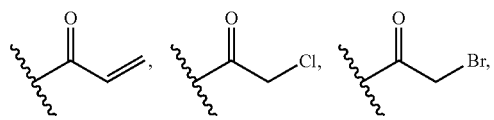

In an embodiment, the kinase binding moiety can be a FKBP, PKC, AMPK, ABL, PK, MAPK, e.g. MAPK1, MAPK11, MAPK12, MAPK13, MAPK14, p38 MAPK, EGFR, FGFR, NGFR, TrkA, ABL, CDK, e.g. CDK2, CDK4, CDK8, PI3K, VEGFR, BRAF, MEK, e.g. MEK1/2, MEK5, AKT, ALK, BTK, BCKDK, FLT3, JAK2, AURKA, c-MET, DDR, INSR, JNK, I⁻B, IKK, Lyn, mTOR, e.g. mTORC-1, PAK, PDK, e.g. PDK1 or PDK2, PTK2/FAK, pyruvate kinases, RAC-, RIPK, TYK2, SHP, aPKC, e.g. PKC-ζ, NOP, GPC family for example; μ opioid receptor or δ opioid receptor, UMPK, SphK, or GSK-3 binding moiety. The kinase binding moiety can comprise a kinase inhibitor or kinase activator. In an embodiment, the kinase inhibitor is a promiscuous kinase inhibitor.

In an embodiment, the kinase inhibitor is sorafenib, SB2035890 or Skepinone B, or an analog or derivative thereof. In an embodiment, the kinase inhibitor is Gefitinib, or an analog or derivative thereof, is Imatinib, or an analog or derivative thereof or is Idelasilib, or an analog or derivative thereof.

The chimeric small molecule may comprise a kinase binding moiety with a half-life shorter than the half-life of the target to which the target binding moiety is capable of binding. In an aspect, the kinase binding moiety half-life is at least 2, 3, 4, 5 times shorter than the half-life of the target bound by the target binding moiety.

The chimeric small molecule can comprise an electrophilic reactive group is selected from N-acyl-N-alkyl sulfonamide (NASA), dibromophenyl benzoate, or N-sulfonyl pyridone. The chimeric small molecule of any of the preceding claims, wherein the electrophilic reactive group is selected from the group consisting of:

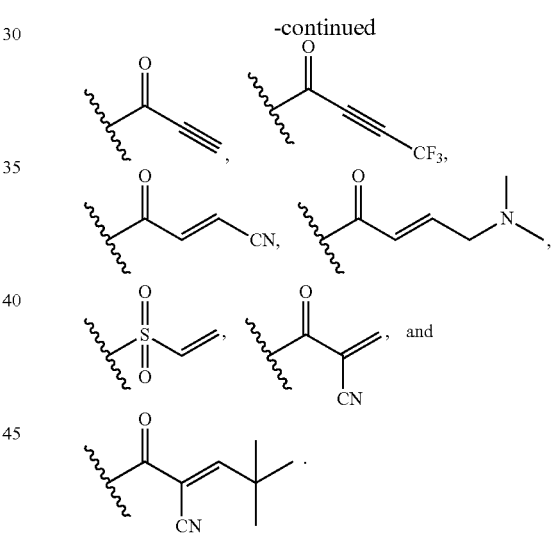

In an aspect, the electrophilic reactive group has the formula:

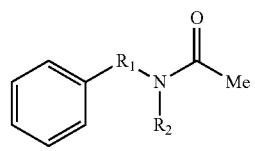

wherein $R_1$ is selected from C—O, $SO_2$, Me-C—O, or Me-$SO_2$, $R_2$ is selected from H, alkane, alkene, alkyne, amine, nitrile, nitro, ether, alcohol, thiol, sulfone, sulfonate, halogen, carbonyl; acyl; ketone; carboxylate ester; amide; enone; anhydride; imide, cyclic hydrocarbon, an unsaturated cyclic hydrocarbon, a heterocycle, one or more fused rings thereof; an aliphatic halide such as —OCF$_2$Cl or any combination thereof, and the benzene ring is optionally substituted at any position.

The chimeric small molecule can comprise a linker as represented by L1 and optionally L2, wherein the linker selected from: alkane; alkene; alkyne; amine; ether; thiol; sulfone; carbonyl; acyl; ketone; carboxylate ester; amide; enone; anhydride; imide; PEG, or any combination thereof. L1 and L2 linkers may be the same or different molecules selected from alkane; alkene; alkyne; amine; ether; thiol; sulfone; carbonyl; acyl; ketone; carboxylate ester; amide; enone; anhydride; imide; PEG, or any combination thereof.

The chimeric small molecule can comprise a kinase binder that further comprises a bio-orthogonal group. In an embodiment, the bio-orthogonal group is selected from tetrazines, triazines, cyclooctenes, cyclopropenes and diazo. The bio-orthogonal group can be selected from the group consisting of:

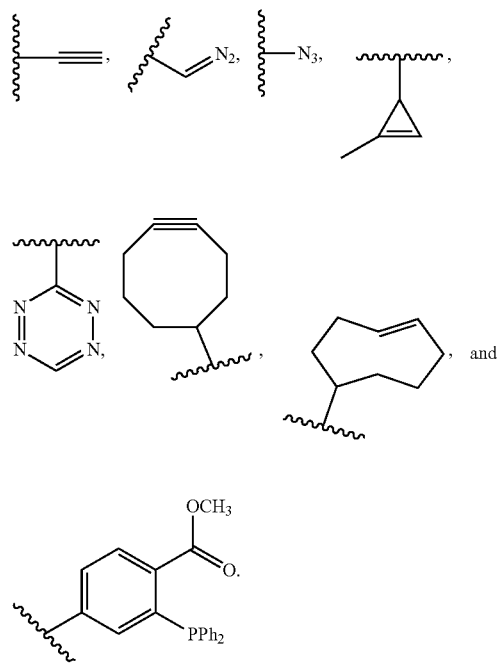

The target of the target binding moiety of the chimeric small molecule is a protein. In an embodiment, the target protein is from a pathogen. The pathogen can be a virus, bacteria, fungi, or protozoa. In an embodiment, the microbial protein is in an intracellular or extracellular pathogen protein. The intracellular pathogen can be *Mycobacterium tuberculosis* or the extracellular pathogen is *Pseudomonas aeruginosa*. The chimeric small molecule can comprise a target binding moiety that is a phosphatase A (PtpA) binder, PtpB binder, SapM binder, ESAT-6 binder, and Rv2966c binder. The chimeric small molecule can comprise a target binding moiety Colistin.

The chimeric small molecule can be capable of covalently labeling a kinase with the kinase binder. In an aspect, the labeling is of a nucleophile disposed on the kinase.

The chimeric small can comprise a targeting binding moiety for a target that is capable of binding an oncogenic target.

The chimeric small molecule can be according to:

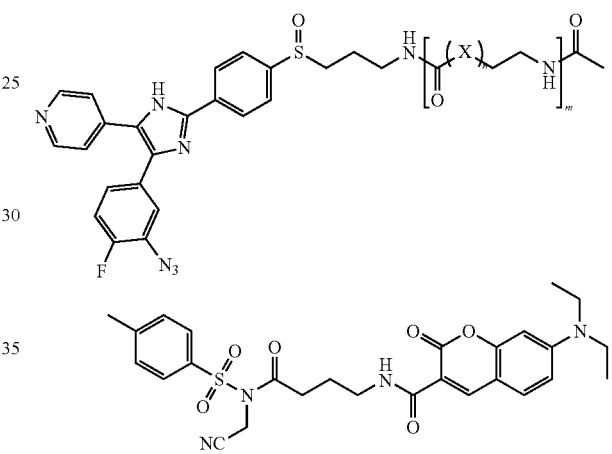

wherein m=0 or 1; n=1, 2, 3, 4 or 5; and X=CH$_2$ or (CH$_2$)$_2$O.

The chimeric small molecule can be according to:

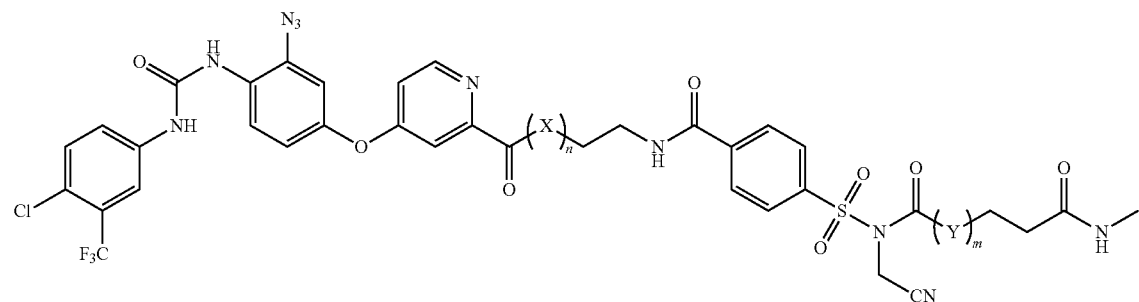

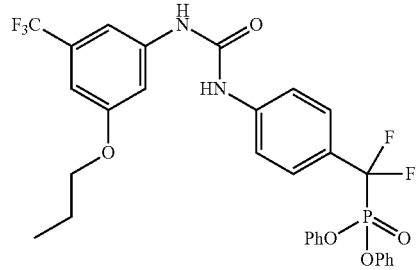

wherein X and Y are independently selected from CH$_2$ or (CH$_2$)$_2$O and n and m are independently selected from 1, 2, 3, 4, 5, or 6.

Embodiments herein comprise methods of inducing modification of a target substrate comprising administering to a cell or cell population a chimeric small molecule as described herein. Methods of modifying a substrate comprising introducing a molecule as described herein to a cell. In an embodiment, the chimeric small molecule electrophilic reactive group can react with a nucleophilic reactive group. In an embodiment, the nucleophilic reactive group is comprised on an amino acid, optionally selected from Cysteine, Serine, Threonine, Tyrosine, Glutamic Acid, Aspartic Acid, Lysine, Arginine, and Histidine.

In one embodiment, methods of modifying a target substrate in a cell, comprising generating a reprogrammed cellular kinase by delivering a chimeric small molecule described herein, wherein A is an kinase binding moiety specific for the cellular kinase to be repurposed/reprogrammed; whereby the chimeric small molecule labels the cellular kinase with the target binding moiety for the target substrate; and modifying the target substrate by binding of the repurposed/reprogrammed kinase to the target substrate via the target binding moiety, whereby the repurposed/reprogrammed cellular kinase introduces one or more modifications to the target substrate.

The methods described herein can further comprise administering a coupling molecule thereby quenching the inhibitory activity of the kinase binding moiety. Methods of modifying can comprise inducing post-translational modification of a target protein. In an aspect, the post-translational modification is phosphorylation.

Methods of treating cancer are provided comprising generating a reprogrammed cellular kinase by administering to a subject in need thereof a chimeric small molecule as detailed herein and target binding moiety B binds to an oncogenic protein to be modified, whereby the chimeric small molecule labels the cellular kinase with the target binding moiety for the target substrate; and modifying the oncogenic protein by binding of the repurposed/reprogrammed kinase to the target substrate via the target binding moiety, whereby the repurposed/reprogrammed cellular kinase introduces one or more modifications to the target substrate. The method may further comprises the step of administering a coupling molecule thereby quenching the activity of the kinase binding moiety. In an aspect, modifying comprises inducing post-translational modification of a target protein; in an aspect, the post-translational modification is phosphorylation.

Methods for treating infection by a pathogen are provided comprising generating a reprogrammed cellular kinase by administering to a subject in need thereof a chimeric small molecule described herein, wherein B is a pathogen protein to be modified, whereby the chimeric small molecule labels the cellular kinase with the target binding moiety for the target substrate; and modifying the pathogen protein by binding of the repurposed/reprogrammed kinase to the pathogen protein via the target binding moiety, whereby the repurposed/reprogrammed cellular kinase introduces one or more modifications to the target substrate. The methods may further comprise administering a coupling molecule thereby quenching the y activity of the kinase binding moiety. In embodiments, modifying comprises inducing post-translational modification of a target protein, optionally wherein the post-translational modification is phosphorylation.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which.

Figure 1:
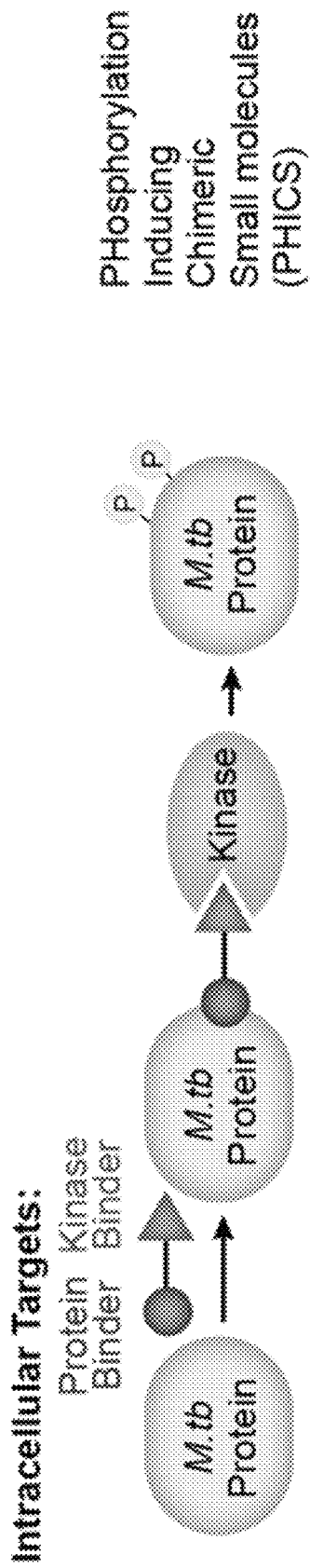
FIG. 1—Exemplary chimeras for recruitment of *Pseudomonas aeruginosa* to antibodies, complement or macrophages and for recruitment of *Mycobacterium tuberculosis* (M.tb) proteins to host kinases.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +1-5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

"Diastereoisomers" are stereoisomers that have at least two asymmetric atoms, but which are not mirror-images of each other. The absolute stereochemistry is specified according to the Cahn-Ingold-Prelog R-S system When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures. In some chemical structures, stereocenters may be identified with "wavy" bonds indicating that the stereocenter may be in the R or S configuration, unless otherwise specified. However, stereocenters without a wavy bond (i.e., a "straight" bond) may also be in the (R) or (S) configuration, unless otherwise specified. Compositions comprising compounds may comprise stereocenters which each may independently be in the (R) configuration, the (S) configuration, or racemic mixtures.

Optically active (R)- and (S)-isomers can be prepared, for example, using chiral synthons or chiral reagents, or resolved using conventional techniques. Enantiomers can be isolated from racemic mixtures by any method known to those skilled in the art, including chiral high pressure liquid chromatography (HPLC), the formation and crystallization of chiral salts, or prepared by asymmetric syntheses.

Optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid. The separation of the mixture of diastereoisomers by crystallization followed by liberation of the optically active bases from these salts affords separation of the isomers. Another method involves synthesis of covalent diastereoisomeric molecules by reacting disclosed compounds with an optically pure acid in an activated form or an optically pure isocyanate. The synthesized diastereoisomers can be separated by conventional means such as chromatography, distillation, crystallization or sublimation, and then hydrolyzed to deliver the enantiomerically enriched compound.

Optically active compounds can also be obtained by using active starting materials. In some embodiments, these isomers can be in the form of a free acid, a free base, an ester or a salt.

In certain embodiments, a disclosed compound can be a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). Tautomerization includes prototropic or proton-shift tautomerization, which is considered a subset of acid-base chemistry. Prototropic tautomerization or proton-shift tautomerization involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

All chiral, diastereomeric, racemic, and geometric isomeric forms of a structure are intended, unless specific stereochemistry or isomeric form is specifically indicated. All processes used to prepare compounds and intermediates made therein are encompassed by the present disclosure. All tautomers of shown or described compounds are also encompassed by the present disclosure.

As used herein, a bond substitution coming out of a ring, e.g,

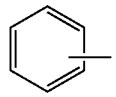

means that the substitution can be at any of the available position on the ring.

A derivative of a compound as used herein is used interchangeably with a structural analog or chemical analog. The derivative of a compound may comprise a variation or change in one or more functional groups, atoms, or substructures relative to the compound.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

"Diastereoisomers" are stereoisomers that have at least two asymmetric atoms, but which are not mirror-images of each other. The absolute stereochemistry is specified according to the Cahn-Ingold-Prelog R-S system When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures. In some chemical structures, stereocenters may be identified with "wavy" bonds indicating that the stereocenter may be in the R or S configuration, unless otherwise specified. However, stereocenters without a wavy bond (i.e., a "straight" bond) may also be in the (R) or (S) configuration, unless otherwise specified. Compositions comprising compounds may comprise stereocenters which each may independently be in the (R) configuration, the (S) configuration, or racemic mixtures.

Optically active (R)- and (S)-isomers can be prepared, for example, using chiral synthons or chiral reagents, or resolved using conventional techniques. Enantiomers can be isolated from racemic mixtures by any method known to those skilled in the art, including chiral high pressure liquid chromatography (HPLC), the formation and crystallization of chiral salts, or prepared by asymmetric syntheses.

Optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid. The separation of the mixture of diastereoisomers by crystallization followed by liberation of the optically active bases from these salts affords separation of the isomers. Another method involves synthesis of covalent diastereoisomeric molecules by reacting disclosed compounds with an optically pure acid in an activated form or an optically pure isocyanate. The synthesized diastereoisomers can be separated by conventional means such as chromatography, distillation, crystallization or sublimation, and then hydrolyzed to deliver the enantiomerically enriched compound.

Optically active compounds can also be obtained by using active starting materials. In some embodiments, these isomers can be in the form of a free acid, a free base, an ester or a salt.

In one example embodiment, a disclosed compound can be a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). Tautomerization includes prototropic or proton-shift tautomerization, which is considered a subset of acid-base chemistry. Prototropic tautomerization or proton-shift tautomerization involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

All chiral, diastereomeric, racemic, and geometric isomeric forms of a structure are intended, unless specific stereochemistry or isomeric form is specifically indicated. All processes used to prepare compounds and intermediates made therein are encompassed by the present disclosure. All tautomers of shown or described compounds are also encompassed by the present disclosure.

As used herein, a bond substitution coming out of a ring, e.g.,

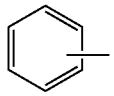

means that the substitution can be at any of the available positions on the ring.

An alkyl generally means a straight or branched chain aliphatic groups. The alkyl groups can be unsubstituted or substituted by halo, hydroxy, alkoxy, amino, alkylamino, dialkylamino, cycloalkyl, aryl, aryloxy, heteroaryl, or heteroaryloxy groups, among other. Alkenyl straight or branched carbon chain having one or more double bonds. Alkynyl comprises a straight or branched carbon chain with at least one triple bond. The alkenyl and alkynyl groups can have one or more double bonds or triple bonds, respectively, or a combination of double and triple bonds. Alkenyl and Alkynyl groups can be unsubstituted or substituted with functional groups as described herein.

As used herein a hydrocarbon substituent means any group exclusively of hydrogen and carbons atoms. This includes alkyls, alkylenes, alkynes as well as saturated and unsaturated rings and fused rings.

As used herein a nitrogen-based substituent means any group comprising one or more nitrogen. Non-limiting examples of nitrogen-based substituent may include aminyl, 4° ammonium cations, amidyl, iminyl, imidyl, azidyl, azo radical, cyano, nitrate, nitrile radical, nitrite radical, nitryl, nitrosyl, oxime, carbamoyl.

As used herein a sulfur-based substituent means any group comprising one or more sulfurs. Non-limiting examples of sulfur-based substituents may include H or R sulfanyl, disulfanyl, sulfinyl, sulfino radical, sulfo radical, alkyl sulfonyl, thiocyanato radical, isothiocyanato radical, thioyl, sulfanylidene, methanethioyl, mercaptocarbonyl, hydroxy(thiocarbonyl), thioester radical, thionoester radical, dithiocarboxy radical, dithiocarboxylic acid ester radical, dithiocarbamate radical.

As used herein an oxygen-based substituent means any group comprising one or more oxygen. Non-limiting examples of oxygen-based substituents may include hydroxyl, carbonyl, formyl, haloformyl, (alkoxycarbonyl) oxy, carboxyl, carboxylate, carboalkoxyl, hydroperoxyl, peroxyl, alkoxyl, dialkoxyl, trialkoxyl, methylenedioxyl, tetralkoxyl, and carboxylic anhydride radical.

As used herein a boron-based substituent means any group comprising one or more boron. Non-limiting examples of boron-based substituents may include boronyl, borono radical, O-[bis(alkoxy)alkylboronyl], hydroxyborino radical, O-[alkoxydialkylboronyl].

As used herein a halogen-based substituent means any group comprising one or more halogen.

As used herein a heterocycle means any molecule that forms a continuous covalent connection and contains an element that is not hydrogen or carbon. Non-limiting examples of heterocycles may include. oxetane, thietane, azetidine, β-lactam, oxirane, thiirane, aziridine, azirine, diaziridine, diazirine, epoxide, tetrahydrofuran, furan, thiolane, thiophene, pyrrolidine, pyrrole, 3-pyrroline, 2-H-pyrrole, benzofuran, coumaran, isobenzofuran, benzothiophene, dibenzothiophene, indoline, indole, indolinine, oxindole, indoxyl, isatin, isoindole, indolizine, pyrrolizine, carbazole, dioxolane, dithiolane, oxazolidine, oxazolidinone, oxazole, isoxazole, thiazole, isothiazole, imidazolidine, 2-imidazoline, imidazole, pyrazolidine, 2-pyrazoline, pyrazole, benzodioxole, benzoxazole, indoxazine, benzothiazole, benzimidazole, 1H-indazole, purine, azaindole, 1,2,3-oxadiazole, 1,3,4-thiadiazole, 1,2,3-triazole, 1,2,4-triazole, tetrazole, benzotriazole, quinuclidine, diazabicyclooctane, diazabicycloundecane, 4H-pyran, tetrahydropyran, dihydropyran, 2H-pyran, piperidine, pyridine, picoline, lutidine, collidine, pyridone, acridine, chromene, coumarin, isocoumarin, xanthene, tetrahydroquinoline, quinoline, isoquinoline, quinolone, 4H-quinolizine, quinolizinium, 1,4-dioxane, morpholine, paraformaldehyde, 1,4-dithiane, 1,3-dithiane, thiomorpholine, trithiane, piperazine, pyrazine, pyrimidine, pyridazine, 1,3,5-triazine, tetrazine, cinnoline, phthalazine, 1,8-naphthyridine, quinoxaline, quinazoline and/or combination thereof including fusing or covalently linking and further optionally substituted with any previously mentioned substituent.

Additional substituents may comprise any combination of the above substituents.

Throughout the description, molecules may be represented with an exemplary bonding location indicated by , however further optimization of binding location of molecules can be performed, including through methods of screening and computational approaches detailed herein and further explored in the examples of the application. Thus, identified binding locations on molecules via depiction with  are not intended to be limiting, merely exemplary, with further optimizations and locations of binding sites implicitly recognized as being identifiable with the methods and guidance as described herein, including at any position on rings within the structures as well as any other substituents of the molecules.

Carbocycle or Cycloalkyl means a mono or bicyclic carbocyclic ring functional group, and includes both substituted and unsubstituted cycloalkyl groups. Cycloalkyl groups can optionally contain double bonds and is intended to encompass cycloalkenyl groups. Unless otherwise indicated, a reference to a ($C_3$-$C_8$) cycloalkyl refers to a cycloalkyl group containing from 3 to 8 carbons, and is intended to encompass a monocyclic cycloalkyl group containing from 3 to 8 carbons and a bicyclic cycloalkyl group containing from 6 to 8 carbons.

Heterocycloalkyl generally refers to a ring functional group having carbon atoms and one or more heteroatoms independently selected from S, N, or. The heterocycloalkyl is intended to encompass 1 or more double bonds which may be between two carbons or a carbon and a heteroatom. For example, an exemplary 5-membered ring heterocycloalkyl can have one carbon-carbon double bond or one carbon-nitrogen bond in the ring, e.g. dihydropyrazoles, pyrrolidinyl.

An aryl group as utilized herein refers to an aromatic hydrocarbon radical that encompasses cyclic, and multicyclic, e.g. bicyclic, tricyclic, aromatic ring moiety. Exemplary aryl groups include phenyl and naphthyl. A phenyl may be unsubstituted or substituted at one or more positions with a substituent, including but not limited to those substituents described above for alkyl groups.

Heteroaryl group as utilized herein refers to an aromatic moiety that encompasses cyclic and multicyclic, e.g., bicyclic, or tricyclic, moiety having carbon atoms and one or more selected from O, S, or N.

All publications, published patent documents, and patent applications cited herein are hereby incorporated by reference to the same extent as though each individual publication, published patent document, or patent application was specifically and individually indicated as being incorporated by reference.

Overview

Small molecules have been classically developed to inhibit enzyme activity. Embodiments disclosed herein define new classes of chimeric small molecules that endow new functions to kinases via proximity-mediated effects. In general, the chimeric small molecules comprise an effector binding moiety connected to a substrate binding moiety via a linker. The chimeric small molecules can be used to improve the kinetics of native proteins modifications by bringing substrate molecules in proximity to the kinase, including using chimeric small molecule configurations that may be more favorable, energetically or otherwise. In addition, the chimeric small molecules may be used to re-target a protein to modify a non-native or neo-substrate.

In one aspect, chimeric small molecule can be configured to facilitate the covalent labeling of a protein with a target-binding moiety. The labeling of a kinase with a target binding moiety can be used to define new substrates not normally targeted or modified by such proteins. In such embodiments, the chimeric small molecule comprises a kinase binding moiety linked to a target binding moiety but further comprising an electrophilic reactive group. The kinase binding moiety non-covalently binds to the kinase of interest and, as a result, leads the electrophilic reactive group—via proximity-driven reactions—to "label" the protein by covalently binding the target binding moiety to a nucleophile located on the protein. In such embodiments, the kinase binding moiety is then released from the labeled kinase, either by inherent kinetics of the molecule or by application of a quencher. The target binding moiety may then direct the labeled kinase to bind and modify new target substrates. This approach also expands the number of kinase binders that may be used. For example, there are several high-quality kinase inhibitors that exist, but such inhibitors are unsuitable for use in targeting chimeras that remain bound to the kinase and thus may otherwise inhibit enzymatic activity of the bound kinase. As discussed in further detail below, selection of appropriate inhibitors, and the optional use of quenching molecules, allows these inhibitors to be used in the aforementioned labeling process without impacting the downstream modification reaction.

Embodiments disclosed herein provide targeting chimera designed for oncogenic targets. In one example embodiment, methods are provided for modification, for example, neo-phosphorylation, of oncogenic targets. Methods of use can comprise eliciting an immune reaction, creation of an autoantigen, and target deactivation. In an exemplary embodiment, hyperphosphorylation or neo-phosphorylation of a target protein may result in immune recruitment to a target, for example via trigger display of neo-epitopes and T-cell attack on cells displaying the epitopes. Modification of kinases and key regulator proteins implicated in cancer are also within the scope of the methods disclosed herein.

Embodiments disclosed herein provide a method of modifying a target substrate in a cell is provided. For example, where the kinase binding moiety is a kinase and the target is a substrate located in a cell, then the kinase labeled with the target binding moiety can bind to the target substrate. The bound kinase can then neo-phosphorylate the target substrate even where a non-cognate substrate of the kinase, thereby modifying it.

Embodiments disclosed herein provide a method of recruiting a host's immune system against cancer is provided. For example, where the target substrate is an oncogenic protein, then a kinase that has been labeled with an oncogenic target binding moiety using a chimeric small molecule can bind to the cancer through the oncogenic protein binding moiety. The bound kinase can then neo-phosphorylate the target oncogenic protein thereby signaling the host's immune system to attack the cancer.

Embodiments disclosed herein provide a method of recruiting a host's immune system against pathogen. For example, where the target substrate is located on the surface of a pathogenic bacteria, then a kinase that has been labeled with a pathogenic protein target binding moiety using a chimeric small molecule can bind to the bacteria through the target protein binding moiety. The bound kinase can then neo-phosphorylate the target pathogenic protein thereby signaling the host's immune system to attack the bacteria.

Chimeric Small Molecules

In one example embodiment, the chimeric small molecule is according to the general formula

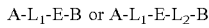

A-L$_1$-E-B or A-L$_1$-E-L$_2$-B wherein A is a kinase binding moiety, B is a target binding moiety, L$_1$ and L$_2$ are each a linker, and E is an electrophilic reactive group.

The embodiments of these formulae may be useful in, but not necessarily limited to, situations where the kinase binding moiety would otherwise inhibit or interfere with the ability of the kinase bound by the kinase binding moiety to modify the target substrate bound by the target binding moiety.

The electrophilic reactive group of the chimeric small molecule may be designed to react with a moiety on the kinase, for example, on an amino acid of the kinase. The electrophilic reactive group can be advantageously designed to react with a moiety in proximity to the binding site of the kinase binding moiety on the kinase. The reaction of the electrophilic reactive group with a moiety on the kinase, for example, a nucleophilic group of an amino acid disposed on the protein, can allow the labeling or binding of the kinase with the target binding moiety. Such binding of a target binding moiety to the kinase can generate a reprogrammed kinase that can modify a target substrate. Accordingly, in an example embodiment, the kinase binding moiety binds to the kinase and is chosen based on the binding pocket and availability of amino acid side chains in proximity to the binding pocket that may be used in a reaction with the electrophilic reactive group of the targeting chimera.

The kinase binding moiety may bind to a kinase and may be specific to one or more kinases. In an embodiment, the kinase binding moiety can further comprise a bio-orthogonal group. The kinase binding moiety, as detailed further herein, can be selected to have a half-life shorter than the half-life of the kinase.

The target binding moiety can be specific for one or more targets of interest. In one example embodiment, the target of interest is a macromolecule, e.g. a protein. The target binding moiety can bind the target of interest (target substrate), thereby bringing the kinase into proximity to the target of interest. In an embodiment, the target of interest may advantageously be a non-cognate substrate of the kinase. The target of interest may be a pathogenic or oncogenic target.

Kinase Binding Moiety

The chimeric small molecule according to the general formula A-L$_1$-E-B or A-L$_1$-E-L$_2$-B comprises a kinase binding moiety A that may comprise any molecule capable of non-covalent bonding to a kinase. The kinase binding moiety, also referred interchangeably herein as a kinase binder, of the chimeric small molecule may target one or more different kinases, or one or more locations on the kinase.

A kinase belongs to a family of phosphotransferases and phosphorylates a substrate by transferring the gamma phosphate of ATP onto hydroxyl groups of the substrate. Substrates may comprise lipids, sugars or amino acids. The kinase binding moiety may be any molecule capable of binding to a kinase. Some kinase binding molecules are known to activate a kinase upon binding while others are known to inhibit a kinase upon binding. In one example embodiment, the kinase binding moiety is a kinase activator. In an example embodiment, the kinase binding moiety is a kinase inhibitor. However, binding of the kinase, rather than its inhibitory or activation behavior of the kinase binding moiety, is the primary objective as the design of the targeting chimeras generates a kinase labeled with a target binding moiety, with the kinase binding moiety utilized for initial binding to the kinase to allow for generation of a repurposed kinase labeled with target binding moiety rather than use of the kinase binding moiety for kinase activation or inhibition properties.

The chimeric small molecule is preferably designed such that one or more nucleophilic groups disposed on the protein, e.g. kinase, readily reacts with the electrophilic reactive group of the chimeric small molecule. The moiety comprising the nucleophilic group of the protein may be an amino acid side chain. Thus, the kinase binding moiety can be chosen based on the binding pocket and availability of amino acid side chains in proximity to the binding pocket that can be used in a reaction with the electrophilic reactive group of the targeting chimera. Further design of exit vectors that are comprised on the kinase binder or linker of the chimeric small molecule may further allow for desired configuration of the kinase binding moiety at the protein binding site.

Half-Life

In one example embodiment, where the chimeric small molecule is being used to label the surface of the kinase with a target binding moiety, the kinase binding moiety may be chosen in part based on its half-life. In one example embodiment, the kinase binding moiety may be chosen based in part on its half-life relative to the half-life of the kinase. In an embodiment, the half-life of the kinase binding moiety is 2, 3, 4, or 5 times shorter than that of the kinase. Without being bound by a particular theory, design of a chimera small molecule with a half-life of the kinase binding moiety shorter than that of the kinase may allow for desirable reaction kinetics when the kinase is labeled with the kinase binding moiety via the electrophilic reactive group. The half-life of the kinase binding moiety and the kinase generally relates to the time required for the concentration of the kinase binding moiety or kinase to decrease to half of its initial concentration. In one example embodiment, the half-life may measure the time it takes to degrade half of the molecules initially measured in a sample, which may comprise a cell, cells, tissue, organoid, or mammal, for example. In one example embodiment, the half-life of the kinase and the kinase binding moiety is measured in the same or similar conditions, for example, in a same cell type, tissue, or organism. In one example embodiment, the measurement of half-life can be measured in a same sample or system that has a particular phenotype, genotype, disease or condition to be studied, treated and/or evaluated.

Measurement of the half-life of the kinase binding moiety may be determined, for example, by dissociation t$_{1/2}$ or receptor occupancy t$_{1/2}$, describing the average time needed to liberate half of the initially occupied receptors under conditions in where association of the protein binding moiety or its rebinding can take place. Dissociation that requires a receptor conformational change or binding pocket size may play a factor in the residence time and can be considered when selected the protein binding moiety. See, e.g. Roskoski R Jr. Classification of small molecule protein kinase inhibitors based upon the structures of their drug-enzyme complexes. *Pharmacol Res.* 2016; 103:26-48. doi: 10.1016/j.phrs.2015.10.021.

The time a compound resides on its target, e.g. residence time, may be used. See, Willemsen-Seegers N, Uitdehaag JCM, Prinsen MBW, et al. Compound Selectivity and Target Residence Time of Kinase Inhibitors Studied with Surface Plasmon Resonance. *J Mol Biol.* 2017; 429(4):574-586. doi:10.1016/j.jmb.2016.12.019, for discussion and identification of residence time and kinetic parameters of exemplary kinase binding moieties, incorporated herein in its entirety, and in particular Table 1,3A-3B, 4A-4C, S3 and S4, for teachings to tyrosine kinase inhibitors, EGFR inhibitors, ponatinib to a variety of kinases, particular kinases and their associated inhibitors, Aurora A and B kinase inhibitors, and P13k lipid kinase inhibitors. Elimination half-life may also be utilized alone or in conjunction with residence time evaluation. Additional pharmacodynamics and pharmacokinetics may also be considered in the evaluation of half-life for the kinase binding moiety. Half-life may be modeled. See, e.g. Callegari D, Lodola A, Pala D, et al. Metadynamics Simulations Distinguish Short- and Long-Residence-Time Inhibitors of Cyclin-Dependent Kinase 8 [published correction appears in *J Chem Inf Model.* 2017 Feb. 27; 57(2):386]. *J Chem Inf Model.* 2017; 57(2):159-169. doi:10.1021/acs.jcim.6b00679, incorporated herein by reference.

The measurement of half-life of the kinase, approaches measuring half-life such as mass spectrometry-based proteomics such as SILAC (stable isotope labeling by amino acids in cell culture)-based proteomics, see, e.g. Matheison et al., Nature Communications volume 9, Article number: 689 (2018), may be used. High throughput proteomics may be used to estimate a kinase half-life in a particular tissue and/or cell, or further predictive modeling may be used to predict such kinase half-life in tissue from cellular properties, see, e.g. Rahman M, Sadygov R G Predicting the protein half-life in tissue from its cellular properties. PLoS ONE 12(7): e0180428. doi.org/10.1371/journal.pone.0180428 (2017).

The kinase binding moiety can be chosen based on the target substrate and the modification to that substrate desired. Advantageously, the kinase binding moiety can be an activator or inhibitor of the kinase. An kinase binding moiety may be chosen based on high kinase abundance in a target cell; kinases with high activity at lower concentrations, e.g. nanomolar activity; available crystal structure and characterization of the kinase active; kinase binding moieties with low residence time; the ability of the kinase binding moiety of the chimeric small molecule to accommodate a bio-orthogonal group, e.g. a small biorthogonal handle, without affecting binding potency and/or residence time; kinases with a high density of amino acids with nucleophilic side chains, e.g. serines/threonines/tyrosines/lysines close to the binding pocket; and/or whether the labeling of the kinase would interfere with its enzymatic activity, which may be based on experimental data and/or modeling. Linker length on the chimeric small molecule may be tuned, allowing modification, e.g. phosphorylation, with increased distance from binding pocket, allowing modification to be targeted to locations, for example, amino acid residues, farther away from the binding pocket. For example, a longer linker length can be utilized when a bioconjugation reaction is desirable further away from a binding pocket but optimized for a length that still allows the target binding moiety, once bound to a target substrate in close proximity to the binding pocket of the kinase. Tuning linker length may also include a level of flexibility or rigidity depending on desired configuration of the target binding moiety for modifications of amino acid residues. A shorter linker length may allow for modification within the binding pocket which may desirable for some applications.

In an example embodiment, the kinase binding moiety is an allosteric modulator. Considerations in selecting a kinase binding moiety may include allosteric signaling, which may include changes associated with networks of non-covalently interacting protein residues, conformational selection, and induced fit with both spatial and temporal aspects. In one example embodiment, the kinase binding moiety may be an allosteric activator or inhibitor of the kinase. Allosteric activators or inhibitors may be discovered computationally. In one example method, high quality drug targets are acquired. Then allosteric site prediction is performed using methods such as perturbation response scanning (PRS) combined with all-atom molecular dynamics (MD) and dynamic residue networks (DRN). Allosteric modulators are then identified using methods such as homology modeling, docking, or essential dynamics. An illustration of this process can be found in FIGS. 2 and 3 of Amamuddy S., et al. *Integrated Computational Approaches and Tools for Allosteric Drug Discovery.* 21 *IJMS,*847 (2020), incorporated herein by reference.

Kinase binding moieties may be chosen based on the type of desired modification to be made by the kinase, for example, post-translational modification of the target substrate. In one example embodiment, the kinase binding moiety is capable of binding an kinase that phosphorylates a target, thus the type of kinase may be chosen for this desired modification of a target substrate. Post-translational modification (PTM) is one type of modification performed. Accordingly, post-translational modification kinases are one set of kinase binding moieties envisaged for use in the present invention.

In one example embodiment, the kinase binding moiety provides a modification to an amino acid, see, e.g. for example Table 1 of Karve et al., Journal of Amino Acids Volume 2011, Article ID 207691, 13 pages, DOI: 10.4061/2011/207691, incorporated herein by reference. Karve et al. summarizes some post-translational modifications and their importance in various diseases as well as normal development. Karve et al. assesses, phosphorylation of amino acids, and is incorporated specifically for the phosphorylation modifications detailed therein.

The reaction of the electrophilic reactive group with a moiety on the kinase, for example, a nucleophilic group disposed on the kinase, can allow the labeling or binding of the kinase with the target binding moiety. Such binding of a target binding moiety to the kinase can generate a reprogrammed kinase that can modify a target substrate. Accordingly, in an example embodiment, the kinase binding moiety binds to the kinase and is chosen based on the binding pocket and availability of amino acid side chains in proximity to the binding pocket that may be used in a reaction with the electrophilic reactive group of the targeting chimera.

Example Kinase Binding Moiety

In an example embodiment, the kinase binding moiety is a kinase activator moiety. The kinase activator moiety can be a small molecule or compound that activates a kinase. As used herein, a kinase is an enzyme that adds a phosphate group to another molecule, typically an amino acid of a protein substrate. An activator of a kinase enhances such phosphorylation activity. In one example embodiment, the kinase activator moiety promotes an active conformation of an enzyme, in one aspect, trough binding interactions with regulatory subunits. See, e.g. Zorn et al *Nat Chem Biol.* 2010 March; 6(3):179-188; doi: 10.1038/nchembio.318. The kinase may act on the amino acid serine, threonine, tyrosine, or a combination thereof.

Activator moieties can be identified from activators known in the art. The activators may be a derivative of activators known in the art, and may comprise fewer or additional functional groups that still permit activator activity, but may enhance or facilitate the desired formation, conformation or attachment sites for the chimeric small molecules described herein. Exemplary modifications may include derivatives for increase solubility, charge, functionality for use with an orienting adaptor or linker, detailed elsewhere in the specification.

In one embodiment, the kinase binding moiety is a kinase inhibitor. A kinase inhibitor (KI) is generally designed to bind with a highly conserved Asp-Phe-Gly (DFG) motif of a kinase. KIs can be classified by the conformation of the DFG binding site. Type I bind to the active, DFG-Asp-in, conformation while Type II inhibitors bind to the inactive, DFG-Asp-out, conformation. Further consideration of kinase inhibitors include competition with ATP-binding, which may include mimicking the hydrogen binding interactions normally formed by the adenosine ring of ATP, or the mechanism of inhibition such as reversible binding or irreversible covalent bonding. See e.g. (Gross et al. *J Clin Invest.* 2015; 125(5):1780-1789)

A consideration of kinase inhibitor design has been the degree of specificity to a particular kinase. While the assumed advantage has been for more specificity, kinase inhibitors with a low degree of specificity for a particular kinase facilitates the recruitment of many types of kinases. A promiscuous kinase inhibitor is advantageous as the kinase is a vehicle for the modification of the target substrate.

In one embodiment, the protein binding moiety is a promiscuous kinase inhibitor (PKI). A promiscuous kinase inhibitor refers to a molecule that binds to more than one kinase. A promiscuous kinase inhibitor is a molecule that has binding specificity to a binding pocket with high conservation across kinases. A promiscuous kinase inhibitor may bind to 2, 3, 4, 5 or more different kinases. In one example embodiment, the promiscuous kinase inhibitor is an ATP-competitive kinase inhibitor. In one example embodiment, the PKIs target one or more kinases selected from PDGFRA, PDGFRB, KIT, CSF1R, DDR1, DDR2, MEK5, and YSK4. See, e.g. Seeliger, M. A., et al. "What Makes a Kinase Promiscuous for Inhibitors?" *Cell Chem. Biol.,* 26 (3), 2019; 390-399. For example, the kinase inhibitor imatinib can inhibit c-KIT, PDGFR-alpha and BCR-ABL kinases (see, e.g. Iqbal N, Iqbal N. Imatinib: a breakthrough of targeted therapy in cancer. Chemother Res Pract. 2014; 2014: 357027. doi: 10.1155/2014/357027. Epub 2014 May 19); similarly, sunitinib, sorafenib, and cabozantinib are also known for their promiscuous activity and are provided as non-limiting examples of promiscuous kinase inhibitors. In one example embodiment, the PKI is modified to contain a bio-orthogonal group.

In one example embodiment, the protein binding moiety is a kinase binding moiety. Example kinases that may be bound by the chimeric small molecules of the present invention include, but are not limited to, PK, PKC, AMPK, MAPK, EGFR, FGFR, NGFR, TrkA, ABL, BCKDK, CDK, PI3K, VEGFR, BRAF, MEK, AKT, ALK, BTK, FLT3, JAK2, AURKA, c-MET, DDR, FKBP, INSR, IKK, JNK, mTOR, PAK, PDK1, PDK2, PTK2/FAK, pyruvate kinases, RAC-α, RIPK, TYK2, SHP, aPKC, NOP, μ (mu) opioid receptor, δ (delta) opioid receptor, UMPK, SphK, or GSK-3.

ABL Binding Moiety

In one example embodiment, the protein binding moiety is an ABL kinase binding moiety. Abelson kinases (ABL) is a ubiquitously expressed, nonreceptor tyrosine kinase which plays a key role in cell differentiation and survival. Simpson, et al., *J. Med. Chem.* 2019 62, 2154-2171. ABL tyrosine kinase can be found in the nucleus, cytoplasm, and mitochondria. ABL proteins are normally under well-orchestrated regulation. However, chromosome translocations that join the ABL genes with genes coding for other proteins give rise to various fusion proteins that are prone to dimerization (or oligomerization) and autophosphorylation. Consequently, ABL kinase becomes constitutively active, leading to myeloproliferative disorders. In one example embodiment, one of the ABL kinase binding moieties as detailed herein is used with a target binding moiety as described herein in a chimeric small molecule.

In one example, embodiment, the ABL kinase binding moiety is an ABL kinase activator. In one example embodiment, the c-Abl Kinase activator is (5-[3-(4-fluorophenyl)-1-phenyl-1H-pyrazol-4-yl]-2,4-imidazolidinedione or 5-(1, 3-diaryl-1H-pyrazol-4-yl)hydantoin):

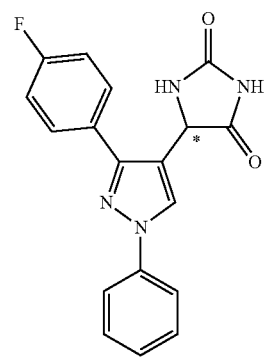 [SMILES: O=C1NC(=O)C(c2cn(-c3ccccc3)nc2-c2ccc(F)cc2)N1]

(DPH) as described in Yang et al., "Discovery and Characterization of a Cell-Permeable, Small-Molecule c-Abl Kinase Activator that Binds to the Myristoyl Binding Site, Chem. & Biol., 18, 177-186, Feb. 25, 2011.

In one example embodiment, the c-Abl kinase activator can be selected from

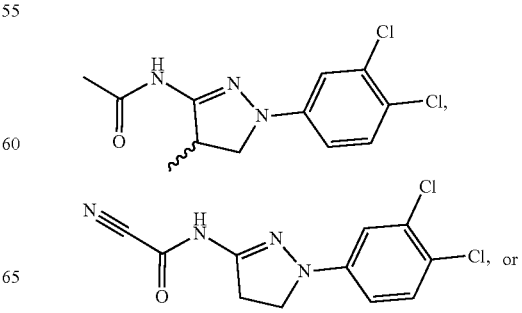

-continued

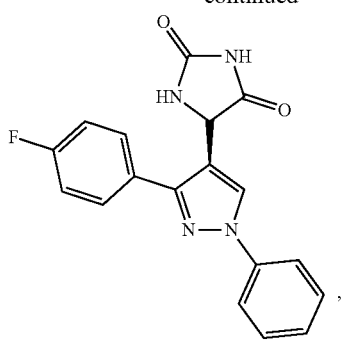

which showed in vivo activation of c-Abl in Simpson, G. L., et al. "Identification and Optimization of Novel Small C-Abl Kinase Activators Using Fragment and HTS Methodologies." *J. Med. Chem.* 2019, 62 (4), 2154-2171. The novel aminopyrazoline small molecule activators described in Simpson et al. at Table 6, are specifically incorporated herein by reference.

In one example embodiment, the c-Abl kinase activator is

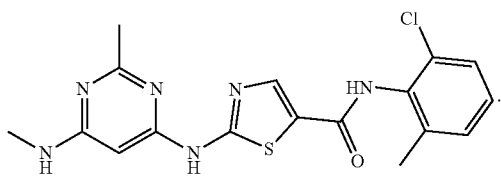 [SMILES: CNc1cc(Nc2ncc(C(=O)Nc3c(C)cccc3Cl)s2)nc(C)n1]

In one example embodiment, the c-Abl kinase binding moiety is a (5-[3-(4-fluorophenyl)-1-phenyl-1H-pyrazol-4-yl]-2,4-imidazolidinedione or 5-(1,3-diaryl-1H-pyrazol-4-yl)hydantoin) (DPH) derivative according to the formula

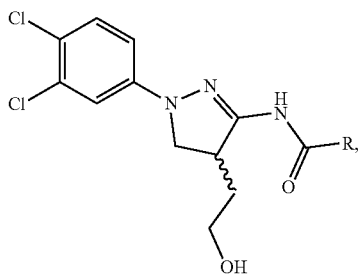

wherein R is

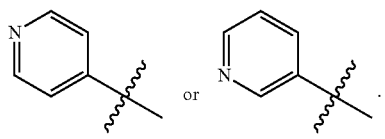 [SMILES: *c1ccncc1 ; *c1cccnc1]

In one example embodiment, the DPH is functionalized:

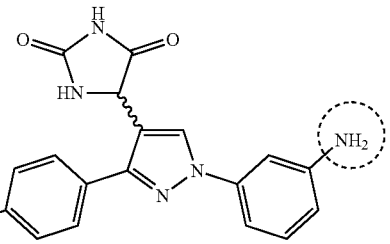

In one example embodiment, the ABL kinase activator is

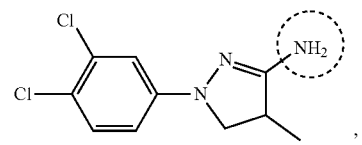

wherein the dashed circle identifies the attachment for the orienting adaptor and/or linker. The functional groups depicted in the dashed circle of the ABL kinase activator can be utilized in methods for attaching a linker and orienting adaptor prior to attachment to the protein binding moiety.

Activator moieties may be functionalized for methods of attaching orienting adaptor and linker. ABL kinase activator parent molecule DPH can be functionalized for methods of attaching orienting adaptor and linker. Exemplary molecules may be:

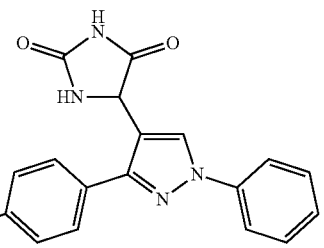

1

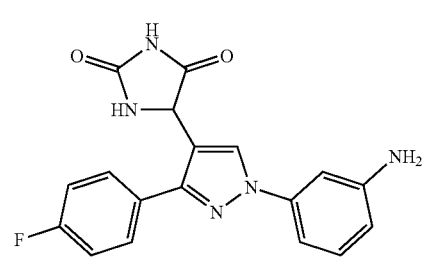

2

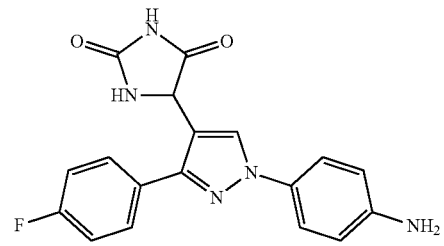

25
-continued
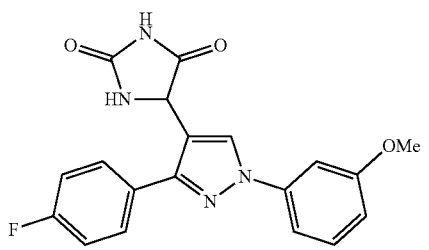
3
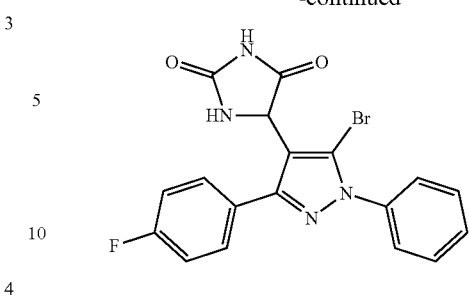
4
26
-continued
5
Once functionalized, the orienting adaptor and linker can be added, either sequentially, or at once, with the orienting adaptor and linker added as one molecule. Exemplary molecules are provided below, with the R group representing the protein binding moiety.
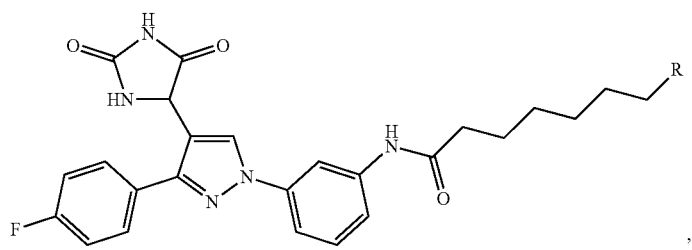
,
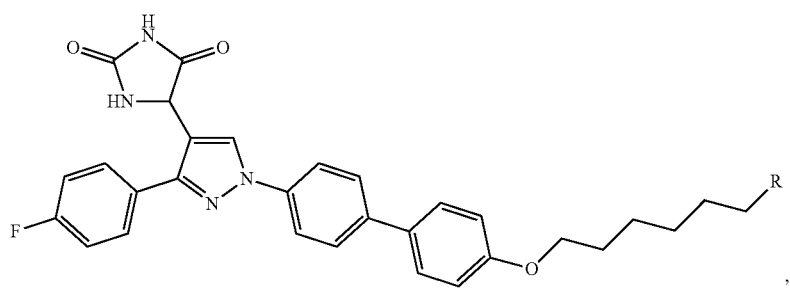
,
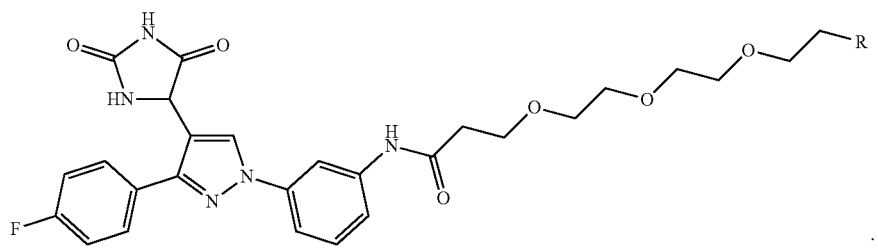
.

Optionally, more than one activator moiety can be attached to the protein binding moiety. In each instance, the activator moiety identified can be functionalized as described herein for methods of attaching a linker and orienting adaptor prior to attachment to the protein binding moiety, for example, utilizing the functional groups depicted in a dashed circle.

In an example embodiment, the Abl kinase activator is DPH or dihydropyrazole activator. An exemplary molecule may comprise

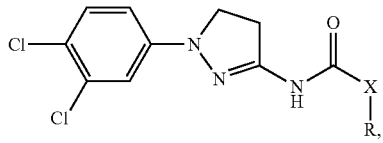

wherein X is $(CH_2)n$, which may be substituted, for example with one or more of amide, acetal, aminal, amine, alkyl, ether, hydrocarbyl, and derivatives thereof, or other groups as described elsewhere herein. In one example embodiment, n is 0 to 20, more preferably n is 1 to 10, or 2 to 7, and R is

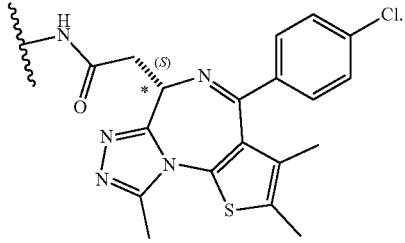

In one example embodiment the attachment to the ABL kinase activator dihydropyrazol is via various types of linkers, see, e.g. (PHICS 10.1-10.5, FIG. 64A of PCT/US2021/012816).

In one preferred embodiment, one of the ABL kinase binding moieties as detailed herein is used with a BRD4 binding moiety as described herein in a chimeric small molecule. In one example embodiment, when the protein binding moiety is for BRD4, an exemplary molecule of may comprise:

PHICS for BRD4
R =

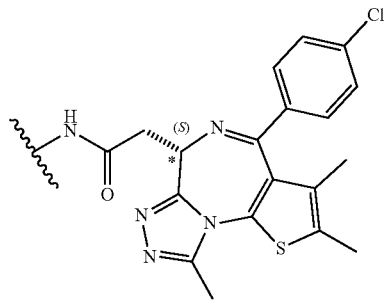

PHICS 10.1: X = $(CH_2)_5$
PHICS 10.2: X = $(CH_2)_3NHC(O)(CH_2)_5$
PHICS 10.3: X = $(CH_2)_2(OC_2H_4)_4$
iPHICS 10.3: X = $(CH_2)_2(OC_2H_4)_4$ with * = (R)
PHICS 10.4: X = $(CH_2)_2NHC(O)CH_2(OC_2H_4)_3$
PHICS 10.5: X = $(CH_2)_2NHC(O)(CH_2)_2(OC_2H_4)_4$ In one embodiment, the kinase binding moiety is an ABL kinase binding moiety according to formula

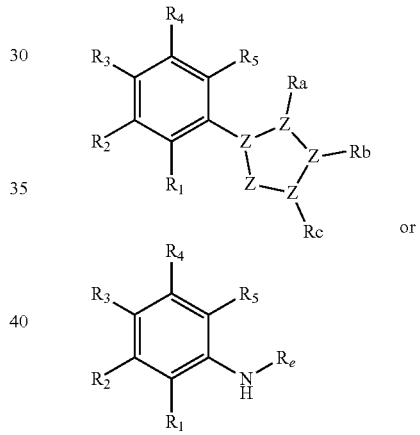

wherein, R1-R5 are independently selected from H, alkane, alkene, alkyne, amine, nitrile, nitro, ether, alcohol, thiol, sulfone, sulfonate, halogen, carbonyl; acyl; ketone; carboxylate ester; amide; enone; anhydride; imide, cyclic hydrocarbon, an unsaturated cyclic hydrocarbon, a heterocycle, one or more fused rings thereof; or an aliphatic halide such as —$OCF_2Cl$; Z is independently selected from B, C, N, O, S, preferably wherein 1 or 2 atoms of Z=N, O, S, or a combination thereof; Ra, Rb, Rc, are independently selected from alkane, alkene, alkyne, ether, alcohol, amine, nitrile, nitro, thiol, sulfone, sulfonate, halogen, carbonyl; acyl; ketone; carboxylate ester; amide; enone; acid anhydride; imide, aliphatic halide such as —$OCF_2Cl$; cyclic hydrocarbon, an unsaturated cyclic hydrocarbon, a heterocycle; one or more fused rings comprising any combination of any previously mentioned rings thereof; and Re is alkane, alkene, alkyne, ether, alcohol, amine, nitrile, nitro, thiol, sulfone, sulfonate, halogen, carbonyl; acyl; ketone; carboxylate ester; amide; enone; acid anhydride; imide, aliphatic halide such as —$OCF_2Cl$; cyclic hydrocarbon, an unsaturated cyclic hydrocarbon, a heterocycle; one or more fused

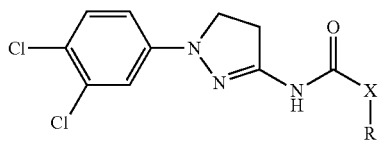

rings thereof at one or more positions, or can form a ring together with $R_1$ or $R_5$, or any combination thereof.

In one embodiment, the one or more of $R_a$, $R_b$, $R_e$ is an amide further bonded to a molecule selected from the group consisting of:

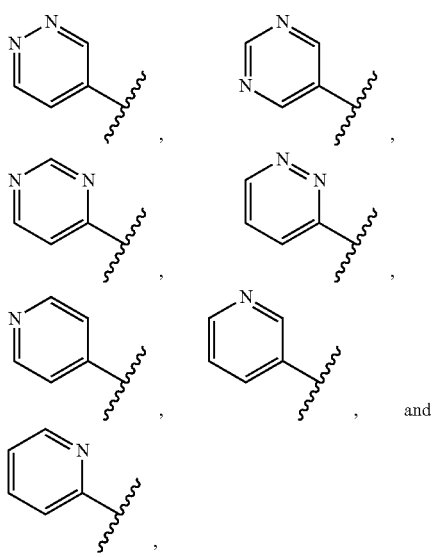

which can be optionally further substituted with alkane, alkene, alkyne, ether, alcohol, amine, nitrile, nitro, thiol, sulfone, sulfonate, halogen, carbonyl; acyl; ketone; carboxylate ester; amide; enone; acid anhydride; imide, cyclic hydrocarbon, an unsaturated cyclic hydrocarbon, a heterocycle; or any combination thereof group at one or more positions.

In one embodiment, the ABL binding moiety is according to formula II(b), wherein Re is selected from the group consisting of:

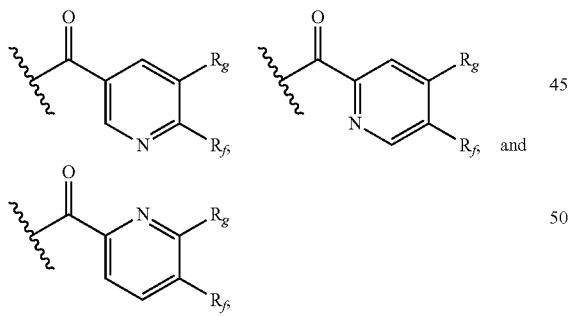

wherein Rf and Rg are selected from cyclic hydrocarbon; an unsaturated cyclic hydrocarbon; a heterocycle; one or more fused rings comprising any combination of any previously mentioned rings optionally substituted at one or more positions alkane, alkene, alkyne, ether, alcohol, amine, nitrile, nitro, thiol, sulfone, sulfonate, halogen, carbonyl; acyl; ketone; carboxylate ester; amide; enone; acid anhydride; imide, cyclic hydrocarbon, an unsaturated cyclic hydrocarbon, a heterocycle; one or more fused rings comprising any combination of any previously mentioned rings. In one example embodiment, wherein Rf and Rg are independently selected from the group consisting of:

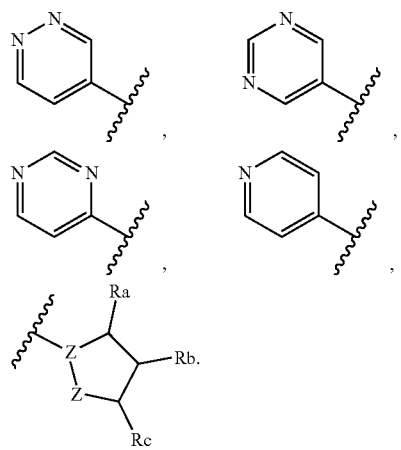

In one embodiment, the kinase binding moiety is selected from the group consisting of:

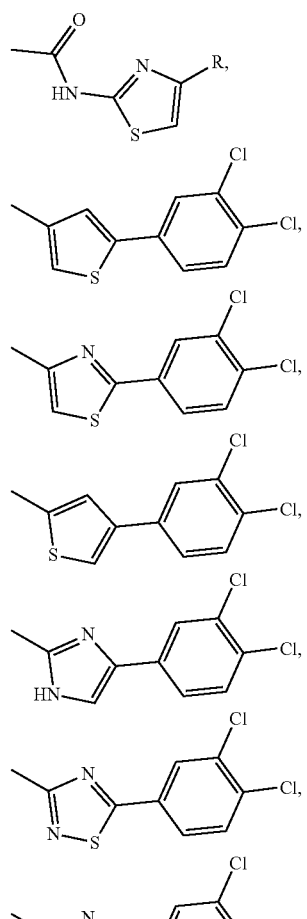

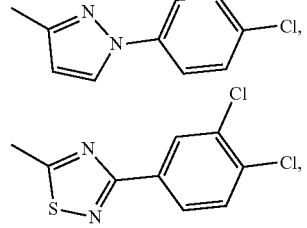

In one example embodiment, the kinase binding moiety is a ABL kinase inhibitor. In one example embodiment, the ABL inhibitor is Imatinib with the formula:

In a one example embodiment, the ABL inhibitor is Nilotinib, Dasatinib, Bosutinib, Ponatinib, or any derivative thereof. In other preferred example embodiments, the kinase binding molecules selected from:

wherein R selected from H, alkane, alkene, alkyne, amine, nitrile, nitro, ether, alcohol, thiol, sulfone, sulfonate, halogen, carbonyl; acyl; ketone; carboxylate ester; amide; enone; anhydride; imide, cyclic hydrocarbon, an unsaturated cyclic hydrocarbon, a heterocycle, one or more fused rings thereof; an aliphatic halides such as —OCF₂Cl or any combination thereof; and optionally selected from

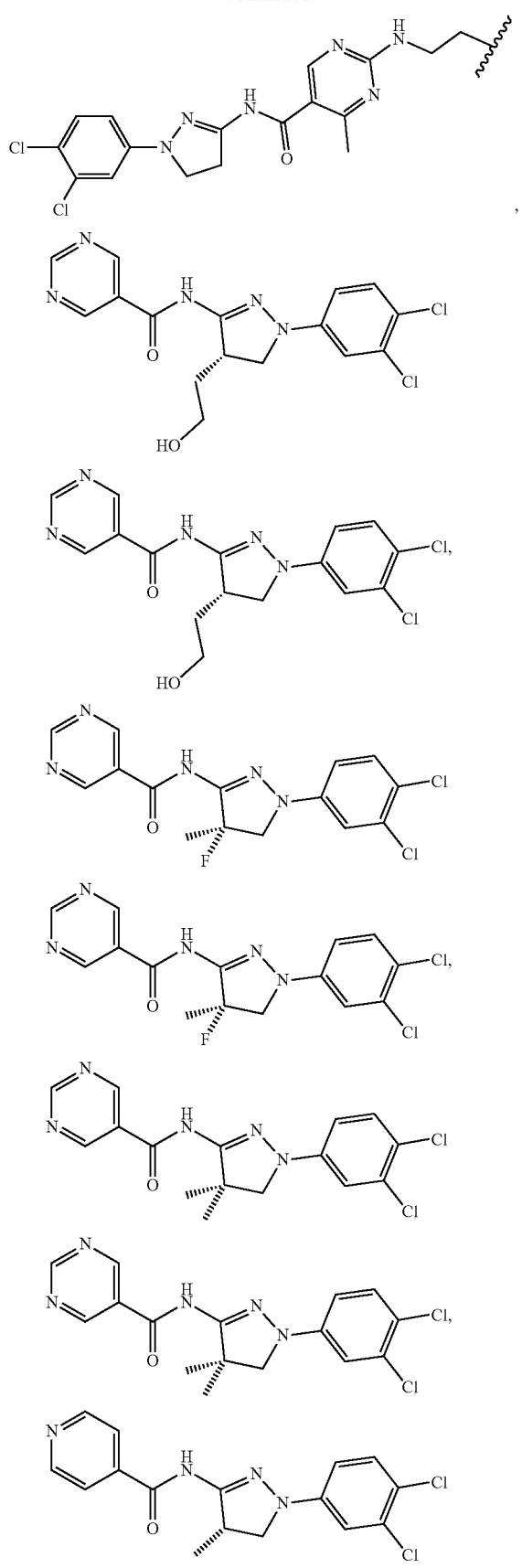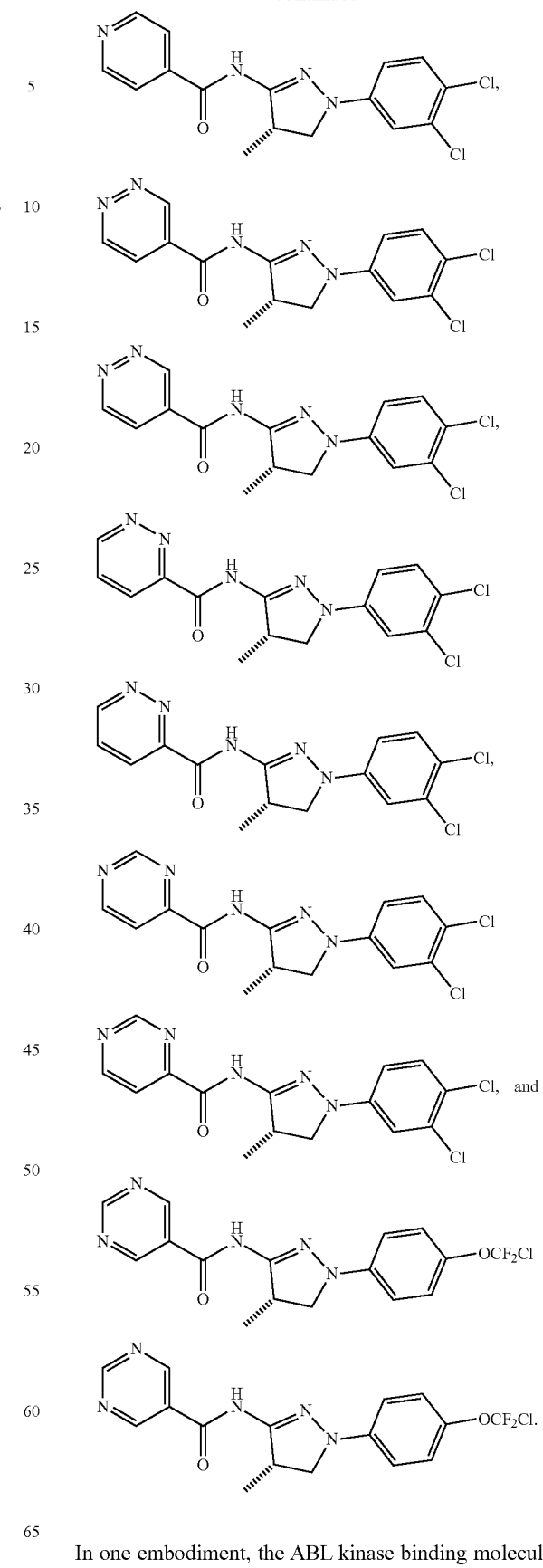
In one embodiment, the ABL kinase binding molecule is selected from the group consisting of:

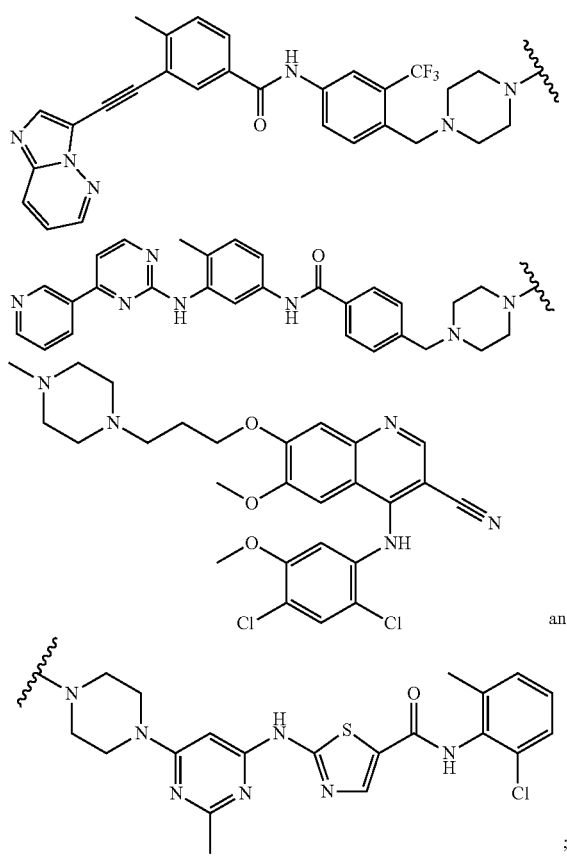
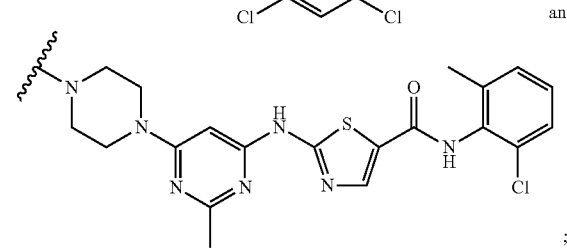
and
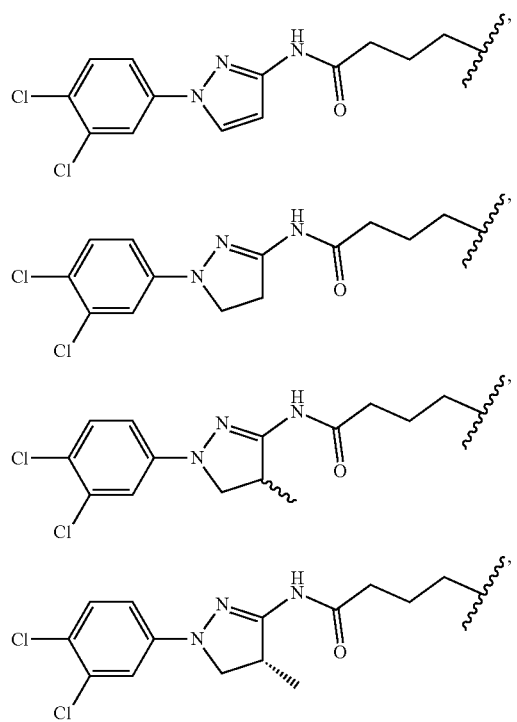
;
In one embodiment, the ABL kinase binding molecule is selected from the group consisting of:
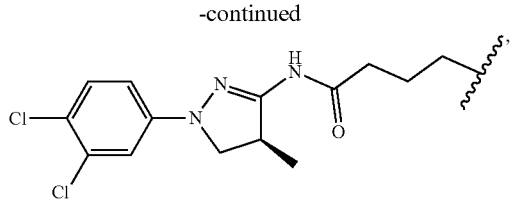
In one embodiment, the ABL kinase binding molecule is selected from the group consisting of:
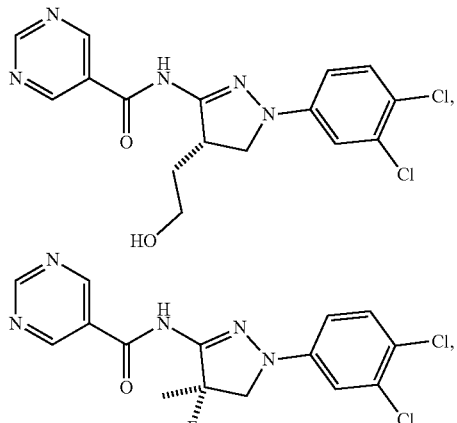
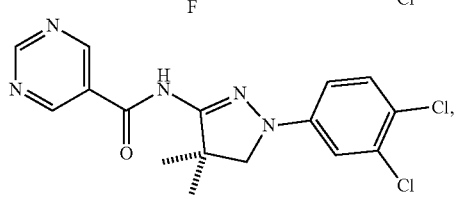
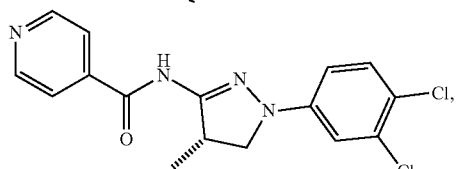
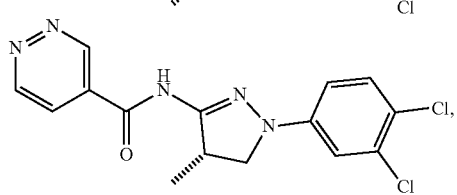
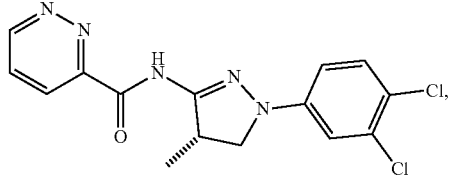

-continued

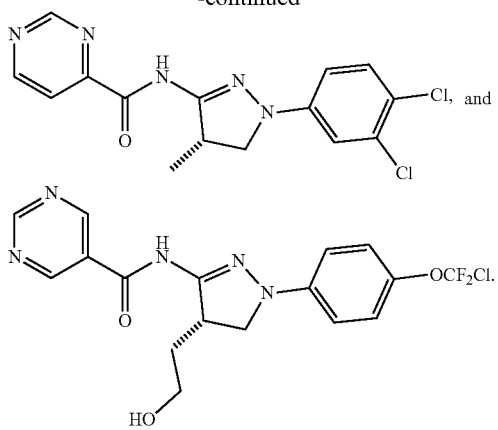

In an example embodiment, the ABL kinase binding moiety is Asciminib, also known as ABL-001, according to the formula:

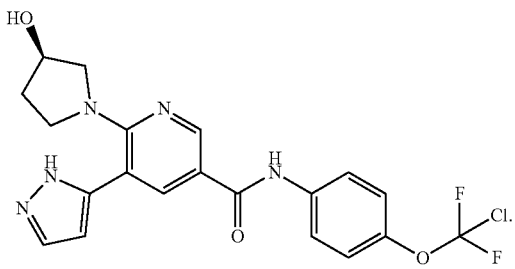 [SMILES: O=C(Nc1ccc(OC(F)(F)Cl)cc1)c1cnc(N2CC[C@@H](O)C2)c(-c2ccn[nH]2)c1]

| Hydrogen bond acceptors | 6 |
| Hydrogen bond donors | 3 |
| Rotatable bonds | 7 |
| Topological polar surface area | 103.37 |
| Molecular weight | 449.11 |
| XLogP | 4.3 |
| No. Lipinski's rules broken | 0 |

Asciminib is a negative allosteric modulator of BCR-ABL1, that induces the kinase to adopt an autoinhibitory, and thereby inactive, conformation. Asciminib-based PROTACs have been given the Fast-Track designation. In the UK, asciminib is available for compassionate use, on a named Organ function impairment and was shown to have minimal effect on platelet function. Asciminib has inhibitory action on cellular proliferation in vitro with $GI_{50}$ 1.5 nM for the wild type ABL1 cell line and 35 nM for the $ABL^{T315I}$ cell line. Asciminib also has an $pIC_{50}$ of 8.6-9.5 for ABL proto-oncogene 1, non-receptor tyrosine kinase. See e.g. Schoepfer, J., et al. "Discovery of Asciminib (ABL001), an Allosteric Inhibitor of the Tyrosine Kinase Activity of BCR-ABL1." *J. Med. Chem.* 2018, 61 (18), 8120-8135, herein incorporated by reference in its entirety. In an aspect, the compound is according to:

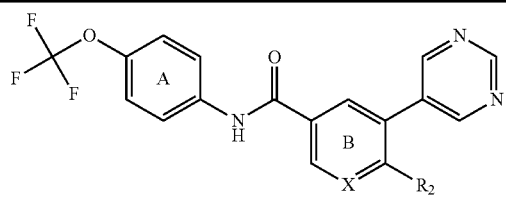

| Cpd | $R^2$ | X | ABL1[164-165] $IC_{50}$ (μM) | Luc-Ba/F3 BCR-$ABL1^{wt}$ $GI_{50}$ (μM) | Luc-Ba/F3 BCR-$ABL1^{T315I}$ $GI_{50}$ (μM) | clogP/ logP | pKa | FASSIF (mM) | HT-Perm calc FA (%) | Rat liver micro- meCL (mL min$^{-1}$ kg$^{-1}$) | hERG dof. Binding $IC_{50}$ (μM) |
|---|---|---|---|---|---|---|---|---|---|---|---|
| 6 | — | | 0.55 ± 0.69 | 0.253; 0.341 | 2.93; >10 | 3.6/4.2 | 6.2 | 0.499 | 100 | 147 | 3.7 |
| 7 | (pyrrolidine-OH) | N | 0.0023 ± 0.0009 | 0.0017 ± 0.0001 | 0.073 ± 0.006 | 2.0/3.0 | 3.3 | 0.59 | 56 | 40 | 9.6 |
| 8 | H | CH | 0.018 ± 0.004 | 0.117 ± 0.065 | 1.80 ± 0.44 | 3.3/4.3 | 3.3 | 0.01 | 100 | 28 | >10 |
| 9 | H | N | 0.024 ± 0.004 | 0.078 ± 0.018 | 1.65 ± 0.44 | 2.5/2.7 | n/a | 0.026 | 98 | 20 | >30 |
| 10 | OMe | CH | 0.011 ± 0.001 | 0.004 ± 0.001 | 0.80 ± 0.09 | 2.9/4.6 | n/a | 0.16 | 100 | 16 | 1.1 |
| 11 | (O-ethyl-pyrrolidine) | CH | 0.019 ± 0.004 | 0.020 ± 0.003 | 1.82; 1.59 | 3.7/>3.4 | 8.9 | 0.5 | 99 | 60 | 0.009 |
| 12 | $NH(CH_2)_3OH$ | N | 0.018 ± 0.008 | 0.004; 0.007 | 0.511; 0.543 | 2.7/3.2 | 3.7 | 0.013 | 36 | 60 | 1.5 |

-continued

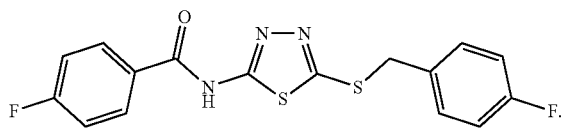 [SMILES: O=C(Nc1nnc(SCc2ccc(F)cc2)s1)c1ccc(F)cc1]

| Cpd | R² | X | ABL1[164-165] IC₅₀ (μM) | Luc-Ba/F3 BCR-ABL1[wt] GI₅₀ (μM) | Luc-Ba/F3 BCR-ABL1[T315I] GI₅₀ (μM) | clogP/ logP | pKa | FASSIF (mM) | HT-Perm calc FA (%) | Rat liver microsomeCL (mL min⁻¹ kg⁻¹) | hERG dof. Binding IC₅₀ (μM) |
|---|---|---|---|---|---|---|---|---|---|---|---|
| 13 | N-piperazinyl-N-Me | N | 0.007 ± 0.001 | 0.005 ± 0.0001 | 0.396 ± 0.043 | 3.1/n/a | 7.4 | 0.151 | 98 | 34 | 0.31 |
| 14 | 3-hydroxypyrrolidinyl | N | 0.004 ± 0.001 | 0.004 ± 0.001 | 0.294 ± 0.066 | 2.0/3.5 | 3.7 | >1 | 40 | 50 | 17 | from Schoepfer et al. (2018).

In an example embodiment, the ABL kinase binding moiety is BO1 according to the formula:

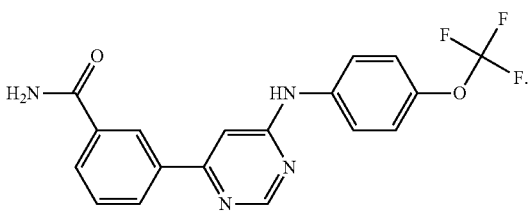 [SMILES: NC(=O)c1cccc(-c2cc(Nc3ccc(OC(F)(F)F)cc3)ncn2)c1]

BO1 is a non-ATP competitive, negative allosteric modulator of mutant BCR-ABL kinase proteins. Interaction of BO1 with the wild type protein shows an ATP-competitive/mixed mechanism of action. BO1 has a $pK_i$ of 7.0-7.4 for ABL proto-oncogene 1, non-receptor tyrosine kinases. See e.g. Radi, M., et al. "Discovery and SAR of 1,3,4-Thiadiazole Derivatives as Potent Abl Tyrosine Kinase Inhibitors and Cytodifferentiating Agents." *Bioorganic & Medicinal Chemistry Letters* 2008, 18 (3), 1207-1211, herein incorporated by reference in its entirety, in particular, compounds 6a-6u:

TABLE 1 c-Src/Abl tyrosine kinase inhibitory activities exerted by compounds 6a-u

| Compound | R¹ | R² | Activity[a] ($K_i$, μM) c-Src | Abl |
|---|---|---|---|---|
| 6a | p-F | p-F | 0.354 | 0.044 |
| 6b | p-Br | p-Cl | 0.217 | 0.047 |
| 6c | H | p-F | 0.464 | 0.070 |
| 6d | m-Cl | p-Cl | 0.195 | 0.073 |
| 6e | p-NO₂ | o-Cl | 0.219 | 0.083 |
| 6f | p-Br | p-F | 0.221 | 0.089 |
| 6g | p-NO₂ | p-Cl | 0.165 | 0.092 |
| 6h | p-F | p-Cl | 0.200 | 0.104 |
| 6i | m-F | p-F | 0.569 | 0.167 |
| 6j | p-OCH₃ | p-Cl | 0.199 | 0.189 |

TABLE 1-continued c-Src/Abl tyrosine kinase inhibitory activities exerted by compounds 6a-u

| Compound | R¹ | R² | Activity[a] ($K_i$, μM) c-Src | Abl |
|---|---|---|---|---|
| 6k | p-OCH₃ | p-F | 0.263 | 0.195 |
| 6l | p-NO₂ | p-F | 0.170 | 0.210 |
| 6m | m-F | p-Cl | 0.064 | 0.217 |
| 6n | p-Br | o-Cl | 0.522 | 0.225 |
| 6o | m-F | o-Cl | 0.718 | 0.272 |
| 6p | m-Cl | p-F | 0.247 | 0.369 |
| 6q | H | p-Cl | 0.334 | 0.400 |
| 6r | p-F | o-Cl | 0.900 | 0.406 |
| 6s | m-Cl | o-Cl | 0.169 | 0.760 |
| 6t | H | o-Cl | 1.137 | 0.920 |
| 6u | p-OCH₃ | o-Cl | 0.272 | 1.260 |
| Imatinib | | | 31 | 0.013 |

In one example embodiment, the ABL kinase binding moiety is GNF-2 according to the formula:

GNF-2 is a highly selective non-ATP competitive inhibitor of Bcr-Abl. It acts as a negative allosteric modulator, binding to a site distant from the ATP pocket. GNF-2 inhibits the Bcr/Abl fusion protein with an IC₅₀ value of 267 nM. See e.g. Zhang, J., et al. "Targeting Bcr-Abl by Combining Allosteric with ATP-Binding-Site Inhibitors." *Nature* 2010, 463 (7280), 501-506, herein incorporated by reference in its entirety.

In one example embodiment, the ABL kinase binding moiety is GNF-5 according to the formula:

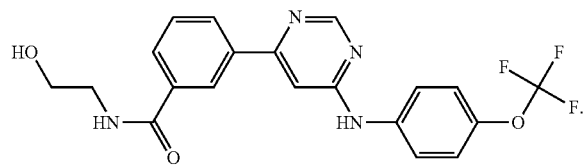 [SMILES: O=C(NCCO)c1cccc(-c2cc(Nc3ccc(OC(F)(F)F)cc3)ncn2)c1]

GNF-5 is a selective and allosteric BCR-ABL inhibitor. GNF-5 can largely overcome the resistance patterns associated with imatinib or nilotinib treatment (except for the gatekeeper mutation T315I). Co-treatment with GNF-2 (GNF-5's original structural incarnation) plus imatinib significantly decreases the emergence of resistant clones in vitro. GNF-5 downregulates BCR-ABL kinase activity by mimicking the effect of myristate binding, which directs the protein towards adopting an inactive conformational state. GNF-5 has pIC$_{50}$ of 6.7 for ABL proto-oncogene 1, non-receptor tyrosine kinase. See e.g. Deng, X., et al. "Expanding the Diversity of Allosteric Bcr-Abl Inhibitors." *J. Med. Chem.* 2010, 53 (19), 6934-6946, herein incorporated by reference in its entirety, and Zhang *Nature* 2010. In an aspect, SAR can be performed around the GNF-2 scaffold, with functionality modified at particular positions:

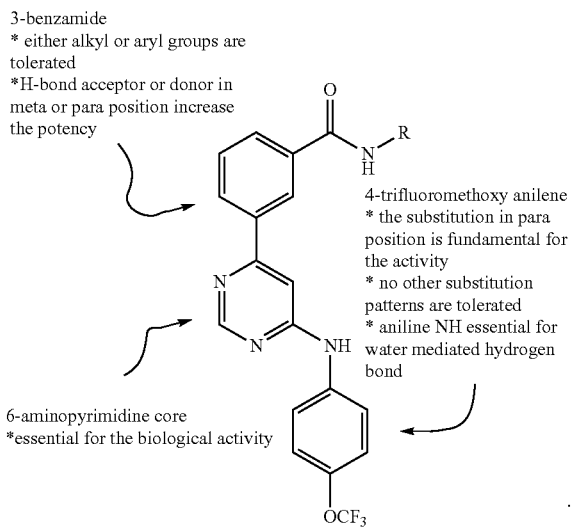

Figure 2:
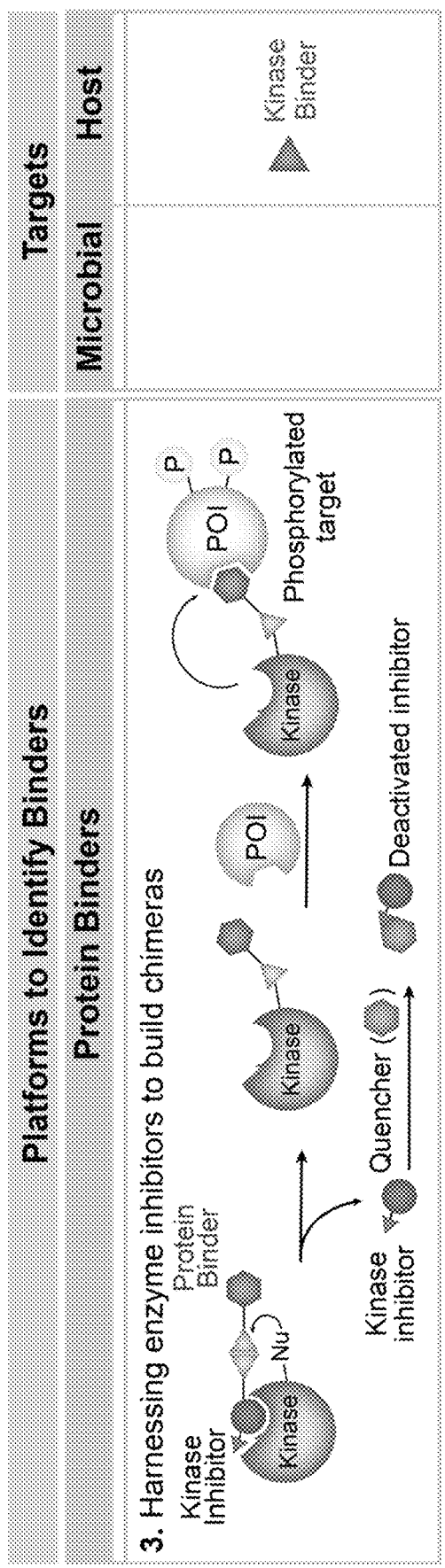
FIG. 2—Binder discovery platforms for microbial targets and host targets.

The crystal structure of GNF-2 bound to the Abl myristoyl pocket can also be utilized for further optimization., see, FIG. 2 of Zhang, Nature, 2010 463, 501-506, incorporated herein by reference. Co-crystal structure of imatinib and GNF-2 in complex with c-Abl is also available (PDB ID:3K5V). Additional targeting moieties can be designed as described in FIG. 3 of Zhang Nature (2010:, FIG. 3, incorporated by reference and depicted below:

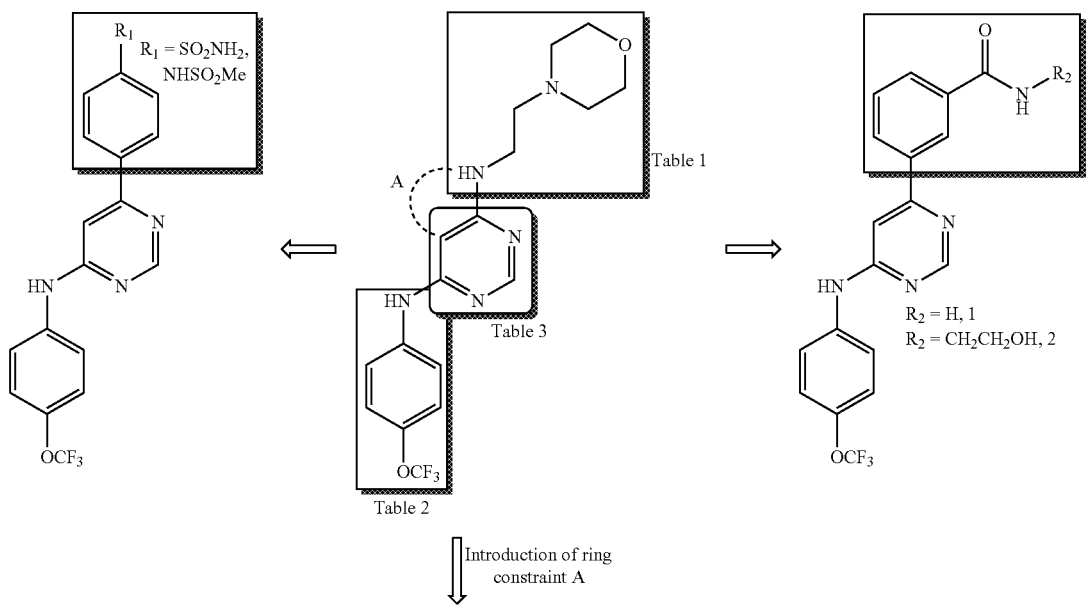

Table 4 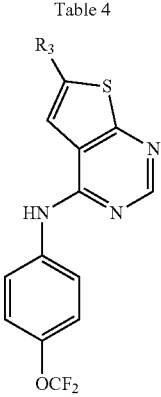 Table 5 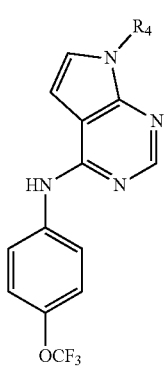 Table 6 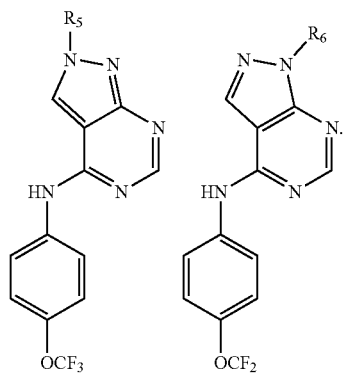

In an example embodiment, the ABL kinase binding moiety is DPH according to the formula:

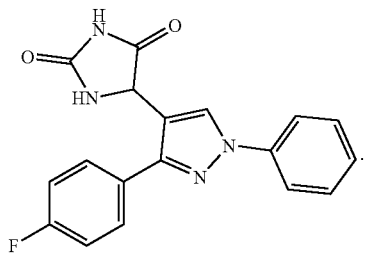 [SMILES: O=C1NC(=O)C(c2cn(-c3ccccc3)nc2-c2ccc(F)cc2)N1]

DPH has an ICW $EC_{50}$ of 6.1, see e.g. Simpson, G. L., et al. "Identification and Optimization of Novel Small C-Abl Kinase Activators Using Fragment and HTS Methodologies." *J. Med. Chem.* 2019, 62 (4), 2154-2171, herein incorporated by reference in its entirety, and may be according to DPH and compounds as identified below:

DPH (1)

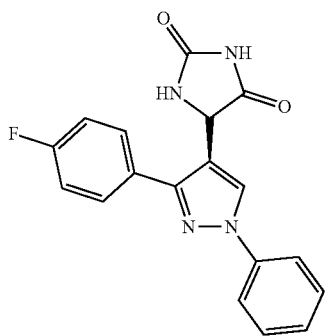

FP Binding $pIC_{50}$: 6.4
IMAP Enzyme Act $pEC_{50}$: 6.6
Cell Act $pEC_{50}$: 6.1

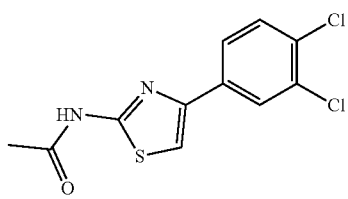

FP Binding $pIC_{50}$: 6.5
IMAP Enzyme Act $pEC_{50}$: 5.6
Cell Act $pEC_{50}$: 4.5

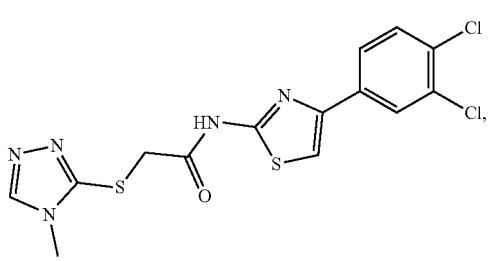

FP Binding $pIC_{50}$: 6.3
IMAP Enzyme Act $pEC_{50}$: 5.0
Cell Act $pEC_{50}$: 4.7 as well as compounds 45 and 32 as adapted from Simpson et al.:

| Cmpd | Structure | cellular activation (ICW EC$_{50}$) | In Vitro Clearance$^c$ (mL/min/mg protein) | In Vivo Plasma Concentration (ng/mL)$^a$ | | Fold Increase phCRKL Vs Total Crk-1. (normalised)$^b$ | |
|---|---|---|---|---|---|---|---|
| | | | | 40 min | 180 min | 40 min | 180 min |
| 1 | 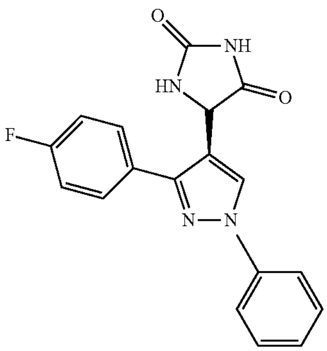 | 6.1 | 0.266 | 15100 ± 1150 | 1050 ± 595 | 13x | 28x |
| 45 | 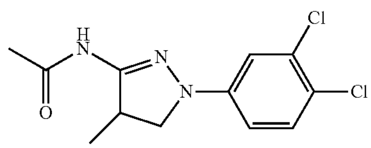 [SMILES: CC(=O)NC1=NN(c2ccc(Cl)c(Cl)c2)CC1C] | 6.3 | 0.408 | 5540 ± 233 | 2540 ± 143 | 1x | 5x |
| 32 | 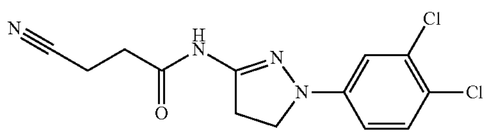 [SMILES: N#CCCC(=O)NC1=NN(c2ccc(Cl)c(Cl)c2)CC1] | 6.1 | <0.01 | 15600 ± 1700 | 17600 ± 3530 | 19x | 35x. |

In another example embodiment, the ABL target binding moiety is any c-ABL kinase activator from Simpson *J. Med. Chem.* 2019.

In an example embodiment, the ABL kinase binding moiety is dihydropyrazole according to the formula:

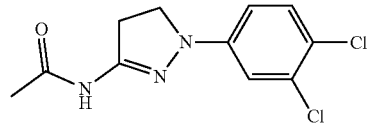

In one example embodiments, the ABL kinase binding moiety is selected from the group consisting of:

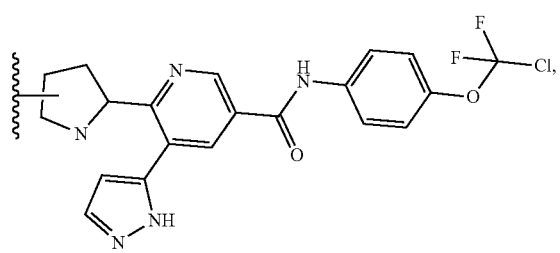

-continued

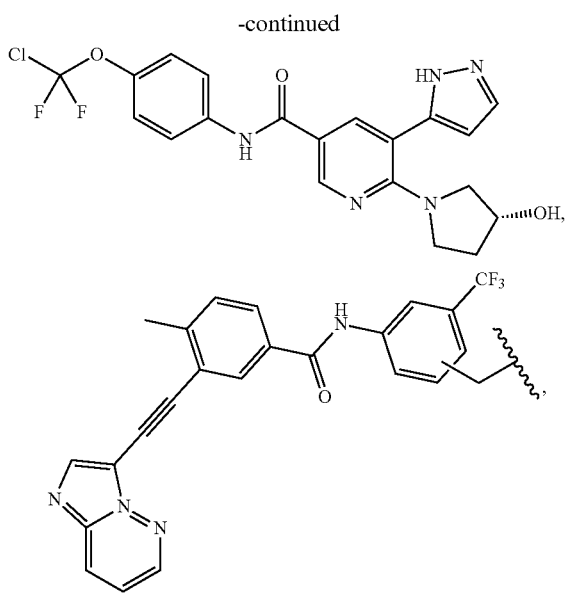

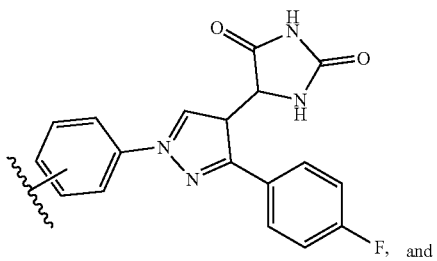

F, and

47

-continued

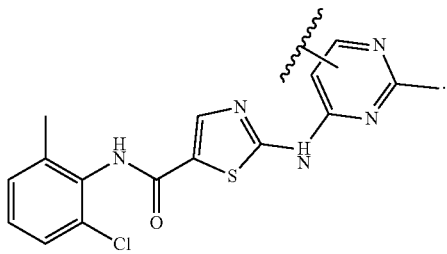

In one embodiment, the ABL kinase binding moiety

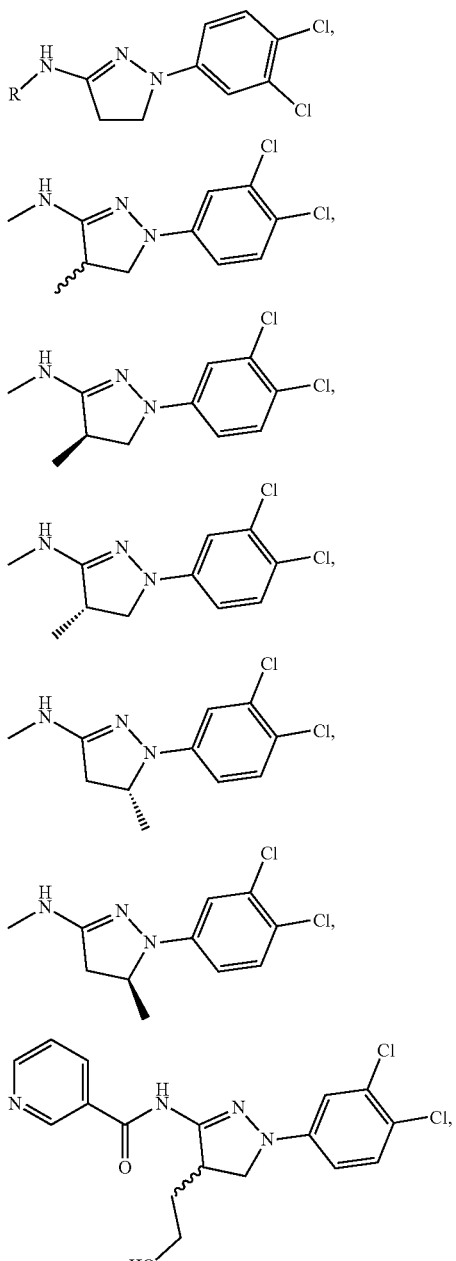

48

-continued

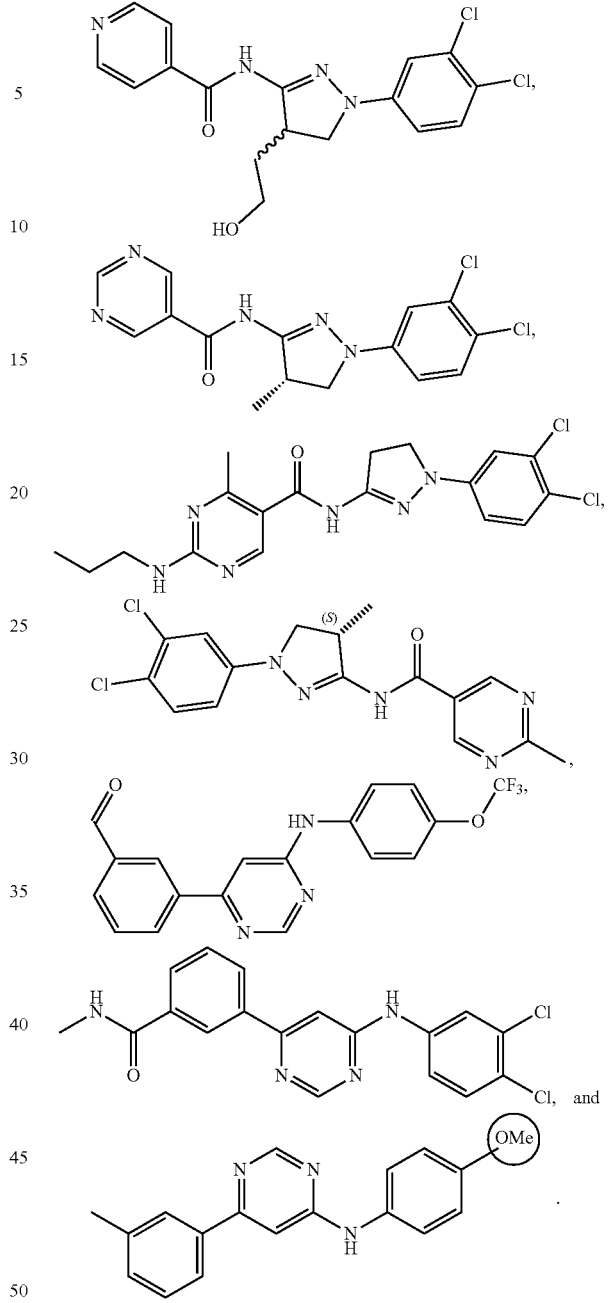

The R in ABL inhibitor formula is optimized for physiochemical properties, such as solubility and/or permeability, and/or pharmacokinetic properties, such as microsomal stability or target binding. In one example embodiment, R is selected from any boron-, carbon-, nitrogen-, oxygen-, sulfur-, halogen-based substituent, heterocycle, fused ring, or any combination thereof. In preferred example embodiments, R is selected from H, alkane, alkene, alkyne, amine, nitrile, nitro, ether, alcohol, thiol, sulfone, sulfonate, halogen, carbonyl; acyl; ketone; carboxylate ester; amide; enone; anhydride; imide, cyclic hydrocarbon, an unsaturated cyclic hydrocarbon, a heterocycle, one or more fused rings thereof; an aliphatic halides such as —OCF$_2$Cl or any combination thereof. In preferred example embodiments, R is selected from

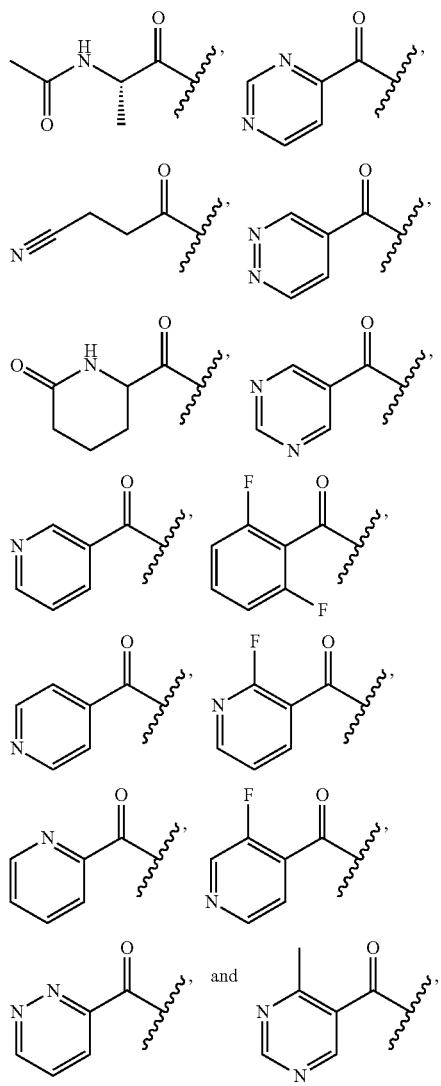

In an example embodiment, the ABL inhibitor kinase binding molecule is selected from

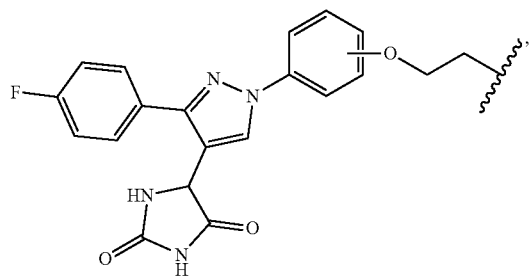

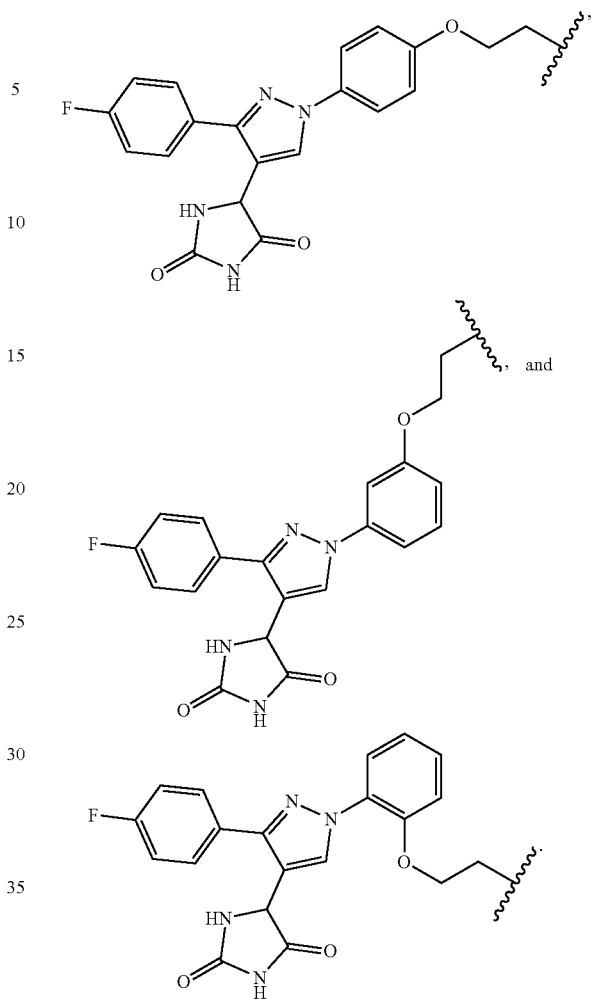

In other example embodiments, the ABL inhibitor kinase binding molecule is selected from the formula

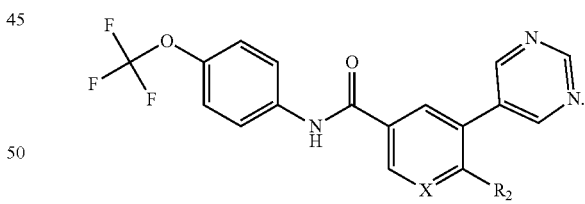

In one example embodiment, X and $R_2$ is optimized for physiochemical properties, such as solubility and/or permeability, and/or pharmacokinetic properties, such as microsomal stability or target binding. In one example embodiment, X is any feasible boron-, carbon-, nitrogen-, oxygen-, or sulfur-based element or compound. In preferred example embodiments, X is selected from C, N, O, and S. In one example embodiment, $R_2$ is selected from any boron-, carbon-, nitrogen-, oxygen-, sulfur-, halogen-based substituent, heterocycle, fused ring, or any combination thereof. In preferred example embodiments, $R_2$ is selected from R2 is selected from H, alkane, alkene, alkyne, amine, nitrile, nitro, ether, alcohol, thiol, sulfone, sulfonate, halogen, carbonyl; acyl; ketone; carboxylate ester; amide; enone; anhydride;

imide, cyclic hydrocarbon, an unsaturated cyclic hydrocarbon, a heterocycle, one or more fused rings thereof; an aliphatic halides such as —OCF$_2$Cl or any combination thereof. In Preferred example embodiments, R2 is selected from

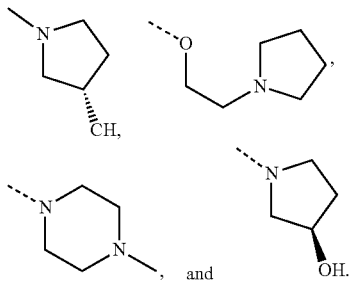

In one example embodiments, the ABL kinase binding molecule is selected from

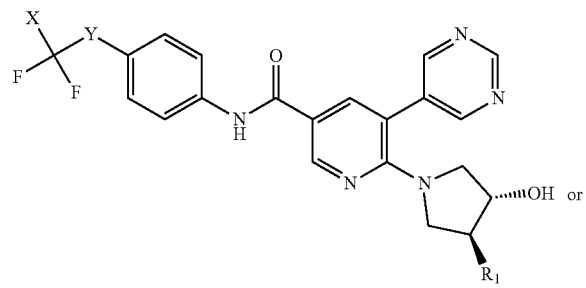

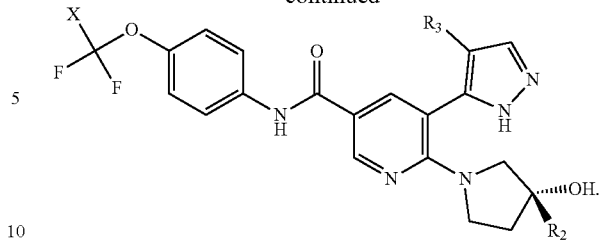

In one example embodiment, X, Y, and R groups are optimized for physiochemical properties, such as solubility and/or permeability, and/or pharmacokinetic properties, such as microsomal stability or target binding. In one example embodiment, X and Y are independently selected from any boron-, carbon-, nitrogen-, oxygen-, sulfur-, halogen-based substituent, heterocycle, fused ring, or any combination thereof. In preferred example embodiments, X is a halogen. In preferred example embodiments, Y is selected from C, N, O, and S. In one example embodiment, $R_1$, $R_2$, and $R_3$ is independently selected from any boron-, carbon-, nitrogen-, oxygen-, sulfur-, halogen-based substituent, heterocycle, fused ring, or any combination thereof. In preferred example embodiments, $R_1$, $R_2$, and $R_3$ is independently selected from H, alkane, alkene, alkyne, amine, nitrile, nitro, ether, alcohol, thiol, sulfone, sulfonate, halogen, carbonyl; acyl; ketone; carboxylate ester; amide; enone; anhydride; imide, cyclic hydrocarbon, an unsaturated cyclic hydrocarbon, a heterocycle, one or more fused rings thereof; an aliphatic halides such as —OCF$_2$Cl or any combination thereof.

In other example embodiments, the ABL inhibitor kinase binding molecule is selected from:

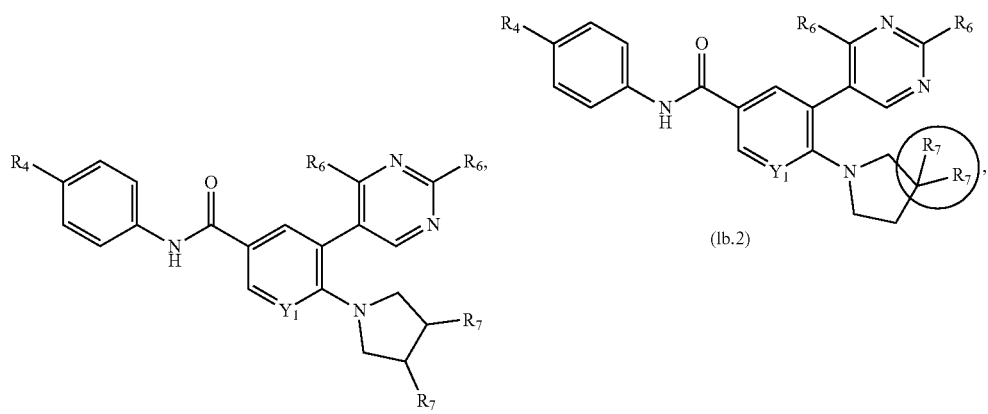

(Ib.2)

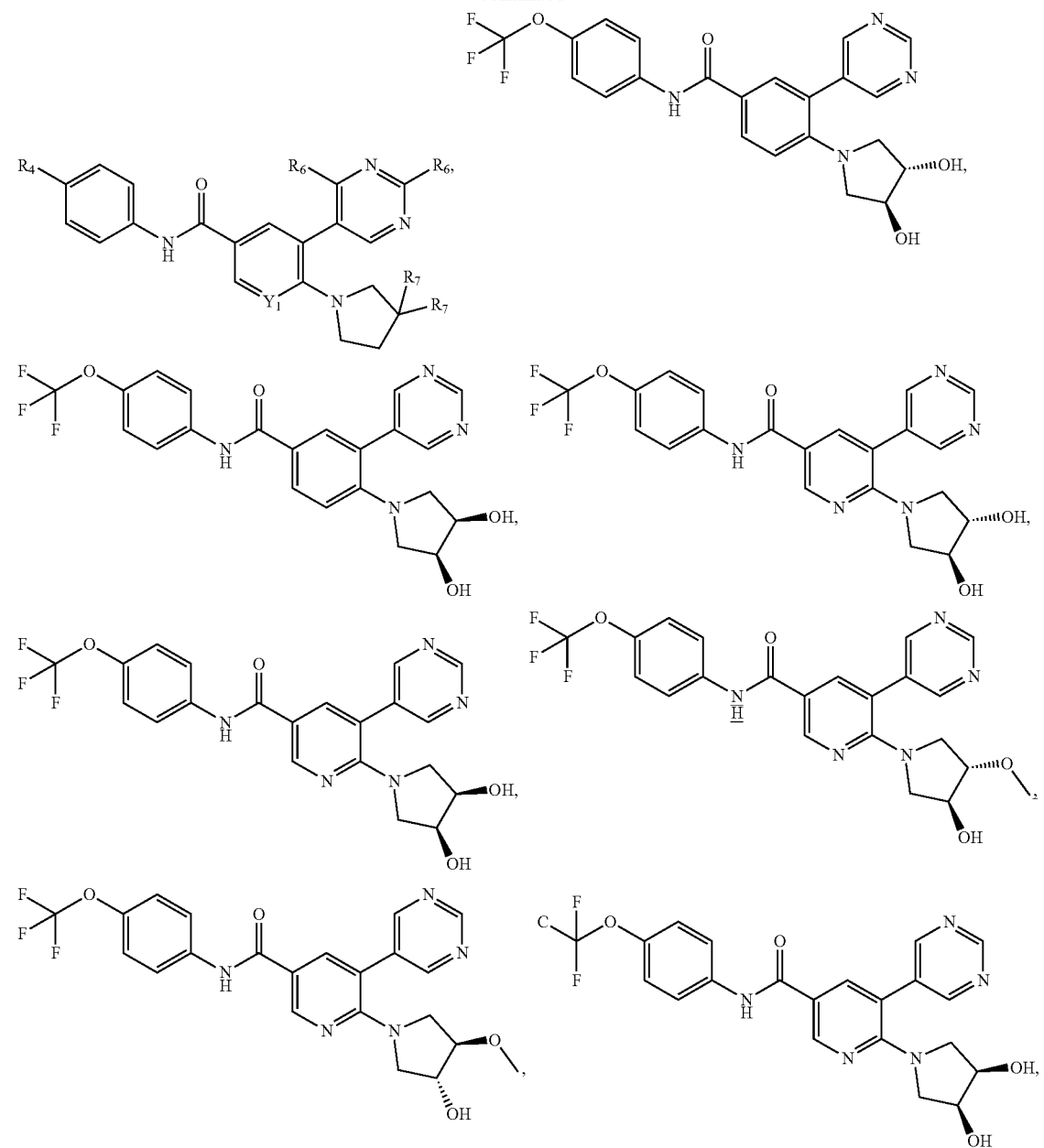
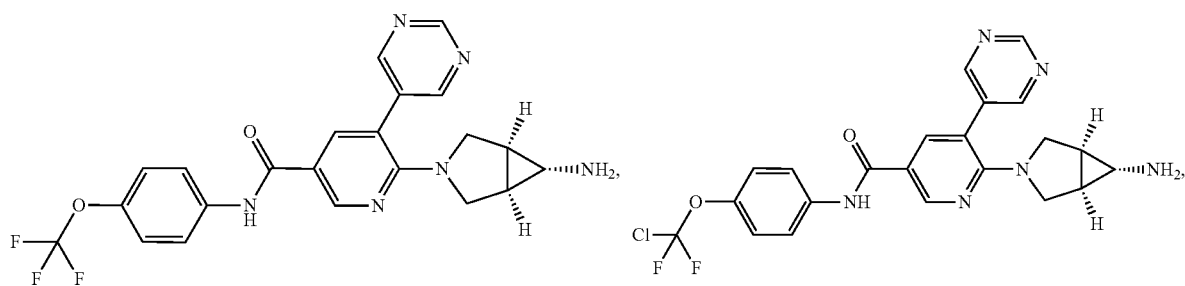

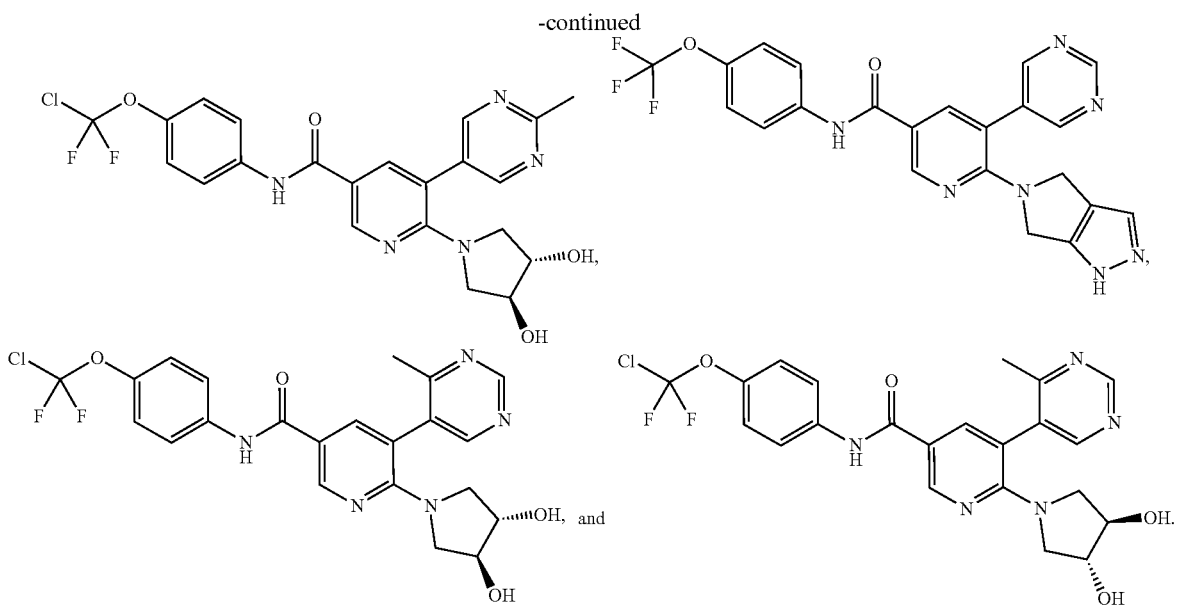

In one example embodiment, the Y groups and R groups are optimized for physiochemical properties, such as solubility and/or permeability, and/or pharmacokinetic properties, such as microsomal stability or target binding. In one example embodiment, Y and $Y_1$ in the previously mentioned formulas is any feasible boron-, carbon-, nitrogen-, oxygen-, or sulfur-based element or compound. In preferred example embodiments, Y and $Y_1$ is selected from C, N, O, and S. In one example embodiment, $R_3$, $R_4$, $R_6$, and $R_7$ in the previously mentioned formulas are independently selected from any boron-, carbon-, nitrogen-, oxygen-, sulfur-, halogen-based substituent, heterocycle, fused ring, or any combination thereof. In Preferred example embodiments, $R_3$, $R_4$, $R_6$, and $R_7$ is independently selected from H, alkane, alkene, alkyne, amine, nitrile, nitro, ether, alcohol, thiol, sulfone, sulfonate, halogen, carbonyl; acyl; ketone; carboxylate ester; amide; enone; anhydride; imide, cyclic hydrocarbon, an unsaturated cyclic hydrocarbon, a heterocycle, one or more fused rings thereof; an aliphatic halides such as —$OCF_2Cl$ or any combination thereof.

In other example embodiments, the ABL kinase inhibitor binding molecule is selected from:

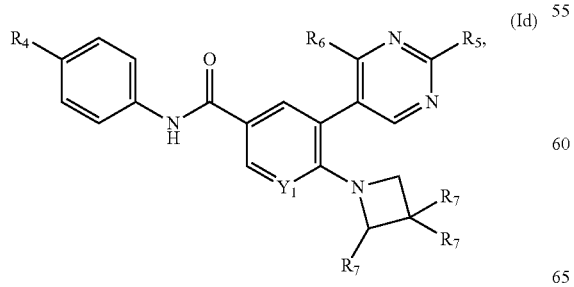
(Id)

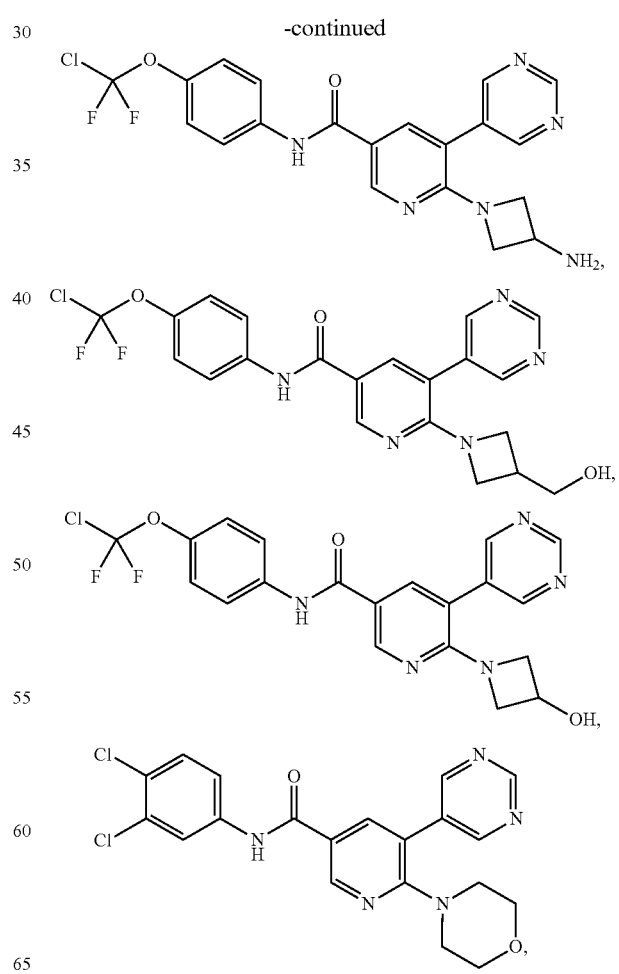

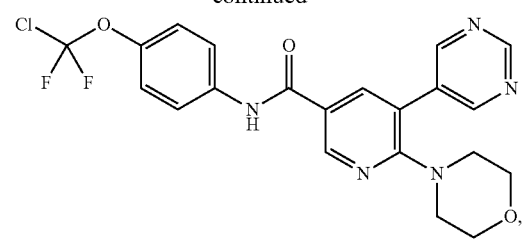
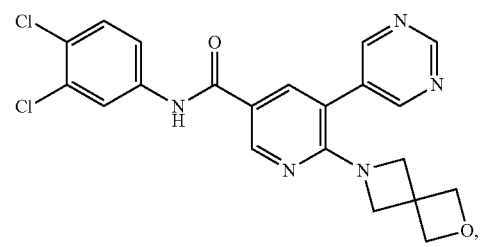
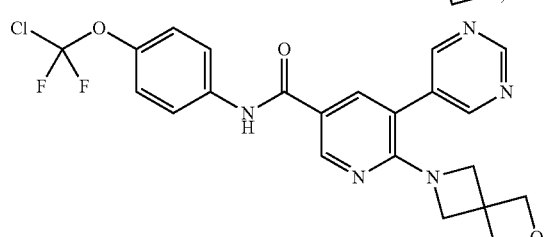
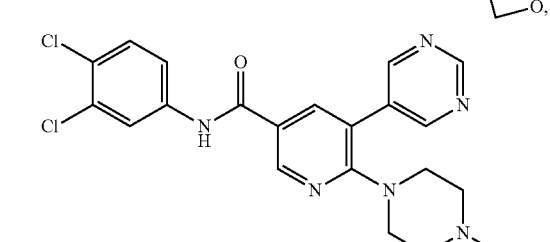
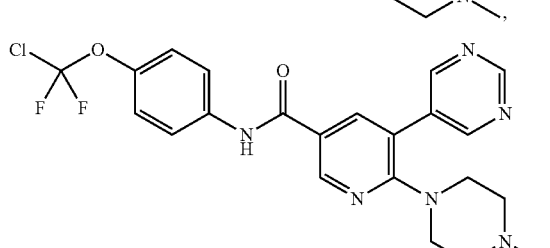
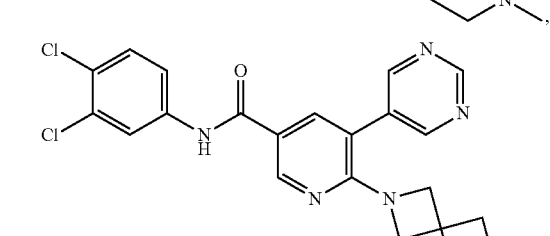
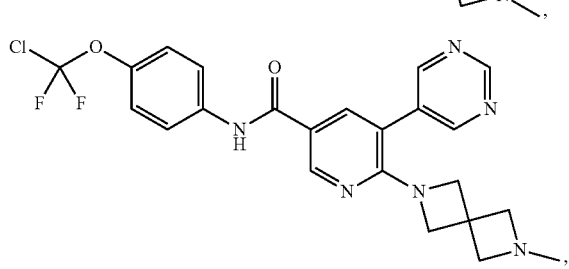

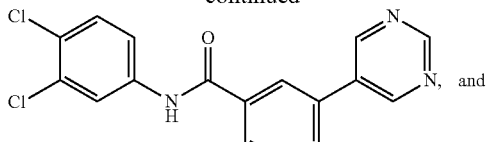
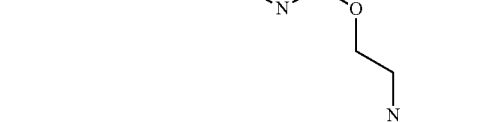
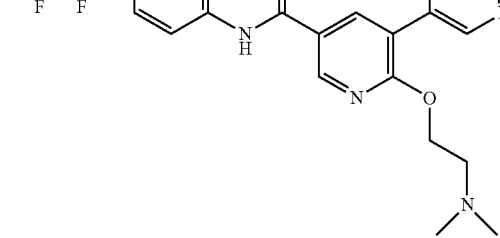

In one example embodiment, $Y_1$ and R groups are optimized for physiochemical properties, such as solubility and/or permeability, and/or pharmacokinetic properties, such as microsomal stability or target binding. In one example embodiment, $Y_1$ in the previously mentioned formulas is any feasible boron-, carbon-, nitrogen-, oxygen-, or sulfur-based element or compound. In Preferred example embodiments, $Y_1$ is selected from C, N, O, and S. In One example embodiment, $R_4$, $R_6$, and $R_7$ in the previously mentioned formulas are independently selected from any boron-, carbon-, nitrogen-, oxygen-, sulfur-, halogen-based substituent, heterocycle, fused ring, or any combination thereof. In preferred example embodiments, $R_4$, $R_6$, and $R_7$ is independently selected from H, alkane, alkene, alkyne, amine, nitrile, nitro, ether, alcohol, thiol, sulfone, sulfonate, halogen, carbonyl; acyl; ketone; carboxylate ester; amide; enone; anhydride; imide, cyclic hydrocarbon, an unsaturated cyclic hydrocarbon, a heterocycle, one or more fused rings thereof; an aliphatic halides such as —OCF$_2$Cl or any combination thereof.

In one example embodiment, the protein binding moiety is an ABL inhibitor. In one example embodiment, the ABL inhibitor is DCC-2036, which is a dual-anchoring inhibitor that binds both the switch control pocket E282/R386 pair and the Met318 ATP hinge with an IC50 value of 0.8 nM according to the formula:

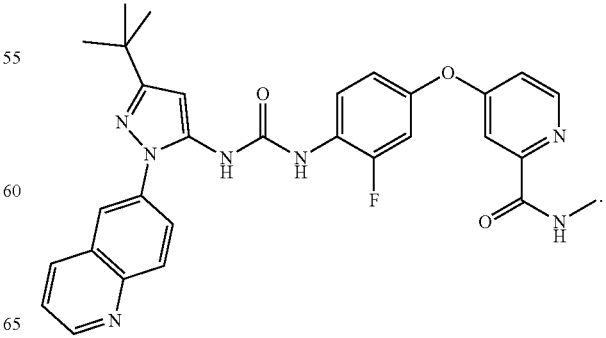

In one example embodiment, the kinase binding moiety is a c-ABL tyrosine kinase inhibitor or any derivative thereof from the International Patent Application WO2019173761, herein incorporated by reference.

AMPK Binding Moiety

In one example embodiment, the kinase binding moiety is an AMPK kinase binding moiety. AMPK is a serine/threonine kinase that assembles into a heterotrimeric complex composed of a catalytic α-subunit and two regulatory β- and γ-subunits. See, e.g. Wells et al. (2012). It is believed that small molecules that mimic AMP binding to the γ-subunit could directly activate AMPK.

In one embodiment, the AMPK kinase binding moiety is according to the formula:

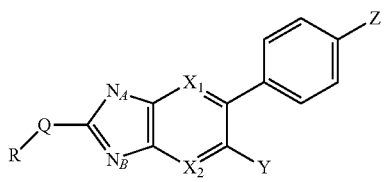

wherein R is selected from the group consisting of:

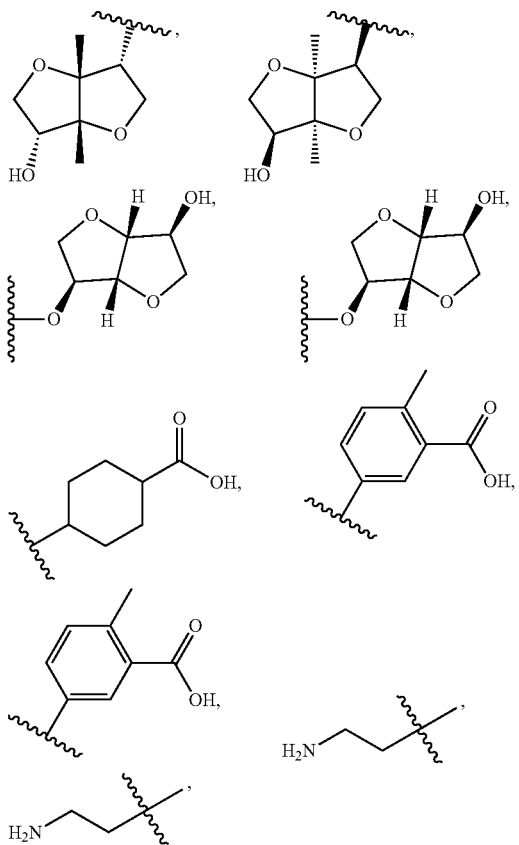

a carbohydrate mimetic, a heterocycle, a diahydrohexitol, a pyranose, or a furanose; Q is selected from the group consisting of: B, C, N, O, S; and wherein a H is located on either $N_A$ or $N_B$; $X_1$ and $X_2$ is independently selected from the group consisting of: C, N and O; Y is selected from the group consisting of: H, OH, a halogen, CN or hydrogen bond donating substituent; and Z is selected from the group consisting of: H, alkane, alkene, alkyne, amine, nitrile, nitro, ether, alcohol, thiol, sulfone, sulfonate, halogen, carbonyl; acyl; ketone; carboxylate ester; amide; enone; anhydride; imide, cyclic hydrocarbon, an unsaturated cyclic hydrocarbon, a heterocycle, one or more fused rings thereof; or an aliphatic halide such as —$OCF_2Cl$ which optionally can be further substituted.

In one example embodiment, Z can be according to the formula:

$$Z_a\text{-}Z_b;$$

wherein $Z_a$ is selected from the group consisting of:

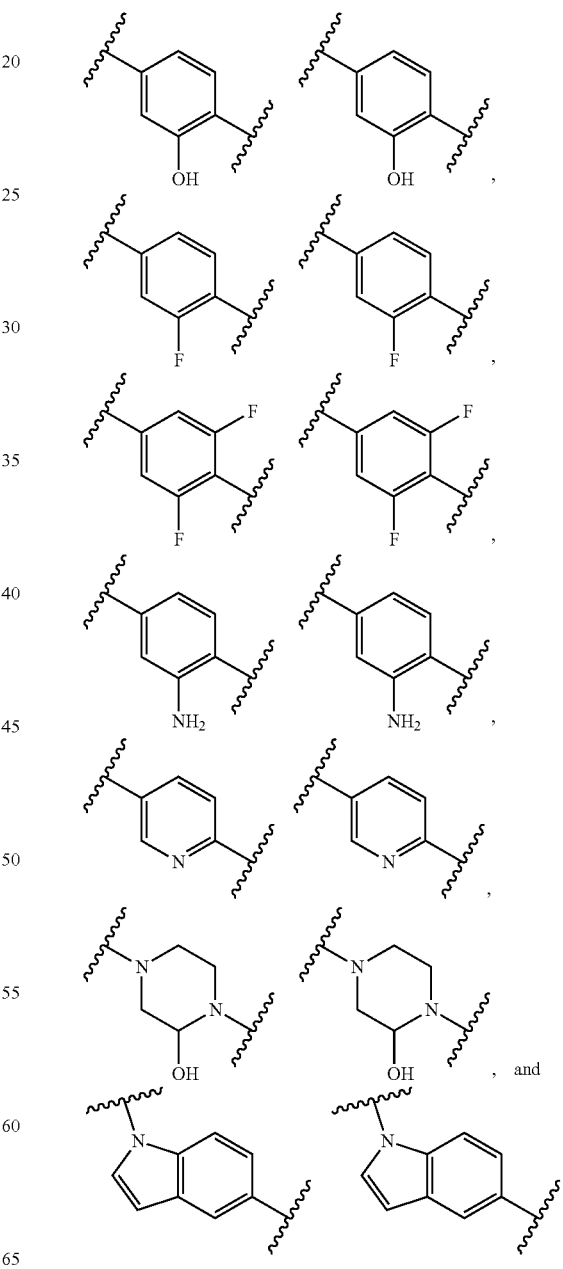

wherein $Z_b$ is selected from the group consisting of:
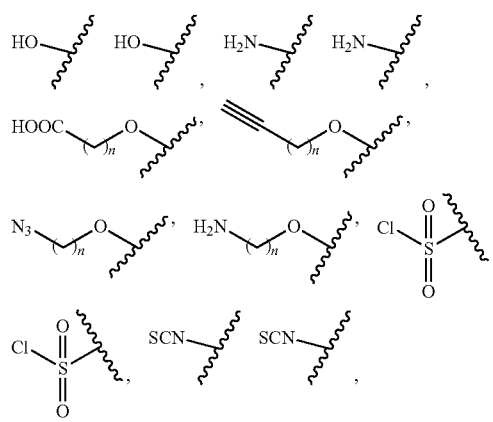
and n is between 0-6.
In one embodiment, the AMPK binding moiety is selected from the group consisting of AMPK binding moiety selected from the group consisting of:
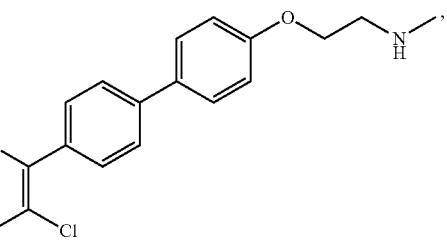
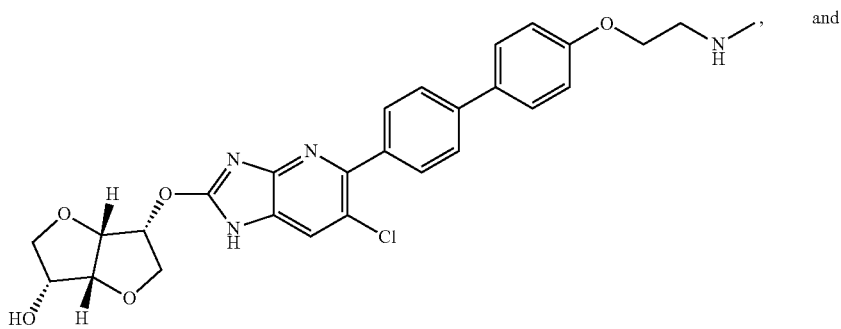
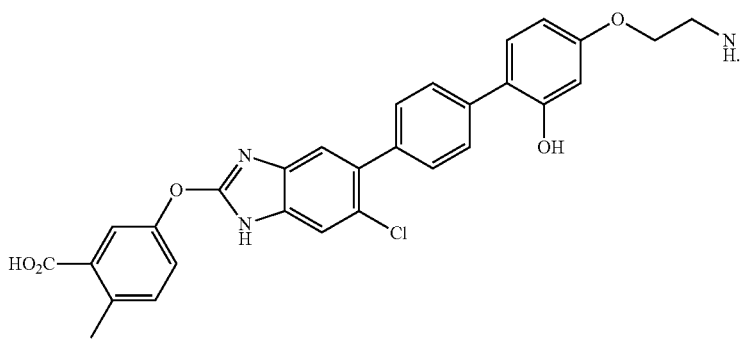

Additional AMPK kinase binding moieties that can be used in accordance with the present invention include Other AMPK activators include A769662 (Cool et al., Cell Metab. 3, 403-416 (2006)) and PT1 (Pang et al., J. Biol. Chem. 283, 16051-16060 (2008), and derivatives thereof and as further modified in accordance with the teachings detailed herein for use and optimization in the chimeric small molecules of the present invention.

AMPK binding moieties can be as described for example in U.S. Patent Publication 20050038068, incorporated herein by reference, and can be according to

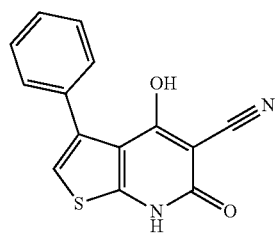

A-592107 or

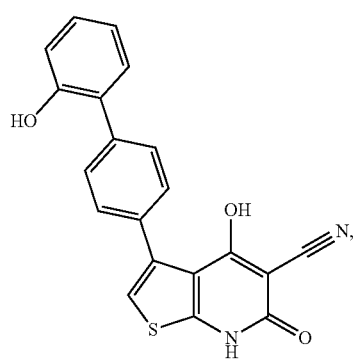

A-769662 or derivatives thereof and as further modified in accordance with the teachings detailed herein for use and optimization in the chimeric small molecules of the present invention.

In one example embodiment, the kinase binding moiety is a AMPK activator. In an example embodiment, the AMPK activator is selected from:

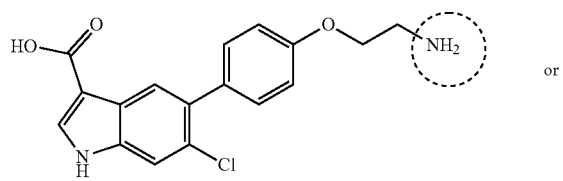

Parent: PF-06409577 (AMPK activator)

or

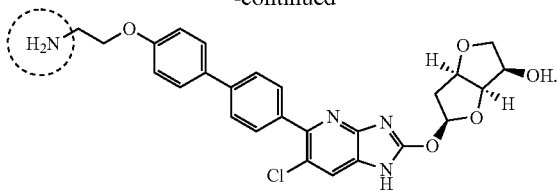

MK-8722 (AMPK activator)

Other AMPK activators include A769662, which has a $pEC_{50}$ value of 6.0, see e.g. Cool, B., et al. "Identification and Characterization of a Small Molecule AMPK Activator That Treats Key Components of Type 2 Diabetes and the Metabolic Syndrome." *Cell Metabolism* 2006, 3 (6), 403-416, herein incorporated by reference in its entirety.

AMPK activators can be as described for example in U.S. Patent Publication 20050038068, incorporated herein by reference, and can be according to

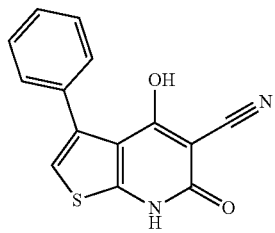

A-592107 or

A-769662

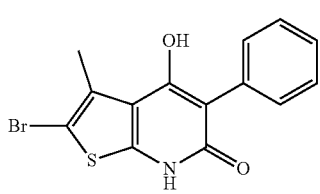

AMPK activators can be as described in International Patent Publications WO2007019914, WO2009124636, WO2009135580, WO2008006432, or WO2009152909, incorporated herein by reference. In one example embodiment, the activator can be according to AlphaScreen: 322%
Delfia: 313%,

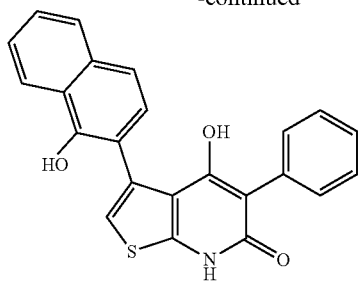

α1β1γ2
Activation at 30 μM:625%,

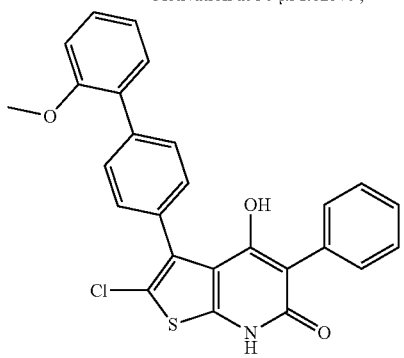

α1β1γ2
Activation at 30 μM:111%,

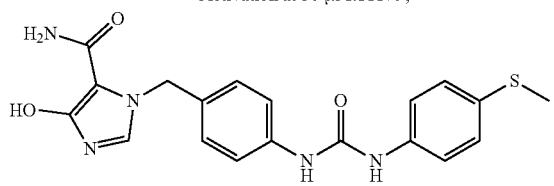

Rat liver AMPK
Activation at 200 μM: 311%, or

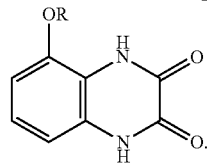

α1β1γ2
Activation at 30 μM
5, R = H, 130%
6, R = Ac, 120%

The AMPK activator can be as described in International Patent Publication WO2009100130, incorporated herein by reference. In one aspect, the AMPK activator is according to

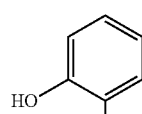

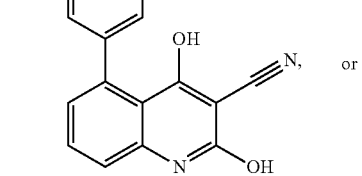

The AMPK activator can be as described in International Patent Publications WO2010036613, WO2010047982, WO2010051176, WO2010051206, WO2011106273, or WO2012116145. In one example embodiment, the AMPK activator is according to

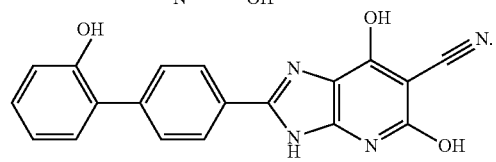

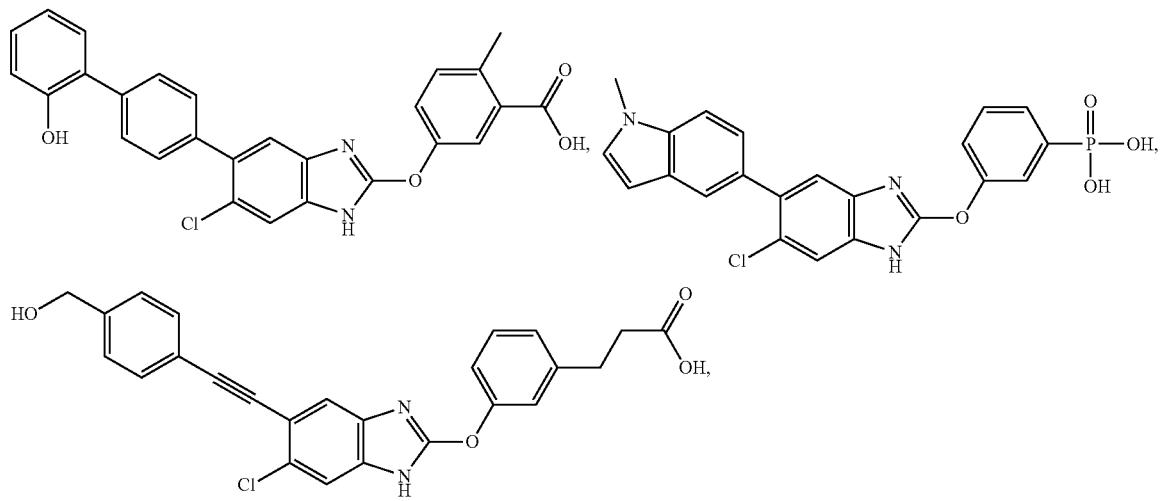

-continued
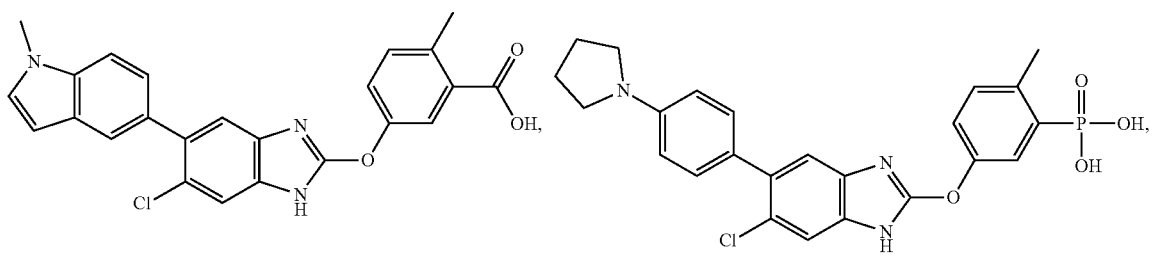
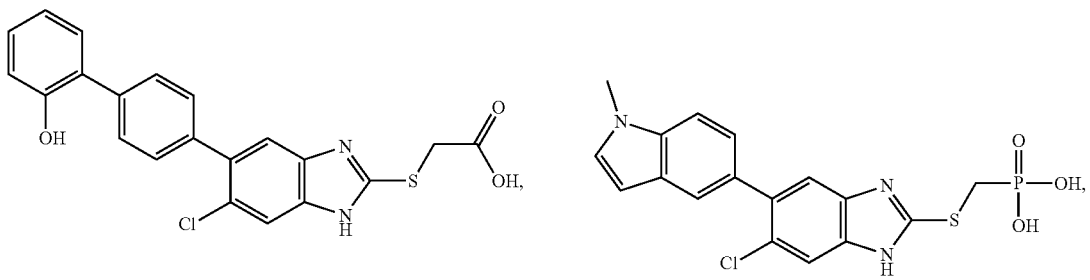
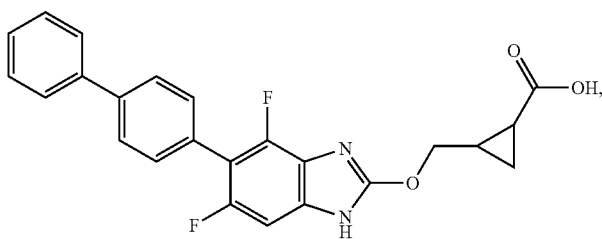
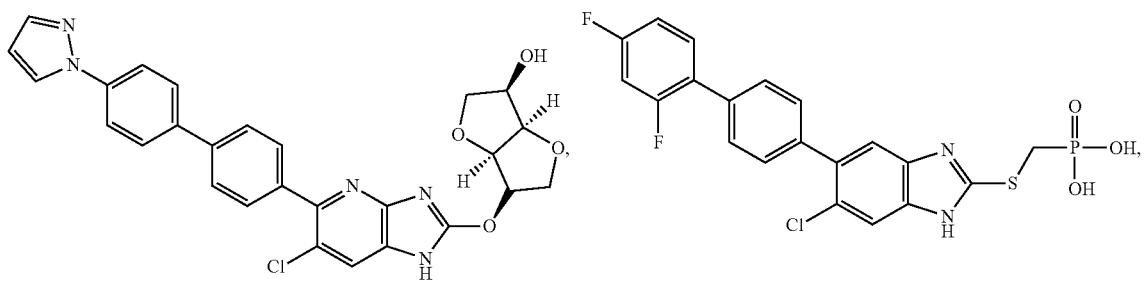
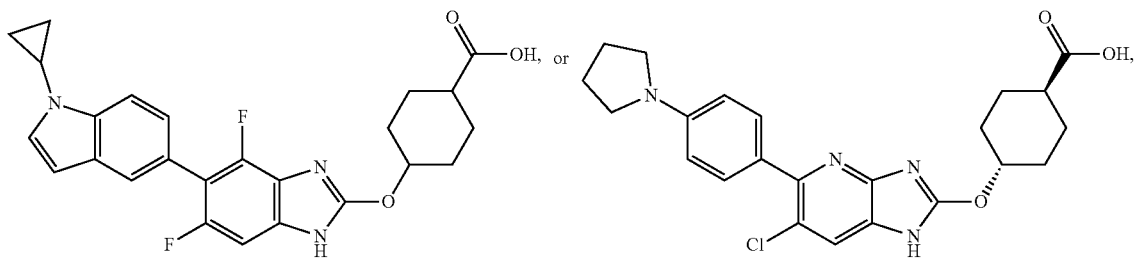

In one example embodiment, the AMPK activator can be as described in International Patent Publications WO2011029855, WO2011138307, WO2012119979, WO2012119978, incorporated herein by reference. In one aspect the AMPK activator can be selected from

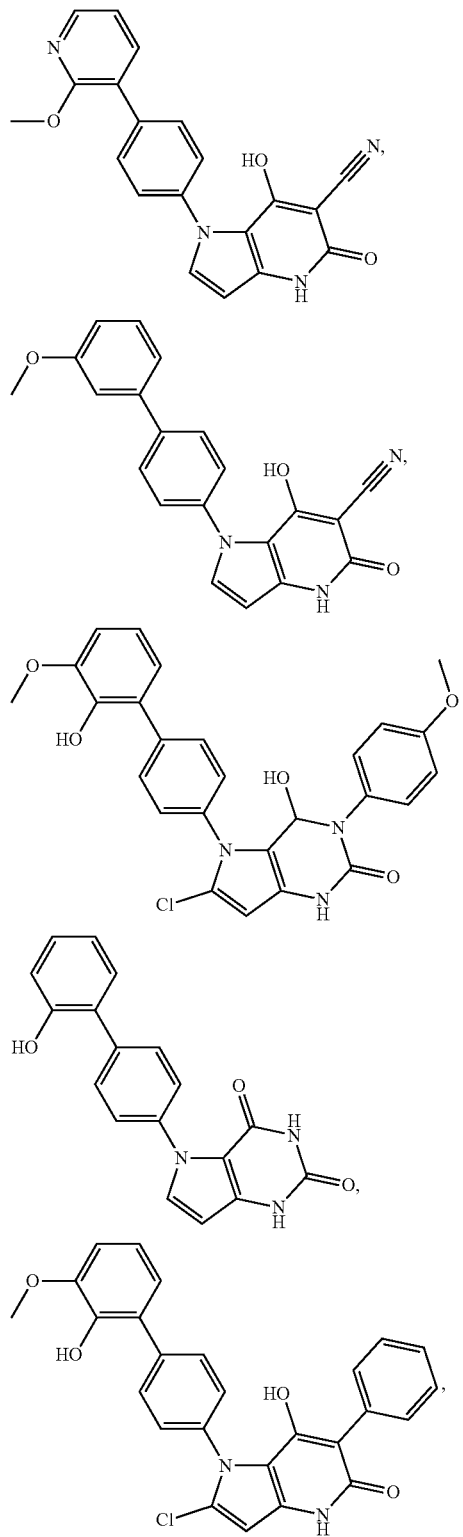

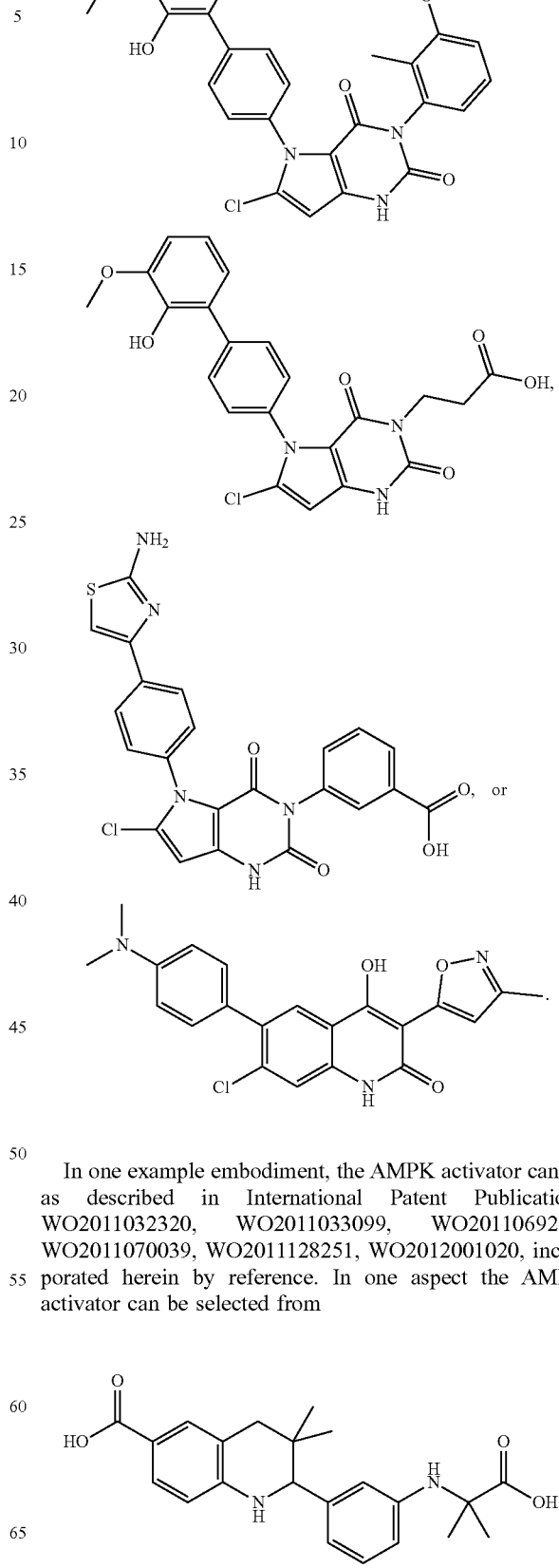

In one example embodiment, the AMPK activator can be as described in International Patent Publications WO2011032320, WO2011033099, WO2011069298, WO2011070039, WO2011128251, WO2012001020, incorporated herein by reference. In one aspect the AMPK activator can be selected from

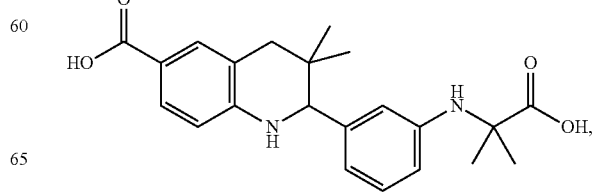

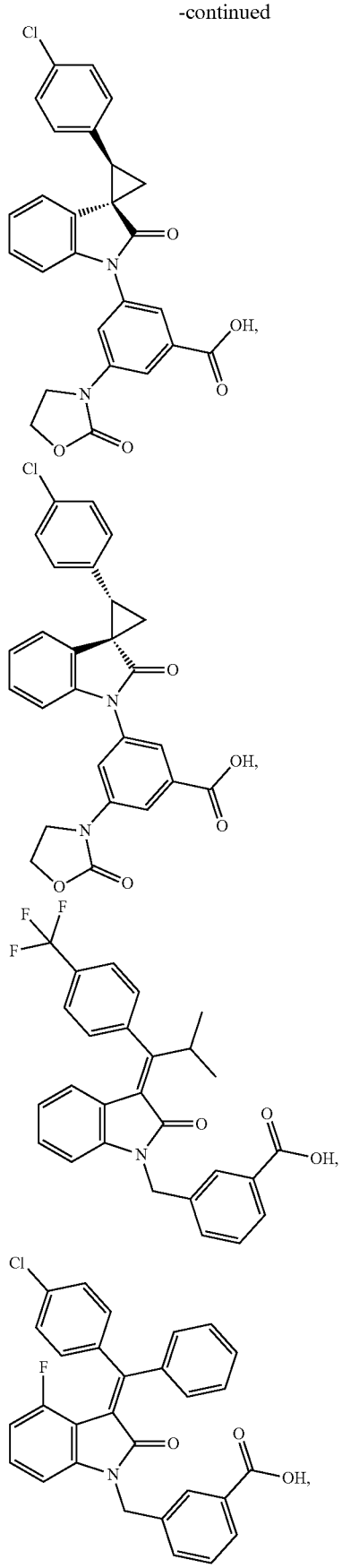
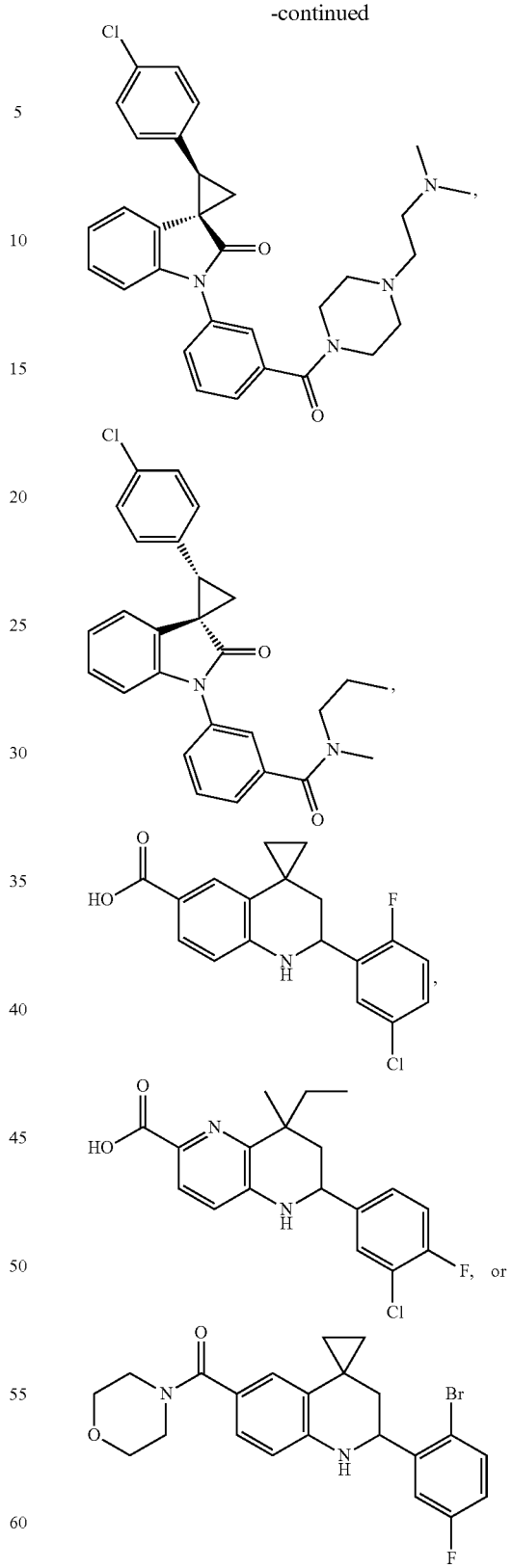
In one example embodiment, the AMPK activator can be as described in International Patent Publication WO2011080277, incorporated herein by reference. In one aspect the AMPK activator can be

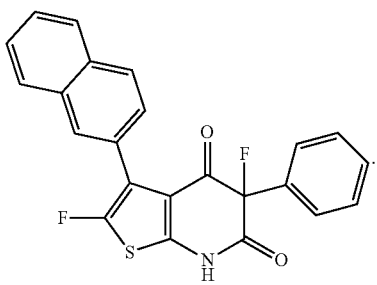 [SMILES: O=C1Nc2sc(F)c(-c3ccc4ccccc4c3)c2C(=O)C1(F)c1ccccc1]

In one example embodiment, the AMPK activator can be as described in International Patent Publication WO2012033149, incorporated herein by reference. In one aspect the AMPK activator can be selected from

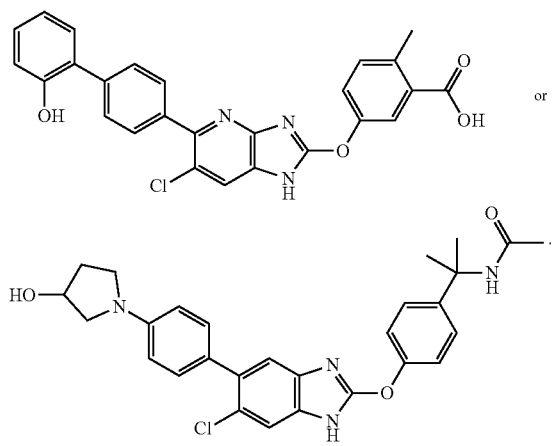

In an example embodiment, the AMPK activator is MT47-100 and has the formula:

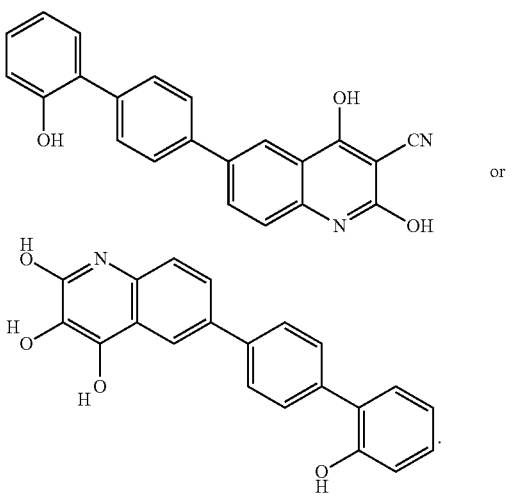

MT47-100 modulates activity of the AMPK but the direction of modulation depends on the subunit composition of the enzyme. MT47-100 acts as a direct activator of β1 subunit-containing AMPK, and as an allosteric inhibitor of β2 subunit-containing AMPK. The $pK_i$ value as an activator is 5.4, while the $pK_i$ value is 4.6 as an allosteric inhibitor. See e.g. Scott, J. W., et al. "Inhibition of AMP-Activated Protein Kinase at the Allosteric Drug-Binding Site Promotes Islet Insulin Release." *Chemistry & Biology* 2015, 22 (6), 705-711, herein incorporated by reference in its entirety.

Additional AMPK binding moieties for use in the present invention can be as described in International Patent Publications WO2007019914, WO2009124636, WO2009135580, WO2008006432, WO2009152909, WO2011029855, WO2011138307, WO2012119979, WO2012119978, WO2011032320, WO2011033099, WO2011069298, WO2011070039, WO2011128251, WO2012001020, WO2011080277, WO2012033149 incorporated herein by reference, and derivatives thereof and as further modified in accordance with the teachings detailed herein for use and optimization in the chimeric small molecules of the present invention.

PKC Binding Moiety

In one example embodiment, the kinase binding moiety is an PKC kinase binding moiety. In one example embodiment, the kinase binding moiety is a PKC activator or inhibitor. Protein Kinase C (PKC) is comprised of multiple isozymes and plays a role in signal transduction pathways, exhibiting a tissue-specific expression and playing a variety of biological roles. In an embodiment, the PKC kinase binding moiety can be utilized in the chimeric small molecules disclosed herein that is selective for a PKC isoform, for example classical (cPKCs-α, βI, βII, γ), novel (nPKCs-δ, ∈, η, θ), atypical (aPKCs-ζ, √λ), and PKCμ (a form between novel and atypical isoforms). In one example embodiment, the PKC binding moiety is according to the formula PKC binding moiety of the formula,

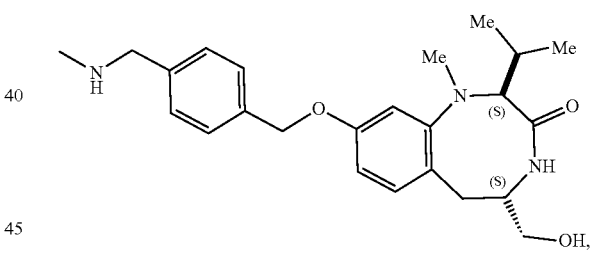

or an analog thereof.

Additional PKC binding moieties that can be configured for use in the molecules described herein are found, for example in International Patent Application PCT/US21/12816 at [0179]-[0194], incorporated specifically herein.

In one example embodiment, the kinase binding molecule can be designed as an activator of a diacylglycerol (DAG) responsive C1 domain-containing protein, such as Protein Kinase C. Protein Kinase C (PKC) is comprised of multiple isozymes and plays a role in signal transduction pathways, exhibiting a tissue-specific expression and playing a variety of biological roles. Activators of PKC can be utilized in the chimeric small molecules disclosed herein, the activating moiety is selective for a PKC isoform.

In one example embodiment, the kinase binding moiety is a DAG activator. The activator of a DAG responsive protein may comprise a DAG-indolactone as described in L. C. Garcia et al., *Bioorg. Med. Chem.*, 22 (2014) 3123-3140. Exemplary DAG-indolactones may be according to the formula

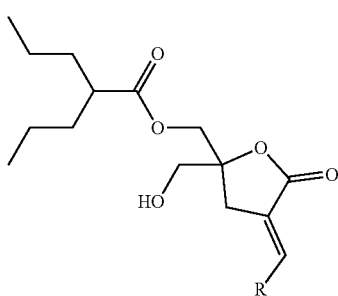

wherein R is an indole. R can be, for example, 1-methyl, 1H-indole5-yl, 1-methyl, 1H-indole6-yl, 1-methyl, 1H-indole4-yl, or. 1-methyl, 1H-indole7-yl. In one example embodiment, the compounds are selective for PKCα or PKCε.

DAG lactones, such as AJH-836, as described in Cooke, et al., *J. Biol. Chem.* (2018) 293(22) 8330-8341. In one example embodiment, the DAG lactone can be according to the formula

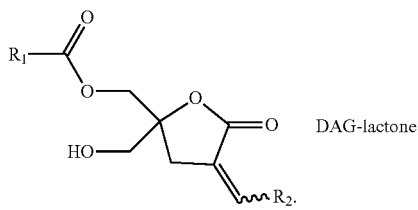

DAG-lactone

As provided in Cooke, AJH-836 formula is

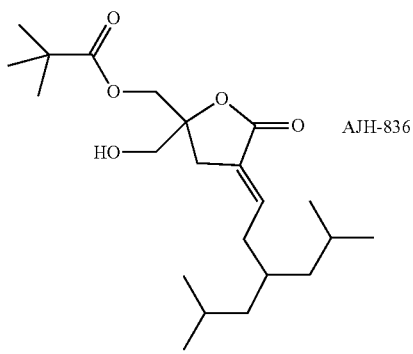 [SMILES: CC(C)CC(C/C=C1\CC(CO)(COC(=O)C(C)(C)C)OC1=O)CC(C)C]

AJH-836 and is selective for PKCδ and PKC.

Teleocidins, such as (−)-indolactam-V (ILV), and benzolactam-V8s, for example, 7-substituted Benzolactam-V8s, can be utilized as PKC activators. The PKC activator can be as described in Ma, et al., Org. Lett. 4:14 (2002) DOI: 10.1021/ol0261251.

In one example embodiment, the PKC activator is according to the formula

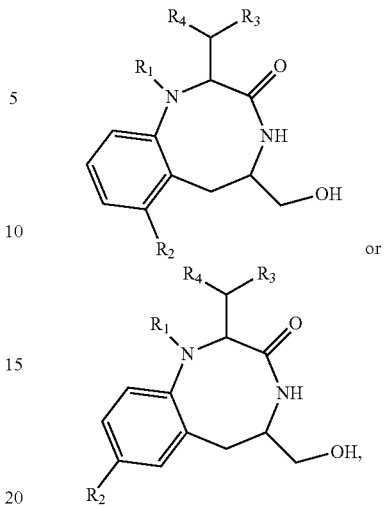

or wherein R1, R3, and R4 are each independently alkyl, alkenyl, alkynyl, and R2 can be selected from divalent hydrocarbon selected from saturated or unsaturated alkylene (e.g., branched alkylene, linear alkylene, cycloalkylene, $C_1$-$C_{22}$ branched alkylene, $C_1$-$C_{22}$ linear alkylene, $C_3$-$C_{22}$ cycloalkylene, $C_1$-$C_{10}$ branched alkylene, $C_1$-$C_{10}$ linear alkylene, $C_3$-$C_{10}$ cycloalkylene, $C_1$-$C_8$ branched alkylene, $C_1$-$C_8$ linear alkylene, $C_3$-$C_8$ cycloalkylene), $C_1$-$C_{22}$ saturated or unsaturated heteroalkylene (e.g., branched heteroalkylene, linear heteroalkylene, heterocycloalkylene, $C_1$-$C_{22}$ branched heteroalkylene, $C_1$-$C_{22}$ linear heteroalkylene, $C_3$-$C_{22}$ heterocycloalkylene, $C_1$-$C_{10}$ branched heteroalkylene, $C_1$-$C_{10}$ linear heteroalkylene, $C_3$-$C_{10}$ heterocycloalkylene, $C_1$-$C_8$ branched heteroalkylene, $C_1$-$C_8$ linear heteroalkylene, $C_3$-$C_8$ heterocycloalkylene), arylene (e.g., $C_5$-$C_{22}$ arylene), heteroarylene (e.g., $C_5$-$C_{22}$ heteroarylene), or combinations thereof; wherein each of the foregoing may have one or more (e.g., two, three, four, five) points of substitution, substituted amides, including those selected from those as described in Table 1 of Kozikowski et al. *J. Med. Chem*, 2003, 46:3, 364-373, Table 1 at page 366, incorporated specifically herein by reference. $R_2$ can be selected from one or more of —$(C(R^a)(R^a))_{1-8}$—, —$(OC(R^a)(R^a))_{1-8}$—, —$(OC(R^a)(R^a)—C(R^a)(R^a))_{1-8}$—, —N($R^a$)—, —O—, —C(O)—, optionally substituted $C_6$ arylene, optionally substituted $C_{5-12}$ heteroarylene, $C_{3-6}$ cycloalkylene substituted with hydroxy, or $C_4$ heterocycloalkylene substituted with hydroxy; wherein each of the foregoing may have one or more (e.g., two, three, four, five) points of substitution; and $R^a$ is independently selected at each occurrence from hydrogen, or alkyl (e.g., $C_1$-$C_7$ alkyl, $C_1$-$C_3$ alkyl).

In one example embodiment, the formula is according to

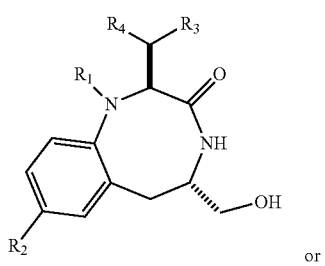

or

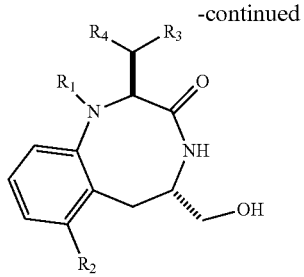

wherein R1, R3, and R4 are each independently alkyl, alkenyl, alkynyl, and R2 can be selected from divalent hydrocarbon selected from saturated or unsaturated alkylene (e.g., branched alkylene, linear alkylene, cycloalkylene, $C_1$-$C_{22}$ branched alkylene, $C_1$-$C_{22}$ linear alkylene, $C_3$-$C_{22}$ cycloalkylene, $C_1$-$C_{10}$ branched alkylene, $C_1$-$C_{10}$ linear alkylene, $C_3$-$C_{10}$ cycloalkylene, $C_1$-$C_8$ branched alkylene, $C_1$-$C_8$ linear alkylene, $C_3$-$C_8$ cycloalkylene), $C_1$-$C_{22}$ saturated or unsaturated heteroalkylene (e.g., branched heteroalkylene, linear heteroalkylene, heterocycloalkylene, $C_1$-$C_{22}$ branched heteroalkylene, $C_1$-$C_{22}$ linear heteroalkylene, $C_3$-$C_{22}$ heterocycloalkylene, $C_1$-$C_{10}$ branched heteroalkylene, $C_1$-$C_{10}$ linear heteroalkylene, $C_3$-$C_{10}$ heterocycloalkylene, $C_1$-$C_8$ branched heteroalkylene, $C_1$-$C_8$ linear heteroalkylene, $C_3$-$C_8$ heterocycloalkylene), arylene (e.g., $C_5$-$C_{22}$ arylene), heteroarylene (e.g., $C_5$-$C_{22}$ heteroarylene), or combinations thereof; wherein each of the foregoing may have one or more (e.g., two, three, four, five) points of substitution, substituted amides, including those selected from those as described in Table 1 of Kozikowski et al. *J. Med. Chem*, 2003, 46:3, 364-373, Table 1 at page 366, incorporated specifically herein by reference.

R2 can be selected from one or more of —(C($R^a$)($R^a$))$_{1-8}$—, —(OC($R^a$)($R^a$))$_{1-8}$—, —(OC($R^a$)($R^a$)—C($R^a$)($R^a$))$_{1-8}$, —N($R^a$)—, —O—, —C(O)—, optionally substituted $C_6$ arylene, optionally substituted $C_{5-12}$ heteroarylene, $C_{3-6}$ cycloalkylene substituted with hydroxy, or $C_4$ heterocycloalkylene substituted with hydroxy; wherein each of the foregoing may have one or more (e.g., two, three, four, five) points of substitution; and $R^a$ is independently selected at each occurrence from hydrogen, or alkyl (e.g., $C_1$-$C_7$ alkyl, $C_1$-$C_3$ alkyl).

In one example embodiments, the formula is according to

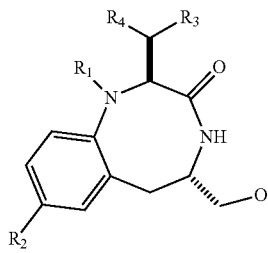

or

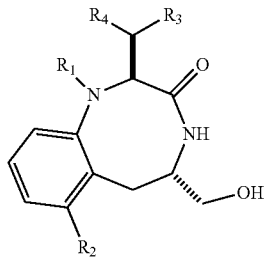

wherein R1, R3 and R4 is independently alkyl, alkenyl, alkynyl, and R2 can be selected from. In one example embodiment, the PKC activator is a benzolactam analogue of ILV, with R can be $CC(CH_2)_7CH_3$ or $(CH_2)_9CH_3$, as described in Kozikowski et al., *J. Med. Chem.*, 1997, 40:9 1316-1326.

In one example embodiment, R1, R3 and R4 are alkyl, in some embodiments, R1, R3 and R4 are methyl. In one example embodiment, the formula is according to:

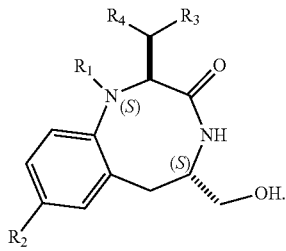

In one example embodiment, the PKC activator is a natural product activator, for example, DPP, prostratin, mezerein, octahydromezerein, thymeleatoxin(–)-octylindolactam V, OAG, or resiniferatoxin, as described in Kazanietz. et al., *Mol. Pharma.* 44:296-307 (1993).

In one example embodiment the PCK binding moiety is according to the formula PKC binding moiety of the formula,

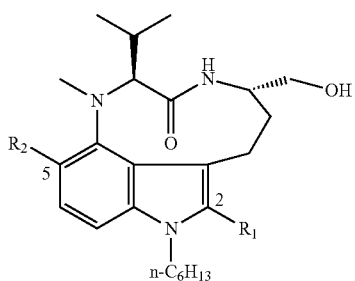

or an analog thereof.

In one example embodiments, the PKC activator is selective for PKCδ. In one example embodiment, the PKC activator is 7α-acetoxy-6β-benzoyloxy-12-Obenzoylroyleanone (Roy-Bz) as described in Bessa et al., Cell Death and Disease (2018) 9:23.

The PKC activator may be an ILV derivative, such as n-hexyl ILV, or a 10 membered ring1-Hexylindolactam-V10, or a derivative thereof, as described in Yanagita, et al., *J. Med. Chem.*, 2008, 51:1, 46-56, incorporated herein by reference. The PKC activator may be wherein R1 and R2=H, R1=H and R2=Cl, or R1=Br and R2=H, and may, in some instance be PKCδ, PKCε or PKCη.

In one example embodiment, the activator moiety is 6-Chloro-5-[4-(1-hydroxycyclobutyl)phenyl]-1H-indole-3-carboxylic Acid (PF-06409577), a benzolactam, DPP, Prostratin, Mezerein, Octahydromezerein, Thymeleatoxin, (−)-Indolactam V, (−)-Octylindolactam V, OAG, or derivatives thereof.

In one example embodiment, the activator moiety is a thieno [2,3-b]pyridine, a thienopyridone, a quinoxalinedione, a imidazo [4,5-b]pyridine, a [2,3-d]pyridine, a benzimidazole, a pyrrolo [2,3-d]pyrimidine, a spirocyclic indolinone, a tetrahydroquinoline, a thieno [2,3-b]pyridinedione, and derivatives thereof. See Expert Opin Ther. Patents (2012) 22(12), incorporated herein by reference.

In other example embodiments, the PKC activators may be selected from Table 1 from PCT/US2021/012816 herein incorporated by reference.

FKBP Binding Moiety

In one example embodiment, the kinase binding moiety is an FKBP kinase binding moiety. In one example embodiment, the kinase binding moiety can be designed as an activator or inhibitor of an FK506-binding protein (FKBP). FKBP belongs to the immunophilin family. FKBPs are present in all eukaryotes, ranging from yeasts to humans, and expressed in most tissues. Mammalian FKBPs can be subdivided into four groups: the cytoplasmic, endoplasmic reticulum, nuclear, and TPR (tetratricopeptide repeats)-containing FKBPs. In one example embodiment, the FKBP is FKBP12, which binds to intracellular calcium release channels and TGF-β type I receptor. In one example embodiment, the FKBP activator moiety is of the formula

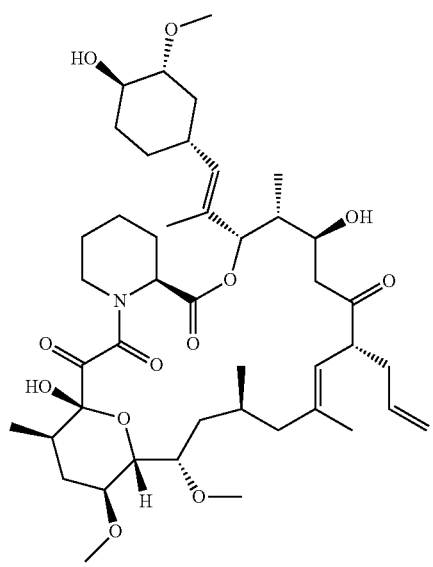

FK506

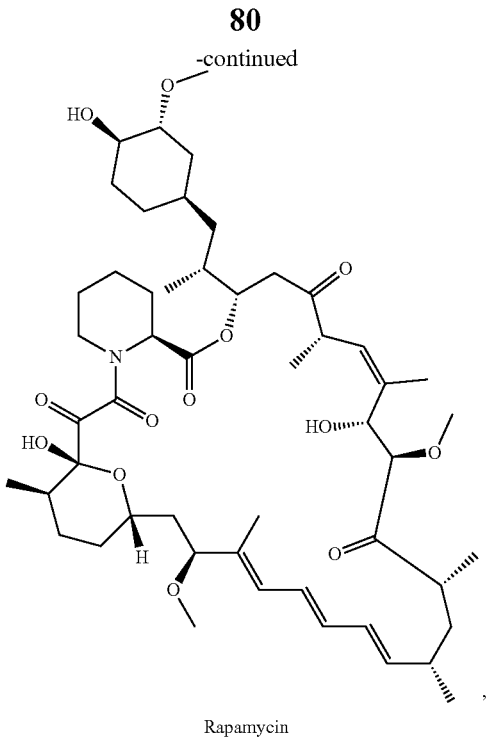

Rapamycin

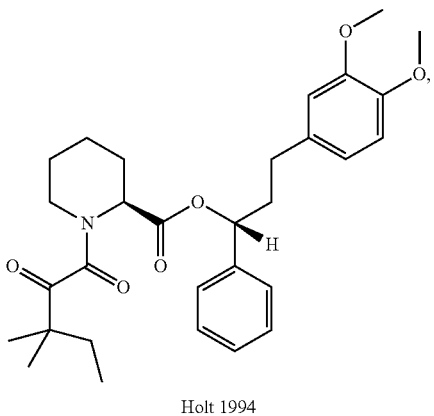

Holt 1994

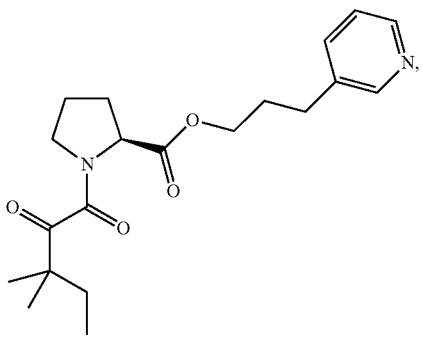

GPI1046

-continued

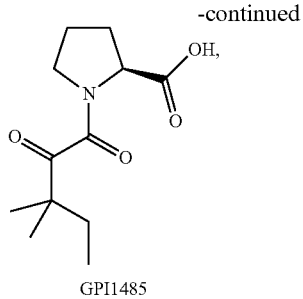

GPI1485

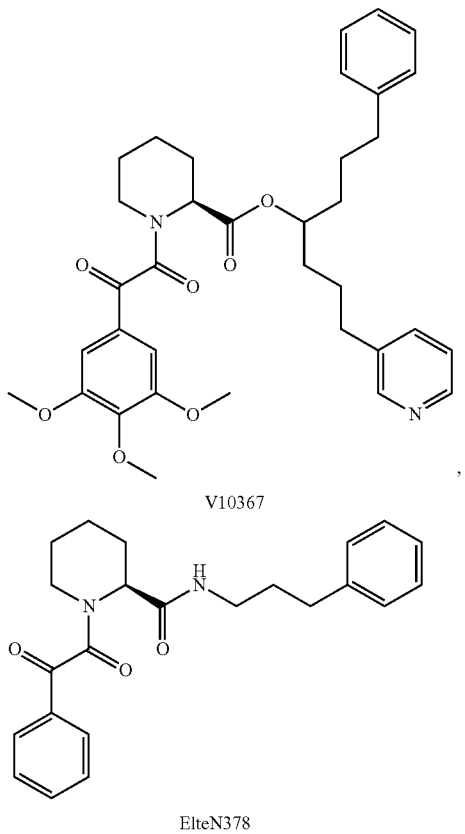

V10367

ElteN378 and any derivative thereof. See e.g. (Kolos et al. FKBP Ligands—Where We Are and Where to Go?Front. (2018) FKBP Ligands—Where We Are and Where to Go?Front. Pharmacol. 9:1425.)

IRTK Binding Moiety

In one example embodiment, the kinase binding moiety is an IRTK kinase binding moiety. The insulin receptor (IR) is a hetero-tetrameric protein consisting of two extracellular α subunits and two transmembrane β subunits. The binding of a ligand to the a subunit of the IR induces conformational changes in the receptor. As a result, the tyrosine kinase activity intrinsic to the β subunit of the IR is stimulated. (Salituro G M et al. Discovery of a small molecule insulin receptor activator. Recent Prog Horm Res. 2001; 56:107-26.) In one example embodiment, the kinase binding moiety is an IR activator or inhibitor. In one example, the activator for IRTK is kojic acid, or a derivative thereof.

In one example embodiment, the target is an Androgen Receptor. In one example embodiment, the localizing moiety may comprise enzalutamide. In one example embodiment, the enzalutamide is attached via an ether bond to a linker comprising an azide end. Thus, in one example embodiment, the addition of alkyne functionality on the activator moiety will enable connection via bioorthogonal click-chemistry. In one example embodiment, the Insulin Receptor is according to the formula:

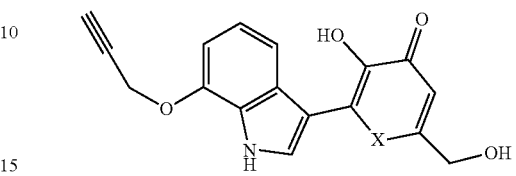

wherein X is C, N, O, S or P. In other example embodiments the IRTK activator is according to the formula:

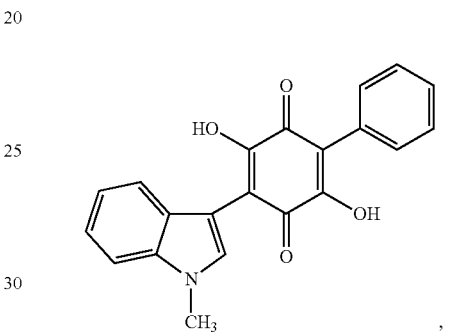

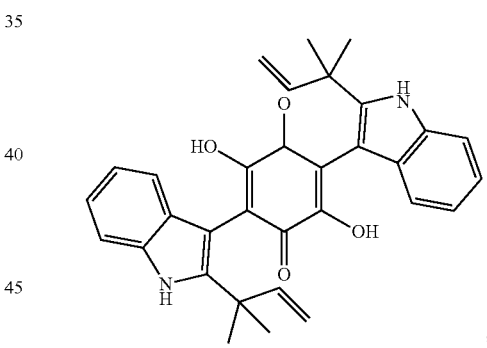

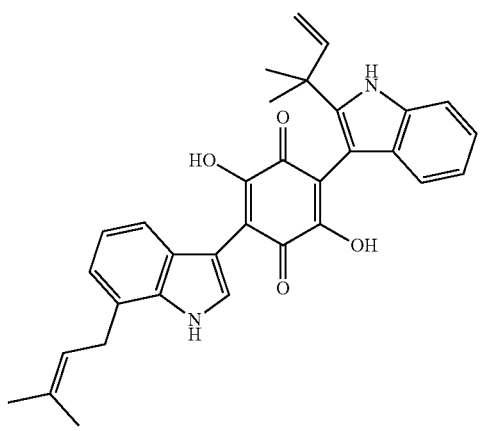

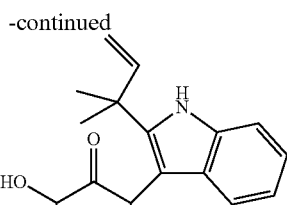

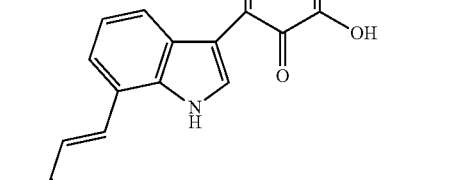

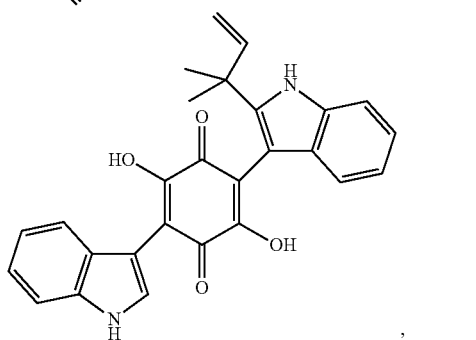

Component 5 and any derivative thereof.

In one example embodiment, the IRTK activator is XMetA, also known as XOMA-159, which is a monoclonal antibody and allosteric partial agonist of the insulin receptor. See e.g. Bedinger D. H., et al. "Differential Pathway Coupling of the Activated Insulin Receptor Drives Signaling Selectivity by XMetA, an Allosteric Partial Agonist Antibody." *J Pharmacol Exp Ther* 2015, 353 (1), 35-43.

Lyn Binding Moiety

In one example embodiment, the kinase binding moiety is an Lyn kinase binding moiety. The Lyn kinase belongs to the Src-family of kinases and is the predominant Src kinase in B cells. The regulatory properties of Lyn play a role in the function of the immune system. See e.g. Xu Y., "Lyn Tyrosine Kinase." Immunity 2005, 22 (1), 9-18. In one example embodiment, the Lyn binding moiety is an activator or inhibitor. In an example embodiment, the Lyn activator is tolimidone, also known as MLR-1023, according to the formula:

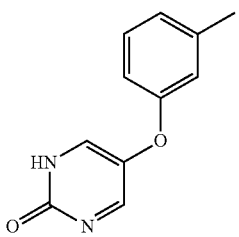

Tolimidone is a selective allosteric activator of Lyn kinas and was developed for the treatment of type 2 diabetes. Experiments with knockout mice revealed tolimidone did not lower glucose when Lyn kinase was absent. Currently, tolimidone is in a Phase 2 study in patients suffering from uncontrolled Type 2 Diabetes. Tolimidone has a $pEC_{50}$ of 7.2. See e.g. Saporito, M. S., et al. "MLR-1023 Is a Potent and Selective Allosteric Activator of Lyn Kinase In Vitro That Improves Glucose Tolerance In Vivo." *J Pharmacol Exp Ther* 2012, 342 (1), 15-22, with the following comparison of activities in cellular and enzyme assays references below and incorporated herein by reference:

Comparison of activities of MLR-1023 and reference compounds in cellular and enzyme assays
MLR-1023 was tested for effects in in vitro and cell-based assays.
Experimental conditions are described under *Materials and Methods*.

| Assay | Control | MLR-1023 (10 μM) | Reference Compound Activity | Reference Compound (μM) |
|---|---|---|---|---|
| Adipocyte differentiation, % differentiation | 4.5 ± 1.2 | 16.7 ± 2.5* | 94.4 ± 3.8 | Rosiglitazone (10 μM) |
| PPARγ, fold activation | 1.0 ± 0.1 | 1.6 ± 0.3 | 22.0 ± 0.4 | Rosiglitazone (10 μM) |
| PPARα, fold activation | 1.0 ± 0.2 | 1.3 ± 0.1 | 3.2 ± 0.5 | Bezafibrate (100 μM) |
| PPARδ, fold activation | 1.0 ± 0.1 | 0.7 ± 0.1 | 13.0 ± 0.8 | L165,041 (100 μM) |
| Adiponectin production, pg/ml | 10 ± 2.3 | 192 ± 11.6* | 1398.2 ± 87.1 | Rosiglitazone (10 μM) |
| DPP-IV, % inhibition | 0.3 ± 0.4 | 0.7 ± 1.5 | 97.3 ± 0.8 | P32/98 (10 μM) |
| Insulin secretion, ng/ml | 3.6 ± 0.1 | 4.4 ± 0.08 | 8.0 ± 0.01 | GLP-1 (5 μM) |
| α-Glucosidase, % inhibition | 0.9 ± 0.2 | 14.6 ± 0.8* | 96.8 ± 0.19 | Castanospermine (2.5 μM) |
| GLP-1R, cAMP, pmol/ml | 17.8 ± 1.1 | 29.4 ± 1.2 | 157 ± 11.1 | GLP-1 (5 μM) |

*Statistical difference ($P < 0.05$) compared with control value.

PK Binding Moiety

In one example embodiment, the kinase binding moiety is a PK kinase binding moiety. Pyruvate kinase (PK) catalyzes the transphosphorylation from phosphoenolpyruvate (PEP) to ADP to generate ATP in glycolysis. PK is expressed in four different isozymic forms: L, R, M1, and M2 in mammalian tissues depending upon the metabolic requirement and their regulatory properties. The M2, L, and R isozymes have homotropic cooperative activation with PEP and heterotropic cooperative activation with FBP. See e.g. Gupta V., et al. "Human Pyruvate Kinase M2: A Multifunctional Protein." *Protein Science* 2010, 19 (11), 2031-2044.

In one example embodiment the PK kinase binding moiety is a PK activator. In an example embodiment, the PK activator is Mitapivat, also known as AG-348, according to the formula:

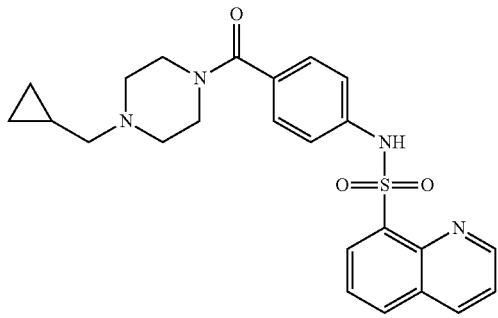 [SMILES: O=C(c1ccc(NS(=O)(=O)c2cccc3cccnc23)cc1)N1CCN(CC2CC2)CC1]

with the following properties

| | | |
|---|---|---|
| Hydrogen bond acceptors | 7 | |
| Hydrogen bond donors | 1 | |
| Rotatable bonds | 7 | |
| Topological polar surface area | 90.99 | |
| Molecular weight | 450.17 | |
| XLogP | 2.75 | |
| No. Lipinski's rules broken | 0. | |

Mitapivat is a small molecule allosteric activator of the pyruvate kinases. It activates the PK isoform that is found in erythrocytes, PKR protein that is expressed from the PKLR gene, and the embryonic PKM2 isoform, expressed from the PKM gene. Mitapivat was developed as a novel therapy for diseases of red blood cells that are associated with inherited PKR deficiency, and for cancer therapy via activation of PKM2. Activation of PK in red cells increases hemoglobin levels. The active drug is the sulfate hydrate. Mitapivat has an $pEC_{50}$ value of >7.0 for PKM2. In one example embodiment, the PK activator is any compound from US Patent number U.S. Pat. No. 8,785,450B2 herein incorporated by reference, or any derivative thereof. In one example embodiment, the PK activator is any compound from International Patent Publication WO2013056153A1, herein incorporated by reference, or any derivative thereof.

In one example embodiment, the kinase binding moiety is a PK inhibitor, see above for more information regarding PK kinase. In an example embodiment, the PK inhibitor is any identified in US Patent U.S. Pat. No. 6,534,501, herein incorporated by reference, or any derivative thereof.

NOP Binding Moiety

The nociceptin opioid peptide (NOP) receptor is part of the opioid receptor family of GPCRs, which couples to Gi/Go and inhibits adenylate cyclase activity. In one example embodiment, the kinase binding moiety or target binding moiety binds to a GPCR opioid receptor. In one example embodiment, the kinase binding moiety is a NOP activator. In an example embodiment, the NOP activator has any of the following formulas:

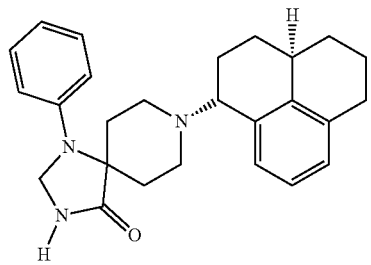

RO 64-6198

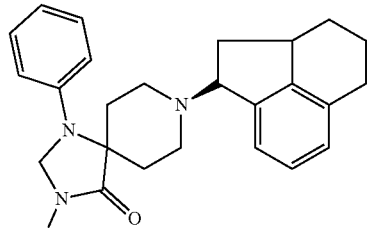

RO 65-6570

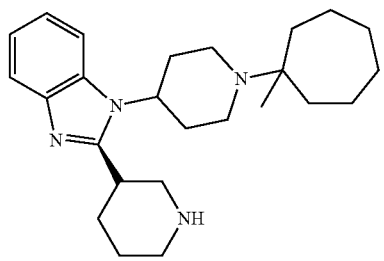

MCOPPB

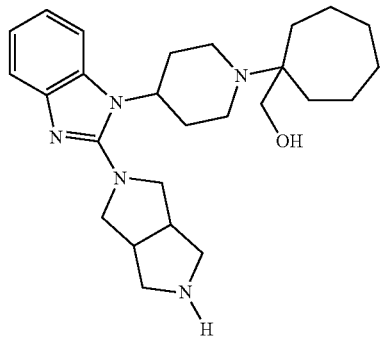

HPCOM

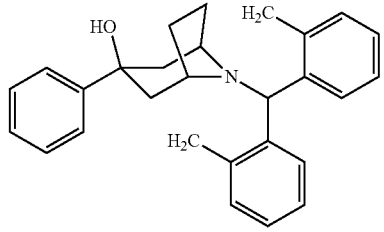

SCH221510

-continued

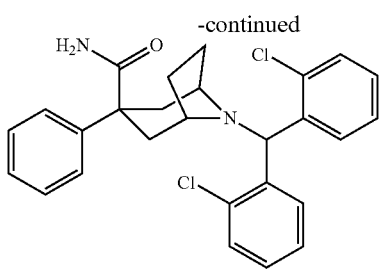

SCH655842

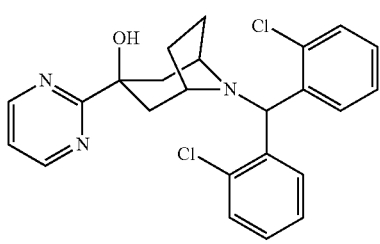

SCH486757

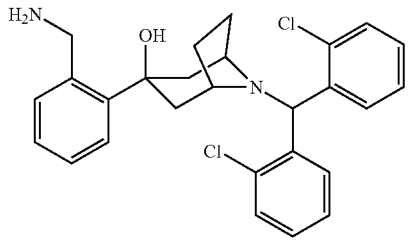

SCH225288

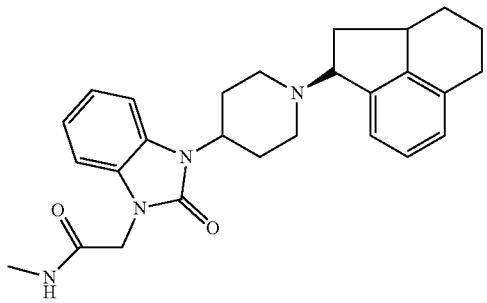

MT-7716

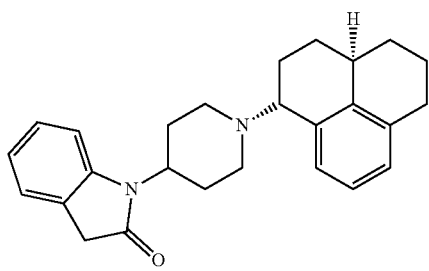

AT-202 (SR16835)

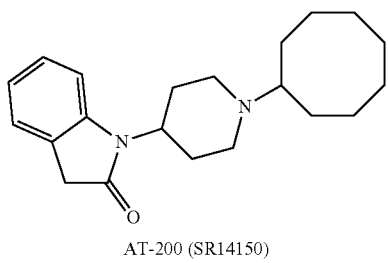

AT-200 (SR14150)

-continued

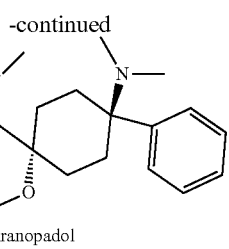

Cebranopadol or any derivative thereof.

In an example embodiment, the NOP activator is the NOP agonist Ser100 according to the formula: Ac-RYYRWKKKKKKK-NH2 (SEQ ID NO: 1). In an example embodiment, the NOP activator is the NOP agonist N/OFQ according to the formula: FGGFTGARKSARK-LANQ (SEQ ID NO: 2). In an example embodiment the NOP activator is JNJ-19385899, see e.g. Zaveri, N. T. "Nociceptin Opioid Receptor (NOP) as a Therapeutic Target: Progress in Translation from Preclinical Research to Clinical Utility." *J. Med. Chem.* 2016, 59 (15), 7011-7028, herein incorporated by reference in its entirety.

A number of proteins such as G protein-coupled receptor kinases, β-arrestins and G proteins clearly regulate NOP receptor functions. It has also been shown sodium and guanyl nucleotides can modify the functional NOP complex and G protein interaction. Other G protein-coupled receptors, such as mu-opioid receptors, appear to be able to form heterodimers with NOP receptors, potentially modifying the receptor protein, see e.g. Wang, H.-L., et al. "Heterodimerization of Opioid Receptor-like 1 and μ-Opioid Receptors Impairs the Potency of μ Receptor Agonist." *Journal of Neurochemistry* 2005, 92 (6), 1285-1294.

In an embodiment, the binder is an allosteric regulator of the delta opioid receptor. In an embodiment, the binder is

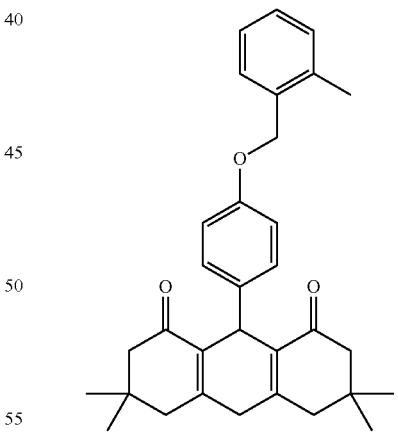

BMS-986187, 3,3,6,6-tetramethyl-9-[4-[(2-methylphenyl) methoxy]phenyl]-4,5,7,9-tetrahydro-2H-xanthene-1,8-dione.

In an embodiment, the binder is an allosteric regulator of the mu opioid receptor.

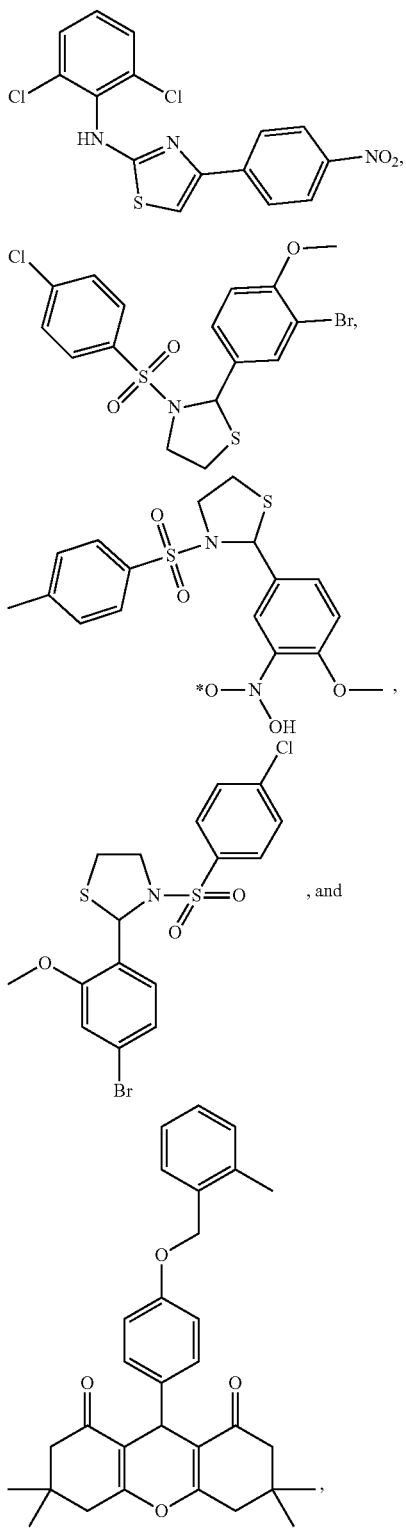

BMS-986121

BMS-986122

, and which may be referenced as BMS-986121 [(4-{2-[(2,6-dichlorophenyl)amino]-1,3-thiazol-4-yl}phenyl)(hydroxy)imino]-λ'-oxidanyl; BMS-986122 2-(3-bromo-4-methoxyphenyl)-3-(4-chlorophenyl)sulfonyl-1,3-thiazolidine; BMS-986123 [hydroxy({2-methoxy-5-[3-(4-methylbenzenesulfonyl)-1,3-thiazolidin-2-yl]phenyl})imino]-λ'-oxidanyl; BMS-986124 2-(4-bromo-2-methoxyphenyl)-3-(4-chlorobenzenesulfonyl)-1,3-thiazolidine; or BMS-986187 3,3,6,6-tetramethyl-9-[4-[(2-methylphenyl)methoxy]phenyl]-4,5,7,9-tetrahydro-2H-xanthene-1,8-dione, respectively.

In one example embodiment, the NOP binder is a NOP antagonist. In an example embodiment, the NOP antagonist has any of the following formulas:

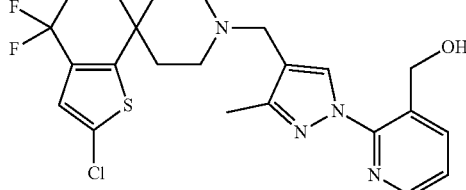

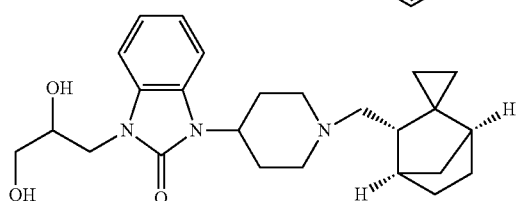

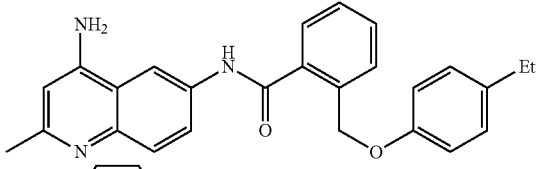

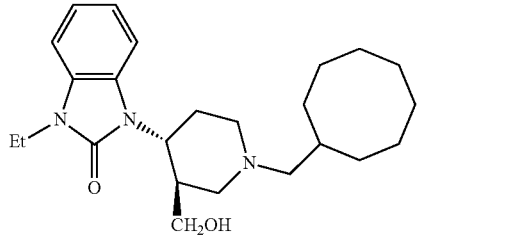

SB-612111

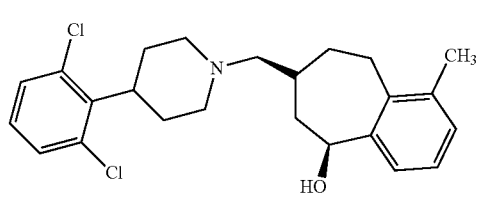

C-24

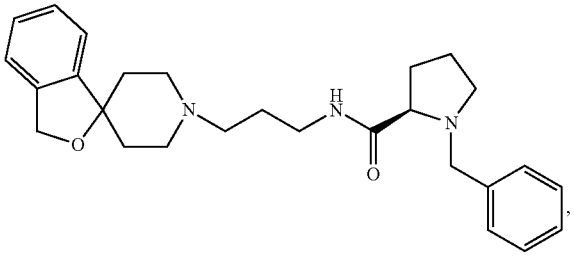

see Zaveri *J. Med. Chem.* 2016.

MAPK Binding Moiety

In one example embodiment, the kinase binding moiety is a mitogen-activated protein kinase (MAPK) binding moiety.

In one example embodiment, the MAPK binding moiety is an inhibitor or activator. MAPK is involved in the signal-transduction pathways. A common feature of MAPKs is their ability to phosphorylate the transactivation domains of transcription factors and, as a result, modulate transcriptional activity. In one example embodiment, the kinase binding moiety is a MAPK inhibitor.

In an example embodiment, the MAPK inhibitor is a p38α MAPK inhibitor comprising:

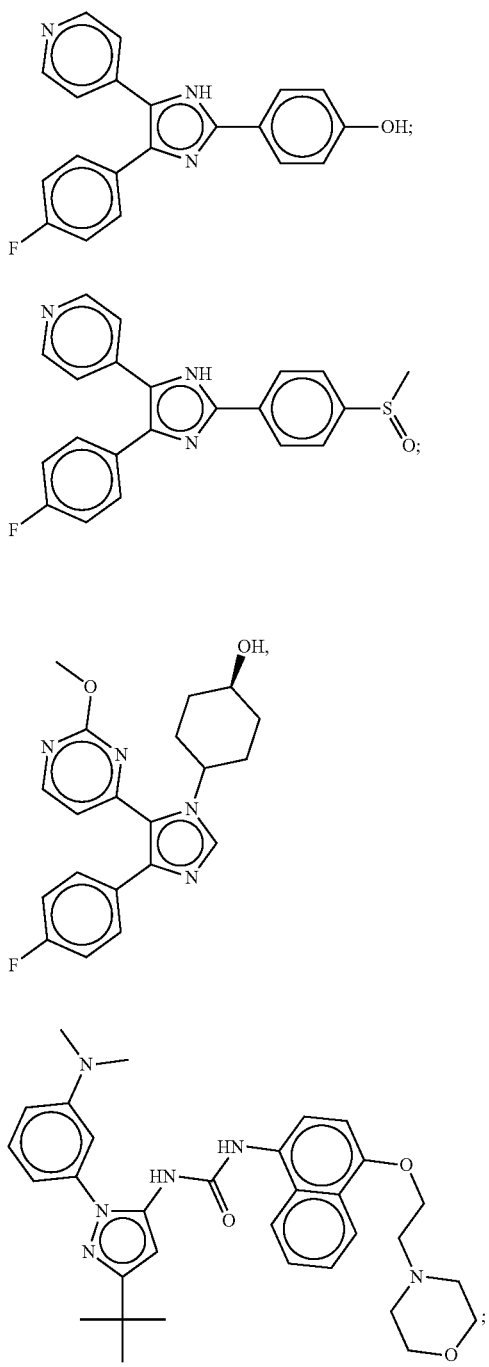

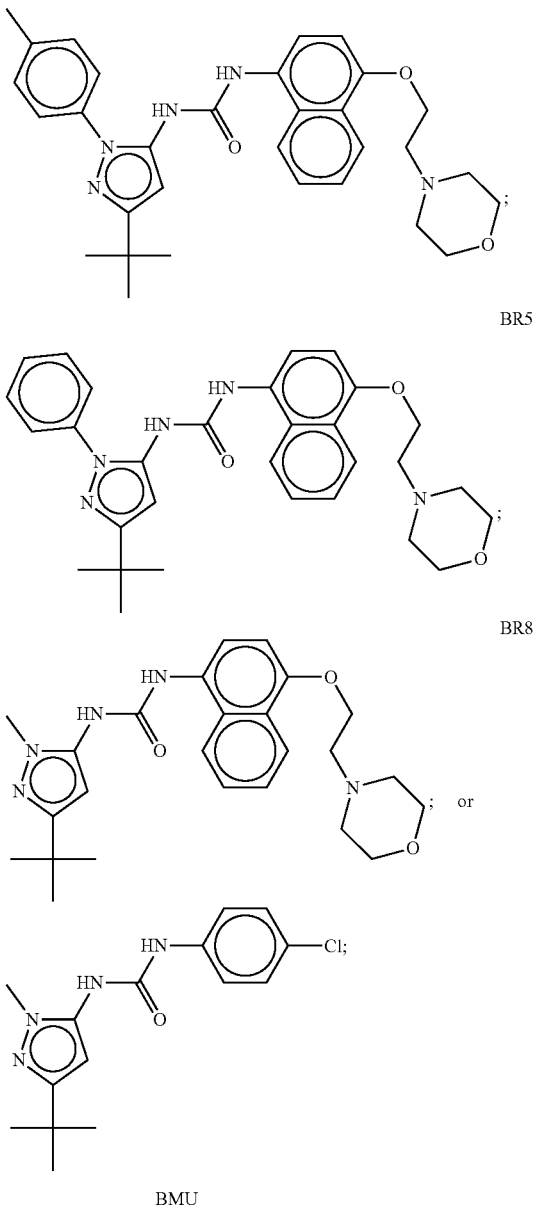

and derivatives thereof, which can be utilized as activating moieties in the chimeric small molecules of the invention. Inhibitor B96 may also be known as Doramapimod, which is an allosteric inhibitor. Doramapimod shows moderate selectivity for the p38alpha, -beta and -gamma isozymes compared to p38delta. It shows moderate selectivity for the p38α, -β and -γ isozymes compared to p38δ. A Kd value of 0.1 nM is reported, and in a screening panel of kinases, doramapimod inhibited many kinases with IC50 values <100 nM. Doramapimod has been shown to block TNFα release in LPS-stimulated THP-1 cells with an IC50 value of 18 nM. Doramapimod inhibits MAPK14 with pKd of 9.4 and pIC50 of 7.7, MAPK11 pIC50 of 8.1, MAPK12 pIC50 of 7.5, and MAPK13 pIC50 of 6.5 See, Moffett, et al., Bioorg. Med. Chem. Lett. 2011, 21, 7155-7165. Further areas for modification when tailoring the molecule for use in the chimeric small molecules are described in Moffett, in particular at FIG. 3 and its associated teachings incorporated by reference. In an aspect, the molecule incorporates non-aromatic fragments which make productive hydrogen bond interactions with Arg 70 on the αC-helix.

In an embodiment, the MAPK inhibitor is the allosteric inhibitor of p38 according to compound 10, which is discussed in further detail in the context of Jnk-1.

In an embodiment, the MAPK inhibitor is SB203580 (SB6). In an embodiment, the MAPK inhibitor is Skepinone-L, with the formula

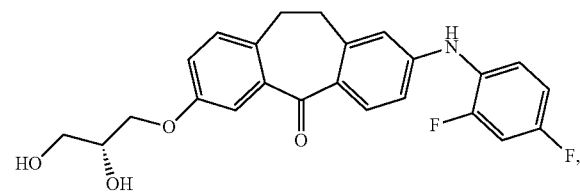 [SMILES: O=C1c2ccc(Nc3ccc(F)cc3F)cc2CCc2ccc(OC[C@H](O)CO)cc21]

and its derivatives. In an embodiment, the MAPK inhibitor is Sorafenib, with the formula

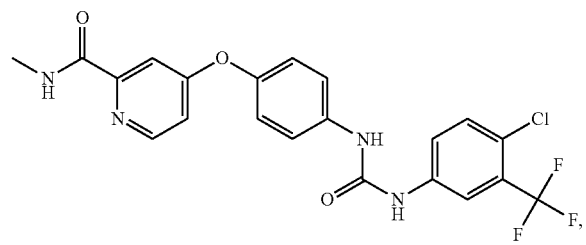 [SMILES: CNC(=O)c1cc(Oc2ccc(NC(=O)Nc3ccc(Cl)c(C(F)(F)F)c3)cc2)ccn1]

and its derivatives.

In one example embodiment, the MAPK inhibitor is the small molecule KC-706.

EGFR Binding Moiety

In one example embodiment, the kinase binding moiety is an EGFR binding moiety. In one example embodiment, the EGFR binding moiety is an inhibitor or activator. EGFR is a tyrosine kinase receptor belonging to the ErbB family of receptors that mediates cell growth, differentiation and repair in cells, especially non-cancerous cells.

In one embodiment, the EGFR binding molecule is of the formula,

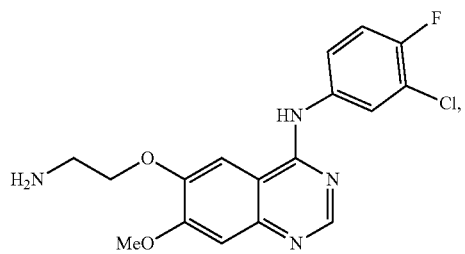 [SMILES: COc1cc2ncnc(Nc3ccc(F)c(Cl)c3)c2cc1OCCN]

or an analog thereof.

In an example embodiment, the EGFR binding molecule is Gefitinib. Gefitinib selectively binds to the ATP-binding site of EGFR thereby causing inhibition. In one example embodiment, the EGFR binding molecule may be any from the group comprising of Erlotinib, Afatinib, Osimertinib, Lapatinib, Neratinib, or any derivatives thereof.

In an embodiment, the kinase is an EGFR mutant. In an embodiment, the EGFR mutant comprises L858R, C797S, T790M, V984R, or a combination thereof.

In an example embodiment, the EGFR inhibitor is EAI001, was designed to overcome clinically acquired EGFR T790M/C797S mutant resistance in NSCLC by binding outside the ATP. EAI001 binds to the allosteric MT3 site of EGFR with the carboxamide forming a hydrogen bond with Asp 855, and Phenyl group forms hydrophobic interactions with the DFG-in pocket and the 1-oxoisoindolinyl extends to the solvent-accessible region. EAI001 is according to the formula:

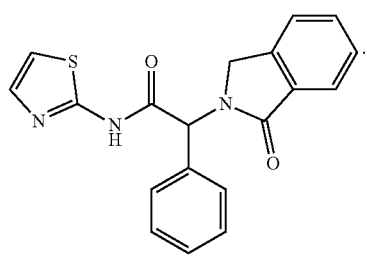 [SMILES: O=C(Nc1nccs1)C(c1ccccc1)N1Cc2ccccc2C1=O]

In an example embodiment, the EGFR inhibitor is an EAI001 analog, for example, EAI045 according to the formula:

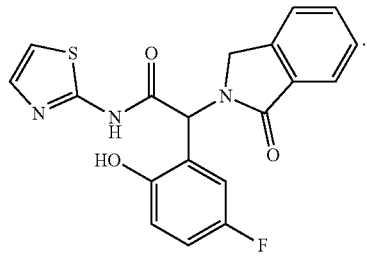 [SMILES: O=C(Nc1nccs1)C(c1cc(F)ccc1O)N1Cc2ccccc2C1=O]

EAI001 and its analogue EAI045 both exhibit potent inhibitory activity against EGFR L858R/T790M with IC50 values of 24 and 3 nm, respectively. EAI045 is an allosteric inhibitor of mutant forms of the EGFR found in lung cancers whilst sparing the wild-type receptor, and inhibits L858R/T790M mutant EGFR with an $IC_{50}$ of 3 nM and is >1000-fold selective for this mutant compared to wild-type receptor. Additional EGFR and its mutants and IC50 for EA1045 are:

|  | EGFR | $EGFR^{L858R}$ | $EGFR^{T790M}$ | $EGFR^{L858R/T790M}$ |
| --- | --- | --- | --- | --- |
| $IC_{50}$ & Target | 1.9 μM ($IC_{50}$) | 0.019 μM ($IC_{50}$) | 0.19 μM ($IC_{50}$) | 0.002 μM ($IC_{50}$) |

In screening panels EA1045 did not inhibit any other kinases by >20% (at 1000 nM EA1045), or show any liability against non-kinase targets, and in xenograft models EAI045 is effective against EGFR(L858R/T790M/C797S) tumors, a mutation profile that is resistant to all currently available ATP-competitive EGFR tyrosine kinase inhibitors. See, Angew. Chem. Int. Ed. 2020, 59, 13764-13776, incorporated herein by reference. EA11045 shows the following properties:

| | |
|---|---|
| Hydrogen bond acceptors | 5 |
| Hydrogen bond donors | 2 |
| Rotatable bonds | 5 |
| Topological polar surface area | 110.77 |
| Molecular weight | 383.07 |
| XLogP | 1.9 |
| No. Lipinski's rules broken | 0. |

In an aspect, the EGFR inhibitor is designed to overcome acquired resistance to current EGFR tyrosine kinase inhibitors which bind to the ATP pocket of the enzyme, which is the location of the many identified resistance mutations In an example embodiment, the EGFR inhibitor is an analog that comprises by addition of phenylpiperazine substituent on the isoindolinone ring of EAI045. The analog may be JBJ-04-125-02 according to the formula:

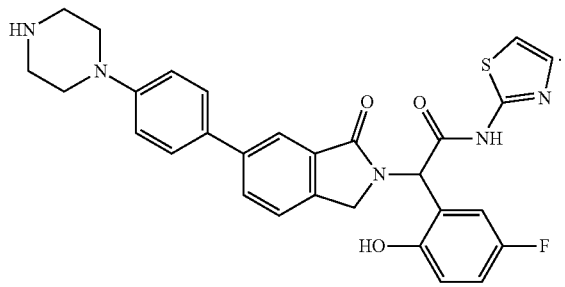 [SMILES: O=C(Nc1nccs1)C(c1cc(F)ccc1O)N1Cc2ccc(-c3ccc(N4CCNCC4)cc3)cc2C1=O]

In an embodiment, JBJ-04-125-02 exhibits sub-nanomolar potency against EGFR L858R/T790M kinase with a biochemical IC50 value of 0.26 nm. Notably, it potently inhibits cell proliferation and EGFR L858R/T790M/C797S signaling in vitro and in vivo as a single agent. X-ray crystal structure of JBJ-04-125-02 and EGFR T790M demonstrates that it binds to the allosteric site of EGFR in a similar manner to EAI001. In an aspect, JBJ-04-125-02 at (0.01-10 uM) inhibited EGFR phosphorylation and demonstrated mutant selectivity by inhibiting mutant EGFR and downstream AKT and ERK1/2 phosphorylation. *Angew. Chem. Int. Ed.* 2020, 59, 13764-13776, incorporated herein by reference in its entirety; see, e.g. To et al., Single and dual targeting of mutant EGFR with an allosteric inhibitor, Cancer Discov. 2019 July; 9(7): 926-943. Doi:10.1158/2159-8290.CD-18-0903.

In an example embodiment, the EGFR inhibitor is an inhibitor or derivative thereof identified in U.S. Pat. No. 8,242,080, herein incorporated by reference.

BCKDK Binding Moiety

In one example embodiment, the kinase binding moiety is a Branched chain alpha-ketoacid dehydrogenase kinase (BCKDK) binding moiety, also referred to as 3-methyl-2-oxoobutanoate-dehydrogenase kinase, binding moiety. In one example embodiment, the BCKDK binding moiety is an inhibitor or activator. BCKDK has been targeted to address conditions such as obesity, maple syrup urine disease and diabetes. In an embodiment, the binding moiety is ADR000362, which is according to the formula

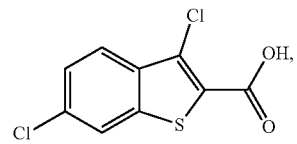 [SMILES: O=C(O)c1sc2cc(Cl)ccc2c1Cl]

or derivatives thereof.

In one embodiment, the allosteric inhibitor is the S-enantiomer of α-chlorophenylpropionate [(S)-CPP]according to the formula

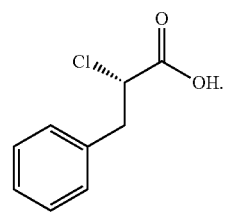 [SMILES: O=C(O)[C@@H](Cl)Cc1ccccc1]

See, Tso S C, Qi X, Gui W J, et al. Structure-based design and mechanisms of allosteric inhibitors for mitochondrial branched-chain α-ketoacid dehydrogenase kinase. Proc Natl Acad Sci USA. 2013; 110(24):9728-9733. doi:10.1073/pnas.1303220110, incorporated herein by reference, specifically, Table 1 inclusive of BCKDK inhibitor compounds and their $IC_{50}$ and $K_d$ values.

In an embodiment, the BCKDK inhibitor is a benzothiophene carboxylate derivative. In an embodiment, the binding moiety is according to the formula 476-116

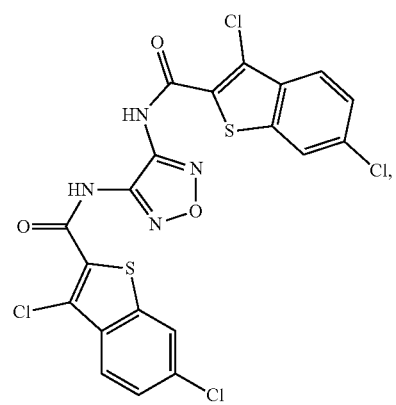

and derivatives thereof. See, Tso et al., Benzothiophene carboxylate derivatives as novel allosteric inhibitors of branched-chain α-ketoacid dehydrogenase kinase. J Biol Chem. 2014 Jul. 25; 289(30):20583-93. doi: 10.1074/jbc.M114.569251.

FGFR Binding Moiety

In one example embodiment, the protein binding moiety is an FGFR kinase binding moiety. In one example embodiment, the FGFR binding moiety is an inhibitor or activator. Fibroblast growth factor receptors (FGFRs) are a family of receptor tyrosine kinases expressed on the cell membrane and consists of four members: FGFR1 to FGFR4. All four FGFR members contain a large extracellular ligand-binding domain from the N- to the C-terminus that comprises three immunoglobulin (Ig)-like subunits (D1, D2 and D3) followed by a single transmembrane helix and an intracellular tyrosine kinase domain. The native ligand of FGFRs is fibroblast growth factors. FGFRs play a crucial role in both developmental and adult cells. See e.g. Dai S., et al. "Fibroblast Growth Factor Receptors (FGFRs): Structures and Small Molecule Inhibitors." Cells 2019, 8 (6), 614.

In an example embodiment, the FGFR inhibitor is SSR128129 according to the formula:

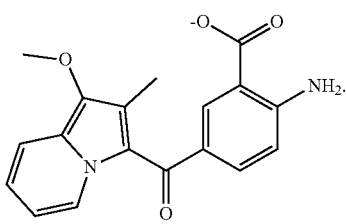

| Hydrogen bond acceptors | 4 |
| Hydrogen bond donors | 2 |
| Rotatable bonds | 4 |
| Topological polar surface area | 94.03 |
| Molecular weight | 324.11 |
| XLogP | 3.76 |
| No. Lipinski's rules broken | 0 |

In an aspect, the SSR128129E is used as the sodium salt. SSR128129E is a negative allosteric modulator of the FGF receptor. The compound inhibits FGF1-induced ERK phosphorylation via FGFR2 with an $IC_{50}$ <100 nM. SSR128129E inhibits FGF ligand induction of receptor dimerization in an allosteric manner without affecting FGF binding, with interaction at Lys279, Thr320, Thr319, Cys 278, Trp290, Phe 276, Wal 274, Tyr 340, I1e329, Tyr328, Leu327, Leu312. See, Cancer Cell, 2013, 23, 477-488, incorporated by reference. For effects of SSR on cellular responses to different FGFRs, reference is made to Table 1 of Cancer Cell, 2013, 23, 4774-88, incorporated specifically herein by reference and showing SSR Concentration resulting in at least 50% inhibition at concentrations of between 10 nM and 100 nM. See also, generally, Herbert et al., Molecular Mechanism of SSR128129E, an Extracellularly Acting, Small-Molecule, Allosteric Inhibitor of FGF Receptor Signaling. Cancer Cell Jul. 11, 2016; doi: 10.1016/j.ccr.2013.02.018, incorporated by reference for chemical structure of the SSR128129E, predicted binding as detailed in FIG. 17 and effects of SSR on cellular responses to different FGFRs as provided in Table 1, each of which is specifically incorporated herein by reference.

HA-NGFR Binding Moiety

In one example embodiment, the protein binding moiety is an allosteric Tropomyosin receptor kinase A (TrkA), or a High affinity nerve growth factor receptors (HA-NGFR) kinase binding moiety. In one example embodiment, the TrkA or HA-NGFR binding moiety is an inhibitor or activator. High affinity nerve growth factor receptors (HA-NGFRs) are a family of receptor tyrosine and regulates the proliferation, differentiation and survival of sympathetic and nervous neurons of the central and peripheral nervous systems. The native ligand of HA-NGFRs is nerve growth factors. The absence of the ligand resulting in lack of activation may promote cell death, making the survival of neurons dependent on trophic factors. See e.g. National Center for Biotechnology Information, 2021. PubChem Protein Summary for NCBI Protein P04629, High affinity nerve growth factor receptor.

In an embodiment, the pan Trk inhibitor is GZ389988, AR786 (allosteric selective TrkA inhibitor), ASP7962 (TrkA receptor antagonist), ONO-4474 (pan Trk inhibitor), or VM902A (allosteric TrkA selective inhibitor). Additional Trk inhibitors are described in Bailey et al, Tropomyosin receptor kinase inhibitors: an updated patent review for 2010-2016, doi: 10.1080/13543776.2017.1297797, and Bailey et al., (2020) Tropomyosin receptor kinase inhibitors: an updated patent review for 2016-2019, Expert Opinion on Therapeutic Patents, 30:5, 325-339, DOI: 10.1080/13543776.2020; both incorporated herein by reference in their entirety.

In an example embodiment, the HA-NGFR is VM-902A or a related compound or analog thereof. In an aspect, the compound can be

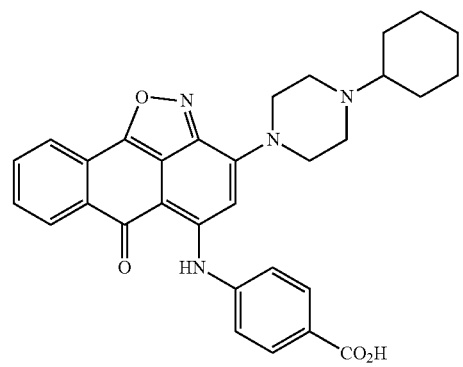

TrkA $IC_{50}$ = 50 nM (cell)
TrkB $IC_{50}$ > 10 µM (cell)
TrkC $IC_{50}$ > 10 µM (cell)

or an analog thereof.

IkappaB Binding Moiety

In one embodiment, the protein binding moiety is an IkappaB kinase binding moiety. In one example embodiment, the IkappaB binding moiety is an inhibitor or activator. In an aspect, the IKappaB kinase binding moiety inhibits one or both subunits IKK-alpha and IKK-beta of IkappaB kinase. In one embodiment, the binding moiety is a selective allosteric inhibitor BMS-345541 and is according to the formula:

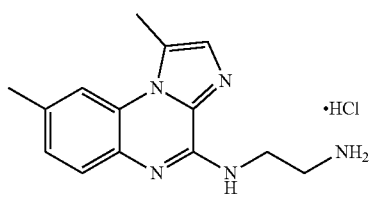 [SMILES: Cc1ccc2nc(NCCN)c3ncc(C)n3c2c1 ; Cl]

with the following properties

| | |
|---|---|
| Hydrogen bond acceptors | 4 |
| Hydrogen bond donors | 2 |
| Rotatable bonds | 3 |
| Topological polar surface area | 68.24 |
| Molecular weight | 255.15 |
| XLogP | 2.15 |
| No. Lipinski's rules broken | 0. |

BMS-345541 has been shown to block NF-kB dependent transcription in mice, and is active against LPS-induced NF-kB activation in mice. In an aspect, the negative allosteric modulator BMS-345541 has a $pK_d$ of 6.9, a $pIC_{50}$ of 6.5 as an inhibitor of nuclear factor kappaB kinase subunit beta, and a $pIC_{50}$ of 5.4 of component of inhibitor of nuclear factor kappa B kinase complex.

CDK Binding Moiety

In one example embodiment, the protein binding moiety is an CDK kinase binding moiety. In one example embodiment, the protein binding moiety is a CDK inhibitor or activator. The cyclin-dependent kinases (CDKs) are characterized by needing a separate subunit, cyclin, that provides domains for enzymatic activity. CDK controls cell division and modulates transcription. The CKD family is divided into three cell-cycle-related subfamilies: CDK1, CDK 2, and CDK 3; CDK4 and CDK6; and CDK5, and CDK14-CDK18 as well as five transcriptional subfamilies: CDK7; CDK8 and CDK 19; CDK9; CDK10 and CDK 11; CDK12 and CDK13; and CDK20. In one example embodiment, the CDK inhibitor comprises Palbociclib, Ribociclib, Abemaciclib, or any derivatives thereof. In an example embodiment, the CDK8 inhibitor is compound 5 with the formula:

CMP-5

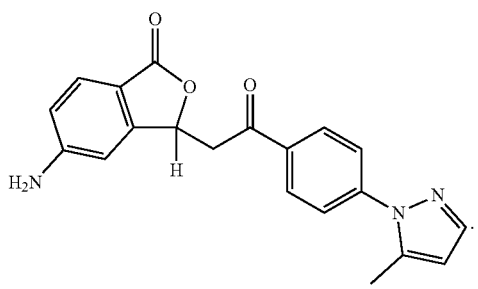

In an example embodiment, the CDK2 inhibitor is a flavopiridol analog. In an example. Embodiment, the CDK2 inhibitor is 8-amidoflavone, 8-sulfonamidoflavone, 8-amido-7-hydroxyflavone, or heterocyclic analogues of flavopiridol. See, Ahn et al., Design, synthesis, and antiproliferative and CDK2-cyclin a inhibitory activity of novel flavopiridol analogues, Bioorganic & Medicinal Chemistry, Volume 15, Issue 2, 2007, Pages 702-713, doi: 10.1016/j.bmc.2006.10.063, incorporated herein by reference. In one embodiment, the compound is selected from the 8 aminoflavopiridol analogues of Table 1 of Ahn, and may be selected based on antiproliferative and inhibitory activities of Table 1, incorporated specifically herein by reference. Modifications to the molecules of Ahn may be made based in part on the desired interactions between the analog and CDK, with exemplary modifications made based on FIG. 2A-2B.

In an example embodiment, the CDK inhibitor is Alvocidib, an inhibitor which causes cell-cycle arrest and is in Phase 2 clinical evaluation for anti-cancer potential, according to the formula:

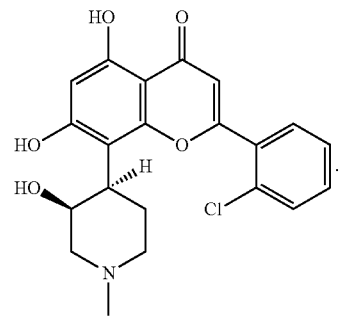 [SMILES: CN1CC[C@H](c2c(O)cc(O)c3c(=O)cc(-c4ccccc4Cl)oc23)[C@H](O)C1]

In an embodiment, Alvocidib is utilized as a CDK2 and/or CDK4 kinase binding moiety, with a CDK4 $pK_i$ of 7.2 and a CDK2 $pIC_{50}$ of 6.4-7.0. and with the following properties:

| | |
|---|---|
| Hydrogen bond acceptors | 3 |
| Hydrogen bond donors | 3 |
| Rotatable bonds | 2 |
| Topological polar surface area | 94.14 |
| Molecular weight | 401.1 |
| XLogP | 3.95 |
| No. Lipinski's rules broken | 0 |

In an aspect, properties can be optimized for use in the chimeric small molecules based on sites for modification which may be identified and optimized in accordance with the formula, and as discussed in Bioorg. Med. Chem. 2007, 15, 702-713:

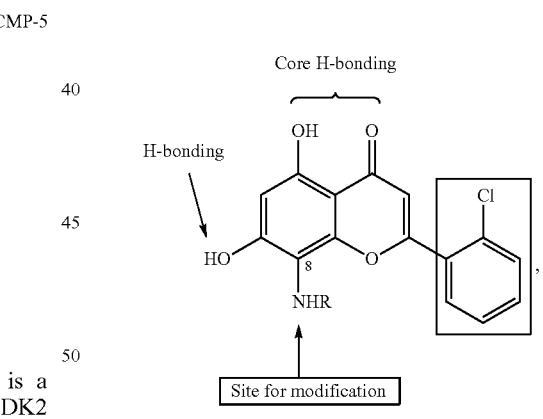

wherein R can be any cyclic hydrocarbon; an unsaturated cyclic hydrocarbon; a heterocycle; one or more fused rings comprising any combination of any previously mentioned rings optionally substituted at one or more positions alkane, alkene, alkyne, ether, alcohol, amine, nitrile, nitro, thiol, sulfone, sulfonate, halogen, carbonyl; acyl; ketone; carboxylate ester; amide; enone; acid anhydride; imide, cyclic hydrocarbon, an unsaturated cyclic hydrocarbon, a heterocycle; one or more fused rings comprising any combination of any previously mentioned rings, preferably a piperideine, pyrrolidine, thiane, or morpholine ring which may be further substituted at any position on the ring. Particular 8 aminoflavopiridol analogues are as detailed in table 1 of Bioorg. Med. Chem. 2007, 15, 702-713:, depicted below:

TABLE 1

Antiproliferative and CDK2-Cyclin A inhibitory activities of 8-aminoflavopiridol analogues

| Compound | ID-8*$IC_{50}$ (μM) | MCF-7*$IC_{50}$ (μM) | CDK2-Cyclin A (μM) |
|---|---|---|---|
| Flavopiridol (I) | 0.0070 | 0.026 | 1.5 |
| 17a | 13 | 7.1 | 417 |
| 17b | 5.5 | 4.6 | 417 |
| 17c | 13 | 15 | 217 |
| 17d | 16 | 10 | N.D. |
| 17e | 5.0 | 3.5 | 383 |
| 19a | N.D. | 8.5 | 91 |
| 19b | N.D. | 13 | 339 |
| 19c | N.D. | 9.7 | 90 |
| 19d | N.D. | 13 | 54 |
| 20a | 9.3 | 20 | 417 |
| 20b | 5.7 | 17 | 417 |
| 20c | 7.9 | 20 | 417 |
| 21a | 104 | 5.5 | N.D. |
| 21b | 12 | 4.5 | 417 |
| 21c | 17 | 2.5 | 417 |
| 21d | 13 | 2.8 | N.D. |
| 22a | 9.8 | 5.5 | 417 |
| 22b | 5.3 | 7.1 | 417 |
| 22c | 5.1 | 4.0 | 417 |
| 22d | 6.2 | 20 | N.D. |
| 23 | 18 | 30 | 417 |
| 24a | 16 | 25 | 219 |
| 24b | 9.5 | 16 | 178 |
| 24c | 24 | 17 | 94 |

PI3K Binding Moiety

In one example embodiment, the protein binding moiety is an PI3K kinase binding moiety. In one example embodiment, the protein binding moiety is a PI3K inhibitor or activator. The phosphoinositide 3-kinase (PI3K) is a superfamily of lipid kinases central to human cancer, diabetes, and aging. There are three different PI3K classes (I, II and III), as well as for the different isoforms (e.g. Class I has 4 isoforms: α, β, γ, δ) and within each class there are distinct roles for each of the PI3Ks. Class I has been implicated in many cancers particularly those with pathogenic mutations. PI3K acts downstream to many growth factors and acts upstream to AKT and mTOR. (Kannaiyan et al. Expert Rev Anticancer Ther. 2018; 18(12): 1249-1270)

In one example embodiment, the PI3K inhibitor is Idelalisib with the formula:

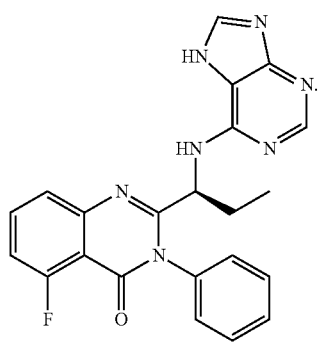 [SMILES: CC[C@H](Nc1ncnc2nc[nH]c12)c1nc2cccc(F)c2c(=O)n1-c1ccccc1]

Idelalisib is a small molecule inhibitor of the delta isoform of PI3K. In an example embodiment, the PI3K inhibitor is PIK-108 according to the formula:

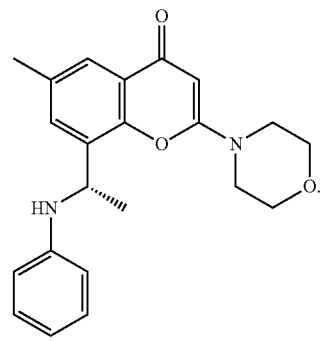 [SMILES: Cc1cc([C@H](C)Nc2ccccc2)c2oc(N3CCOCC3)cc(=O)c2c1]

PIK-108 is an allosteric inhibitor of the lipid modifying kinases, phosphatidylinositol-4,5-bisphosphate 3-kinase catalytic subunits β and δ (PI3Kβ/δ). The compound binds at an allosteric site close to the mutation hotspot of H1047R in the mouse PI3Kα C-lobe, in addition to binding at the ATP-binding pocket. See e.g. Certal, V., et al. "Discovery and Optimization of New Benzimidazole- and Benzoxazole-Pyrimidone Selective PI3Kβ Inhibitors for the Treatment of Phosphatase and TENsin Homologue (PTEN)-Deficient Cancers." J. Med. Chem. 2012, 55 (10), 4788-4805, herein incorporated by reference in its entirety with specific mention of Table 2 and 3 and the Biochemical and Cellular Activity of Pyrimidone Benzimidazoles and their substitutions.

VEGFR Binding Moiety

In one example embodiment, the protein binding moiety is a VEGFR binding moiety. In one example embodiment, the VEGFR binding moiety is an inhibitor or activator. Vascular endothelial growth factors (VEGFs) are a family of polypeptides with conserved receptor-binding domain comprising of a disulfide-knot structure. There are two VEGFs, VEGF-A and VEGF-B, that bind to VEGFR which are receptor tyrosine kinases located on vascular endothelial cells. In one example embodiment, the kinase binding moiety is a VEGFR inhibitor. In an example embodiment, the VEGFR inhibitor is Sorafenib, Sunitinib, Pazopanib, Axitinib, Cabozantinib, Lenvatinib, Vandetanib, or Regorafenib.

BRAF Binding Moiety

In one example embodiment, the kinase binding moiety is a BRAF binding moiety. In one example embodiment, the binding moiety is a BRAF inhibitor or activator. BRAF is a member of the Rapidly Accelerated Fibrosarcoma family of serine/threonine kinases and is frequently activated in patients with cancer through genetic aberrations. BRAF has three conserved regions: conserved region 1 (CR1) is a Ras-GTP-binding self-regulatory domain; conserved region 2 (CR2) is a serine-rich region that functions as a hinge on the molecule; and conserved region 3 (CR3) is a catalytic protein kinase domain. In one example embodiment, the kinase binding moiety is a BRAF inhibitor. In one embodiment, the BRAF inhibitor comprises Vemurafenib or Dabrafenib.

MEK Binding Moiety

In one example embodiment, the protein binding moiety is a MEK binding moiety. In one example embodiment, the MEK binding moiety is an inhibitor or activator. MEK is a kinase enzyme that phosphorylates mitogen activated protein kinases (MAPK). Seven MEK subtypes have been identified, all mediate cellular responses to different growth signals. In one example embodiment, the kinase binding moiety is a MEK inhibitor. In one embodiment, the binding moiety is a Type-3 kinase inhibitor. In one embodiment, the MEK inhibitor comprises Trametinib according to the formula:

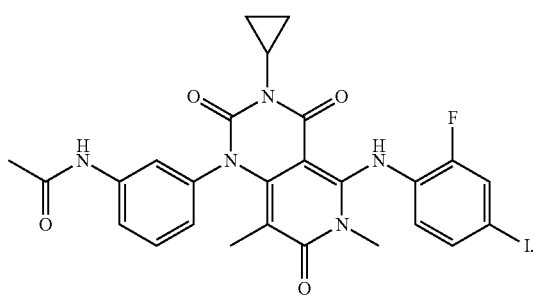 [SMILES: CC(=O)Nc1cccc(-n2c(=O)n(C3CC3)c(=O)c3c(Nc4ccc(I)cc4F)n(C)c(=O)c(C)c32)c1]

Trametinib has been used for the adjuvant treatment of patients with BRAF V600E or V600K mutated melanoma inhibiting MAP2K1 and MAP2K2 (aka MEK1 and 2) in the p42/p44 MAPK pathway. Absorption/distribution of an oral dose of trametinib tablet is 72%. Trametinib is 97.4% bound to human plasma proteins, which can be utilized when determining dosage for small molecules detailed herein. See, Gilmartin, et al., GSK1120212 (JTP-74057) Is An Inhibitor of MEK Activity and Activation with Favorable Pharmacokinetic Properties for Sustained In Vivo Pathway Inhibition. Clin Cancer Res. 2011 Mar. 1; 17(5):989-1000. doi: 10.1158/1078-0432.CCR-10-2200. Epub 2011 Jan. 18. Trametinib has a MAPK1 inhibition $pIC_{50}$ of 9/0-9.1 and a MAPK2 $pIC_{50}$ inhibition of 8.7. Trametinib was shown to have sustained suppression of p-ERK1/2 for more than 24 hours, with high potency, selectivity and long circulating half-life.

In one example embodiment, the MEK inhibitor comprises Cobimetinib, an allosteric inhibitor of MEK serine/threonine protein kinases, with a selectivity for MEK 1 and MEK2. Cobimetinib selectively inhibits the activity of the MEK serine/threonine protein kinase and is according to the formula:

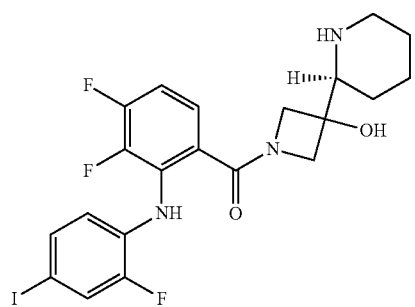 [SMILES: O=C(c1ccc(F)c(F)c1Nc1ccc(I)cc1F)N1CC(O)([C@@H]2CCCCN2)C1]

with the following properties:

| | |
|---|---|
| Hydrogen bond acceptors | 5 |
| Hydrogen bond donors | 3 |
| Rotatable bonds | 5 |
| Topological polar surface area | 64.6 |
| Molecular weight | 531.06 |
| XLogP | 4.82 |
| No. Lipinski's rules broken | 0 |

Additional in vitro activity of cobimetinib and related analogs was explored in Rice et al., "Novel Carboxamide-Based Allosteric MEK Inhibitors: Discovery and Optimization Efforts toward XL518 (GDC-0973)" ACS Med. Chem. Lett. 2012, 3, 5, 416-421, incorporated herein by reference in particular, at Tables 1 and 3.

In an example embodiment, the MEK inhibitor comprises Pimasertib according to the formula:

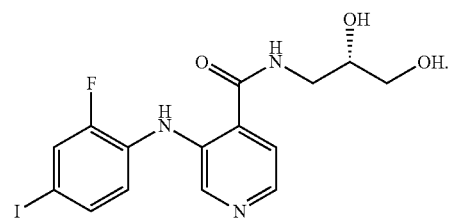 [SMILES: O=C(NC[C@H](O)CO)c1ccncc1Nc1ccc(I)cc1F]

Pimasertib is an orally bioavailable small-molecule inhibitor of the mitogen-activated protein kinases MEK1 and MEK2 (MEK1/2) with potential antineoplastic activity. It binds to an allosteric site, distinct from the ATP binding site and as such prevents activation rather than inhibiting catalysis. Pimasertib (AS703026) is cytotoxic against CD138-purified multiple myeloma (MM) cells from patients with relapsed and refractory MM, with IC50 values ranging from 2-200 nM. MEK1/2 (MAP2K1/K2) are dual-specificity threonine/tyrosine kinases that play key roles in the activation of the RAS/RAF/MEK/ERK pathway and are often upregulated in a variety of tumor cell types. Selectively binds to and inhibits the activity of MEK1/2, preventing the activation of MEK1/2-dependent effector proteins and transcription factors, which may result in the inhibition of growth factor-mediated cell signaling and tumor cell proliferation. See, Yoon J, Koo K H, Choi K Y. MEK1/2 inhibitors AS703026 and AZD6244 may be potential therapies for KRAS mutated colorectal cancer that is resistant to EGFR monoclonal antibody therapy. Cancer Res. 2011 Jan. 15; 71(2):445-53. doi: 10.1158/0008-5472.

In an example embodiment, the MEK inhibitor comprises CI-1040 according to the formula:

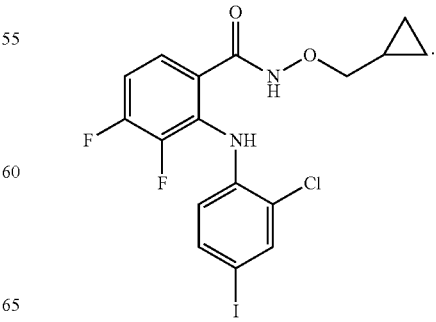

In an example embodiment, the MEK1 and MEK2 inhibitor is Selumetinib (AZD6244, ARRY-142886) according to the formula:

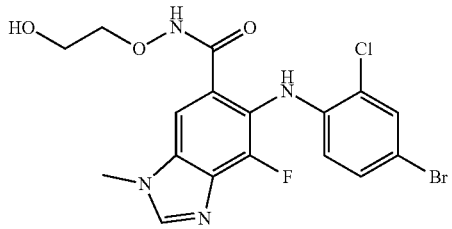 [SMILES: Cn1cnc2c(F)c(Nc3ccc(Br)cc3Cl)c(C(=O)NOCCO)cc21]

and with the following properties:

| | |
|---|---|
| Hydrogen bond acceptors | 4 |
| Hydrogen bond donors | 3 |
| Rotatable bonds | 7 |
| Topological polar surface area | 88.41 |
| Molecular weight | 456 |
| XLogP | 3.7 |
| No. Lipinski's rules broken 34 | 0 |

Selumetinib is an orally bioavailable non-ATP competitive inhibitor that is highly specific for MEK1/2. It is a negative allosteric modulator of MEK1 with a pIC50 of 7.8-7.9. Sensitivity to selumetinib in a panel of NSCLC and CRC cell lines showed sensitivity to particular mutations of KRAS in GEO cells with amino acid change p.G12A, SW480 cells with amino acid change G12V, SW620 cells with amino acid change p.G12V, and in HCT116 cells with amino acid change G13D and PIK3CA amino acid change p.H1047R, and in H1299 cells with NRAS amino acid change p.Q61K.

In an example embodiment, the allosteric MEK inhibitor is a 3,4-difluoro-2-(2-halo-4-iodo-phenylamino)-N-2-hydroxy-ethoxy)-benzamide according to the formula

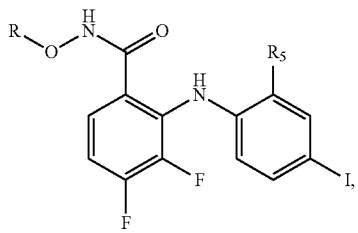

wherein R and $R_5$ are selected from the table below

| Compound | R | $R_5$ | C26 $IC_{50}$ (nM) | Sol (pH 6.5) (μg/mL) |
|---|---|---|---|---|
| 24 (CI-1040) | —CH$_2$$^c$Pr | Cl | 35 | <1 |
| 29 | —CH$_2$$^c$Pr | F | 1.0 | <1 |
| 30 | —CH$_2$CH$_2$OH | Cl | 3.5 | <1 |
| 31 | —CH$_2$CH$_2$OH | F | 0.07 | 5 |
| 32 | (±)-CH$_2$CHOH(CH$_2$OH) | Cl | 19 | — |
| 33 | (±)-CH$_2$CHOH(CH$_2$OH) | F | 0.48 | 147 |
| 34 (PD 0325901) | R-(−)-CH$_2$CHOH(CH$_2$OH) | F | 0.33 | 190 |
| 35 | S-(+)-CH$_2$CHOH(CH$_2$OH) | F | 0.82 | 255, | as described in Hartung et al., Optimization of allosteric MEK inhibitors, Part 1: Venturing into underexplored SAR territories, Bioorganic and Medicinal Chemistry Letters 23 (2013) 2384-2390, incorporated herein by reference.

In one example embodiment, the MEK inhibitor is Mirdametinib (PD 0325901) a selective and non-ATP-competitive MEK inhibitor that has been explored in advanced KRAS mutant colorectal cancer, non-small-cell lung cancer, melanoma, colonic neoplasms and breast cancer, and is according to the formula:

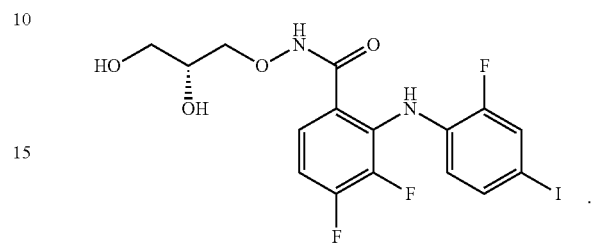

Mirdametinib has a EK1 inhibition $pIC_{50}$ value of 8.1 and has the following properties:

| | |
|---|---|
| Hydrogen bond acceptors | 4 |
| Hydrogen bond donors | 4 |
| Rotatable bonds | 8 |
| Topological polar surface area | 90.82 |
| Molecular weight | 482 |
| XLogP | 3.4 |
| No. Lipinski's rules broken | 0 |

In one example embodiment, the MEK binding moiety comprises allosteric inhibitor refametinib:
or an analog thereof, for example,

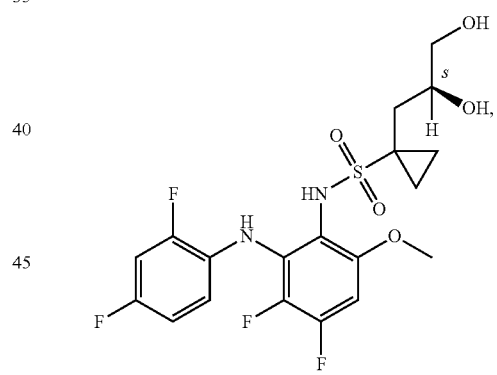

or a derivative thereof.

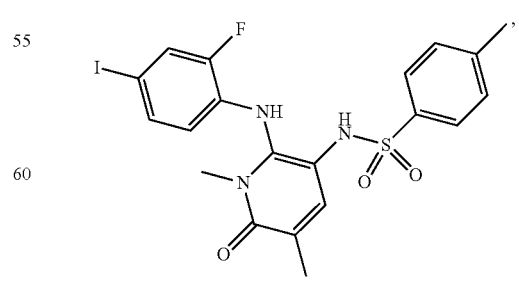

In an example embodiment, the MEK inhibitor is Binimetinib according to the formula:

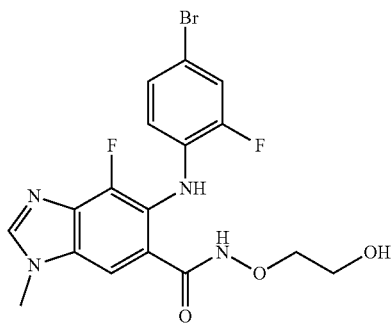 [SMILES: Cn1cnc2c(F)c(Nc3ccc(Br)cc3F)c(C(=O)NOCCO)cc21]

and has the following properties:

| | |
|---|---|
| Hydrogen bond acceptors | 4 |
| Hydrogen bond donors | 3 |
| Rotatable bonds | 7 |
| Topological polar surface area | 88.41 |
| Molecular weight | 440.03 |
| XLogP | 3.23 |
| No. Lipinski's rules broken | 0 |

Binimetinib has received FDA approval as a treatment for advanced BRAF-mutant melanoma in conjunction with the BRAF mutant kinase inhibitor encorafenib. See, Dummer et al., Encorafenib plus binimetinib versus vemurafenib or encorafenib in patients with BRAF-mutant melanoma (CO-LUMBUS): a multicenter, open-label, randomized phase 3 trial. Lancet Oncol. 2018 May; 19(5):603-615. doi: 10.1016/S1470-2045(18)30142-6.

Additional exploration in other solid tumor types, neuroblastoma, and hematological cancers are being explored. See, e.g. Woodfield S E, Zhang L, Scorsone K A, Liu Y, Zage P E. Binimetinib inhibits MEK and is effective against neuroblastoma tumor cells with low NF1 expression. BMC Cancer. 2016 Mar. 1; 16:172. doi: 10.1186/s12885-016-2199-z. Binimetinib is a negative allosteric modulator with a MEK1 and a MEK2 pIC50 of 7.9.

AKT Binding Moiety

In one example embodiment, the protein binding moiety is an AKT binding moiety. In one example embodiment, the AKT binding moiety is an inhibitor or activator. RAC-alpha serine/threonine-protein kinase (AKT) in humans has three isozymes (AKT1, 2, and 3, also known as PKB-α, -β and -γ). Each isozyme contains an amino (N)-terminal PH domain, inter-domain linker, kinase domain and 21-residue carboxy (C)-terminal hydrophobic motif. In an example embodiment, the ATK inhibitor is Borussertib with the formula:

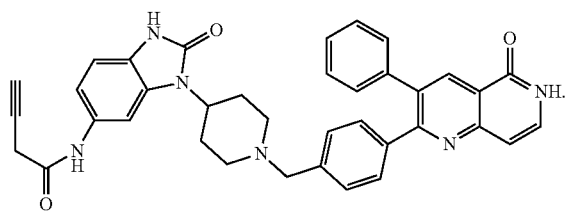

In an example embodiment the kinase inhibitor is MK-2206 with the formula:

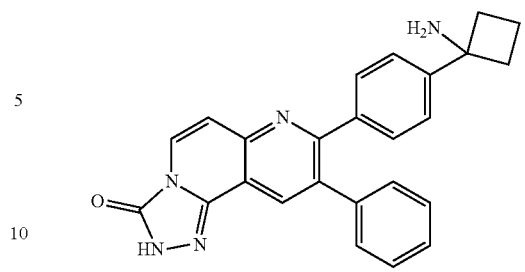

with the following properties:

| | |
|---|---|
| Hydrogen bond acceptors | 4 |
| Hydrogen bond donors | 2 |
| Rotatable bonds | 3 |
| Topological polar surface area | 89.07 |
| Molecular weight | 407.17 |
| XLogP | 5.13 |
| No. Lipinski's rules broken | 1. |

MK-2206 is an orally bioavailable allosteric inhibitor of the serine/threonine protein kinase AKT (protein kinase B) with potential antineoplastic activity. MK-2206 has $pIC_{50}$ values of 8.3, 7.9, and 7.2 for AKT1, 2, and 3 respectively. MK-2206 is able to enhance the antitumor efficacy of standard chemotherapeutic agents or molecular targeted drugs in vitro and in vivo. As of 2018, ClinicalTrilas.gov had 50 registered MK-2206 trials. Many have been withdrawn, terminated or completed. The ring fused to the pyridine may be modified to mono-, bi-, tricyclic linear fused rings, or angular tricycles. The pyridine may be modified to a pyrazine. The moiety of substituted benzene may also be modified. The strained cyclobutene may be substituted for any substituent known in the art. Furthermore, the hydrogens on the amine in the moiety may be substituted for any substituent known in the art. For further design guidance see Kettle, J. G., et al. "Diverse Heterocyclic Scaffolds as Allosteric Inhibitors of AKT." J. Med. Chem. 2012, 55 (3), 1261-1273, herein incorporated by reference in its entirety.

In one example embodiment, the AKT inhibitor is any inhibitor from International Patent Application WO2008070016A2, herein incorporated by reference in its entirety, and any derivative thereof. In addition, see e.g. Wu, W.-I., et al. "Crystal Structure of Human AKT1 with an Allosteric Inhibitor Reveals a New Mode of Kinase Inhibition." PLoS ONE 2010, 5 (9), e12913, herein incorporated by reference in its entirety. In an embodiment, inhibitors of AKT or derivatives thereof can be according to:

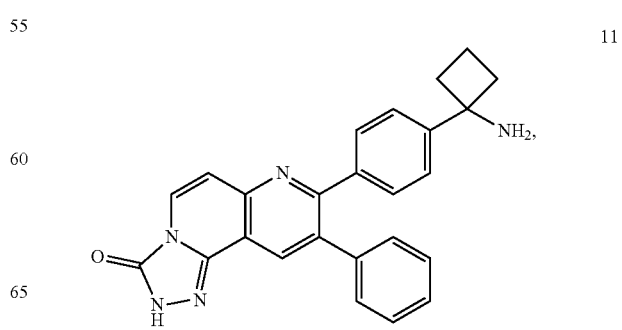

-continued

12

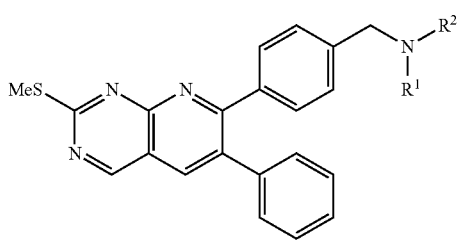

13

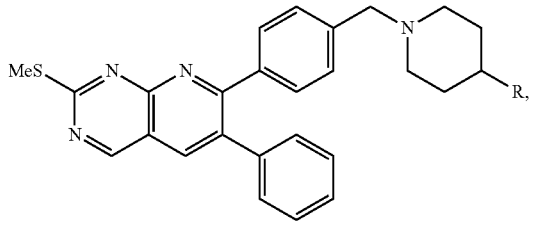

wherein R1=H and R2=

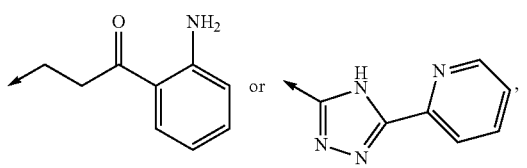

where any N in the ring can be substituted with C, N, O, S, B or P;

or according to

14

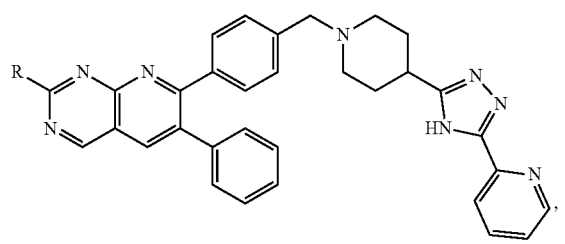

wherein R=NHMe. See, Bioorg. Med. Chem. Let. 2008, 18, 4191-4194; doi:10.1371/journal.pone.0012913, incorporated herein by reference. Optimization of allosteric inhibition of AKT can be performed based on the following guidance:

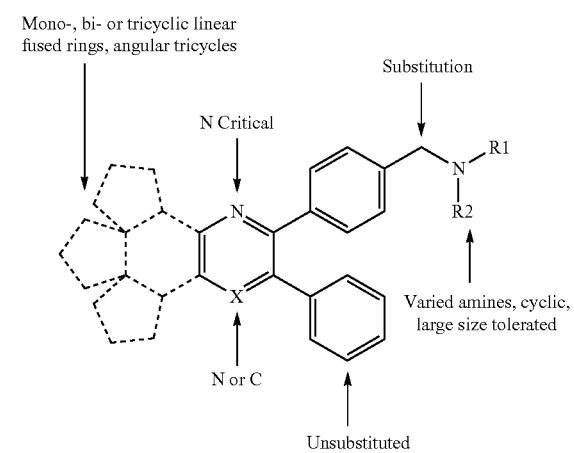

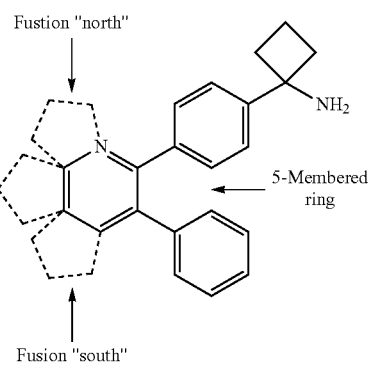

Strategy for combining potency and reducing hERG affinity for AKT binders can be based in whole or in part on the following:

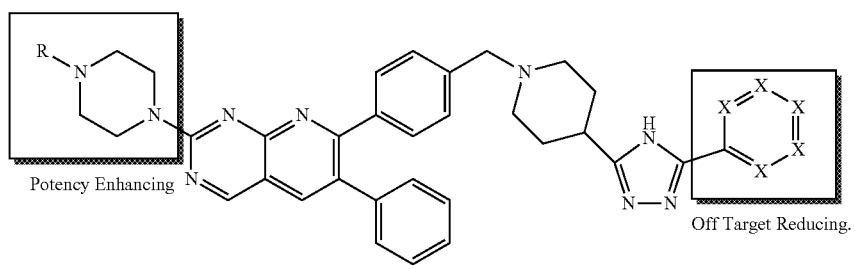

In an example embodiment, the kinase inhibitor is AKT Inhibitor VIII, also known as compound 16h, with the formula:

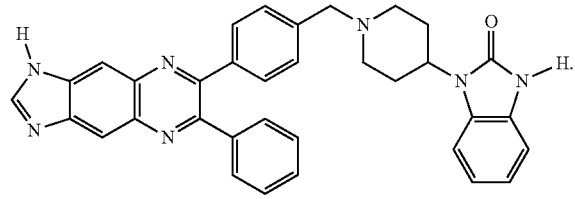

AKT Inhibitor VII is a cell-permeable quinoxaline compound that has been shown to potently, selectively, allosterically, and reversibly inhibit AKT (protein kinase B), with selectivity for AKT1 and 2 over AKT3. The $pIC_{50}$ values of AKT Inhibitor VIII is 7.2, 6.7, and 5.7 for AKT1, 2, and 3 respectively. See Lindsley, C. W., et al. "Allosteric Akt (PKB) Inhibitors: Discovery and SAR of Isozyme Selective Inhibitors." *Bioorganic & Medicinal Chemistry Letters* 2005, 15 (3), 761-764, herein incorporated by reference in its entirety with specific mention of Table 1 and Table 2, reproduced below:

TABLE 1

Structures and activities for pyrazinones 13/14

| Compd | R | Akt1 $IC_{50}$ (nM)[a] | Akt2 $IC_{50}$ (nM)[a] | Akt3 $IC_{50}$ (nM)[a] |
|---|---|---|---|---|
| 13a | H | 3029 | 15,700 | >50,000 |
| 14a |  | 1500 | >50,000 | >50,000 |
| 13b | CH$_3$ | 760 | 24,000 | >50,000 |
| 14b |  | 1003 | 1179 | 33,100 |
| 13c | benzyl | 17,000 | >50,000 | >50,000 |
| 14c |  | >50,000 | 1755 | 3973 |
| 13d | 4-hydroxybenzyl | 21,670 | 45,270 | >50,000 |
| 14d |  | >50,000 | 5407 | >50,000 |
| 13e | sec-butyl | 17,000 | >50,000 | >50,000 |
| 14e |  | >50,000 | 4517 | >50,000 |
| 13f | isobutyl | >50,000 | 18,000 | >50,000 |
| 14f |  | 21,200 | 325 | 21,870 |

TABLE 2

Structures and activities for quinoxalines 16

| Compd | R | Akt1 $IC_{50}$ (nM)[a] | Akt2 $IC_{50}$ (nM)[a] | Akt3 $IC_{50}$ (nM)[a] |
|---|---|---|---|---|
| 16a | 6-COOH | 240 | 281 | >50,000 |
| 16b | 7-COOH | 166 | 388 | 3200 |
| 16c | 6-(2H-tetrazole) | 63 | 65 | 1228 |
| 16d | 7-(2H-tetrazole) | 20 | 144 | 1613 |
| 16e | 6-(2-Me-tetrazole) | 1089 | 1877 | >50,000 |
| 16f | 7(-2-Me-tetrazole) | 55 | 332 | >50,000 |

TABLE 2-continued

Structures and activities for quinoxalines 16

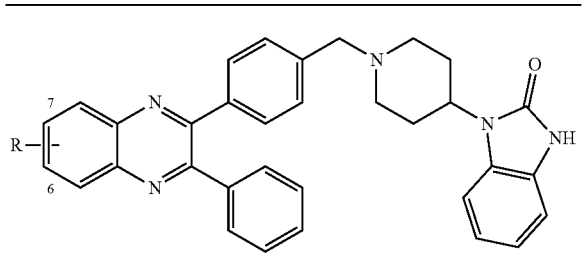

| Compd | R | Akt1 IC$_{50}$ (nM)$^a$ | Akt2 IC$_{50}$ (nM)$^a$ | Akt3 IC$_{50}$ (nM)$^a$ |
|---|---|---|---|---|
| 16g | 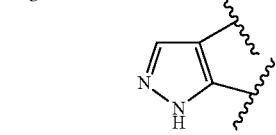 | 85 | 300 | 2400 |
| 16h | 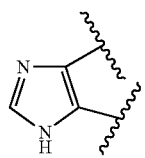 [SMILES: *c1nc[nH]c1*] | 58 | 210 | 2119 |

In an example embodiment, the kinase inhibitor is miransertib, also known as ARQ-092, according to the formula:

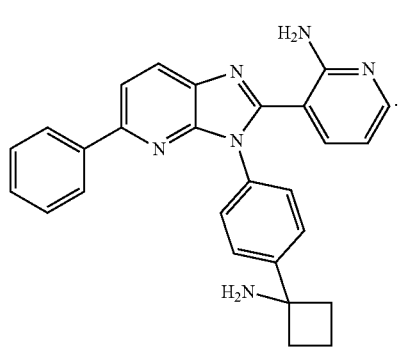 [SMILES: Nc1ncccc1-c1nc2ccc(-c3ccccc3)nc2n1-c1ccc(C2(N)CCC2)cc1]

Miransertib is an orally active, selective, and potent allosteric AKT inhibitor. Miransertib has pIC$_{50}$ values of 8.3, 8.4, and 7.8 for AKT1, 2, and 3. Miransertib has progressed to Phase 1 and 2 development in solid and liquid tumors. See e.g. "Discovery of 3-(3-(4-(1-Aminocyclobutyl)Phenyl)-5-Phenyl-3H-Imidazo[4,5-b]Pyridin-2-Y1)Pyridin-2-Amine (ARQ 092): An Orally Bioavailable, Selective, and Potent Allosteric AKT Inhibitor." J. Med. Chem. 2016, 59 (13), 6455-6469, herein incorporated by reference in its entirety with specific mention of Tables: 1, 2, 3, 4, 6, and 9, with Tables 2 and 4 reproduced below:

TABLE 2

Structure-Activity Relationship for Subsitution on the Pyridine Ring$^a$

| cmpd | R$_1$ | R$_2$ | R$_3$ | IC$_{50}$ (μM)$^b$ | | |
|---|---|---|---|---|---|---|
| | | | | AKT1 | AKT2 | AKT3 |
| 6 | H | H | H | 1.7 | 9.3 | >100 |
| 7a | Me | H | H | 0.5 | NT | NT |
| 7b | H | Me | H | 0.27 | 5.3 | >10 |
| 7c | H | Me | Me | >1 | NT | NT |
| 7d | H | H | Cl | 0.27 | 1.9 | 2.6 |
| 7e | H | Pr | H | 0.32 | NT | NT |
| 9a | H | H | Ph | 0.0037 | 0.033 | 0.43 |
| 9b | H | H | 3-NHAc-Ph | 0.013 | 0.024 | 0.086 |
| 9c | H | H | 4-NHAc-Ph | 0.072 | 0.079 | 0.70 |
| 9d | H | H | 1H-pyrazol-4-yl | 0.017 | 0.014 | 0.065 |
| 9e | H | pyridin-3-yl | H | 0.036 | 3.5 | >10 |

$^a$See Experimental Sections for assay details.
NT means not tested.
$^b$Assay conducted with unphosphorylated enzymes.

TABLE 4

Structure-Activity Relationship of-Substituted Analogs

| Compd | R | IC$_{50}$ (μM) for un-phosphorylated and phosphorylated forms of AKT isoforms | | | | | |
|---|---|---|---|---|---|---|---|
| | | AKT1 | | AKT2 | | AKT3 | |
| | | Inactive | Active | Inactive | Active | Inactive | Active |
| 21a | phenyl | 0.0027 | 0.0050 | 0.014 | 0.0045 | 0.0081 | 0.016 |
| 21b | 3-acetamidophenyl | 0.0028 | 0.0023 | 0.0071 | 0.0032 | 0.0054 | 0.022 |
| 23 | 3-aminophenyl | 0.0019 | 0.0026 | 0.0054 | 0.0028 | 0.0040 | 0.0090 |
| 21c | pyridin-3-yl | 0.006 | 0.034 | 0.0025 | 0.036 | 0.026 | 0.34 |

In an example embodiment, the kinase inhibitor is ARQ 751. In one example embodiment, the kinase inhibitor is any inhibitor from Ashwell, M. A., et al. "Discovery and Optimization of a Series of 3-(3-Phenyl-3H-Imidazo[4,5-b]Pyridin-2-Y1)Pyridin-2-Amines: Orally Bioavailable, Selective, and Potent ATP-Independent Akt Inhibitors." *J. Med. Chem.* 2012, 55 (11), 5291-5310 or any derivative thereof with specific mention of Tables 3, 4, 6, and 8, reproduced below for reference:

TABLE 3

Akt1 Biochemical and Biophysical Results for Scaffold 24[a]

R2 = H

| Compd | R$_1$ | R$_3$ | R$_4$ | Akt1 ΔTm (° C.) | Akt1 IC$_{50}$ (μM) |
|---|---|---|---|---|---|
| 3a | H | 4-tert-butylphenyl | pyridin-3-yl | no shift | >300 |
| 3b | H | 4-tert-butylphenyl | 2-aminopyridin-3-yl | 1.9 | 3.9 |
| 3c | H | 2-methoxybenzyl | 2-aminopyridin-3-yl | no shift | 58 |
| 3d | Br | 1-(2-methoxyphenyl)ethyl | 2-aminopyridin-3-yl | no shift | >300 |
| 3e | Br | 1-(2-methoxyphenyl)ethyl | pyridin-4-yl | no shift | >300 |
| 3f | H | 4-tert-butylphenyl | pyridin-4-yl | no shift | 185 |
| 3g | Br | 2-(4-tert-butylphenyl)propan-2-yl | 2-aminopyridin-3-yl | 0.9 | >300 |
| 3h | H | 3-tert-butylphenyl | 2-aminopyridin-3-yl | no shift | >300 |

TABLE 3-continued

Akt1 Biochemical and Biophysical Results for Scaffold 24[a]

$R_2$ = H

| Compd | $R_1$ | $R_3$ | $R_4$ | Akt1 ΔTm (°C.) | Akt1 IC$_{50}$ (μM) |
|---|---|---|---|---|---|
| 5a | H | 4-(aminomethyl)phenyl | 2-aminopyridin-3-yl | 2.6 | 0.93 |
| 5b | H | 4-(aminomethyl)phenyl | pyridin-3-yl | no shift | 8.8 |
| 5c | H | 4-(NHAc)phenyl | 2-aminopyridin-3-yl | 3.7 | 1.3 |
| 5d | H | 4-aminophenyl | 2-aminopyridin-3-yl | 4.1 | 0.74 |

TABLE 4

Akt1 Structure-Activity Relationship for Para-Substituents[a]

| Compd | R | ΔTm (°C.) | IC$_{50}$ (μM) |
|---|---|---|---|
| 5e | 4-(NHC(O)Ph) | 7.3 | 0.014 |
| 7 | 4-(NHC(O)CH$_2$Ph) | 7.9 | 0.028 |

TABLE 4-continued

Akt1 Structure-Activity Relationship for Para-Substituents[a]

| Compd | R | Akt1 ΔTm (° C.) | IC$_{50}$ (μM) |
|---|---|---|---|
| 8a | 4-CH$_2$NHC(O)Ph | 7.7 | 0.023 |
| 8b | 4-CH$_2$NHC(O)-cyclohexyl | 5.7 | 0.25 |
| 8c | 4-CH$_2$NHC(O)CH$_2$Ph | 4.7 | 0.66 |
| 8d | 4-CH$_2$NHC(O)CH$_3$ | 2.3 | 0.81 |
| 8g | 3-CH$_2$NHC(O)Ph | no shift | 13 |
| 8h | 4-CH$_2$NHCH$_2$Ph | 4.9 | 0.26 |

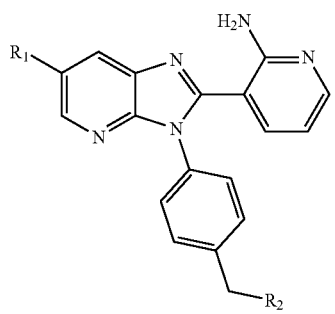
| | | | Akt1 | | Akt2 | | Akt3 | |
|---|---|---|---|---|---|---|---|---|
| Compd | R₁ | R₂ | ΔTm (° C.) | IC$_{50}$ (μM) | ΔTm (° C.) | IC$_{50}$ (μM) | ΔTm (° C.) | IC$_{50}$ (μM) |
| 7 | H | −C(O)NH−phenyl | 6.7 | 0.028 | 1.2 | 0.70 | no shift | 22 |
| 8a | H | −NHC(O)−phenyl | 6.4 | 0.023 | 1.3 | 0.66 | no shift | 24 |
| 8c | Br | −NHC(O)−phenyl | 8.1 | 0.027 | 3.0 | 0.13 | | >10 |
| 9 | cyclopentyl | −NHC(O)−phenyl | 6.0 | 0.11 | 3.3 | 0.80 | no shift | >100 |
| 12d | phenyl | −NHC(O)−phenyl | 5.61 | 0.033 | 1.2 | 51 | no shift | >100 |
| 12e | 3-pyridyl | −NHC(O)−phenyl | 9.2 | 0.008 | 4.8 | 0.030 | 1.6 | 6.66 |
| 12g | 3-pyridyl | −NHC(O)−(3-F-phenyl) | 9.4 | 0.0052 | 5.4 | 0.027 | 1.5 | 0.40, |

TABLE 8

In Vivo Pharmacokinetic and Pharmacodynamic Results For 12e and 12j[a]

| compd | po dose (mg/kg) | time (h) | % inhibition p-Akt (S473) | p-Akt (T308) | p-p7056 (T389) | plasma concn (µM) | tumor concn (µM) |
|---|---|---|---|---|---|---|---|
| 12e | 100 | 2 | 82 | 25 | 76 | 14.1 | 8.4 |
| 12j | 250 | 2 | 62 | 57 | 90 | 62.0 | 1.2 |
|  |  | 4 | 51 | 67 | 86 | 1.2 | 0.6 |

In an example embodiment, the kinase inhibitor is borussertib with the formula:

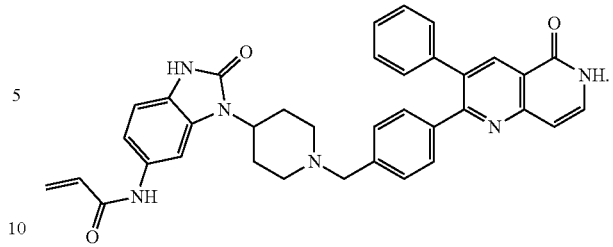

Borussertib is a covalent-allosteric inhibitor of AKT, with an $IC_{50}$ of 0.8 m< and a $K_i$ of 2.2 nM for $AKT^{wt}$. The $EC_{50}$ values for Borussertib are 191±90 nM, 48±15 nM, 5±nM, 277±90 nM, 373±54 nM, 7770±641 nM in AN3CA (endometrium), T47D (breast), ZR-75-1 (breast), MCF-7 (breast), BT-474 (breast), and KU-19-19 (bladder) cell lines, respectively. In an aspect, the allosteric inhibitor can be according to Table reproduced below:

TABLE 1

Biochemical evaluation of covalent-allosteric Akt inhibitors

| Cpd | R | X | $IC_{50}$ [nM] | $K_i$ [nM] | $k_{inact}$[min$^{-1}$] | $k_{inact}/K_i$ [µM$^{-1}$ s$^{-1}$] |
|---|---|---|---|---|---|---|
| 1 | (structure) | C | 0.8 ± 0.3 | 2.2 ± 0.3 | 0.111 ± 0.020 | 0.853 ± 0.038 |
| 24a | (structure) | C | 1.2 ± 0.3 | 4.1 ± 0.7 | 0.110 ± 0.023 | 0.447 ± 0.074 |
| 24b | (structure) | C | 3.0 ± 0.3 | 10.7 ± 0.5 | 0.121 ± 0.016 | 0.190 ± 0.025 |

TABLE 1-continued

Biochemical evaluation of covalent-allosteric Akt inhibitors

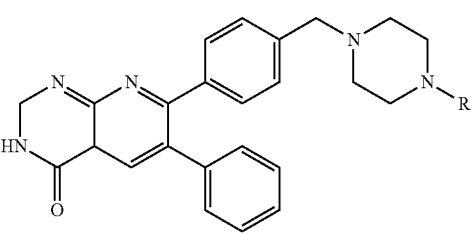

| Cpd | R | X | IC$_{50}$ [nM] | K$_i$ [nM] | k$_{inact}$[min$^{-1}$] | k$_{inact}$/K$_i$ [µM$^{-1}$ s$^{-1}$] |
|---|---|---|---|---|---|---|
| 24c | 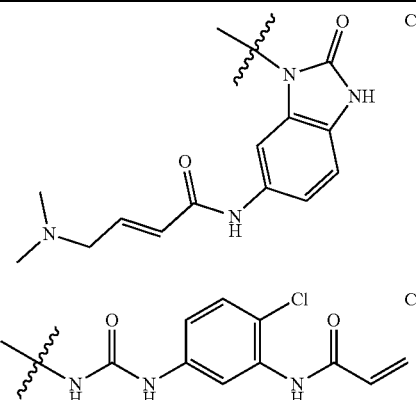 | C | 18.1 ± 4.9 | 33.0 ± 2.4 | 0.050 ± 0.009 | 0.025 ± 0.005 |
| 27 | 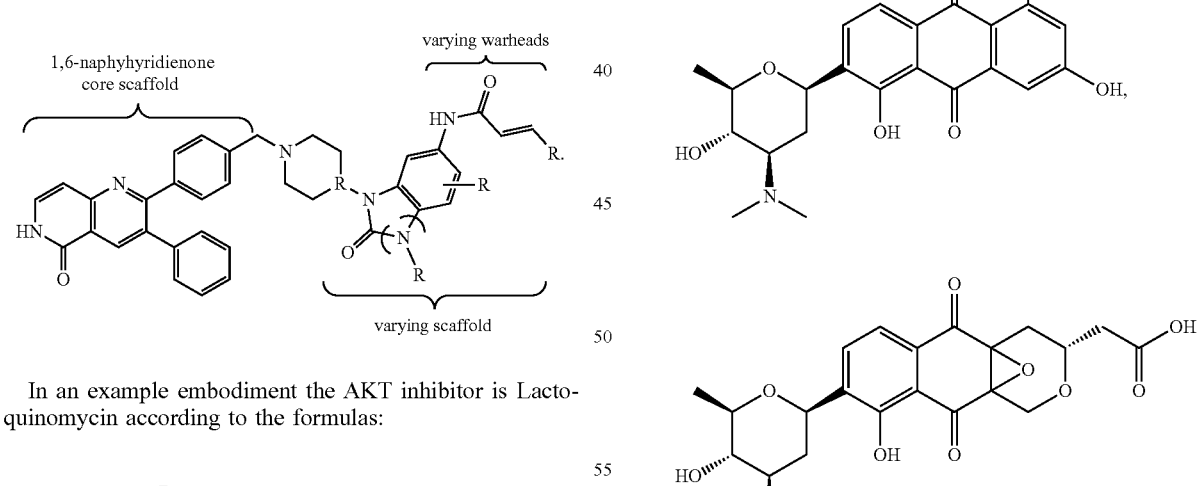 | C | 9.1 ± 1.5 | 17.5 ± 3.6 | 0.081 ± 0.019 | 0.080 ± 0.008. |

Varying of the scaffold can be according to the following scheme:

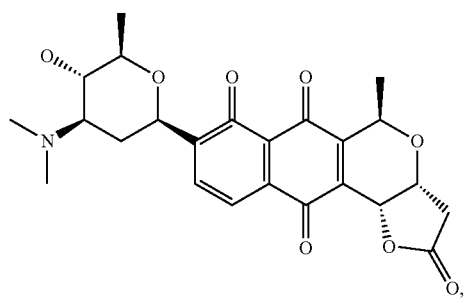

In an example embodiment the AKT inhibitor is Lactoquinomycin according to the formulas:

or any derivative thereof, see e.g. "Lactoquinomycin C and D, Two New Medermycin Derivatives from the Marine-Derived *Streptomyces* Sp. SS17A." *Natural Product Research* 2019, 34 (9), 1213-1218. In an example embodiment, the Lactoquinomycin is Medermycin.

In an example embodiment, the AKT inhibitor is BIND-2206, also known as MK-2206 or NSC-749607, according to the formula:

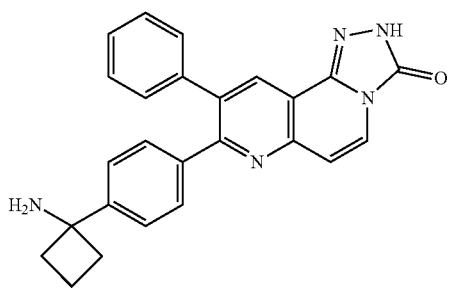 [SMILES: NC1(c2ccc(-c3nc4ccn5c(=O)[nH]nc5c4cc3-c3ccccc3)cc2)CCC1]

with the following properties

| | |
|---|---|
| Hydrogen bond acceptors | 4 |
| Hydrogen bond donors | 2 |
| Rotatable bonds | 3 |
| Topological polar surface area | 89.07 |
| Molecular weight | 407.17 |
| XLogP | 5.13 |
| No. Lipinski's rules broken | 1. |

AKT moieties can be synthesized according to the guidance and design provided herein in view of AKT binding moieties as disclosed, for example, in Panicker et al. Adv Exp Med Biol 1163:253-278 (2019); Botello-Smith et al. PLoS Comp Biol 13(8):e1005711 (2017); Mou et al. Chem Biol Drug Des 89(5):723-731 (2017); Ruiz-Carillo et al. Sci Rep 8:7365 (2018), and Budas et al. Biochem Soc Trans 35:1021-1026 (2007). Further information on AKT allosteric inhibitors may be found in Wu, W.-I., et al. "Crystal Structure of Human AKT1 with an Allosteric Inhibitor Reveals a New Mode of Kinase Inhibition." PLoS ONE 2010, 5 (9), e12913.

ALK Binding Moiety

In one example embodiment, the protein binding moiety is an ALK kinase binding moiety. In one example embodiment, the ALK binding moiety is an inhibitor or activator. Anaplastic Lymphoma Kinase also known as ALK tyrosine kinase receptor or CD246. ALK participates in cellular communication and the development and function of the nervous system. Upon binding of a ligand, a full-length receptor ALK dimerizes, changes conformation, and auto-activates its own kinase domain. An autoactivated ALK dimer will phosphorylate other ALK receptors on specific tyrosine amino acid residues. ALK phosphorylated residues are binding sites for the recruitment of several adaptor. In one example embodiment, the ALK inhibitor comprises Crizotinib, Ceritinib, Alectinib, Brigatinib, or Lorlatinib.

In an embodiment, the ALK inhibitor is CH5424802, according to the formula:

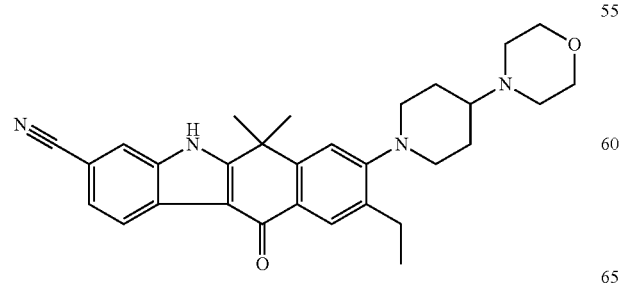

or a derivative thereof.

BTK Binding Moiety

In one example embodiment, the protein binding moiety is an BTK kinase binding moiety. In one example embodiment, the BTK binding moiety is an inhibitor or activator. Bruton's tyrosine kinase (Btk) is involved in multiple signaling cascades, and plays a role in B-cell development and oncogenic signaling. See, e.g. Singh et al., 2018; Pal et al., 2018. In an example embodiment, the BTK inhibitor is ibrutinib, acalabrutinib or a derivative thereof.

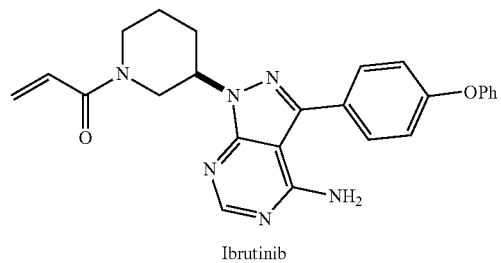

Ibrutinib

Exemplary derivatives include

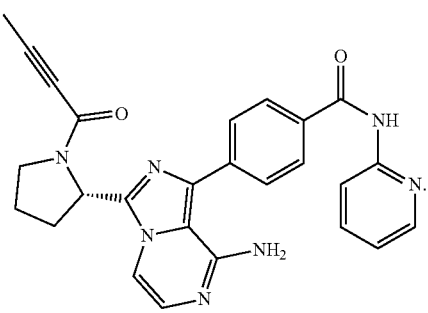

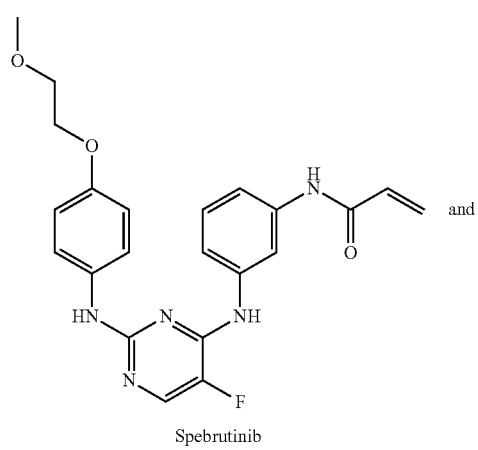

Spebrutinib

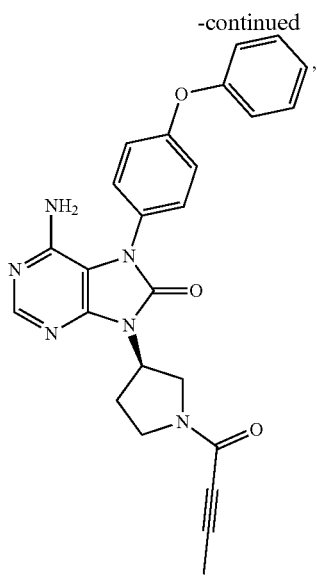

Tirabrutinib as detailed in Liclican et al, Biochimica et Biophysica Acta (BBA) 1864(4): 129531, DOI:10.1016/j.bbagen.2020.129531.

In one example embodiment, the BTK activator is selected from

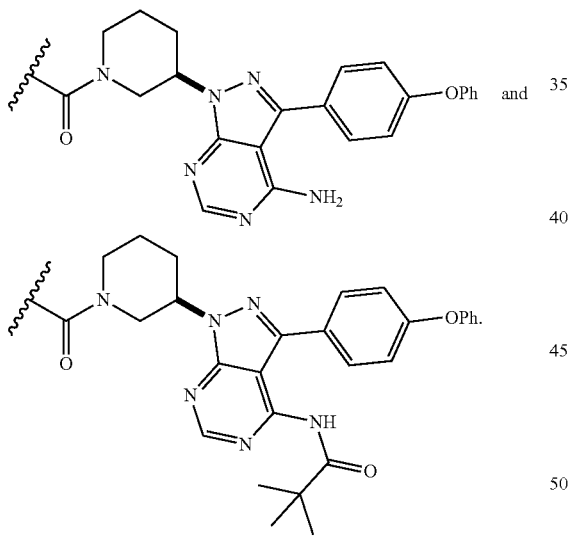

In one example embodiment, the BTK activator moiety is provided with a targeting moiety of

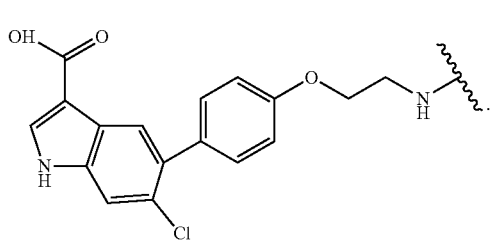 [SMILES: *NCCOc1ccc(-c2cc3c(C(=O)O)c[nH]c3cc2Cl)cc1]

FLT3 Binding Moiety

In one example embodiment, the protein binding moiety is an FLT3 kinase binding moiety. In one example embodiment, the FLT3 binding moiety is an inhibitor or activator. FMS-like tyrosine kinase 3 (FLT3) is a receptor tyrosine kinase that belongs to the subclass III family. FLT3 contain five immunoglobulin-like domains in the extracellular region and an intracellular tyrosine kinase domain split in two by a specific hydrophilic insertion. In one example embodiment, the FLT3 inhibitor comprises Midostaurin.

JAK2 Binding Moiety

In one example embodiment, the protein binding moiety is an JAK2 kinase binding moiety. In one example embodiment, the JAK2 binding moiety is an inhibitor or activator. Janus kinase 2 (JAK2) is a non-receptor tyrosine kinase and belongs to the Janus kinase family. JAK2 lacks the Src homology binding domains, SH2 and SH3, but includes seven JAK homology domains, JH1-JH7. In one example embodiment, the JAK2 Inhibitor comprises Ruxolitinib, also known as INCB018424, according to the formula:

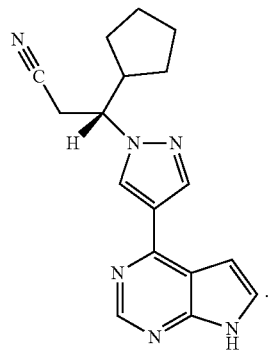 [SMILES: N#CC[C@H](C1CCCC1)n1cc(-c2ncnc3[nH]ccc23)cn1]

In another example embodiment, the JAK2 inhibitor is Tasocitinib, also known as CP690550, according to the formula:

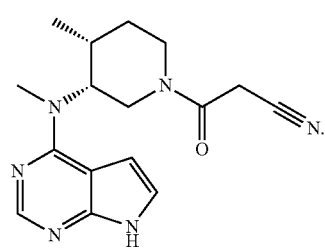 [SMILES: C[C@@H]1CCN(C(=O)CC#N)C[C@@H]1N(C)c1ncnc2[nH]ccc12]

AURKA Binding Moiety

In one example embodiment, the protein binding moiety is an AURKA kinase binding moiety. In one example embodiment, the AURKA binding moiety is an inhibitor or activator. Aurora A kinase (AURKA) is a member of Setr/Thr kinases whose orthologous control progression through miotic cell division. The other members of the Aurora family are Aurora B and C and they all share a relatively conserved kinase catalytic domain at the carboxy-(C) terminus. In an example embodiment, the Aurora A inhibitor is AurkinA with the formula:

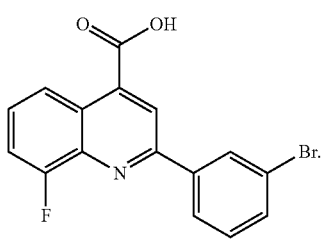

AurkinA has an $IC_{50}$, in μM, of 12.7 and $K_i$, in μM, of 2.7.

In an example embodiment, the Aurora A inhibitor is AA29 with the formula:

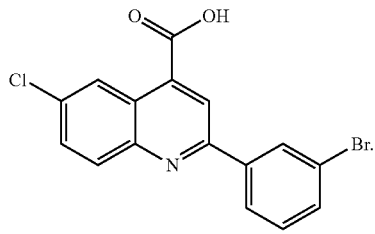 [SMILES: O=C(O)c1cc(-c2cccc(Br)c2)nc2ccc(Cl)cc12]

AA29 has an $IC_{50}$, in μM, of 34.4 and $K_i$, in μM, of 7.4.

In an example embodiment, the Aurora A inhibitor is AA30 with the formula:

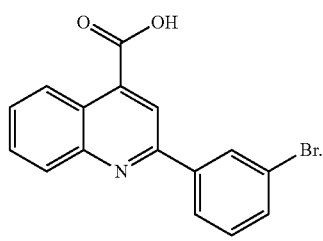 [SMILES: O=C(O)c1cc(-c2cccc(Br)c2)nc2ccccc12]

AA30 has an $IC_{50}$, in μM, of 25.6 and $K_i$, in μM, of 5.5. In an aspect, the compound can be according to

| Compound | (iso)quinoline core | Aromatic group | Average $IC_{50}$/μM | Calculated $K_i$/μM |
|---|---|---|---|---|
| 3 | quinoline-CO₂H with 2-aryl | phenyl | 289 | 62.5 |
| 24 | | 4-CN-phenyl | >500 | >100 |
| 26 | | 3-F-phenyl | 75.9 | 16.5 |
| AA30 | | 3-Br-phenyl | 25.6 | 5.5 |
| 33 | | 3-Cl-5-F-phenyl | 20.5 | 4.4 |

-continued

| Compound | (iso)quinoline core | Aromatic group | Average IC$_{50}$/μM | Calculated K$_i$/μM |
|---|---|---|---|---|
| 32 | | 3,5-difluorophenyl | 36.0 | 7.8 |
| 34 | | 3-CF$_2$-phenyl | 26.5 | 5.7 |
| 31 | 6-Cl-quinoline-4-CO$_2$H, 2-linked | pyridin-3-yl | 163 | 35.5 |
| 25 | | phenyl | 205 | 44.7 |
| 27 | | 3-fluorophenyl | 107 | 23.3 |
| AA29 | | 3-bromophenyl | 34.4 | 7.4 |
| 28 | 6-Br-quinoline-4-CO$_2$H, 2-linked | 3-fluorophenyl | >500 | >100 |
| AurkinA | 8-F-quinoline-4-CO$_2$H, 2-linked | 3-bromophenyl | 12.7 | 2.7 |
| 50 | isoquinoline-1-CO$_2$H, 3-linked | phenyl | 213 | 46.3 |

| Compound | (iso)quinoline core | Aromatic group | Average IC$_{50}$/μM | Calculated K$_i$/μM |
|---|---|---|---|---|
| 51 | | 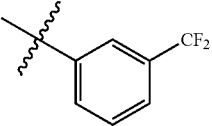 | 106 | 22.8, | see, Janeček, M., Rossmann, M., Sharma, P. et al. Allosteric modulation of AURKA kinase activity by a small-molecule inhibitor of its protein-protein interaction with TPX2. Sci Rep 6, 28528 (2016). Doi:rep28528, incorporated herein by reference. In one example embodiment, the kinase binding moiety is a monobody that targets Aurora A as described by Zorba A., et al. "Allosteric Modulation of a Human Protein Kinase with Monobodies." Proc Natl Acad Sci USA 2019, 116 (28), 13937-13942, herein incorporated by reference.

In one example embodiment, the Aurora inhibitor is an Aurora inhibitor or any derivative thereof identified in the US Patent Applicant US20080051327, herein incorporated by reference.

c-MET Binding Moiety

In one example embodiment, the protein binding moiety is an c-MET kinase binding moiety. In one example embodiment, the c-MET binding moiety is an inhibitor or activator. c-MET is a receptor tyrosine kinase involved in cellular signaling pathways. After binding with a hepatocyte growth factor, it activates signaling pathways such as proliferation, motility, migration and invasion among others, see e.g. Organ, S. L., et al. "An Overview of the C-MET Signaling Pathway." Ther Adv Med Oncol 2011, 3, S7-S19. In one example embodiment, the c-MET inhibitor is tivantinib, also referred to as ARQ-197, according to the formula

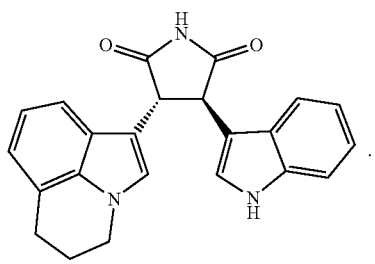 [SMILES: O=C1NC(=O)[C@@H](c2cn3c4c(cccc24)CCC3)[C@@H]1c1c[nH]c2ccccc12]

In an embodiment, the tivantinib binder, or derivative thereof, targets the MET proto-oncogene, receptor tyrosine kinase, is an allosteric inhibitor, and has one or more of the following properties: the tivantinib or derivative thereof, is a non-ATP competitive, MET-specific inhibitor that is 10-100 time more selective for c-Met that other kinases tested (See, Munshi et al., Moll. Can. Ther. doi:10.1158/1535-7163.MCT-09-1173), with an Enzyme IC$_{50}$ of 50 nM, phosphor-MET IC$_{50}$ of 100 nM, viability IC$_{50}$ of 100 nM, and Invasion IC$_{50}$ of 80 nM, each in NCI-H441 cells. Tivantinib has shown inhibition of growth in breast carcinoma, prostate carcinoma, colon carcinoma and pancreatic carcinoma xenografts as well as inhibit metastasis formation in experimental metastatic models of orthotopic colon cancer xenografts. Additionally, the tivantinib inhibitor has a pKi value of 6.4. These features allow for appropriate selection and modification for design of chimeric small molecules, as detailed elsewhere herein.

DDR Binding Moiety

In one example embodiment, the protein binding moiety is an DDR kinase binding moiety. In one example embodiment, the DDR binding moiety is an inhibitor or activator. Discoidin domain receptor (DDR) belongs to the receptor tyrosine kinase family and are distinguished by the ligand that actives it, fibrillar collagen. Furthermore, their activation and inactivation kinetics are slow and exist as dimers on the cell surface absent their ligand. See e.g. Grither, W. R., et al. "Inhibition of Tumor-Microenvironment Interaction and Tumor Invasion by Small-Molecule Allosteric Inhibitor of DDR2 Extracellular Domain." Proc Natl Acad Sci USA 2018, 115 (33), E7786-E7794.

In one example embodiment, the DDR inhibitor is selected from:

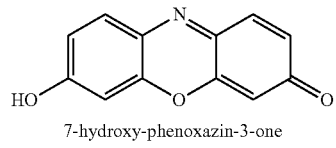

7-hydroxy-phenoxazin-3-one

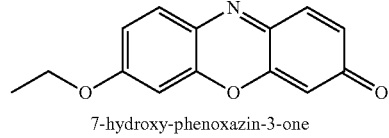

7-hydroxy-phenoxazin-3-one

WRG-1

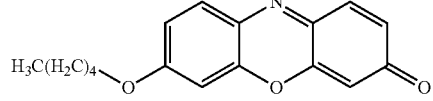

WRG-2

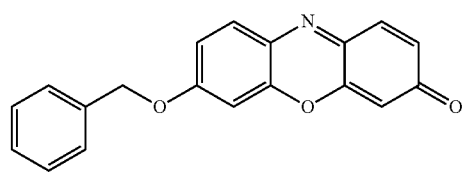

WRG-3

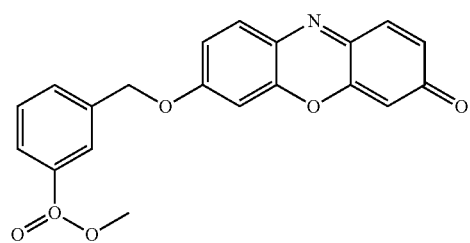

WRG-5
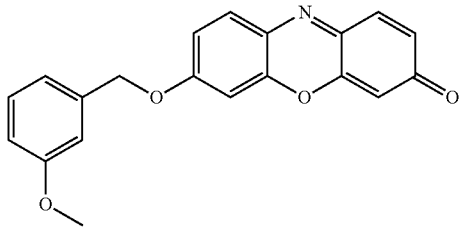

WRG-6
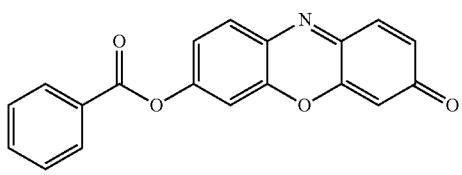

WRG-7
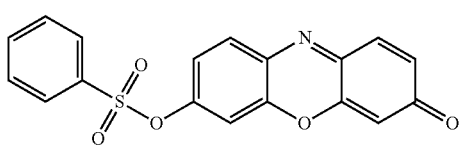

WRG-9
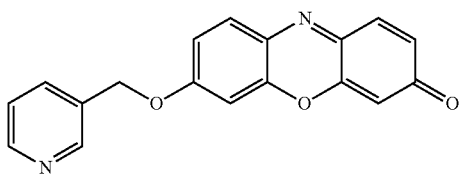

WRG-10
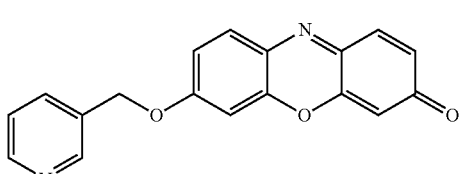

WRG-11
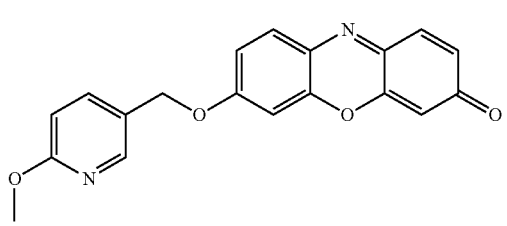

WRG-27
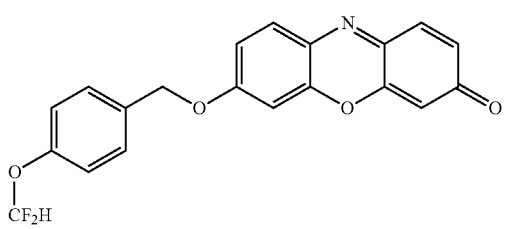

WRG-28
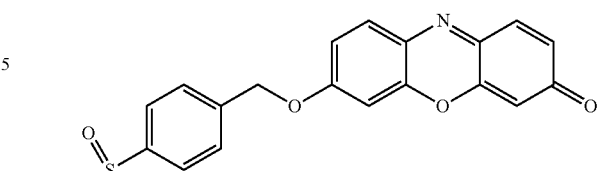

WRG-30

or a derivative thereof.

In one example embodiment, the DDR inhibitor is WRG-28, with an $IC_{50}$ of 230 nM according to the formula:

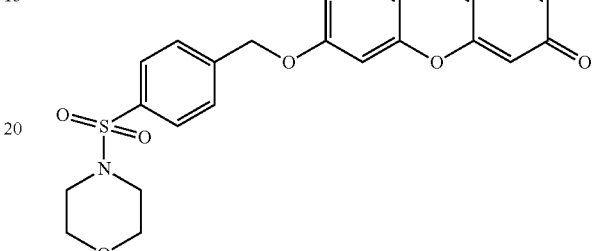

In one embodiment, the WRG-28 or derivative thereof, is an extracellularly acting allosteric inhibitor which inhibits receptor-ligand interactions via allosteric modulation of the receptor. WRG-28 has been shown to inhibit tumor invasion and migration as well as tumor-supporting roles of the stroma, and inhibits metastatic breast tumor cell colonization in the lungs by targeting DDR2.

INSR Binding Moiety

In one example embodiment, the protein binding moiety is an INSR kinase binding moiety. In one example embodiment, the INSR binding moiety is an inhibitor or activator. The insulin receptor (INSR) is located in a plasma membrane glycoprotein and member of the receptor tyrosine kinase (RTK) family that modulates insulin. The INSR family comprises of RTKs including the insulin like growth factor-1 receptor (IGF1R) and insulin receptor-related receptor. See e.g. Hubbard, S. R. "The Insulin Receptor: Both a Prototypical and Atypical Receptor Tyrosine Kinase." *Cold Spring Harbor Perspectives in Biology* 2013, 5 (3). In one example embodiment, the kinase binding moiety is an INSR inhibitor. In an example embodiment, the INSR inhibitor is XMetD, also known as RZ-358 or XOMA358, which is a human anti-INSR IgG2 monoclonal antibody. XMetD is a negative allosteric modulator of the INSR. See e.g. Patel P., et al. "A Unique Allosteric Insulin Receptor Monoclonal Antibody That Prevents Hypoglycemia in the SUR-1-/-Mouse Model of KATP Hyperinsulinism." *mAbs* 2018, 10 (5), 796-802.

In an embodiment, the protein is an insulin receptor and the binding moiety is RZ-358, also known as XOMA-358 that is fully human negative allosteric modulating insulin receptor antibody. RZ358 can be intravenously administered and binds to a site on the insulin receptor present in the liver, fat and muscle. The RZ358 molecule has high selectivity to the insulin receptor with no IGF-1 interaction and still allows insulin to bind and signal, dampening the insulin signal only when insulin is elevated. Clinical trials have been performed with dowsing ranging from 0.1 to 9 mg/kg and has been studied in congenital hyperinsulinism and. Post-gastric bypass hypoglycemia.

Additional selective allosteric antibodies to the Insulin receptor, including XMetD have been identified using a research platform and can be utilized in small molecules disclosed herein. See, J Journal of Diabetes Science and Technology 2014, 8, 865-873, doi:10.4161/mabs.26871. In an embodiment, the binding moiety is an allosteric insulin receptor antibody, for example XOMA358. Phase 2 clinical trials show ZOMA358 exhibits an inhibition on insulin signaling in patients with improper insulin signaling, including congenital hyperinsulinism. Treatment using the antibody in volunteers ranges from 01.mg/kg to 9 mg/kg. See, Johnson et al., Attenuation of Insulin Action by an Allosteric Insulin Receptor Antibody in Healthy Volunteers. J Clin Endocrinol Metab. 2017 Aug. 1; 102(8):3021-3028. doi: 10.1210/jc.2017-00822.

IKK Binding Moiety

In one example embodiment, the kinase binding moiety is an IKK kinase binding moiety. In one example embodiment, the IKK binding moiety is an inhibitor or activator. The IκB kinase (IKK) complex comprises of three subunits: IKKα, IKKβ, and IKKγ/NEMO. The subunits IKKα and IKKβ are catalytic and IKKγ/NEMO is regulatory. See e.g. Karin, M. "The IκB Kinase—a Bridge between Inflammation and Cancer." *Cell Res* 2008, 18 (3), 334-342. In an example embodiment, the IKK inhibitor is BMS-345541 according to the formula:

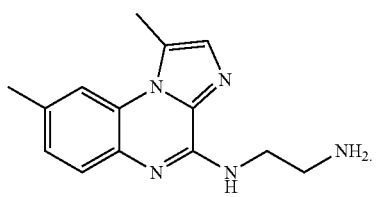 [SMILES: Cc1ccc2nc(NCCN)c3ncc(C)n3c2c1]

mTOR Binding Moiety

In one example embodiment, the protein binding moiety is an mTOR kinase binding moiety. In one example embodiment, the mTOR binding moiety is an inhibitor or activator. Mammalian target of rapamycin (mTOR) is a serine/threonine protein kinase of the PI3K-related protein kinase family. mTOR is large, approximately 300-500 kDa, and contains a conserved kinase catalytic domain. mTOR also includes HEAT repeats, FAT domains, FATC domains, and a FRB (FKBP12/rapamycin-binding) domain that binds the drug rapamycin in complex with its intracellular receptor protein FKBP12. See e.g. Ballou L. M., et. al. "Rapamycin and MTOR Kinase Inhibitors." *J Chem Biol* 2008, 1 (1-4), 27-36.

In an example embodiment, the mTOR inhibitor is Sirolimus, also known as Rapamycin, according to the formula:

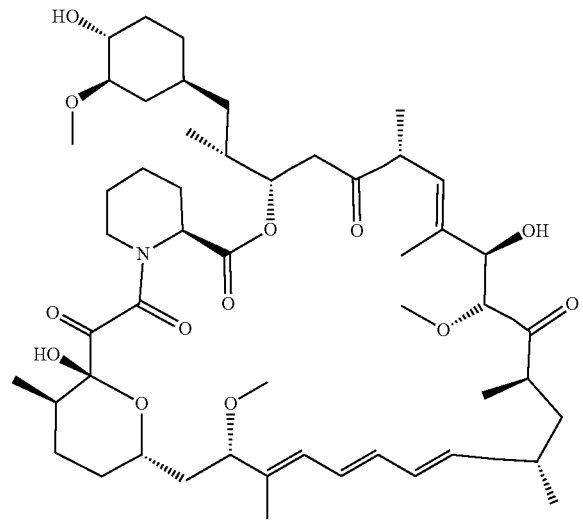

and has the following properties

| | |
|---|---|
| Hydrogen bond acceptors | 14 |
| Hydrogen bond donors | 3 |
| Rotatable bonds | 6 |
| Topological polar surface area | 195.43 |
| Molecular weight | 913.56 |
| XLogP | 4.32 |
| No. Lipinski's rules broken | 1. |

Sirolimus is a macrolide produced by the bacteria *Streptomyces hygroscopicus*. It has potent immunosuppressive and antiproliferative properties. Sirolimus binds to the FK506 binding protein 12 (FKBP12), creating a complex which inhibits mammalian target of rapamycin (mTOR). Sirolimus inhibition of FKBP prolyl isomerase 1A has a p$K_i$ of 9.7.

The FKBP12-sirolimus complex is reported to bind to a site distinct from the kinase domain of mTOR and acts as a negative allosteric modulator of mTOR activity. This action reduces mTOR-induced proliferation of activated T-cells, the cells which would normally be involved in the immunological attack on transplanted tissue. See, *Am. J. Health-Syst. Pharm.* 2000, 57, 437-448. In vitro studies have been performed and these show that sirolimus inhibits MERS-CoV infection of Huh7 cells. This mechanism could also be applied to SAR-CoV-2 infection. Sirolimus has been used in renal transplantation.

In an example embodiment the mTOR inhibitor is any inhibitor or derivative thereof encompassed in the International Patent Application WO2014177123, herein incorporated by reference.

PAK Binding Moiety

In one example embodiment, the protein binding moiety is an p21 kinase binding moiety. In one example embodiment, the PAK binding moiety is an inhibitor or activator. p21-activated kinases (PAKs) are serine/threonine protein kinases. PAKs can be divided into two groups: group I comprising of PAK1-3 and group II comprising of PAK4-6. They are effectors of Rac/Cdc42 GTPases and play an important role in cell proliferation, survival, motility, and angiogenesis. See e.g. Karpov A. S., et al. "Optimization of a Dibenzodiazepine Hit to a Potent and Selective Allosteric PAK1 Inhibitor." *ACS Med. Chem. Lett.* 2015, 6 (7), 776-781. In an example embodiment, the PAK inhibitor is compound 3, PMID 26191365, according to the formula:

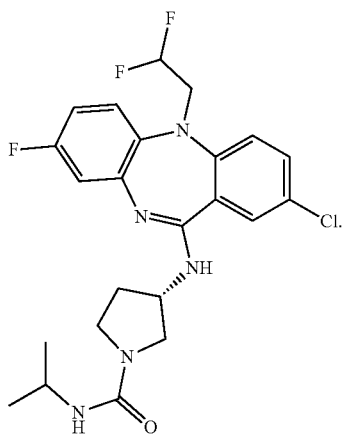 [SMILES: CC(C)NC(=O)N1CC[C@H](NC2=Nc3cc(F)ccc3N(CC(F)F)c3ccc(Cl)cc32)C1]

Compound 3 is a highly selective, negative allosteric regulator of the protein kinase, p21 protein (Cdc42/Rac)-activated kinase 1 with favorable physicochemical properties. Compound 3 binds to a site adjacent to the kinase's ATP binding site. Compound 3 has $pK_d$ values of 8.1 and 6.4 for PAK1(RAC1) and PAK2(RAC1) respectively. See e.g. Karpov, A. S. et al. "Optimization of a Dibenzodiazepine Hit to a Potent and Selective Allosteric PAK1 Inhibitor." *ACS Med. Chem. Lett.* 2015, 6 (7), 776-781, herein incorporated by reference in its entirety. In one example embodiment, the PAK inhibitor is a PAK inhibitor from Karpov *ACS Med. Chem. Lett.* 2015.

SAR of PAK1 Inhibitors, Selectivity versus other PAK inhibitors is detailed in Table 3 of ACS Med. Chem. Lett, 2015, 6, 776-781 and reproduced below:

TABLE 2

SAR of PAK1 Inhibitor; Selectivity vs. Other PAK Isoforms[a]

| Compound | X | R₁ | PAK1 dephos IC₅₀ (μM) | PAK1 Kd (nM) | PAK2 Kd (nM) | PAK3 Kd (nM) | PAK4 Kd (nM) | PAK6 Kd (nM) |
|---|---|---|---|---|---|---|---|---|
| 1 | H, F | *piperazine* | 12000 | 340 | >40000 | >40000 | >40000 | >40000 |
| 5 | CH₃,Cl | | 900 | | | | | |
| 11 | CH₃CH₂, Cl | | 323 | | | | | |
| 13 | CH₃CH₂, Cl | *Boc-aminopyrrolidine* | 190 | 130 | >40000 | >40000 | >40000 | >40000 |

TABLE 2-continued

SAR of PAK1 Inhibitor; Selectivity vs. Other PAK Isoforms[a]

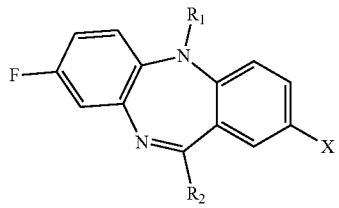

| Compound | $R_1$, X | $R_1$ | PAK1 dephos $IC_{50}$ (μM) | PAK1 Kd (nM) | PAK2 Kd (nM) | PAK3 Kd (nM) | PAK4 Kd (nM) | PAK6 Kd (nM) |
|---|---|---|---|---|---|---|---|---|
| 2 | $CH_3CH_2$, Cl | | 18 | 9.9 | 1100 | | >40000 | >40000 |
| 3 | $CHF_2CH_2$, Cl | | 5.2 | 7 | 400. | | | |

In an example embodiment, the PAK inhibitor is IPA-3 according to the formula:

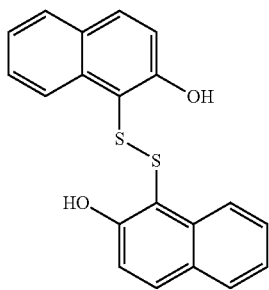 [SMILES: Oc1ccc2ccccc2c1SSc1c(O)ccc2ccccc12]

and has the following properties:

| | |
|---|---|
| Hydrogen bond acceptors | 0 |
| Hydrogen bond donors | 2 |
| Rotatable bonds | 3 |
| Topological polar surface area | 91.06 |
| Molecular weight | 350.04 |
| XLogP | 6.19 |
| No. Lipinski's rules broken | 1. |

LPA-3 is a cell-permeable, non-ATP-competitive, allosteric, and selective inhibitor of p21 protein (Cdc42/Rac)-activated kinase 1 (PAK1). IPA-3 binds covalently to the autoregulatory domain of PAK1, preventing its activation by Cdc42. IPA-3 has a $pIC_{50}$ of 5.6 for PAK1(RAC1). See e.g. Viaud, J.; Peterson, J. R. "An Allosteric Kinase Inhibitor Binds the P21-Activated Kinase Autoregulatory Domain Covalently." *Mol Cancer Ther* 2009, 8 (9), 2559-2565 and Deacon, S. W., et al. "An Isoform-Selective, Small-Molecule Inhibitor Targets the Autoregulatory Mechanism of P21-Activated Kinase. Chemistry & Biology 2008, 15 (4), 322-331, both herein incorporated by reference in their entirety.

In an example embodiment, the PAK inhibitor is KPT-9274 according to the formula:

KPT-9274 is a small molecule that inhibits PAK4 and NAMPT. KPT-9274 acts as an allosteric modulator of PAK4 that does not interfere with the enzyme's kinase activity, in contrast to the PAK kinase inhibitor PF-3758309. KPT-9274 has begun Phase 1 clinical evaluation for non-Hodgkin lymphoma and for solid tumors. KPT-9274 inhibits recombinant human NAMPT with an $IC_{50}$ of 120 nM in a cell-free assay. KPT-9274 inhibits proliferation of MS751 cervical carcinoma and Z138 B cell acute lymphoblastic leukemia cell lines with $IC_{50}$ values <100 nM in vitro, and induces shrinkage of Molt-4 (T cell acute lymphoblastic leukemia) xenografts in SCID mice. In addition, KPT-9274 inhibits B-ALL cell lines: KOPN-8; RS4; REH; 697 cells; OP-1;

Nalm6; SupB15; SEM with IC$_{50}$ values, in nM, of 2.4; 5.6; 14.3; 16.7; 18.0; 19.0; 22.6; and >10,000 respectively. KPT-9274 also inhibits PDX B-ALL: LAX2; LAX7R; and ICN13 with IC$_{50}$ values, in nM, of 19.4; 32.7; and 25.9.

PDK1 Binding Moiety

In one example embodiment, the protein binding moiety is an PDK1 kinase binding moiety. In one example embodiment, the PDK1 binding moiety is an inhibitor or activator. Phosphoinositide-dependent protein kinase-1 (PDK1) regulates the AGC family of kinases. PDK1 comprises three ligand binding sites: the substrate binding site, the catalytic ATP binding site, and the PDK1 Interacting Fragment (PIF) binding site. The PIF binding site, which is hydrophobic, has two functions: the recruitment of the downstream substrate kinases harboring the hydrophobic motif (HM) and the stimulation of the intrinsic activity of PDK1. See e.g. "The Chemical Diversity and Structure-Based Discovery of Allosteric Modulators for the PIF-Pocket of Protein Kinase PDK1." *Journal of Enzyme Inhibition and Medicinal Chemistry* 2019, 34 (1), 361-374. In one example embodiment, the kinase binding moiety is a PDK1 inhibitor. In one example embodiment, the kinase binding moiety is a PDK1 inhibitor. In an example embodiment, the PDK1 inhibitor is PS48 according to the formula:

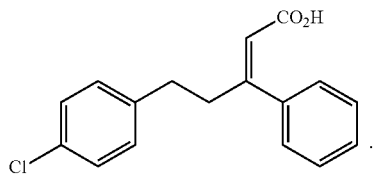 [SMILES: O=C(O)/C=C(/CCc1ccc(Cl)cc1)c1ccccc1]

Figure 3:
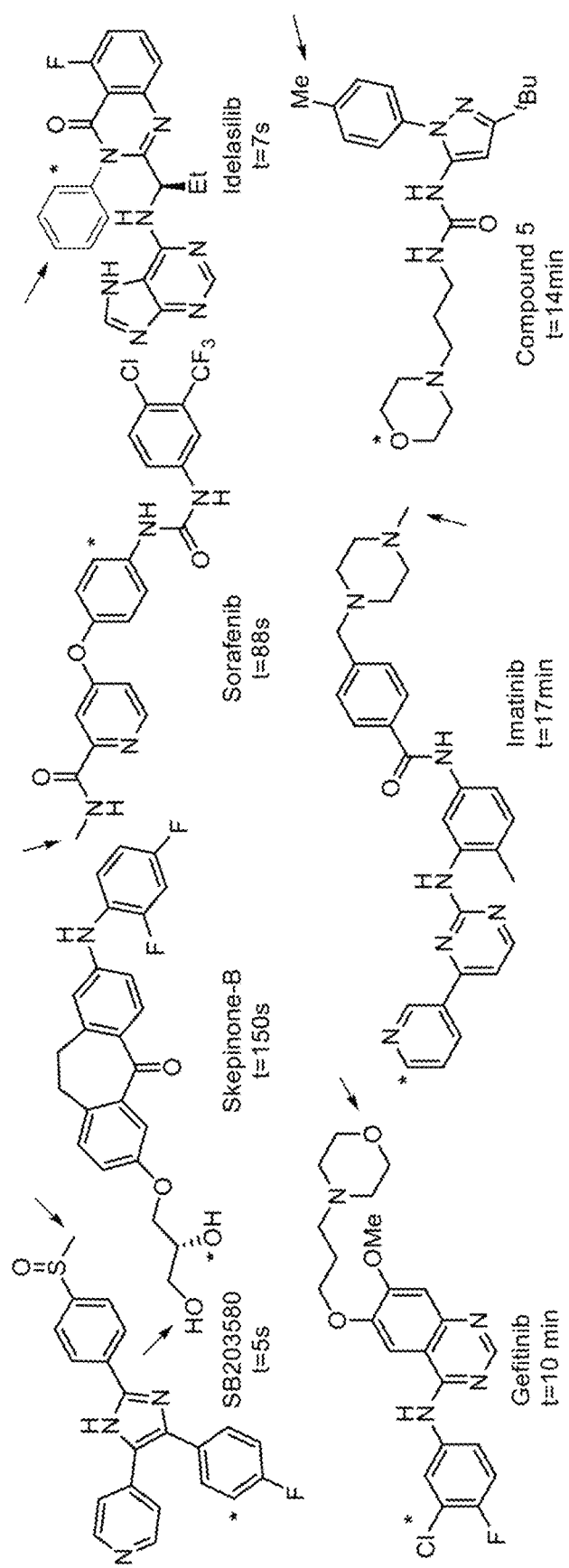
FIG. 3—Selected inhibitors for covalent labeling of kinases with their residence times. Sites of the linker and bio-orthogonal group attachments are shown by arrow and star (*), respectively.
Figure 4:
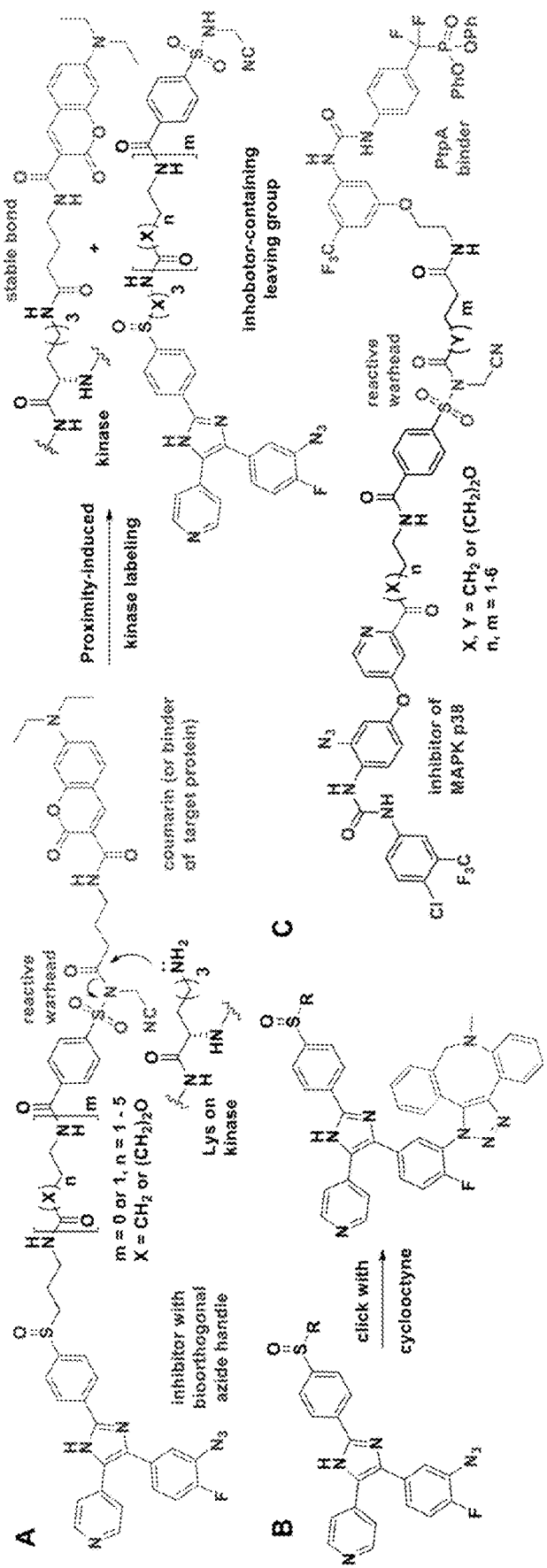
FIG. 4A-4C—(A) Representative example of chimeric small molecule designed for proximity-induced labeling of MAPK p38α based on its inhibitor SB203580 and mechanism of covalent modification. (B) exemplary deactivation of inhibitor via click reaction with bulky cyclooctyne, bulky group makes inhibitor not bind to the kinase. C. Exemplary embodiment of Sorafenib-based chimeric small molecule designed for proximity-induced labeling of MAPK p38α with binder of PtpA.
Figure 5:
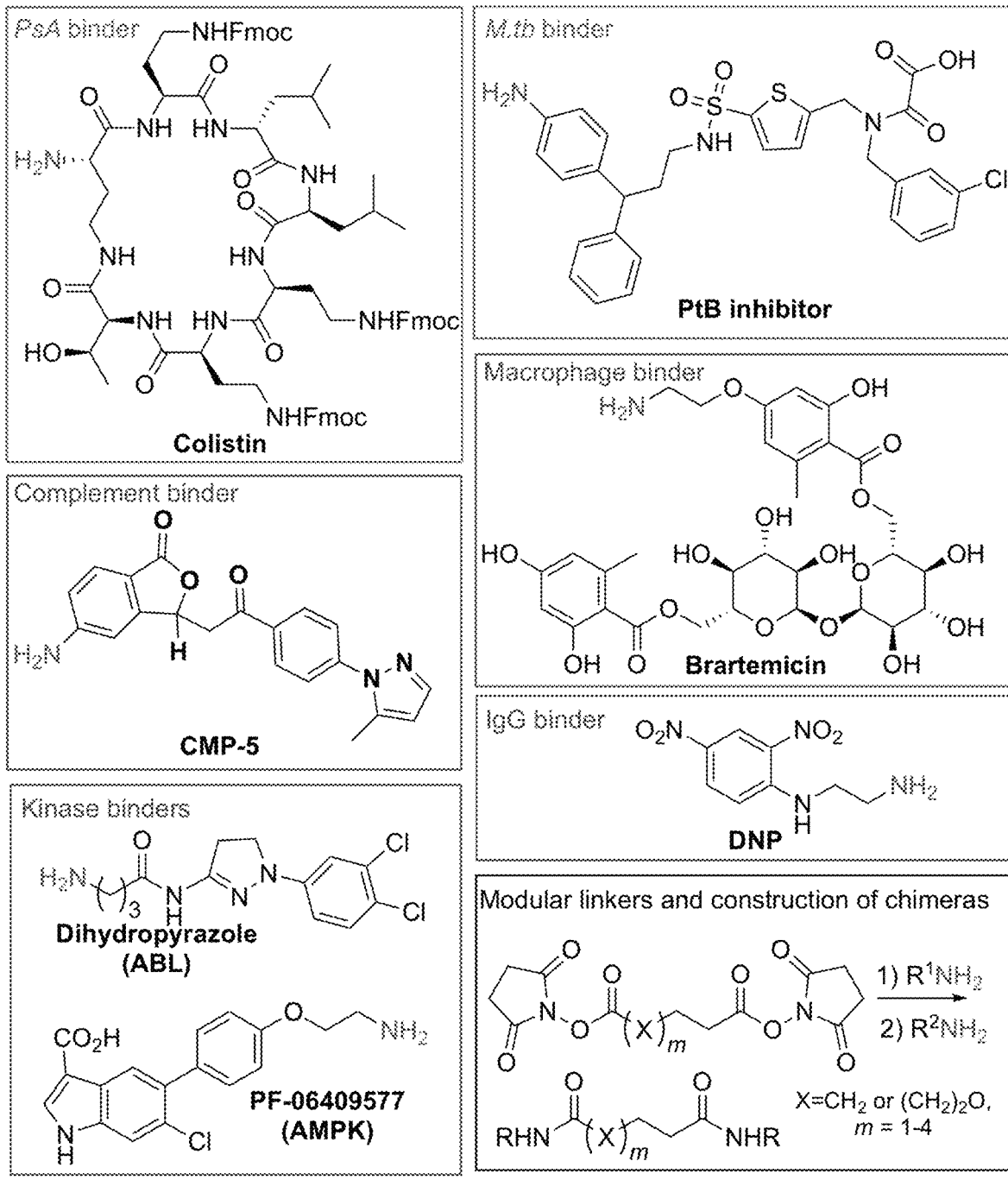
FIG. 5—Modular components for exemplary chimeras: known binders (blue) to microbial targets and known binders (green) to host targets. Applicants used these to optimize the assays. Applicants will also use these building blocks to create pseudo-chimeras, which consist of a known binder (shown here) and a binder identified from the screen.
Figure 6:
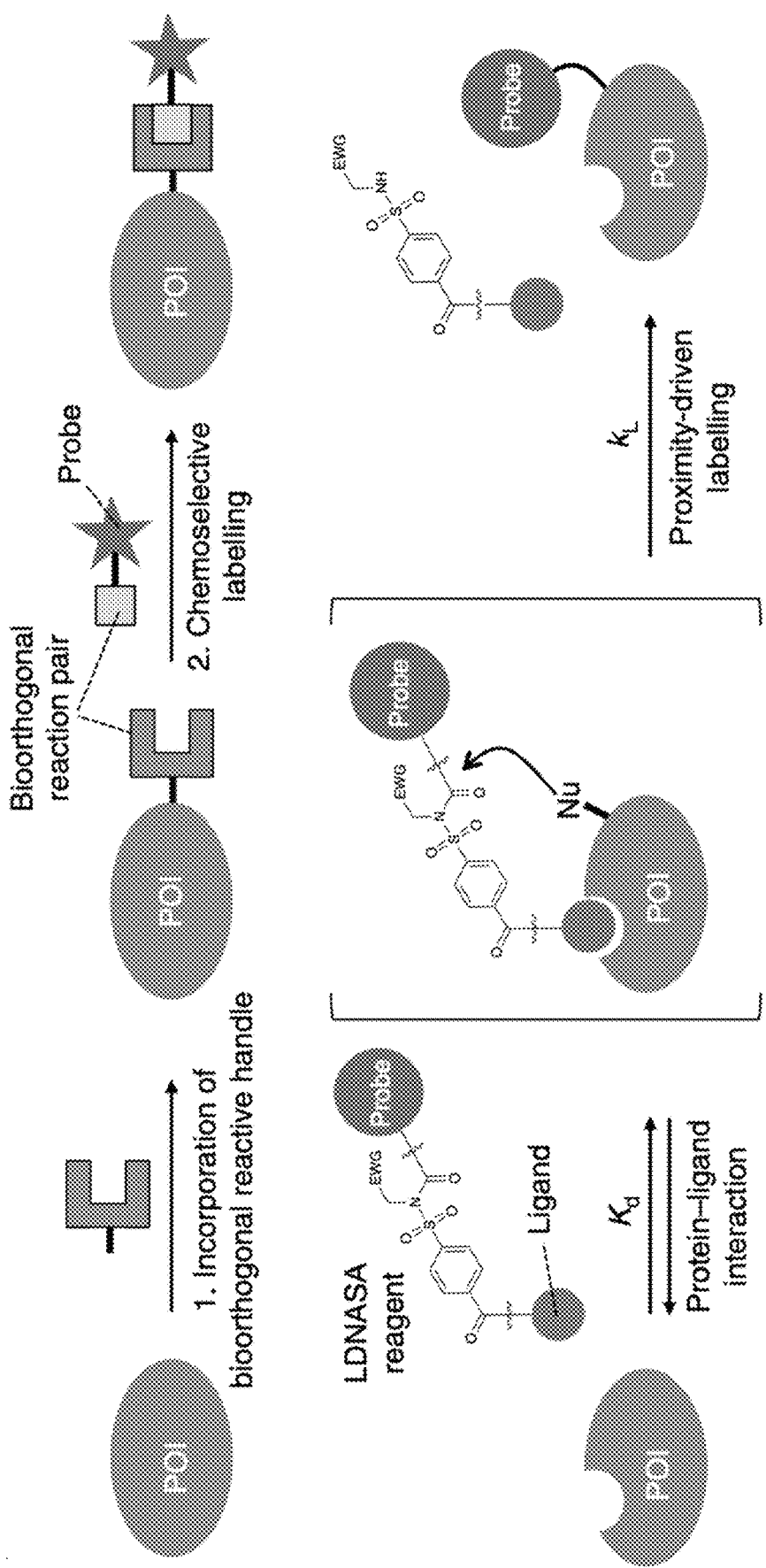
FIG. 6—Exemplary platform of target labeling chimeras.
Figure 7:
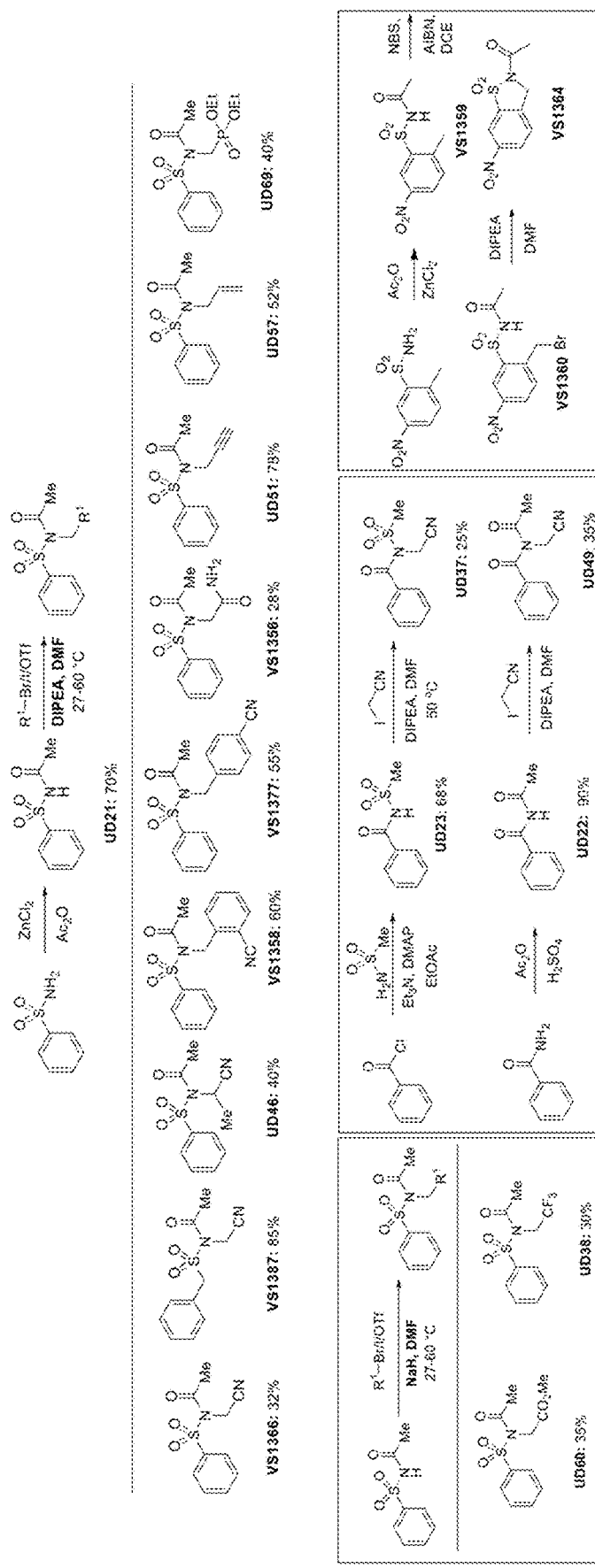
FIG. 7—General strategies for preparation of NASA and its analogs/alternatives.
Figure 8:
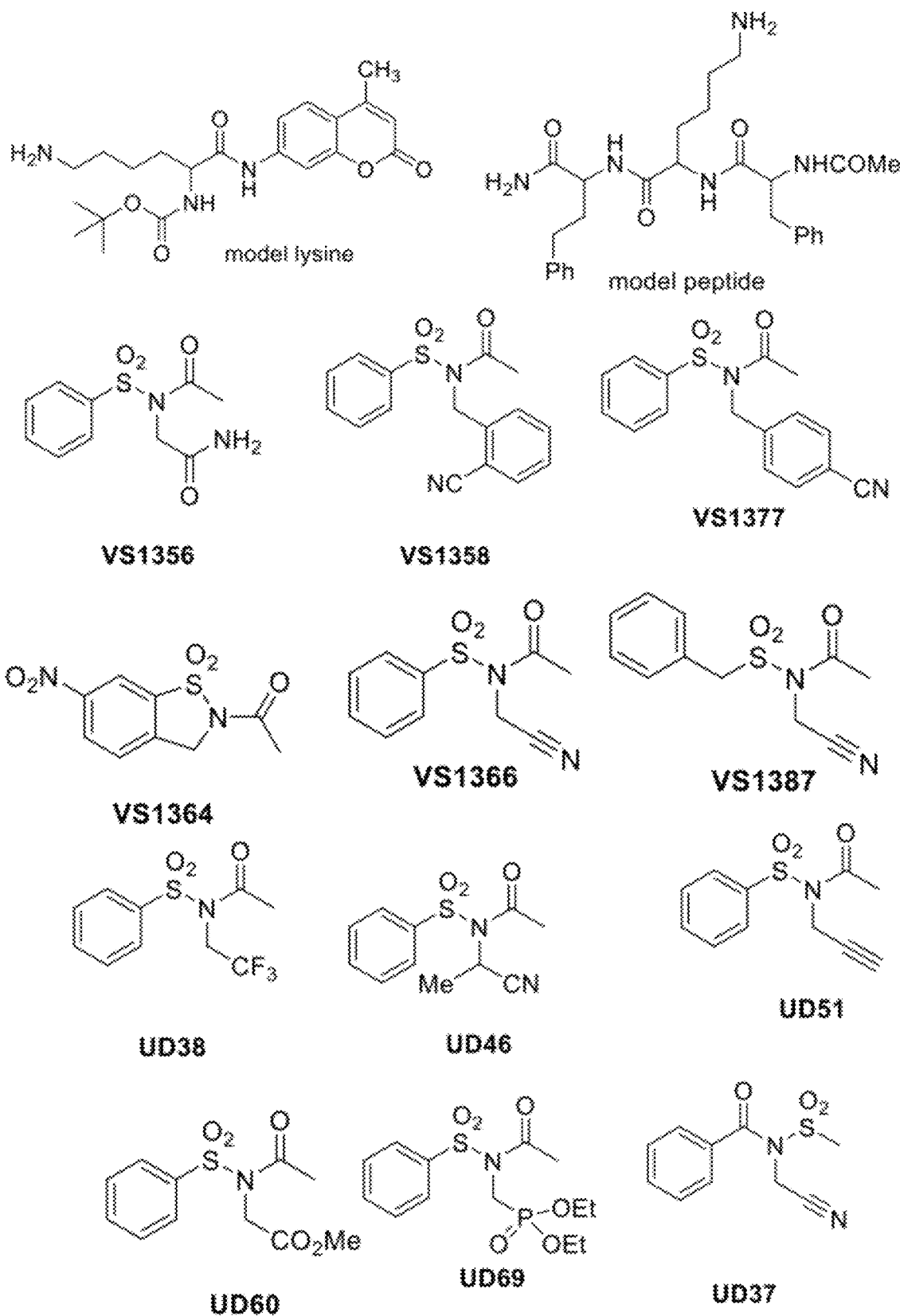
FIG. 8—Additional exemplary NASA analogs/alternatives fr use in embodiments of the invention.
Figure 8:
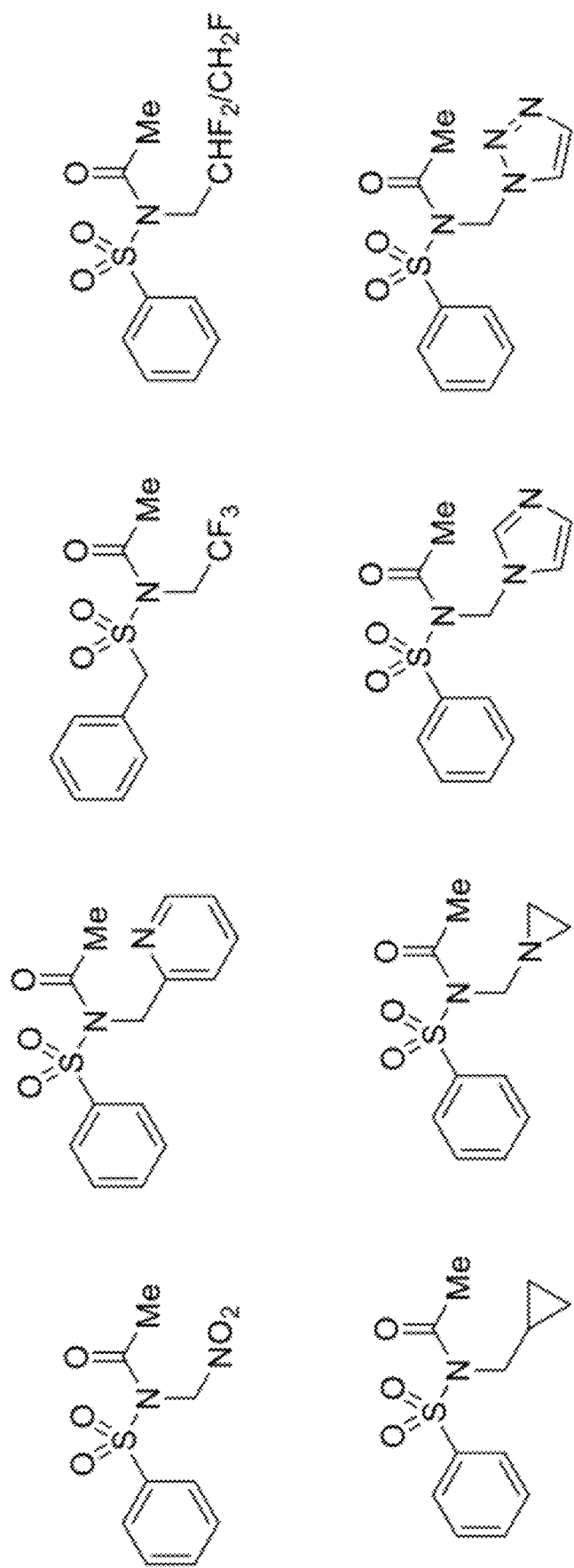

PS48 has an AC$_{50}$ value of 8.0 μM. See e.g. Hindie, V., et al. "Structure and Allosteric Effects of Low-Molecular-Weight Activators on the Protein Kinase PDK1." *Nat Chem Biol* 2009, 5 (10), 758-764, incorporated by reference in its entirety with specific reference to FIG. 3 depicting binding pocket and Table 1, depicted below:

TABLE 1

Thermodynamic parameters of PDK1 interaction with low-molecular-weight compound activators

| | Isomer | N | $K_q$ (M$^{-1}$)$^a$ | $K_a$ (μm)$^a$ | ΔH (kcal mol$^{-1}$)$^b$ | ΔG (kcal mol$^{-1}$)$^b$ |
|---|---|---|---|---|---|---|
| PS48 | Z | 1.0 (0.05) | 9.7 × 10$^4$ (1.2 × 10$^4$) | 10.3 | −1.82 (0.15) | −6.73 (0.08) |
| PS08 | Z | 1.01 (0.05) | 1.62 × 10$^5$ (0.14 × 10$^4$) | 6.2 | −1.79 (0.08) | −7.15 (0.05) |

See also Stroba, A., et al. "3,5-Diphenylpent-2-Enoic Acids as Allosteric Activators of the Protein Kinase PDK1: Structure-Activity Relationships and Thermodynamic Characterization of Binding as Paradigms for PIF-Binding Pocket-Targeting Compounds" *J. Med. Chem.* 2009, 52 (15), 4683-4693, both incorporated herein by reference in their entirety. Table 1 from Stroba, entitled Effect of Compounds on Catalytic Activity of PDK1 and Thermodynamic Characterization of Binding is particularly incorporated by reference and is reproduced below:

|  |  | Kinase activity assay | | ITC | | | | | |
| --- | --- | --- | --- | --- | --- | --- | --- | --- | --- |
| No. | Structure | $A_{max}{}^a$ fold | $AC_{50}{}^{a,b}$ μM | $K_a{}^c$ M$^{-1}$ | $K_d{}^c$ μM | $\Delta H^d$ kcal/mol | $T\Delta S^e$ kcal/mol | $\Delta G^f$ kcal/mol | $\Delta H/\Delta G$ % |

Ar structure:

![Ar-CH2-CH2-C(=CHCOOH)-Ph core structure]

| No. | Ar | $A_{max}$ | $AC_{50}$ | $K_a$ | $K_d$ | $\Delta H$ | $T\Delta S$ | $\Delta G$ | $\Delta H/\Delta G$ |
| --- | --- | --- | --- | --- | --- | --- | --- | --- | --- |
| 2Z | 4-Cl-C6H4 | 4.0$^a$ | 6.0$^a$ | 9.67E4 | 10.3 | −1.82 | 4.87 | −6.73 | 27.1 |
| 2E |  | n.e. | n.e. | — | n.b. |  |  |  |  |
| 3Z | 3-Cl-C6H4 | 2.2 | 9.5 | — | n.d. |  |  |  |  |
| 3E |  | n.e. | n.e. | — | n.d. |  |  |  |  |
| 4Z | 4-F-C6H4 | 3.3 | 41.0 | — | n.d. |  |  |  |  |
| 4E |  | n.e. | n.e. | — | n.d. |  |  |  |  |
| 5Z | 4-Br-C6H4 | 3.9 | 9.8 | 4.78E4 | 20.9 | −3.07 | 3.20 | −6.32 | 48.6 |
| 5E |  | n.e. | n.e. | — | n.d. |  |  |  |  |
| 6Z | 4-CF3-C6H4 | 4.4 | 7.1 | 9.66E4 | 10.4 | −1.94 | 4.79 | −6.73 | 28.8 |
| 6E |  | n.e. | n.e. | — | n.d. |  |  |  |  |
| 7Z | 3,4-diCl-C6H3 | 2.4 | 2.8 | 7.18E4 | 13.9 | −3.71 | 2.80 | −6.56 | 56.6 |
| 7E |  | n.e. | n.e. | — | n.d. |  |  |  |  |
| 8Z | 2,4-diCl-C6H3 | 2.1 | 4.7 | 1.71E5 | 5.9 | −2.08 | 4.93 | −7.07 | 29.5 |
| 8E |  | n.e. | n.e. | — | n.d. |  |  |  |  |
| 9Z | 2-F-4-Br-C6H3 | 3.9 | 4.0 | 1.62E5 | 6.2 | −1.79 | 5.19 | −7.15 | 25.0 |
| 9E |  | n.e. | n.e. | — | n.b. |  |  |  |  |

-continued

| No. | Structure | Kinase activity assay $A_{max}^a$ fold | $AC_{50}^{a,b}$ μM | ITC $K_a^c$ $M^{-1}$ | $K_d^c$ μM | $\Delta H^d$ kcal/mol | $T\Delta S^e$ kcal/mol | $\Delta G^f$ kcal/mol | $\Delta H/\Delta G$ % |
|---|---|---|---|---|---|---|---|---|---|
| 10Z | 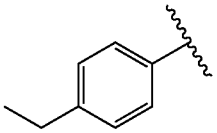 [SMILES: *c1ccc(CC)cc1] | 1.4 | >30 | — | n.d. | | | | |
| 10E | | n.e. | n.e. | — | n.d. | | | | |
| 11Z | 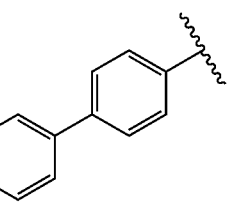 | 3.2 | 6.0 | — | n.d. | | | | |
| 11E | | n.e. | n.e. | — | n.d. | | | | |
| 12Z | 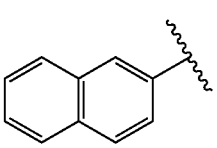 [SMILES: *c1ccc2ccccc2c1] | 3.5 | 6.0 | 7.26E4 | 13.8 | −4.56 | 1.96 | −6.67 | 68.3 |
| 12E | | n.e. | n.e. | — | n.d. | | | | |
| 13Z | 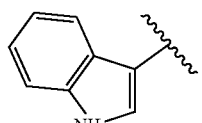 | 3.1 | 7.6 | 9.63E4 | 10 | −4.09 | 2.60 | −6.73 | 60.8 |
| 13E | | 2.2 | 8.8 | — | n.b. | | | | |

In an example embodiment, the PDK1 inhibitor is RS1 according to the formula:

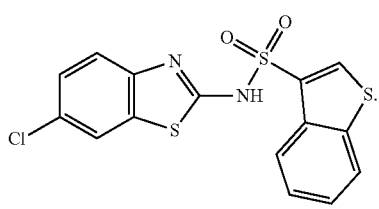 [SMILES: O=S(=O)(Nc1nc2ccc(Cl)cc2s1)c1csc2ccccc12]

RS1 binds to PDK1 selectively. In an example embodiment, the PDK1 inhibitor is RS2 according to the formula:

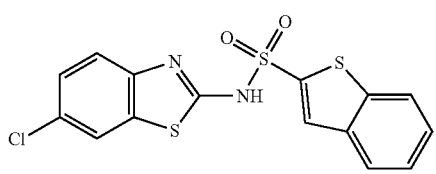 [SMILES: O=S(=O)(Nc1nc2ccc(Cl)cc2s1)c1cc2ccccc2s1]

RS1 and RS2 bound to PDK1 with a Kd of 1.5 μM and 9 μM, respectively.

In an example embodiment, the PDK1 inhibitor is a peptide docking motif (piftide). A piftide is a synthetic peptide. In one example embodiment, the piftide is REPRIL-SEEEQEMFRDFDYIADW (SEQ ID NO: 3). In an example embodiment, the piftide is a small molecule mimic of the peptide. See e.g. Rettenmaier T. J., et al. "A Small-Molecule Mimic of a Peptide Docking Motif Inhibits the Protein Kinase PDK1. Proc Natl Acad Sci USA 2014, 111 (52), 18590-18595, herein incorporated by reference in its entirety.

In an example embodiment, the PDK1 inhibitor is PS210 according to the formula:

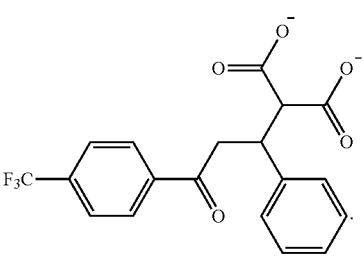 [SMILES: O=C(CC(c1ccccc1)C(C(=O)[O-])C(=O)[O-])c1ccc(C(F)(F)F)cc1]

PTK2/FAK Binding Moiety

In one example embodiment, the protein binding moiety is an PTK2/FAK kinase binding moiety. In one example embodiment, the PTK2/FAK binding moiety is an inhibitor or activator. Protein tyrosine kinase 2 (PTK2), also known as Focal adhesion kinase (FAK), is a non-receptor tyrosine kinase but only distantly related to other tyrosine kinases. PTK2/FAK plays an essential role in mammalian development and numerous physiological functions, most notably cell migration, by integrating signals from integrins as well as growth factor receptors. See e.g. Hirt U. A., et al. "Efficacy of the Highly Selective Focal Adhesion Kinase Inhibitor BI 853520 in Adenocarcinoma Xenograft Models Is Linked to a Mesenchymal Tumor Phenotype." *Oncogenesis* 2018, 7 (2).

In an example embodiment, the PTK2/FAK inhibitor is compound 30, PMID 23414845, according to the formula:

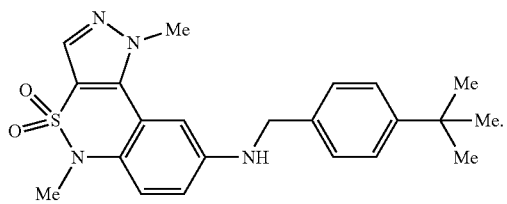 [SMILES: CN1c2ccc(NCc3ccc(C(C)(C)C)cc3)cc2-c2c(cnn2C)S1(=O)=O]

Compound 30 is a selective inhibitor of the tyrosine kinase PTK2 (aka FAK). It is a type III inhibitor in that it binds to an allosteric site, not to the ATP active site of the kinase. In vitro, compound 30 inhibits autophosphorylation of PTK2 with and $IC_{50}$ of 7.1 µM in prostate cancer cells. PTK2 plays a key role in control of cell proliferation, migration and invasion, and helps regulate resistance to apoptosis. This enzyme is over-expressed in a number of cancers, and reduction of PTK2 activity has growth inhibitory action in vitro and in vivo. These factors make inhibition of PTK2 a novel mechanism for diseases of cellular over-proliferation. In another experiment compound 30 had a $pIC_{50}$ of 6.2 for the inhibition of PAK2. See e.g. Tomita, N., et al. "Structure-Based Discovery of Cellular-Active Allosteric Inhibitors of FAK." *Bioorganic & Medicinal Chemistry Letters* 2013, 23 (6), 1779-1785, herein incorporated by reference in its entirety with specific reference to Tables 1, 3, and 5, depicting evaluation of SAR of substituents with Tables 1 and 5 reproduced below for binders that can be used herein:

TABLE 1

SAR of substituents on the benzene ring

| Compound | $R^3$ | FAK $IC_{50}^a$ (µM) |
|---|---|---|
| 1 | Et | 0.96 |
| 20 | $CONH_2$ | 3.5 |
| 21 | (acyl-NH-CH2CH2-OH) | 0.99 |
| 22 | (acyl-N-piperidinyl-CH2CH2-OH) | 0.50 |

TABLE 5

SAR of amino substituents

| Compound | $R^4$ | FAK $IC_{50}^a$ (µM) | Cell pFAK $IC_{50}$ (µM) |
|---|---|---|---|
| 24 | 4-F-phenyl | 4.3 | >30 |
| 28 | 4-F-benzyl | 0.32 | 19 |
| 29 | 4-Br-benzyl | 1.4 | >30 |
| 30 | 4-(C(Me)3)-benzyl | 0.64 | 7.1 |

RIPK Binding Moiety

In one example embodiment, the protein binding moiety is an RIPK kinase binding moiety. In one example embodiment, the RIPK binding moiety is an inhibitor or activator. Receptor-interacting protein kinase (RIPK)-1 is involved in RIPK3-dependent and -independent signaling pathways leading to cell death and/or inflammation. See e.g. Degterev A., et al. "Targeting RIPK1 for the Treatment of Human Diseases." *Proc Natl Acad Sci USA* 2019, 116 (20), 9714-9722. In an example embodiment, the RIPK inhibitor is RIPA-56 according to the formula.

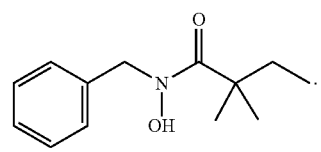 [SMILES: CCC(C)(C)C(=O)N(O)Cc1ccccc1]

RIPA-56 is a highly potent, selective, and metabolically stable type III (allosteric) inhibitor of RIPK1. RIPA-56 is also known as compound 92 in patent WO2016101885, herein incorporated by reference. RIPA-56 is a drug candidate for the treatment of systemic inflammatory response syndrome (SIRS). RIPA-56 is active against human and mouse RIPK1 and is efficacious in animal models. It is devoid of off-target IDO inhibiting activity. RIPA-56 has an $pIC_{50}$ value of 7.9 for RIPK-1. See e.g. Ren, Y., et al.

"Discovery of a Highly Potent, Selective, and Metabolically Stable Inhibitor of Receptor-Interacting Protein 1 (RIP1) for the Treatment of Systemic Inflammatory Response Syndrome." *J. Med. Chem.* 2017, 60 (3), 972-986, herein incorporated by reference in its entirety with specific mention of Table 5.

TYK2 Binding Moiety

In one example embodiment, the protein binding moiety is an TYK2 kinase binding moiety. In one example embodiment, the TYK2 binding moiety is an inhibitor or activator. Tyrosine kinase 2 (TYK2) is a member of the JAK kinase family that regulates signal transduction downstream of receptors. TYK2 pairs with JAK2 to regulate the IL-23/IL-12 pathways and JAK1 to regulate the type I interferon family. In an example embodiment, the TYK2 inhibitor is compound 29 according to the formula:

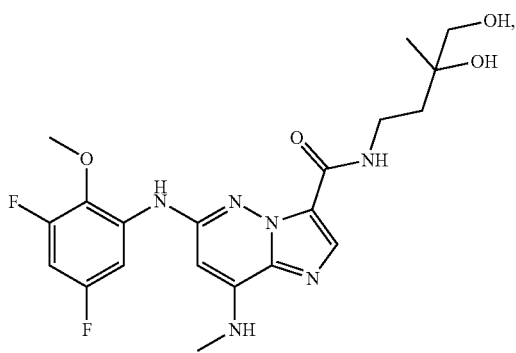 [SMILES: CNc1cc(Nc2cc(F)cc(F)c2OC)nn2c(C(=O)NCCC(C)(O)CO)cnc12]

see e.g. Moslin R., et al. "Identification of Imidazo[1,2-b] Pyridazine TYK2 Pseudokinase Ligands as Potent and Selective Allosteric Inhibitors of TYK2 Signalling." *Med. Chem. Commun.* 2017, 8 (4), 700-712.

In an example embodiment, the TYK2 inhibitor is Deucravacitinib, also known as BMS-986165, according to the formula:

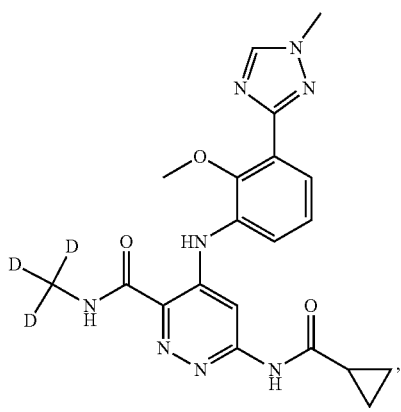

wherein D is deuterium. The deuteromethyl amide group confers selectivity by virtue of binding to a pocket in the TYK2 JH2 ligand binding domain. Deucravacitinib is a selective, orally active, and allosteric inhibitor of the TYK2 where it binds to the JH2 (pseudokinase) domain. Deucravacitinib is kinome selective and does not bind to JAKs1-3 or to the TYK2 JH1 (ATP) binding domain. Deucravacitinib has been shown in inhibit IFNα production with an $IC_{50}$ of 5 nM in vitro. In particular, Deucravacitinib has a $pK_i$ value of 10.7 for TYK2 and a $pIC_{50}$ of 9.7 and 9.0 for TYK2 and JAK1 respectively. Currently Deucravacitinib has advanced to evaluation in clinical studies in patients with systemic lupus erythematosus and ulcerative colitis (both Phase 2) and moderate-to-severe psoriasis (Phase 3). See e.g. Wrobleski, S. T., et al. "Highly Selective Inhibition of Tyrosine Kinase 2 (TYK2) for the Treatment of Autoimmune Diseases: Discovery of the Allosteric Inhibitor BMS-986165." *J. Med. Chem.* 2019, 62 (20), 8973-8995 and "Tyrosine Kinase 2 (TYK2) Allosteric Inhibitors To Treat Autoimmune Diseases." *J. Med. Chem.* 2019, 62 (20), 8951-8952, incorporated herein by reference in its entirety. Tables 1 and 3 from Wrobleski et al. are specifically incorporated herein by reference. Table 1 shows JAK Family Biochemical Potencies for clinical inhibitors. And Table 3, reproduced below, provides Expansion of C3' Amide SAR:

TABLE 3

Expansion of C3' Amide SAR

| | R | TYK2 JH2 ($IC_{50}$, nM)$^a$ | IFNα ($IC_{50}$, nM)$^a$ | hWB ($IC_{50}$, nM)$^a$ |
|---|---|---|---|---|
| 22 | —NH$_2$ | 0.5 ± 0.1 | 30 ± 16 | 62 ± 11 |
| 23 | —NHMe | 0.5 ± 0.1 | 47$^c$ | 140$^c$ |
| 24 | —NHEt | 0.4 ± 0.1 | 28 ± 14 | 280 ± 180 |
| 25 | —N(Me)$_2$ | 1.7 ± 0.5 | 130 ± 45 | 750 ± 92 |
| 26 | —NHCH$_2$-cPr | 1.1 ± 0.2 | 64 ± 17 | 870 ± 360 |
| 27 | —NH(CH$_2$)$_2$OH | 0.8 ± 0.2 | 220 ± 53 | 270 ± 21 |
| 28 | (morpholinoethylamino) | 0.7 ± 0.5 | 51 ± 45 | 160 ± 17 |
| 29 | (pyridylmethylamino) | 0.3 ± 0.2 | 22 ± 9 | 180 ± 35. |

SHP Binding Moiety

In one example embodiment, the protein binding moiety is an Scr kinase binding moiety. In one example embodiment, the Scr kinase binding moiety is an inhibitor or activator. Src homology 2 (SH2) domain-containing phosphatase 2 (SHP2) belongs to protein tyrosine phosphatase (PTP) family and is a positive transducer of proliferative and antiapoptotic signals from receptor tyrosine kinases. SHP2 is composed of three folded domains and a C-terminal tail. SHP2 modulates phosphatase activity by binding phosphopeptides at the N-terminal SH2 and C-terminal SH2 domains. The PTP domain harbors the catalytic functionality in the conserved signature motif HCX5R. The disordered C-terminal tail contains has a putative regulatory function. See e.g. Marasco M., et al. "Molecular Mechanism of SHP2 Activation by PD-1 Stimulation." Sci. Adv. 2020, 6 (5), eaay4458. In an example embodiment the SHP3 inhibitor is any from the International Patent Application WO2020076723, herein incorporated by reference.

aPKC Binding Moiety

In one example embodiment, the protein binding moiety is an atypical PKC kinase binding moiety. In one example embodiment, the aPKC binding moiety is an inhibitor or activator. Atypical protein kinase C (aPKC) belongs to the protein kinase C family that are categorized into three groups based on their structure and cofactor regulation. The aPKC isozymes: ζ and λ, are the least understood and differ significantly in structure from the other two classes. First, the C1 domain contains one Cys-rich motif, instead of two. Second, aPKC isozymes do not appear to contain key residues that maintain the C2 fold. In additional feature of aPKCs is they have been reported to not respond to phorbol esters in vivo or in vitro. See e.g. Newton, A. C. "Protein Kinase C: Structure, Function, and Regulation." *Journal of Biological Chemistry* 1995, 270 (48), 28495-28498.

In an example embodiment, the aPKC inhibitor is an inhibitor or any derivative thereof identified in the International Patent Application WO2015075051, herein incorporated by reference.

In an example embodiment, the PKC Inhibitor is a PKC-zeta (PKCζ) inhibitor. See, Abdel-Halim, Discovery and Optimization of 1,3,5-Trisubstituted Pyrazolines as Potent and Highly Selective Allosteric Inhibitors of Protein Kinase C-ζ, Journal of Medicinal Chemistry 2014 57 (15), 6513-6530, DOI: 10.1021/jm500521n, incorporated herein by reference in its entirety with specific mention of Tables 1 and 2, reproduced below:

TABLE 1

Inhibition of Recombinant PKCζ and the NF-κB Pathway is Cells

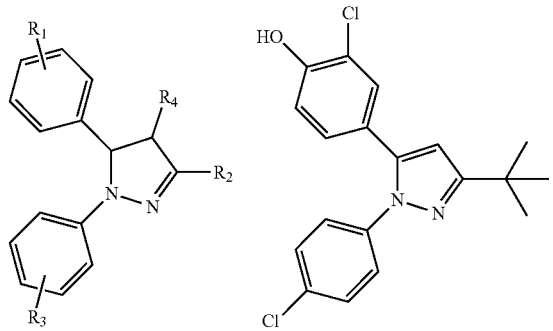

11

| | | | | | cell-free assay | | NF-κB reporter gene assay (U(37 cells)) | |
|---|---|---|---|---|---|---|---|---|
| compd | $R_1$ | $R_2$ | $R_3$ | $R_4$ | % inhibn at 62.5 (μM)$^a$ | $IC_{50}$ ± SD (μM) | % inhibn at 5 (μM)$^a$ | $IC_{50}$ ± SD (μM) |
| 1a | 4-OH | t-Bu | 4-Cl | H | 91.5 | 10.7 ± 0.54 | 75.1 | 3.2 ± 0.22 |
| 1b | 4-OH | t-Bu | 4-F | H | 95.5 | 9.4 ± 0.19 | 63.8 | ND$^a$ |
| 1c | 4-OH | t-Bu | 4-Br | H | 93.2 | 11.4 ± 1.25 | 58.4 | ND |
| 1d | 4-OH | t-Bu | 4-CF$_3$ | H | 94.2 | 8.8 ± 0.53 | ND$^b$ | ND |
| 1e | 4-OH | t-Bu | 4-CH$_3$ | H | 88.8 | 12.6 ± 1.13 | 62.9 | ND |
| 1f | 4-OH | t-Bu | 4-isopropyl | H | 54.9 | ND | ND$^b$ | ND |
| 1g | 4-OH | t-Bu | 4-COOH | H | 47.9 | ND | 40.7 | ND |
| 1h | 4-OH | t-Bu | 3-Cl | H | 96.8 | 5.2 ± 0.67 | 64.6 | ND |
| 1i | 4-OH | t-Bu | 3-F | H | 98.1 | 2.2 ± 0.09 | 73.5 | ND |
| 1j | 4-OH | t-Bu | 3-CF$_3$ | H | 96.1 | 2.7 ± 0.08 | 89.7 | 2.7 ± 0.32 |
| 1k | 4-OH | t-Bu | 3-CH$_3$ | H | 91.7 | 3.5 ± 0.35 | 73.7 | ND |
| 1l | 4-OH | t-Bu | 2-Cl | H | 57.1 | ND | 23.5 | ND |
| 1m | 4-OH | t-Bu | 2-F | H | 57.6 | ND | 48.7 | ND |
| 1n | 4-OH | t-Bu | 2,4-dichloro | H | 71.0 | ND | 50.2 | ND |
| 1o | 4-OH | t-Bu | 2,4-difluoro | H | 68.0 | ND | 51.8 | ND |
| 1p | 4-OH | t-Bu | 2,4-dimethyl | H | 59.9 | ND | 41.5 | ND |

TABLE 2

Inhibition of PKCl at 20 μM$^a$

| compd | PKC$_l$ % inhibn at 20 μM | compd | PKC$_l$ % inhibn at 20 μM | compd | PKC$_l$ % inhibn at 20 μM |
|---|---|---|---|---|---|
| 1a | 0 | 2a | 31.6 | 4a | 17.4 |
| 1h | 43.5 | 2b | 45.5 | 4d | 29.7 |
| 1i | 19.3 | 2c | 13.4 | 4e | 0 |
| 1j | 17.0 | 2h | 21.4 | 4g | 44.1 |
| 1k | 13.9 | 2i | 45.9 | 4h | 25.2 |
| 1r | 31.6 | 2j | 24.1 | 4i | 45.2 |

TABLE 2-continued

Inhibition of PKCl at 20 μM[a]

| compd | PKC$_l$ % inhibn at 20 μM | compd | PKC$_l$ % inhibn at 20 μM | compd | PKC$_l$ % inhibn at 20 μM |
|---|---|---|---|---|---|
| 1s | 23.7 | 2k | 20.3 | 4j | 39.2 |
| 1t | 7.8 | 2l | 38.7 | 9 | 23.1. |

[a]Values are the mean of at least two experiments; standard deviation <15%.

In an aspect, the binding moiety is a 1,3,5-trisubstituted pyrazoline according to the formula:

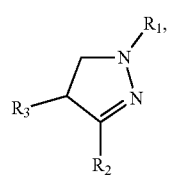

more preferably wherein the binding molecule is selected from

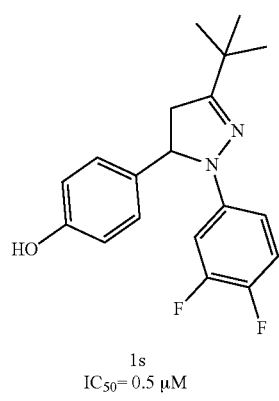

1s
IC$_{50}$= 0.5 μM

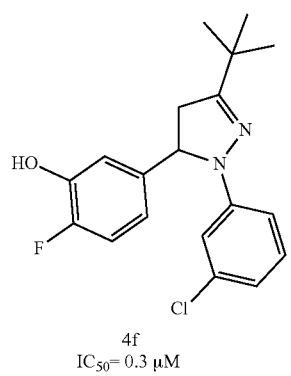

4f
IC$_{50}$= 0.3 μM

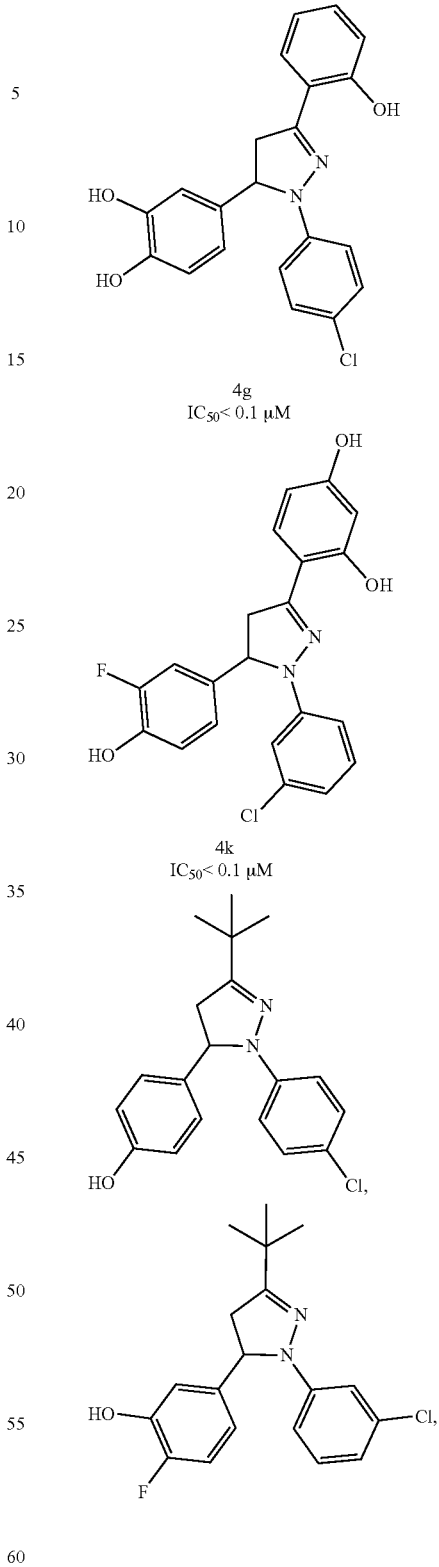

or any derivative thereof. 1,3,5-trisubstituted pyrazolines is potent and selective allosteric PKCζ inhibitors. Phenolic group on the 5-phenyl was essential for the inhibitory activity, with a catechol providing the best activity. Presence of a lipophilic (halogen or alkyl) substituent on the 1-phenyl proved to be essential for the generation of high potency.

SphK Binding Moiety

In one example embodiment, the protein binding moiety is an SphK kinase binding moiety. In one example embodiment, the SphK binding moiety is an inhibitor or activator. Sphingosine kinases (SphKs) are biological lipid kinases that regulate the sphingolipid metabolic pathway and control multiple important cell processes. SphKs are the only enzymes that catalyze ATP-dependent phosphorylation of sphingosine to sphingosine-1-phosphate. SphKs have five conserved domains, C1-C5. The C4 domain appears to be unique SphKs while the C1-C3 domains are also found in ceramide kinase (CERK) and diacylglycerol kinases (DAGK). The two SphK isoforms are SphK1 and SphK2. SphK2 has ~240 more amino acids than SphK1. See e.g. Cao M., "Sphingosine Kinase Inhibitors: A Patent Review." *Int J Mol Med* 2018.

In an example embodiment, the SphK inhibitor is an inhibitor or derivative thereof identified in the International Patent Application WO2014118556, herein incorporated by reference.

GSK-3 Binding Moiety

In one example embodiment, the protein binding moiety is an GSK-3 kinase binding moiety. In one example embodiment, the GSK-3 binding moiety is an inhibitor or activator. Glycogen synthase kinase-3 (GSK3) comprises two isoforms, GSK3a and GSK3p, that regulate many interactions such as intracellular receptor-coupled signaling proteins, insulin receptors, and several ionotropic neurotransmitter receptors. GSK3 can be found in the cytosol, mitochondria and nucleus, as well as other subcellular compartments. The two key functional domains of GSK3 are the primed-substrate binding domain that recruits substrates to GSK3, and the kinase domain that phosphorylates the substrate. See e.g. Glycogen Synthase Kinase-3 (GSK3): Regulation, Actions, and Diseases. Pharmacology & Therapeutics 2015, 148, 114-131. In an example embodiment, the GSK3 inhibitor is an inhibitor or derivative thereof identified in the US Patent U.S. Pat. No. 9,757,369, herein incorporated by reference.

JNK Binding Moiety c-Jun N-terminal kinases (JNKs) participate in stress signaling pathways implicated in gene expression, neuronal plasticity, regeneration, cell death, and regulation of cellular senescence. JNKs are one of the three families of MAP kinases. JNKs have three isoforms: JNK1 and JNK2, which is found throughout tissue; and JNK3, which is found in neurons, the heart, and the testis. See e.g. Yarza, R., et al. "C-Jun N-Terminal Kinase (JNK) Signaling as a Therapeutic Target for Alzheimer's Disease." *Front. Pharmacol.* 2016, 6. In one example embodiment, the kinase binding moiety is a JNK binding moiety. In one example embodiment, the JNK binding moiety is an inhibitor or activator. In one example embodiment, the JNK inhibitor is compound 10, according to the formula:

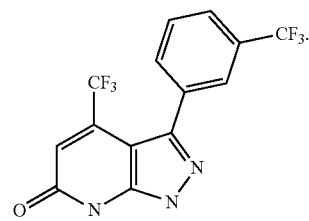 [SMILES: O=c1cc(C(F)(F)F)c2c(-c3cccc(C(F)(F)F)c3)n[nH]c2[nH]1]

Compound 10 has $IC_{50}$ values, in µM, of: 1.2 in 0.1 mM p38α assay; 0.8 in 0.1 mM MKK6/p38α cascade assay; 1.4 in 0.01 mM p38α/MK2 cascade assay; >100 in 0.1 mM MKK6 assay; >40 in 0.01 mM MK2 assay; >40 in 0.1 mM p38β assay; >40 in 0.1 mM p38γ assay; and >40 in 0.1 mM p28δ assay, see e.g. Comess, K. M., et al. "Discovery and Characterization of Non-ATP Site Inhibitors of the Mitogen Activated Protein (MAP) Kinases." ACS Chem. Biol. 2011, 6 (3), 234-244, incorporated herein by reference. In an aspect, compound 10 binds the lipid binding pocket. Additional JNK1 non-ATP site inhibitors can also be used in the small molecules disclosed herein, including biaryl-tetrazole based Jnk-1 Activation inhibitors. In an embodiment, the biaryl-tetrazole based binding moiety for Jnk-1 are selected from Table 2 of ACS Chem. Biol. 2011, 6, 234-244, reproduced below:

| No. | Structure | $IC_{50}$ (MKK7-Jnk1)[a] | $IC_{50}$ (Jnk1)[b] | $IC_{50}$ (P-cJun)[c] |
|---|---|---|---|---|
| 2 | 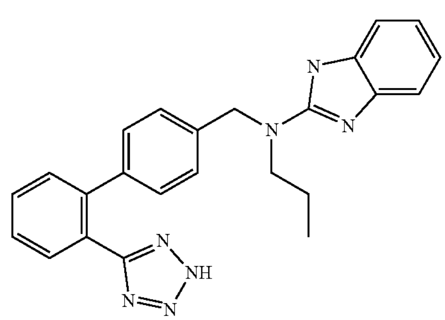 [SMILES: CCCN(Cc1ccc(-c2ccccc2-c2nn[nH]n2)cc1)c1nc2ccccc2[nH]1] | 7.8 | >100 | >30 |

-continued

| No. | Structure | IC$_{50}$ (MKK7-Jnk1)$^a$ | IC$_{50}$ (Jnk1)$^b$ | IC$_{50}$ (P-cJun)$^c$ |
|---|---|---|---|---|
| 3 | 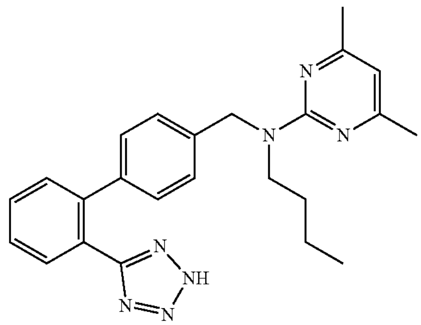 [SMILES: CCCCN(Cc1ccc(-c2ccccc2-c2nn[nH]n2)cc1)c1nc(C)cc(C)n1] | 7.7 | >10 | >30 |
| 4 | 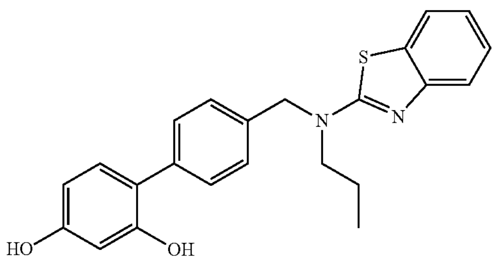 [SMILES: CCCN(Cc1ccc(-c2ccc(O)cc2O)cc1)c1nc2ccccc2s1] | 2.9 | >100 | >10 |
| 5 | 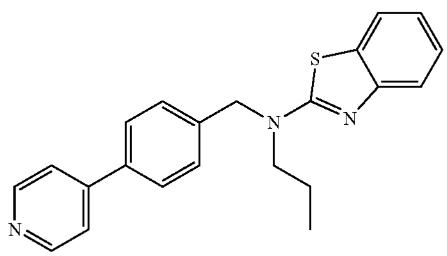 [SMILES: CCCN(Cc1ccc(-c2ccncc2)cc1)c1nc2ccccc2s1] | 2.8 | 68.6 | >10 |
| 6 | 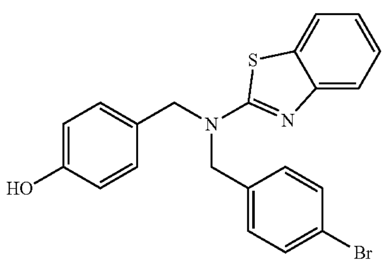 [SMILES: Oc1ccc(CN(Cc2ccc(Br)cc2)c2nc3ccccc3s2)cc1] | 3.1 | ND | >10 |
| 7 | 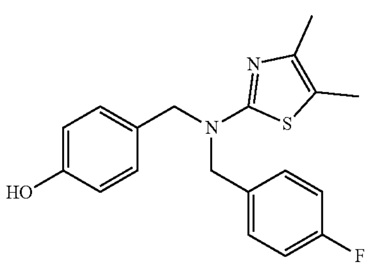 [SMILES: Cc1nc(N(Cc2ccc(O)cc2)Cc2ccc(F)cc2)sc1C] | 3.8 | >100 | 4.0 |

| No. | Structure | IC$_{50}$ (MKK7-Jnk1)$^a$ | IC$_{50}$ (Jnk1)$^b$ | IC$_{50}$ (P-cJun)$^c$ |
|---|---|---|---|---|
| 8 | 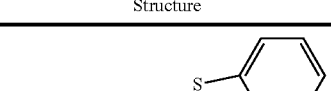 | 4.7 | 82.3 | >10. |

Further details regarding biaryl-tetrazole affinity and coupled assay data for JNK isoforms and related MAP kinase protein from Table 1 of ACS Chem. Biol. 2011, 6, 234-244 is also provided, and is adapted below for reference

| No. | Structure | IC$_{50}{}^a$ Jnk-1 | IC$_{50}{}^a$ MKK7cp$^b$ | Kd$^c$ Jnk1-u$^d$ | Kd$^c$ Jnk1-a$^a$ | Kd$^c$ p38α-u$^a$ | Kd$^c$ ERK2-u$^d$ |
|---|---|---|---|---|---|---|---|
| 2 | 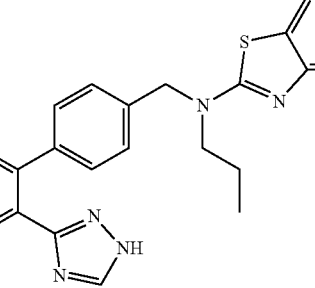 | >100 | 7.8 | 11 | >50 | 18 | 18 |
| 3 | 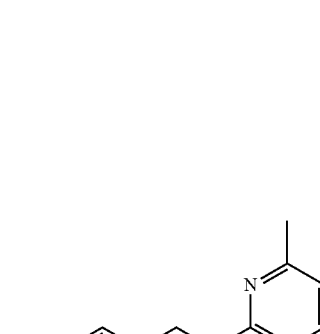 | 62 | 7.7 | 16 | >50 | 17 | 32 |

In an example embodiment, the binding moiety is selected from:

| Compound IC$_{50}$(µM) JNK1 IC$_{50}$(µM) JNK2 | Structure |
|---|---|
| 1<br>0.88 ± 0.19<br>1.2 ± 0.3 | 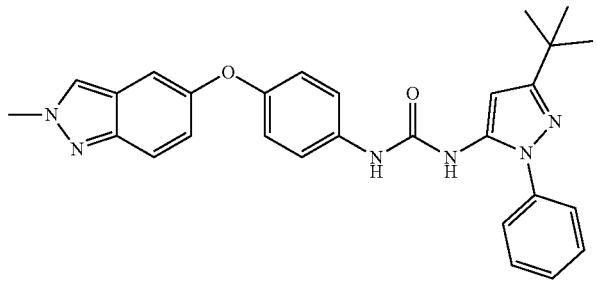 [SMILES: Cn1cc2cc(Oc3ccc(NC(=O)Nc4cc(C(C)(C)C)nn4-c4ccccc4)cc3)ccc2n1] |
| 2<br>0.48 ± 0.27<br>2.8 ± 1.1 | 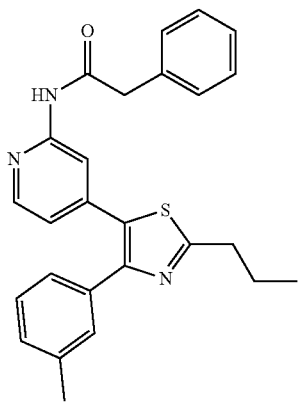 [SMILES: CCCc1nc(-c2cccc(C)c2)c(-c2ccnc(NC(=O)Cc3ccccc3)c2)s1] |
| 3<br>17 ± 11<br>15 ± 4 | 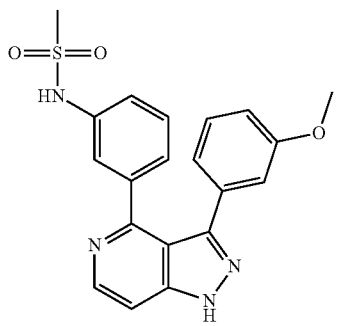 [SMILES: COc1cccc(-c2n[nH]c3ccnc(-c4cccc(NS(C)(=O)=O)c4)c23)c1] |
| 4<br>0.070 ± 0.023<br>0.59 ± 0.15 | 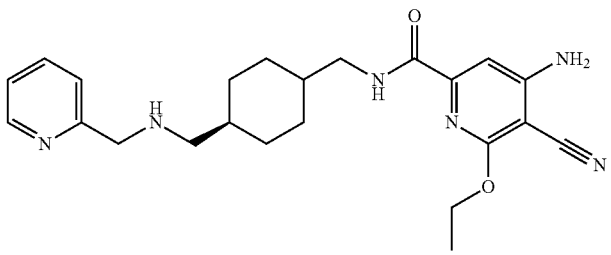 |
| 5<br>19 ± 5<br>0.99 ± 0.33 | 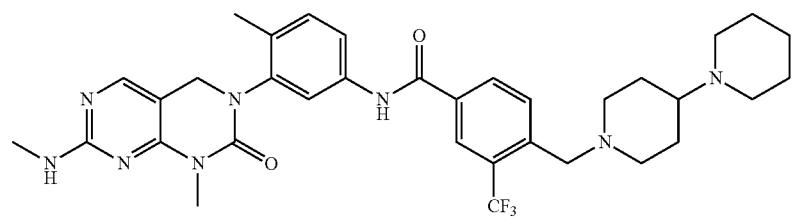 [SMILES: CNc1ncc2c(n1)N(C)C(=O)N(c1cc(NC(=O)c3ccc(CN4CCC(N5CCCCC5)CC4)c(C(F)(F)F)c3)ccc1C)C2] |

-continued
| Compound<br>IC$_{50}$(μM) JNK1<br>IC$_{50}$(μM) JNK2 | Structure |
|---|---|
| 6<br><0.0018<br><0.0026 | 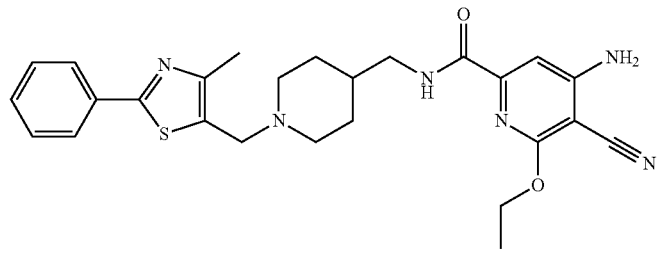 [SMILES: CCOc1nc(C(=O)NCC2CCN(Cc3sc(-c4ccccc4)nc3C)CC2)cc(N)c1C#N] |
| 7<br>>30<br>34 ± 12 | 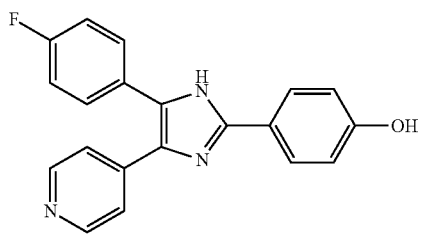 [SMILES: Oc1ccc(-c2nc(-c3ccncc3)c(-c3ccc(F)cc3)[nH]2)cc1] |
| 8<br>1.3 ± 0.5<br>>30 | 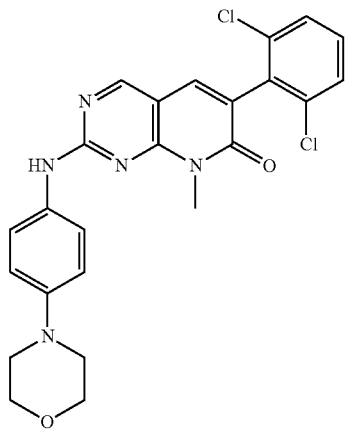 [SMILES: Cn1c(=O)c(-c2c(Cl)cccc2Cl)cc2cnc(Nc3ccc(N4CCOCC4)cc3)nc21] |
| 9<br>0.97 ± 0.30<br>1.3 ± 0.4 | 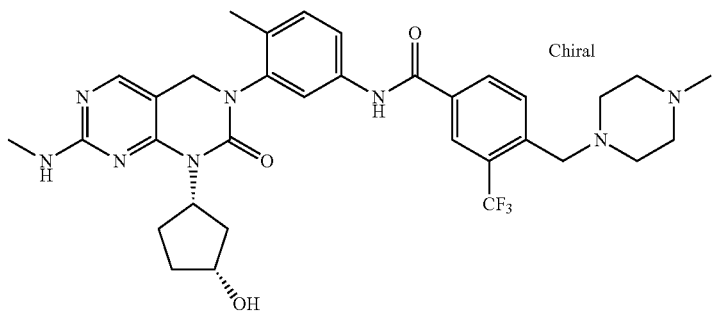 |

-continued

| Compound IC$_{50}$(µM) JNK1 IC$_{50}$(µM) JNK2 | Structure |
|---|---|
| 10<br>0.10 ± 0.03<br>0.14 ± 0.03 | 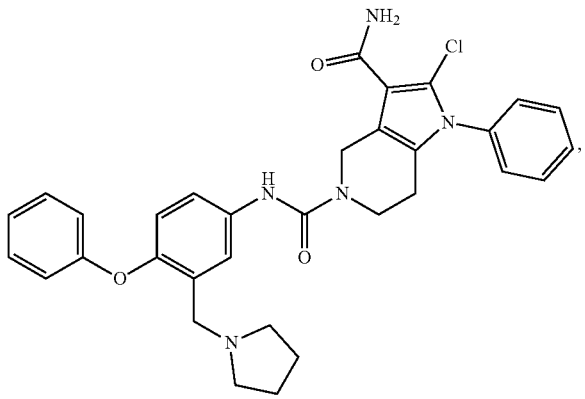 [SMILES: NC(=O)c1c2c(n(-c3ccccc3)c1Cl)CCN(C(=O)Nc1ccc(Oc3ccccc3)c(CN3CCCC3)c1)C2] | as adapted from Lombard et al. Allosteric modulation of JNK docking-site interactions with ATP-competitive inhibitors. Biochemistry. Author manuscript: available in PMC 2019 Oct. 9, FIG. 1B, incorporated herein by reference.

TRK Binding Moiety

The Neurotrophic Tyrosine Kinase Receptor 1 gene (NTRK1) encodes the Tropomyosin-related kinase A (TRKA) receptor tyrosine kinase. TRKA is a high affinity receptor for Nerve Growth Factor (NGF) and a member of the neurotrophin receptor family of receptor tyrosine kinases. TRKA is critical for the development and maturation of the central and peripheral nervous systems during embryogenesis. It is implicated in pain and temperature sensing in sympathetic and sensory nerves as well as memory processes in adults it is expressed in the basal forebrain. NGF-mediated dimerization actives TRKA, which induces autophosphorylation of specific tyrosine residues and transphosphorylation of additional substrates, leading to activation of the PI3K/AKT, Ras/MAPK and PLC-γ pathways. See, e.g., Ardini, E., et al. "The TPM3-NTRK1 Rearrangement Is a Recurring Event in Colorectal Carcinoma and Is Associated with Tumor Sensitivity to TRKA Kinase Inhibition." *Molecular Oncology* 2014, 8 (8), 1495-1507.

In one example embodiment the protein binding moiety is a TRK binding moiety. In one example embodiment, the TRK binding moiety is an inhibitor or activator. In one example embodiment, the TRK inhibitor is any one of compounds 13-16, according to the formulas:

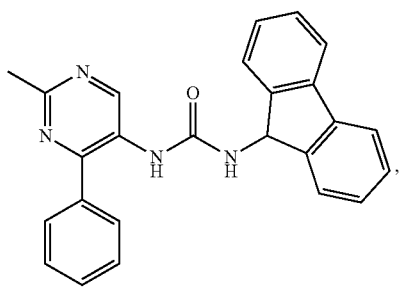

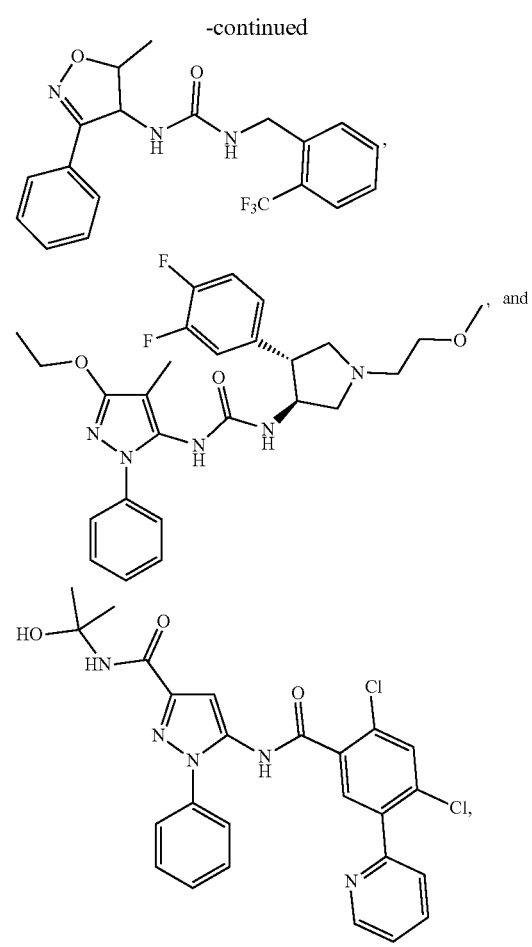

respectively. Compound 13, an allosteric inhibitor of TRKA, has an IC$_{50}$ of 99 nM and good selectivity over TRKB and TRKC, each of which has an IC$_{50}$ value of 81 mM and 25 mM respectively. In addition, Compound 15 also demonstrated good selectivity for TRKA over TRKB. Crystal structures of TRKA and Compounds 13, 15 and 16 from Patent Application No. CN103649076, in particular, FIGS. 10 and 11 are incorporated herein by reference (PDB codes:

5KMI, 5H3Q). In another example embodiment, the TRK inhibitor is any pyrrolidinyl urea or pyrrolidinyl thiourea as described in the International Patent Application WO2012158413A2, herein incorporated by reference, as well as any derivates thereof.

Additional Trk inhibitors are described in Bailey et al, Tropomyosin receptor kinase inhibitors: an updated patent review for 2010-2016, Expert Opinion on Therapeutic Patents doi: 10.1080/13543776.2017.1297797, and Bailey et al., (2020) Tropomyosin receptor kinase inhibitors: an updated patent review for 2016-2019, Expert Opinion on Therapeutic Patents, 30:5, 325-339, DOI: 10.1080/13543776.2020; both incorporated herein by reference in their entirety.

PDGFR Binding Moiety

Platelet-derived growth factor (PDGF) system includes two receptors: PDGFRA and PDGFRB and four ligands: PDGFA; PDGFB; PDGFC; and PDGFD. Ligand binding induces receptor dimerization, enabling autophosphorylation of specific tyrosine residues and subsequent recruitment of a variety of signal transduction molecules. PDGFR regulates normal cellular growth and differentiation, and expression of activated PDGFR promotes oncogenic transformation, see e.g. McDermott, U., et al. "Ligand-Dependent Platelet-Derived Growth Factor Receptor (PDGFR)-α Activation Sensitizes Rare Lung Cancer and Sarcoma Cells to PDGFR Kinase Inhibitors. Cancer Res 2009, 69 (9), 3937-3946. In one example embodiment, the kinase binding moiety is a PDGFR targeting molecule. In one example embodiment, the PDGFR binding moiety is an inhibitor or activator. In an example embodiment, the PDGFR targeting molecule is imatinib, nilotinib, or dasatinib.

Target Substrates

The target substrate may be a natural substrate of the enzyme bound by the kinase binding moieties above. However, the target binding moieties discussed below, may also be used to direct the enzyme to modify a non-natural or neo-substrate for that kinase. Target substrates polypeptides, a nucleic acid, polynucleotides, lipids, and oligosaccharides. The target binding moiety may be chosen for a specific substrate of interest, which may be located in different localization sites of the cell, e.g. nucleus, cytoplasm, mitochondria, cell surface.

Target Binding Moiety

The target binding moiety equips the chimeric small molecule with a mechanism to bind or associate with a target, including the target substrates noted above. The target binding moiety of the chimeric small molecule binds the target substrate and brings the target substrate into proximity with a kinase via the kinase binding moiety or by virtue of the target binding moiety bound or labeled on the kinase. The reaction can allow the protein to modify a larger number of substrates, non-natural target substrates of the protein, and to increase the kinetics/efficiency of such substrate modifications. For that purpose, the target binding moiety should be capable of binding the desired substrate of interest and capable of being linked to a kinase binding moiety via a linker to allow for modification of the substrate.

Polynucleotide Binding Moieties

In one example embodiment, the target binding moiety binds polynucleotides. Example polynucleotide binding moieties include small molecules. Small molecules that target polynucleotides include groove binders and intercalators, see e.g. Wang M., et al. "Recent Advances in Developing Small Molecules Targeting Nucleic Acid." *IJMS* 2016, 17 (6), 779 and Warner K. D., et al. "Principles for Targeting RNA with Drug-like Small Molecules." *Nat Rev Drug Discov* 2018, 17 (8), 547-558, herein incorporated by reference. Additional example polynucleotide binding moieties include polynucleotide binding proteins. Polynucleotide binding proteins can be identified from nucleotide-binding folds in the proteins, such as the Rossmann-type (see, e.g. Kleiger et al., J. of Mol. Biol. 323: 69-76) and the P-loop containing nucleotide hydrolase folds (see, e.g., Saraste et al., Trends in Bio Sci, 15: 430-434). Chauhan et al. has developed methods for the identification of ATP and GTP binding residues and Ansari et al. has designed a method specifically for NAD. Parca et al. (2012), identified nucleotide-binding sites in protein structures, and include nucleotides bound by the protein, protein name and name of organism in Table S1 of DOI: 10.1371/journal-.pone.0050240, incorporated herein by reference. Accordingly, nucleotide binding moieties are known in the art and can be identified by one of skill in the art for use as a target binding moiety in the present compositions.

Oligosaccharide Binding Moieties

In one example embodiment, the target binding moiety is an oligosaccharide binding moiety. Oligosaccharide binding moieties include small molecules. For example, small molecules that include boronic acid are typically used to bind to oligosaccharides. See e.g. Jin S., et al. "Carbohydrate Recognition by Boronolectins, Small Molecules, and Lectins. Med. Res. Rev. 2009, herein incorporated by reference. Other oligosaccharide binding moieties include carbohydrate binding proteins, are important targets when considering antiviral and anticancer drugs. The localizing moiety can be, for example, a lectin, facilitating interaction sites for carbohydrates. Exemplary molecules include small molecule boronolectins, nucleic acid-based boronolectins, and peptidoboronolectins. See, e.g. Jin et al., Med. Res Rev. 2010 March; 30(2): 171-257; doi: 10.1002/med.20155, incorporated herein by reference, specifically FIGS. 1-50 for binding molecules and the complexes formed. Publicly available computational methods are available using developed bioinformatics to select small molecules capable of binding carbohydrates, see, e.g., Zhao et al., Current Protocols in Protein Science 94: 1 10.1002/cpps.75; Shionyu-Mitsuyama C, Shirai T, Ishida H, Yamane T (2003) Protein Eng 16: 467-478; and Kulharia M, Bridgett S J, Goody R S, Jackson R M (2009) InCa-SiteFinder: a method for structure-based prediction of inositol and carbohydrate binding sites on proteins. J Mol Graph Model 28: 297-303.

Analysis of binding site residues along with stabilizing residues in protein-carbohydrate complexes can allow for identification of folding and binding of the complexes to understand interactions in addition to non-covalent interactions of hydrogen bonding and non-polar interactions. See, e.g., Shanmugam et al., doi.:10.2174/0929866525666180221122529. Utilizing publicly available tools, carbohydrate binding moieties, including binding sites and predicted folding can be used for the design of chimeric small molecules comprising such a carbohydrate binding moiety.

Lipid Binding Moieties

In one example embodiment, the target binding moiety is a lipid binding moiety. Lipid binding moieties can be utilized as target binding moieties in the chimeric small molecules disclosed herein. As regulators of cellular stabilization and signaling, modifications in their composition, distribution or trafficking would be useful in treatment, regulation and/or modification of pathways, processes and conditions. Lipids include charged lipids, e.g. phosphatidylserine (PS), phosphatidic acid (PA), phosphatidylinositol (PI), and the PI-phosphate, -bisphosphate, and -trisphosphate (PIPs—a family of seven anionic charged lipids), and ganglioside (GM). Zwitterionic lipids, e.g., phosphatidylcholine (PC), phosphatidylethanolamine (PE), and sphingomyelin (SM) lipids, Ceramides (CER), diacylglycerol (DAG), and lysophosphatidylcholine (LPC) lipids, sphingolipids, glycerophospholipids, cholesterol, phosphatidylglycerols.

Lipid binding moieties may be incorporated into chimeric small molecules. For example, certain steroids are capable of targeting and binding to lipids. Other lipid binding moieties such as proteins can either bind lipids specifically, where a clear binding site for a given lipid can be identified, or nonspecifically, where lipids act as a medium, and physical properties like thickness, fluidity, or curvature regulate the protein function. Phosphoinositide binding domains such as FYVE or PX, or the FRRG motif in the β-propeller of PROPPINs are more common domains that can be used to identify lipid binding proteins. The FYVE domain, named after the first four proteins to contain the motif (Fab1, YOTB, Vac1 EEA1) contains several conserved regions, which can also be utilized to identify related domains. See, e.g., A. H. Lystad, A. Simonsen Phosphoinositide-binding proteins in autophagy, FEBS Lett., 590 (2016), pp. 2454-2468, 10.1002/1873-3468.12286. Additional FYVE domain-containing proteins include SARA, FRABIN, DFCP1 FGD1, ANKFY1, EEA1 FGD1, FGD2, FGD3, FGD4, FGD5, FGD6, FYCO1, HGS MTMR3, MTMR4, PIKFYVE, PLEKHF1, PLEKHF2, RUFY1, RUFY2, WDF3, WDFY1, WDFY2, WDFY3, ZFYVE1, ZFYVE16, ZFYVE19, ZFYVE20, ZFYVE21, ZFYVE26, ZFYVE27, ZFYVE28, ZFYVE9.

Eukaryotic cells can degrade intracellular components through a lysosomal degradation pathway called macroautophagy, with pathway malfunction linked to several diseases. Dikic et al., Mechanism and medical implications of mammalian autophagy. Nat. Rev. Mol. Cell Biol., 19 (2018), pp. 349-364, doi: 10.1038/s41580-018-0003-4. Accordingly, autophagy related (ATG) proteins may be utilized as lipid binding moiety in the present invention, including LC3A, LC3B, LC3C, GABARAP, GABARAPL1 and GABARAPL2. De la Ballina (2019), doi.org/10.1016/j.jmb.2019.05.051. Lipid-binding proteins include protein HCLS1 binding protein 3 (HS1BP3) that is able to negatively regulate the activity of phospholipase D1 (PLD1).

Target Protein Binding Moiety

As detailed herein, target protein binding moieties for exemplary proteins of interest to be targeted for modification are provided. The target protein binding moiety is chosen based on the desired association and modification. Accordingly, the modifications desired, which may be tailored based on a particular condition, disease, treatment, or other desired effect, will be a design consideration when choosing the protein binding moiety.

The target protein binding moiety may be chosen for a specific protein of interest, which may be located in different localization sites of the cell, e.g. nucleus, cytoplasm, mitochondria, cell surface. Example target protein binding moieties are disclosed for example in, Sun et al., Signal Transduction and Targeted Therapy, 4:64 (2019), which provides exemplary proteins and corresponding ligands (i.e. target polypeptide binding moieties, see in particular FIGS. 5-48, which is incorporated herein by reference). The target protein binding moiety may bind to proteins which undergo conformation change upon binding.

The target protein binding moiety may bind to proteins which undergo conformation change upon binding, for example, an androgen receptor (AR). In one embodiment, activation of the protein results in modification of the target substrate by the protein at one or more new modification sites that would otherwise remain unmodified by the protein when not activated by the chimeric small molecule. The target substrate is not required to be a natural substrate of the protein. The target substrate may be a protein, and discussion herein of genes includes the products of the gene expression.

In one embodiment, the target protein binding moiety is capable of binding a protein that is an ATPase or GTPase. Exemplary GTPases may be from the Ras, Rho, Rab, Arf or Ran family, see, e.g. Yoshimi Takai, Takuya Sasaki, and Takashi Matozaki, Small GTP-Binding Proteins, Physiological Reviews 2001 81:1, 153-208; doi: 10.1152/ohysrev.2001.81.1.153. Exemplary molecules targeting may include molecules such as Ibrutinib (BTK), Dasatinib (BCR-ABL), MRTX (KRAS), MI-1061 (MDM2), Gefitinib (EGFR), Palbociclib (CDK4/6) and Foretinib (C-MET), or analogs thereof.

In one example embodiment the target substrate is modified with an orthogonal tag, e.g. FKBP12$^{F36V}$ SNAP-, CLIP-, ACP- and MCP-tags, and the target binding moiety is a binder of the orthogonal tag. See, e.g. neb.com/tools-and-resources/feature-articles/snap-tag-technologies-novel-tools-to-study-protein-function, incorporated herein by reference.

The following provide examples of further, non-limiting, target protein binding moieties to various target proteins of interest in oncology and infectious disease contexts and the use of which will discussed further in the Methods of Use section below.

KRAS

In one example embodiment, the target protein binding moiety is a KRAS binding moiety. In one example embodiment, the target protein binding moiety is a KRAS binder according selected from the group consisting of;

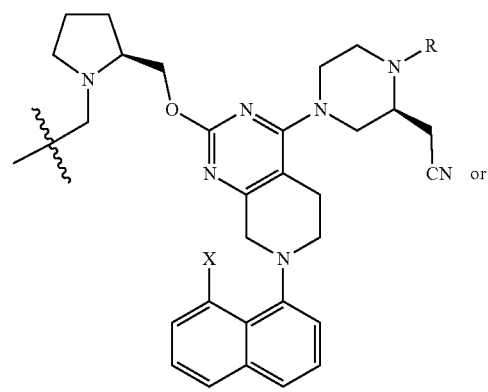

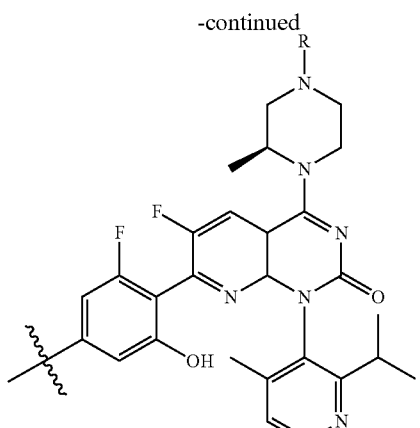

wherein R is a covalent warhead; X is the formula

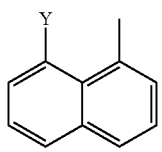

and Y is selected from the group consisting of: H, alkane, alkene, alkyne, amine, nitrile, nitro, ether, alcohol, thiol, sulfone, sulfonate, halogen, carbonyl, acyl, ketone, carboxylate ester, amide, enone, anhydride, imide, cyclic hydrocarbon, an unsaturated cyclic hydrocarbon, a heterocycle, one or more fused rings thereof, or an aliphatic halides such as —OCF$_2$Cl.

In one example embodiment, the target binding moiety is a hydrogen bond surrogate (HBS) Son of Sevenless (SOS) peptide mimics (PM). In one example embodiment, the HBS-SOS-PM is HBS 1-7 according to the sequences: XFE*GIYRTDILRTEEGN-NH2 (SEQ ID NO: 4); XFE*GIYRTELLKAEEAN-NH2 (SEQ ID NO: 5); XFE*GIYRLELLKAEEAN-NH2 (SEQ ID NO: 6); XFE*GIYRLELLK-NH2 (SEQ ID NO: 7); XFE*AIYRLELLKAEEAN-NH2 (SEQ ID NO: 8); XFE*GIYRLELLKAibEEAibN-NH2 (SEQ ID NO: 9); and XAE*GIYRLELLKAEAAA-NH2 (SEQ ID NO: 10), respectively, wherein X denotes a 4-pentenoic acid residue and the asterisk (*) denotes N-allyl residue (*G, N-allylglycine). In one example embodiment, the target binding moiety is a KRAS binding molecule HB3 according to the formula: XFE*GIYRLELLKAEEAN-NH2 (SEQ ID NO: 6). In one example embodiment, the target binding moiety is a KRAS binding molecule HB7 according to the formula: XAE*GIYRLELLKAEAAA-NH2 (SEQ ID NO: 10). See Nickerson et al., An Orthosteric Inhibitor of the RAS-SOS Interaction, doi: 10.1016/B978-0-12-420146-0.00002-0 incorporated herein by reference in its entirety with specific mention of Table 2.1.

In one example embodiment, the target binding moiety is a KRAS binding molecule according to the formula:

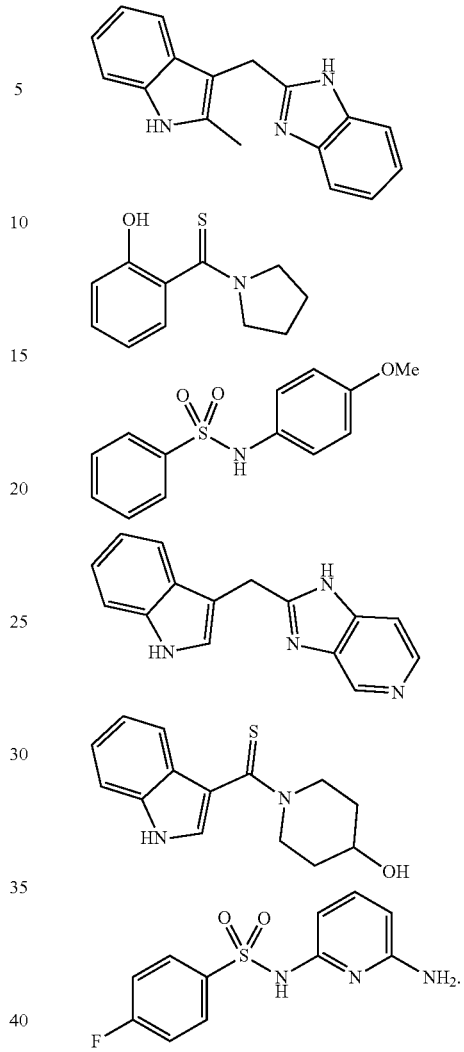

In one example embodiment, the target binding moiety is a KRAS binding moiety according to the formula:

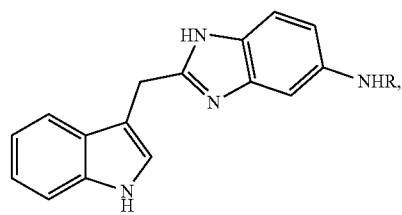

wherein R may be H, Gly, Ala, β-Ala, Val, Ile, Pro, or any other feasible substituent known in the art. In one example embodiment, the target binding moiety is a KRAS binding moiety is an indole, phenol, sulfonamide, or any modified version thereof. See Sun et al., Angew Chem Int Ed Engl. 2012 Jun. 18; 51(25): 6140-6143. doi: 10.1002/anie.201201358, herein incorporated by reference in its entirety.

In one example embodiment, the target binding moiety is a KRAS binding molecule according to the formula:

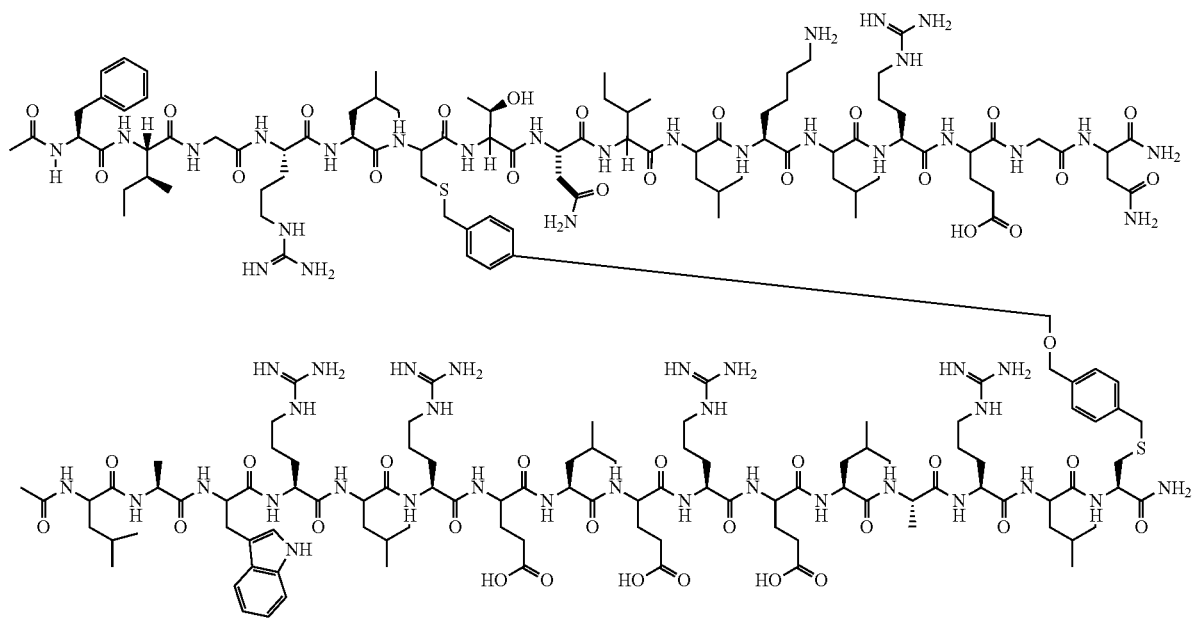
CHD$^{Sos}$-1
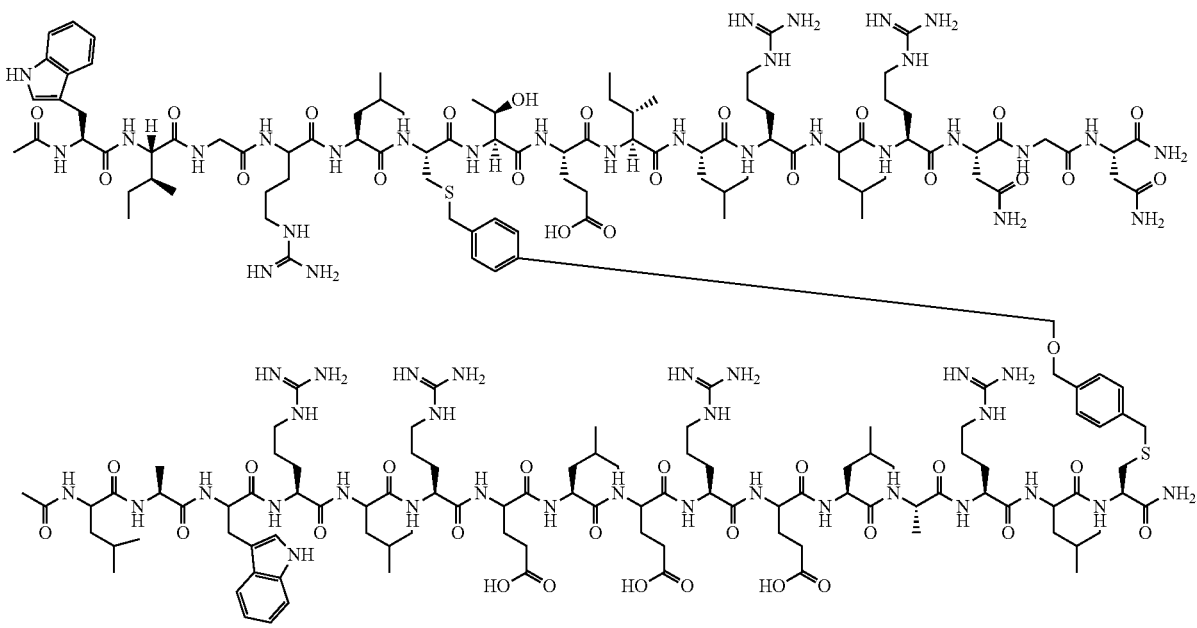
CHD$^{Sos}$-2

CHD<sup>Sos</sup>-2
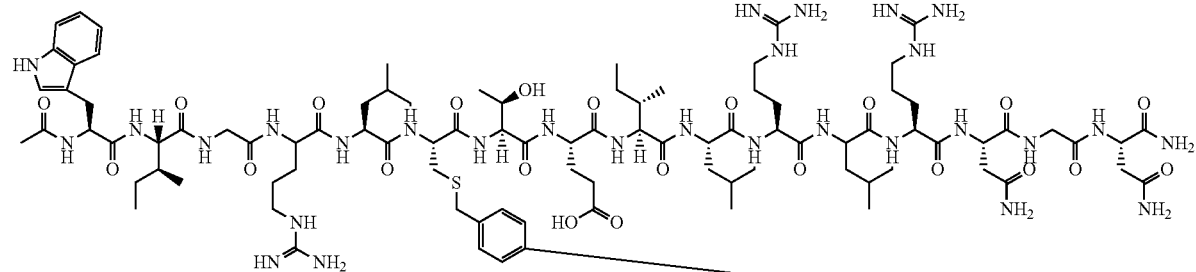
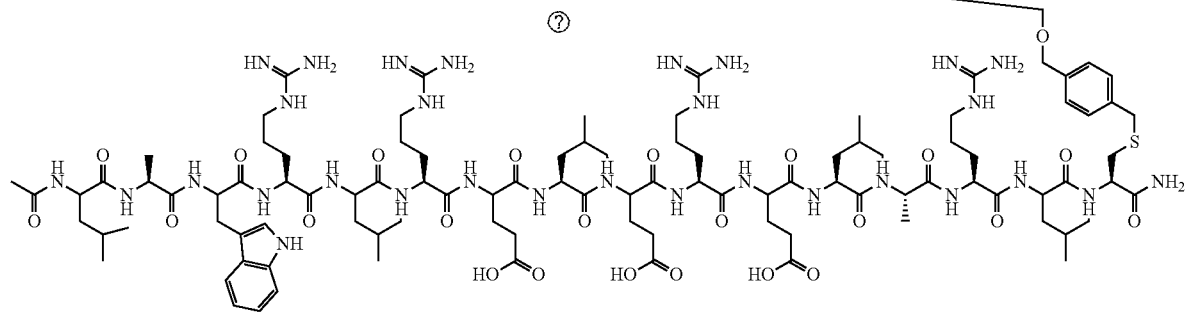
CHD<sup>Sos</sup>-3
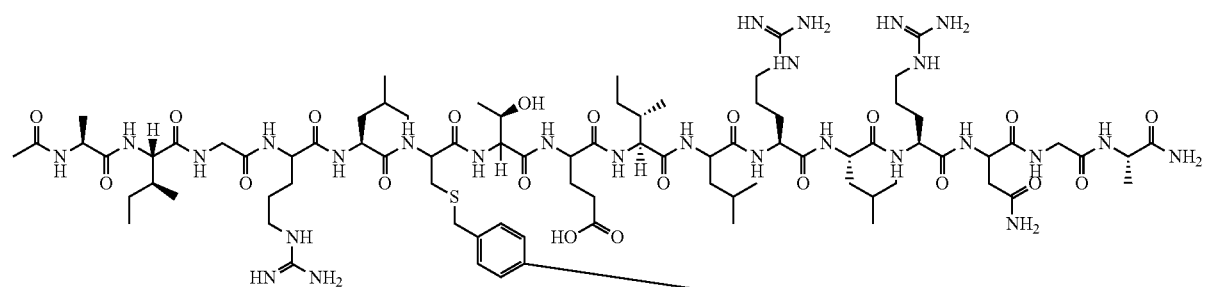
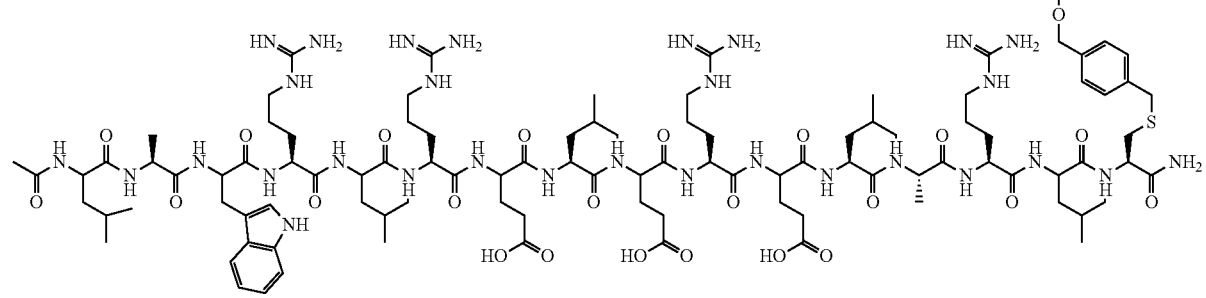

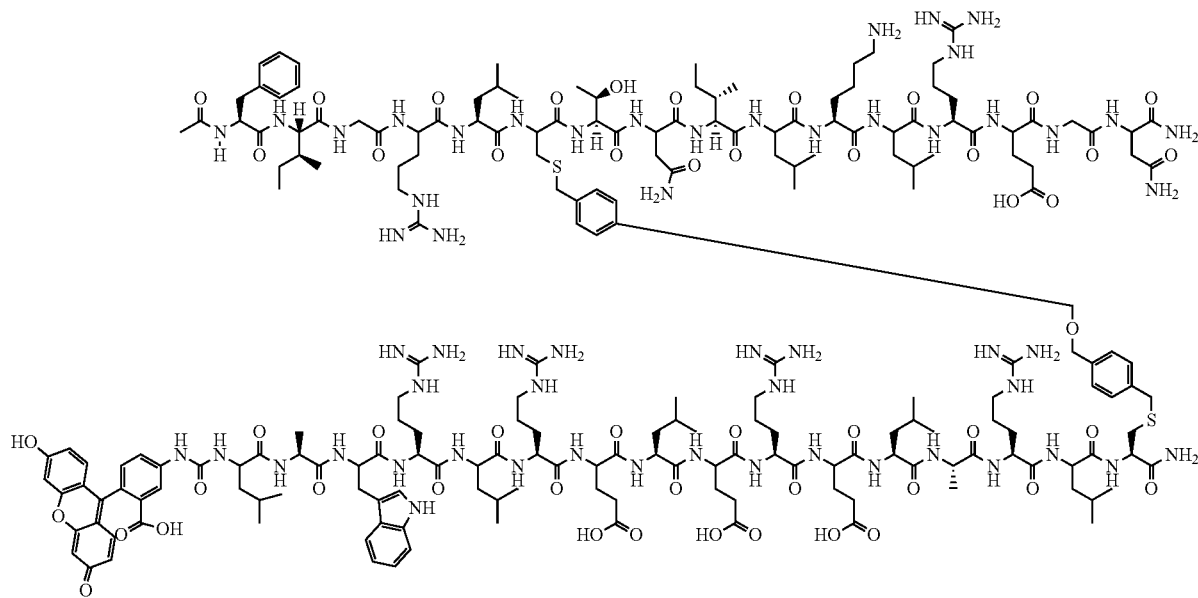
FITC-CHD<sup>Sos</sup>-1
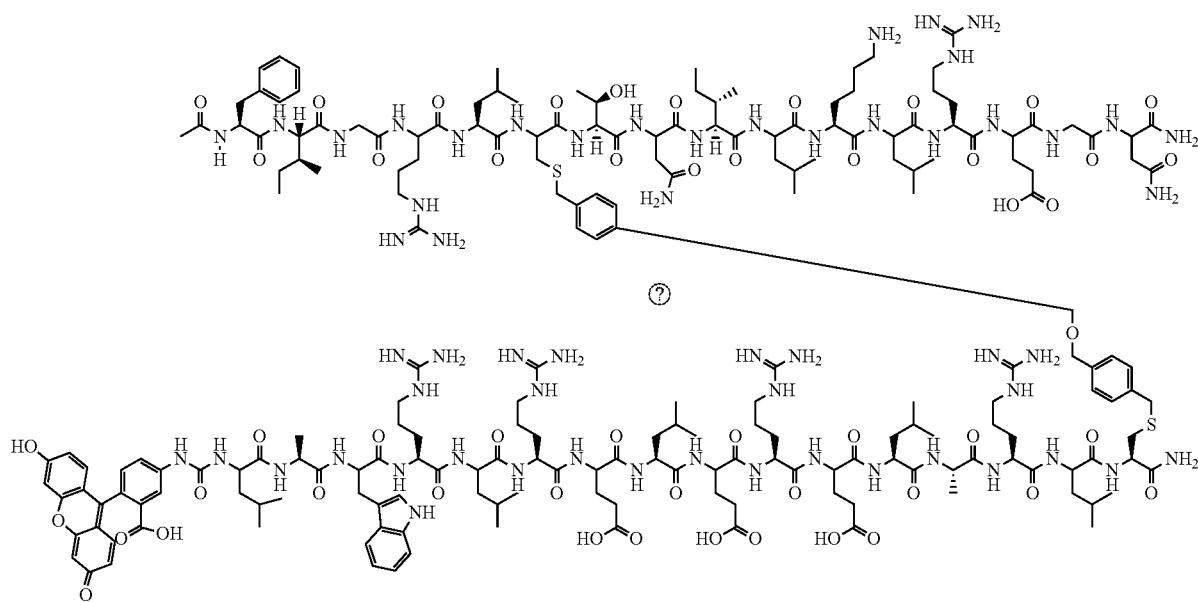
FITC-CHD<sup>Sos</sup>-1

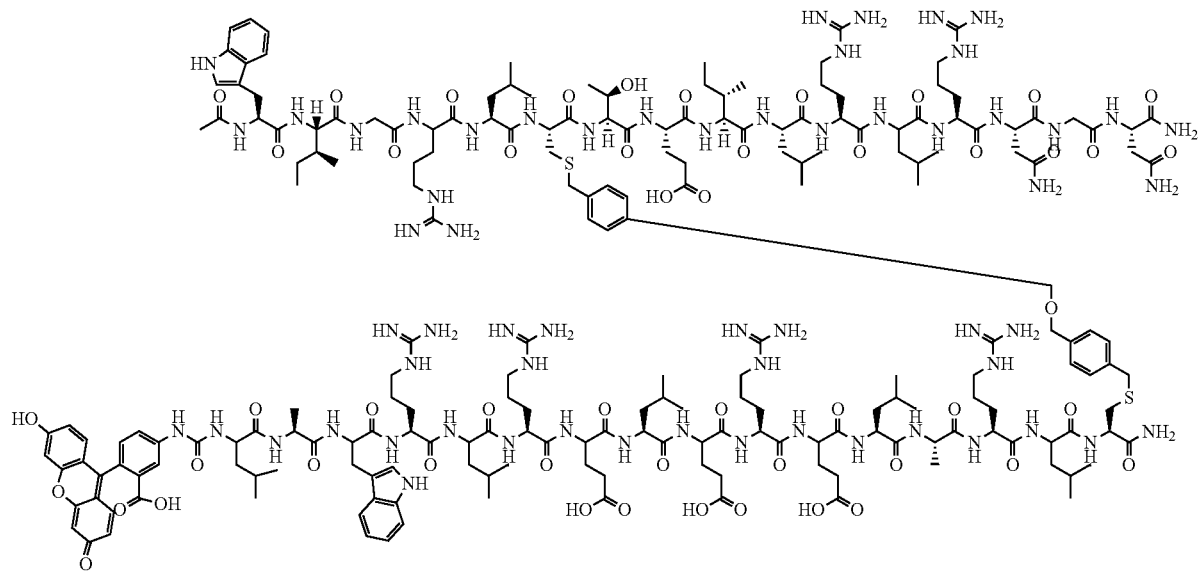
FITC-CHD^Sos-2
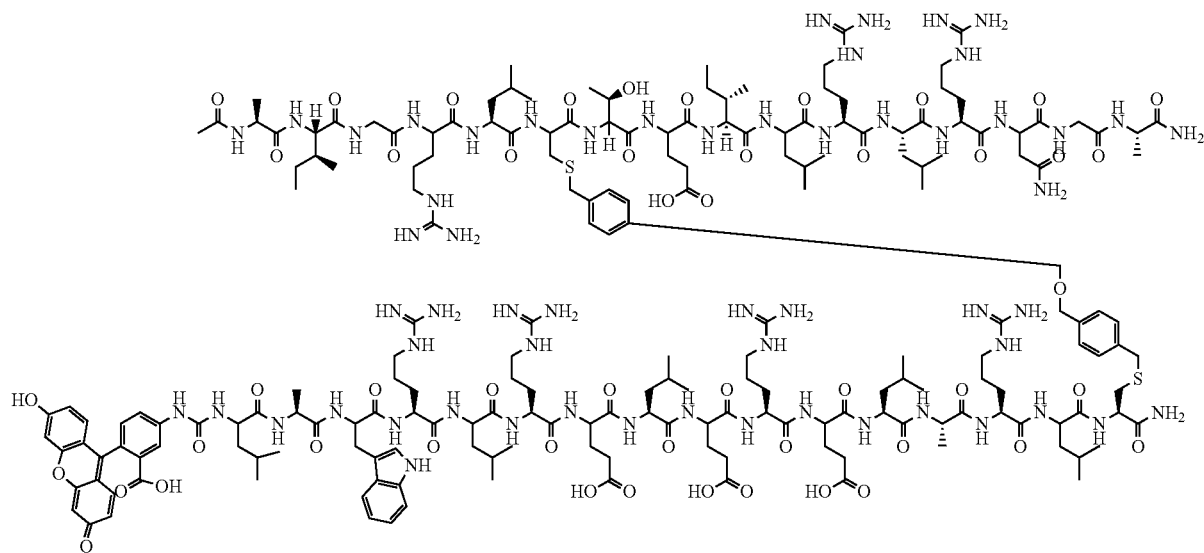
FITC-CHD^Sos-3

-continued
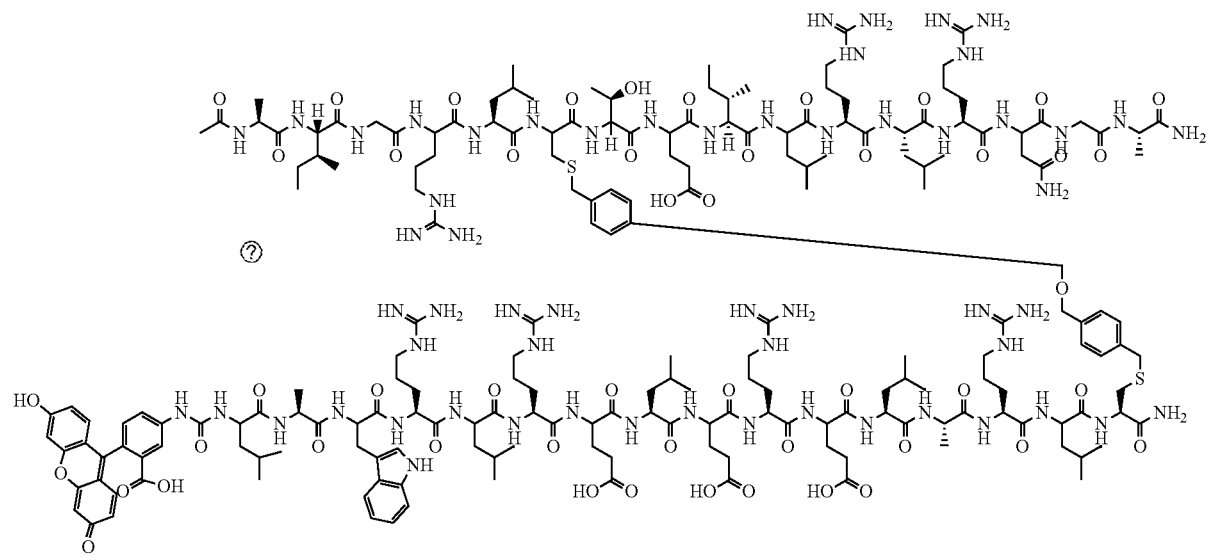
FITC-CHD^Sos-3
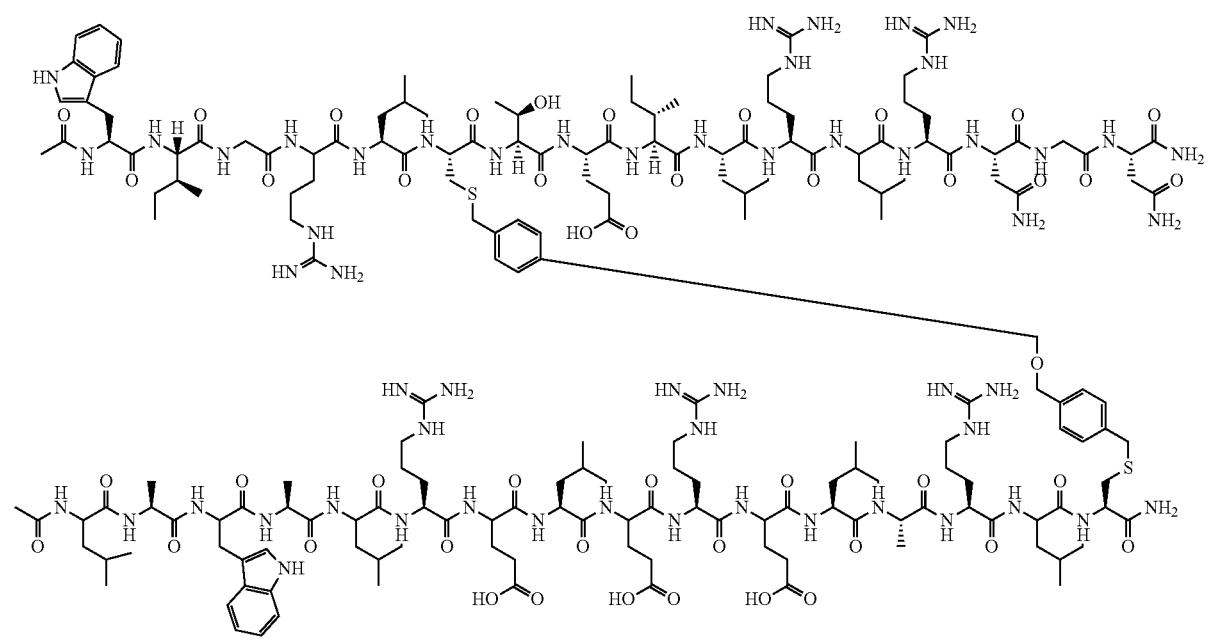
CHD^Sos-4

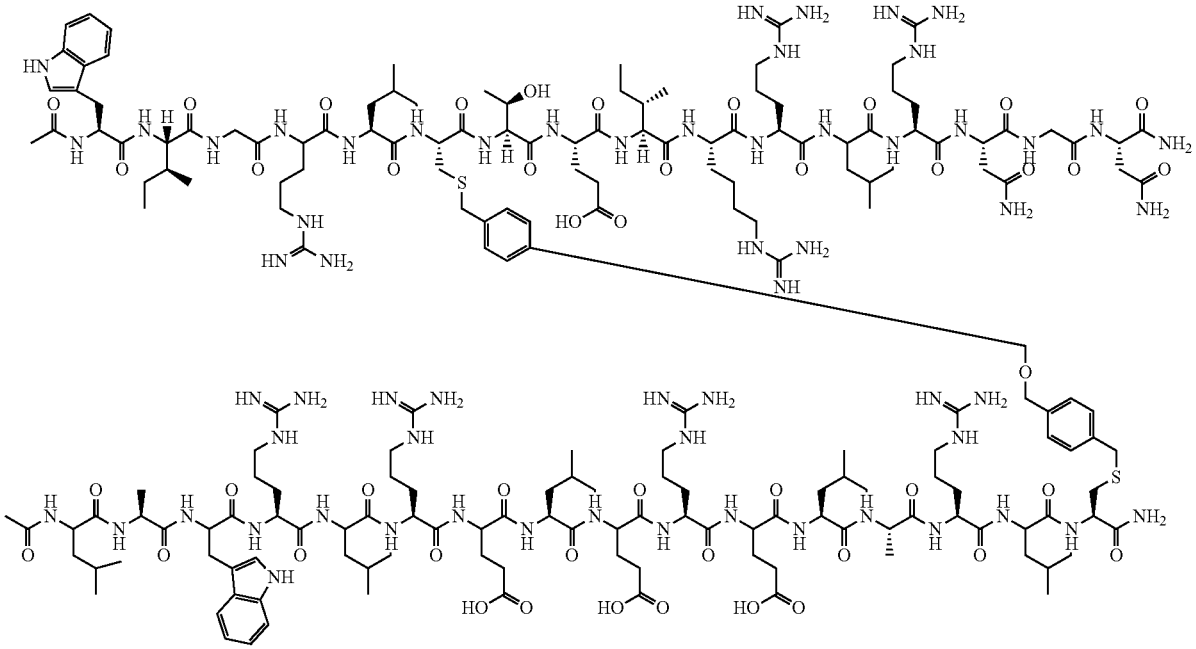
CHD<sup>Sos</sup>-5
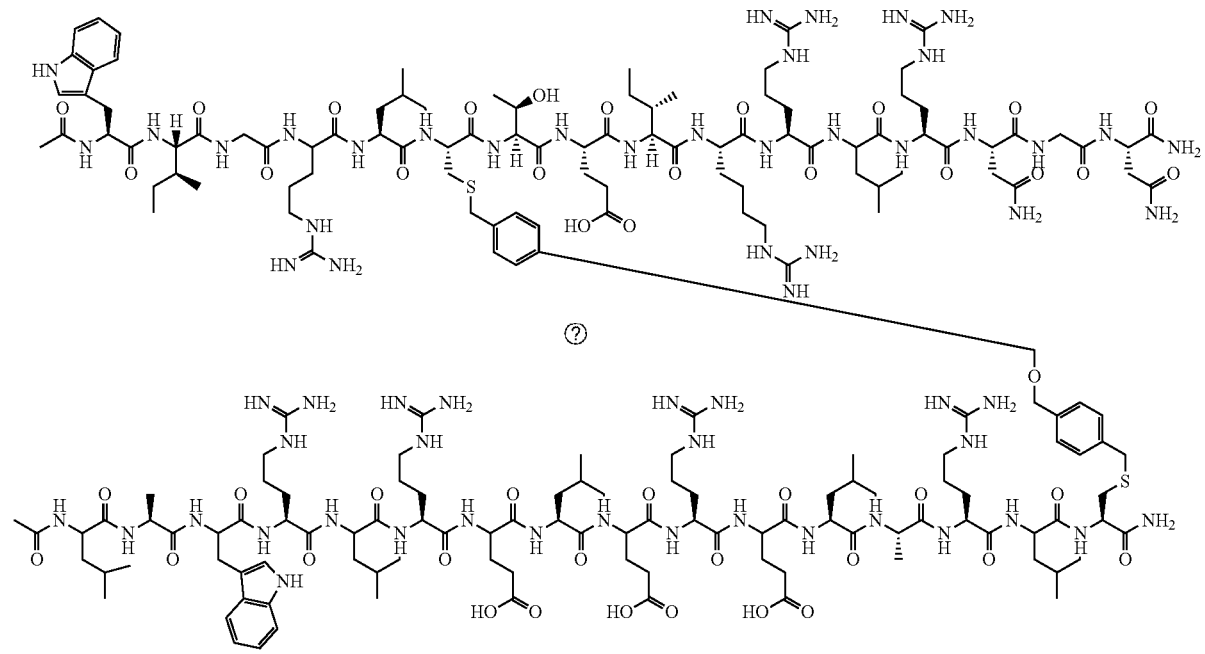
CHD<sup>Sos</sup>-5

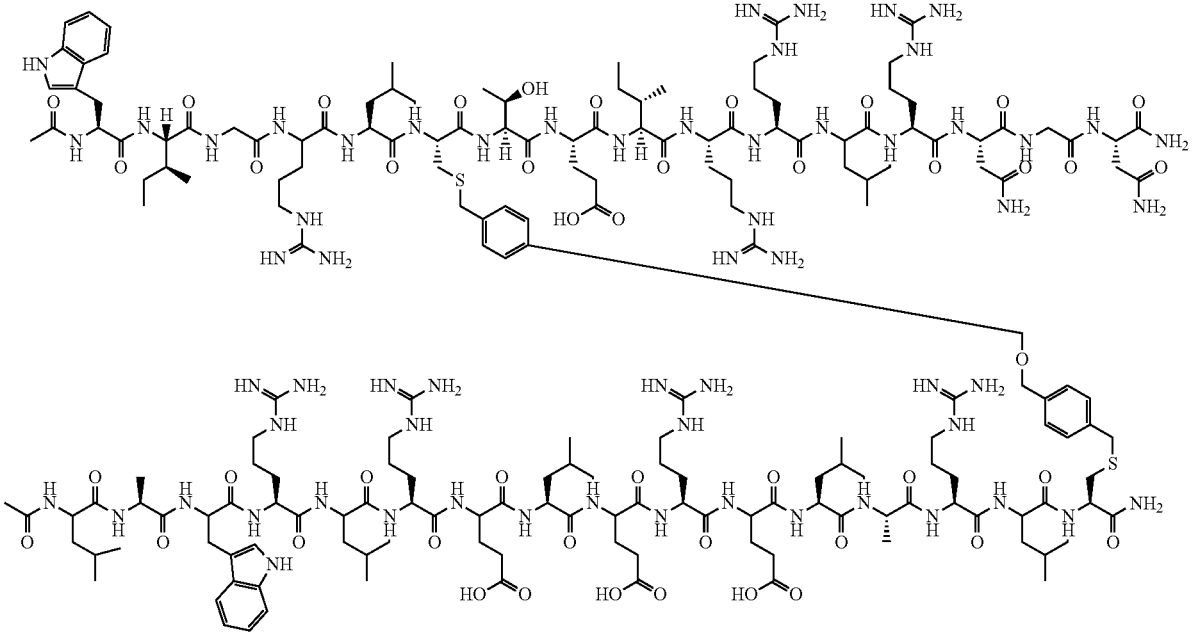
CHD<sup>Sos</sup>-6
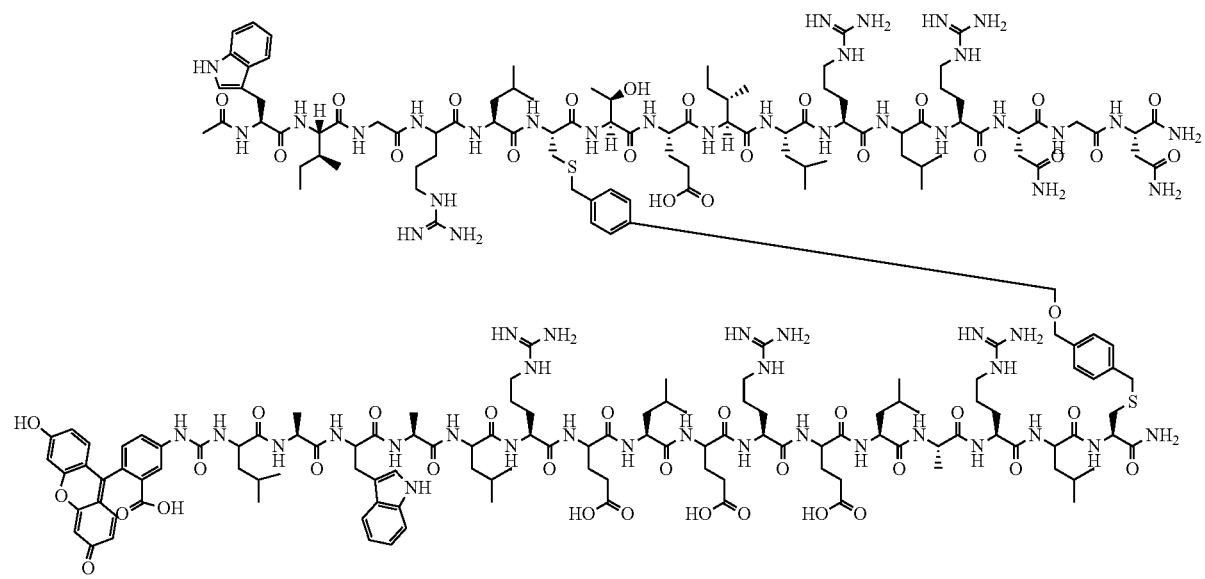
FITC-CHD<sup>Sos</sup>-4

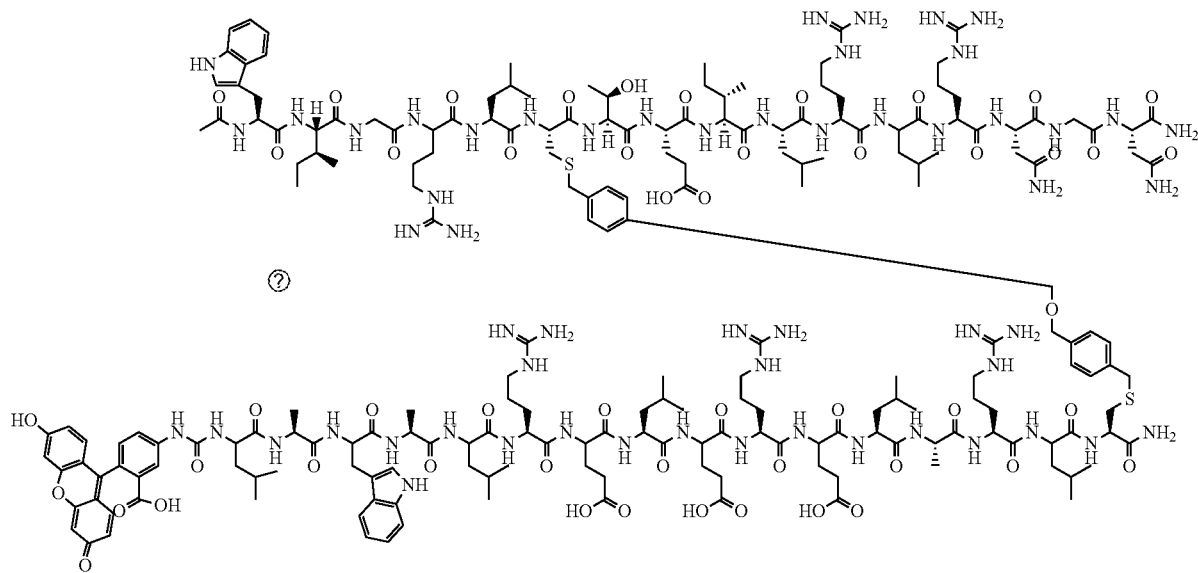
FITC-CHD^Sos-4
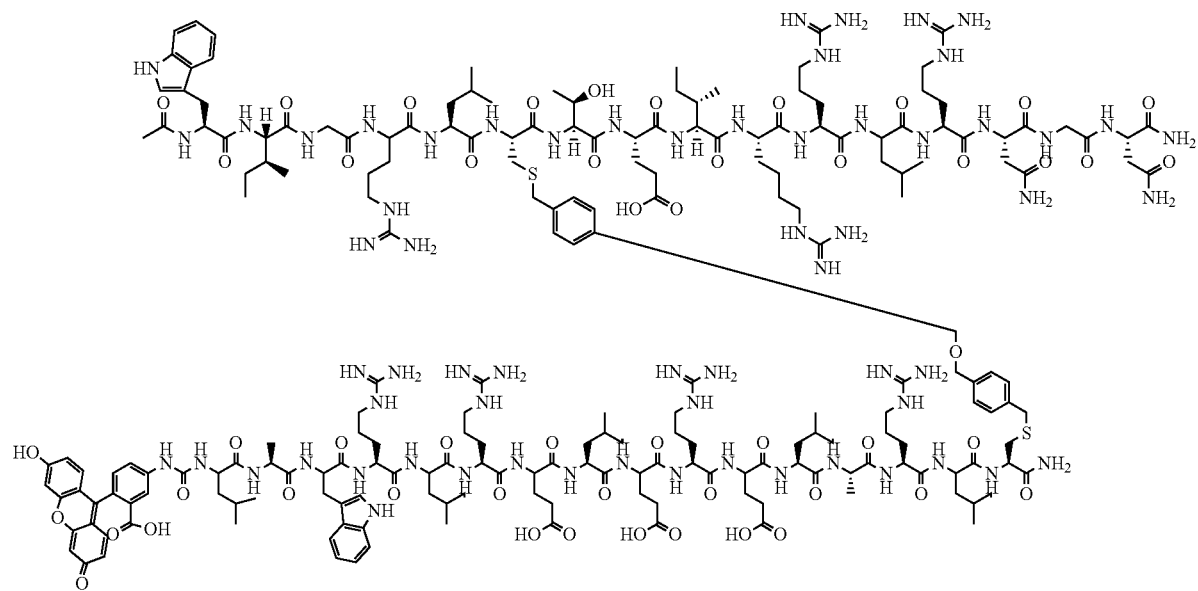
FITC-CHD^Sos-5

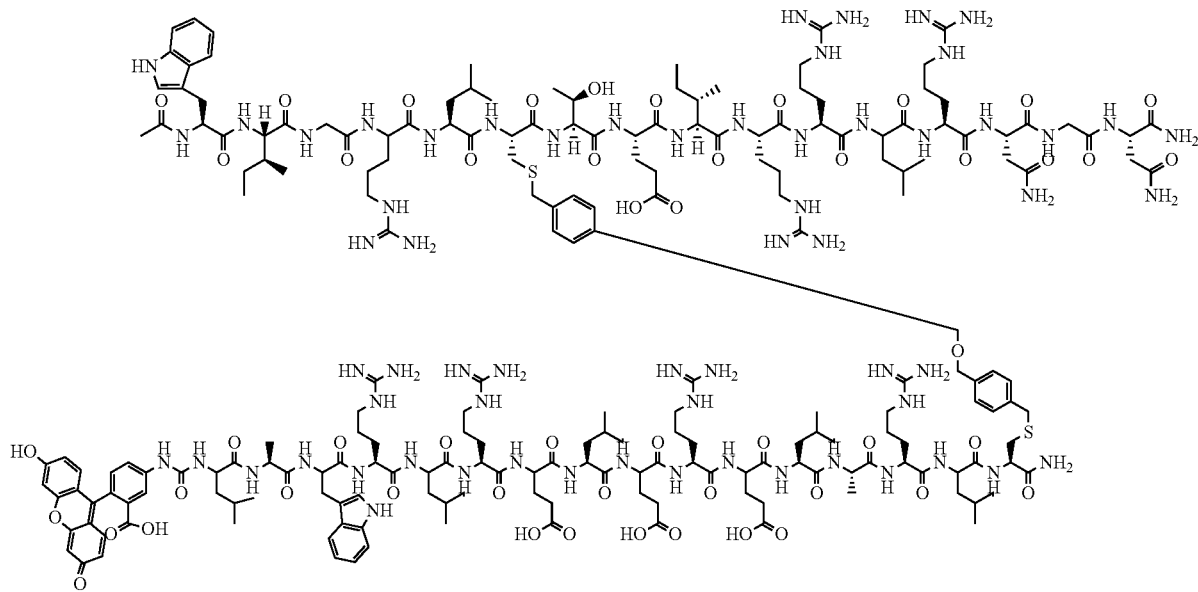
FITC-CHD$^{Sos}$-6
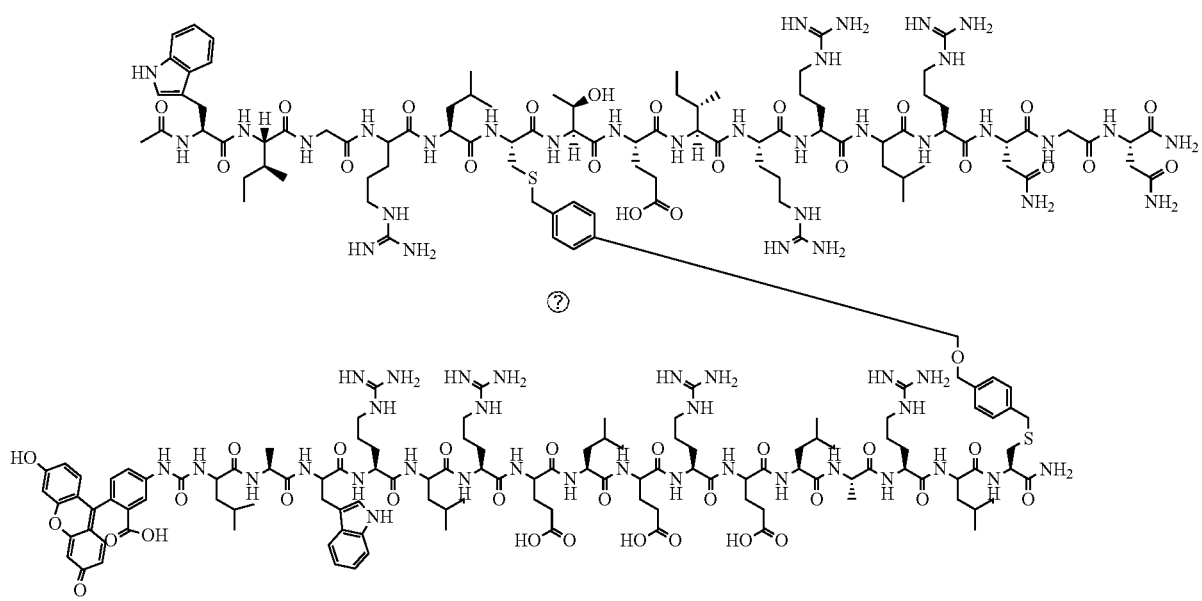
FITC-CHD$^{Sos}$-6

-continued
DZ1-CHD$^{Sos}$-5
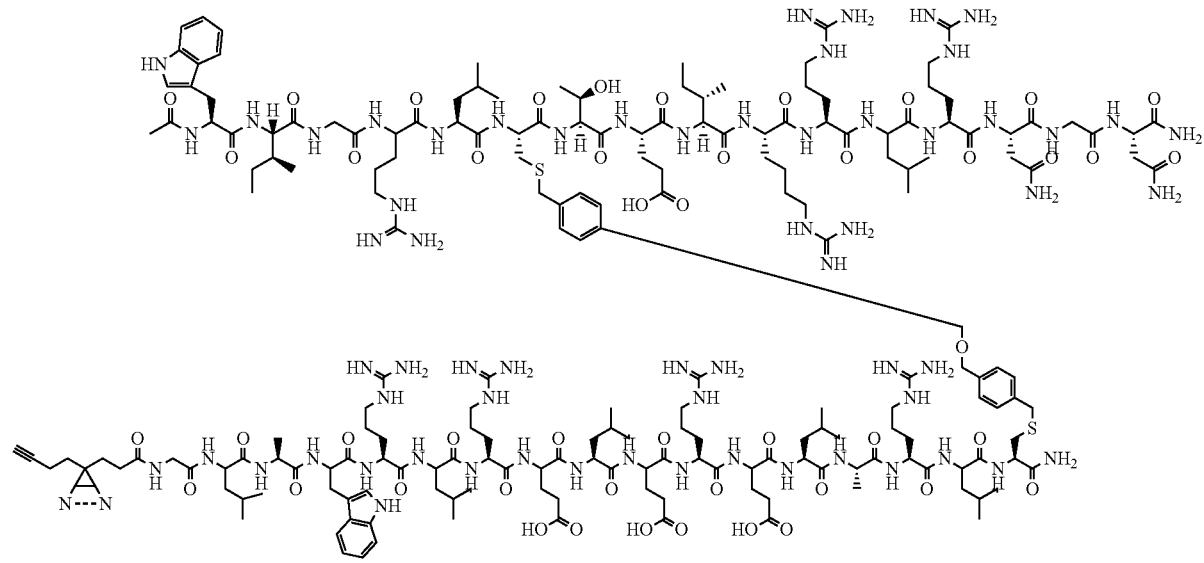
DZ2-CHD$^{Sos}$-5
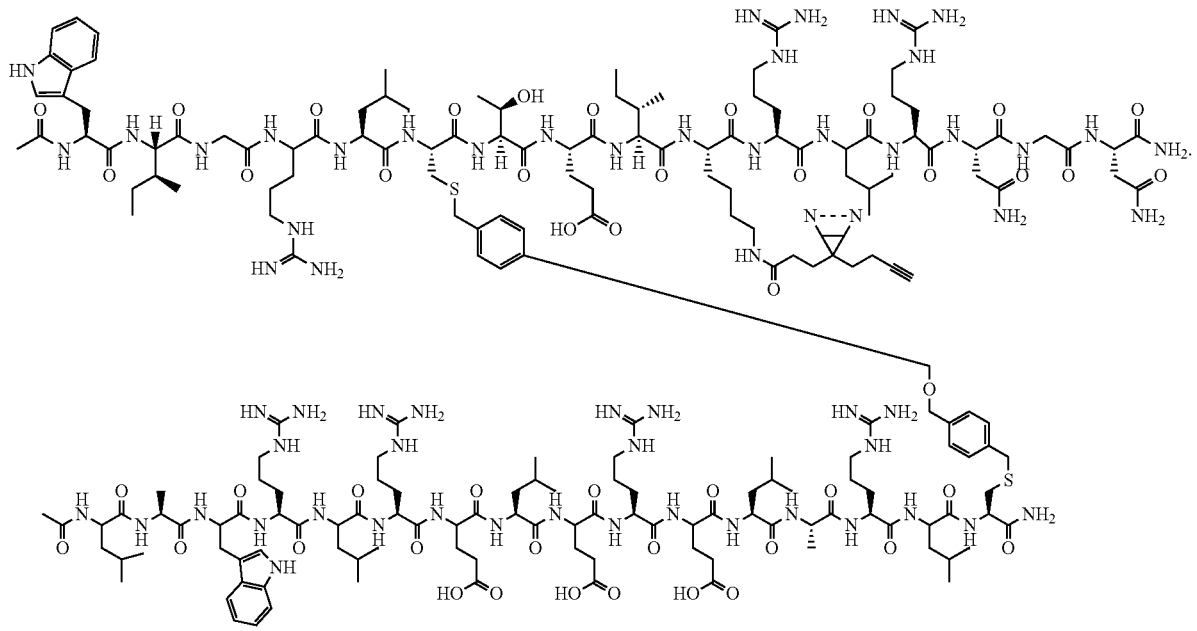

-continued

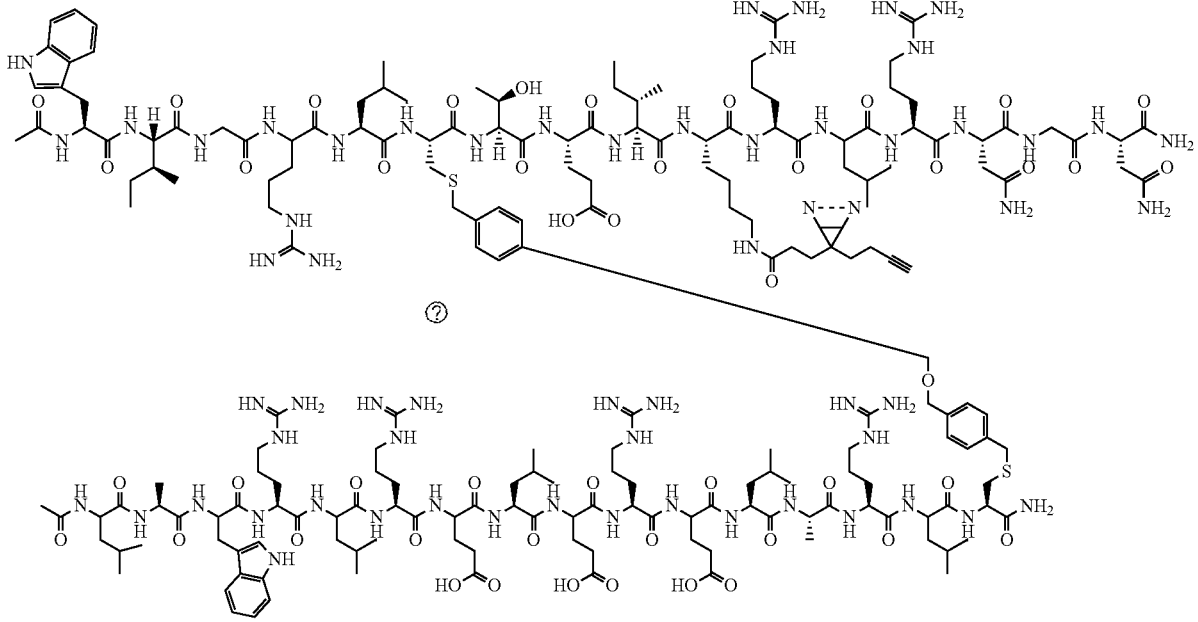

In one example embodiment, the target binding moiety is a SOS peptide mimic according to the formula: Ac-FI-GRLCTEILKLREGN-NH2 (SEQ ID NO: 11); Ac-LAWRLRELERELARLC-NH2 (SEQ ID NO: 12); Ac-WIGRLCTEILRLRNGN-NH2 (SEQ ID NO: 13); Ac-LAWRLRELERELARLC-NH2 (SEQ ID NO: 14); Ac-AIGRLCTEILRLRNGA-NH2 (SEQ ID NO: 15); Ac-LAWRLRELERELARLC-NH2 (SEQ ID NO: 16); Ac-WIGRLCTEILRLRNGN-NH2 (SEQ ID NO: 17); Ac-LAWALRELERELARLC-NH2 (SEQ ID NO: 18); Ac-WIGRLCTEIR$^H$RLRNGN-NH2 (SEQ ID NO: 19); Ac-LAWRLRELERELARLC-NH2 (SEQ ID NO: 20); Ac-WIGRLCTEIRRLRNGN-NH2 (SEQ ID NO: 21); Ac-LAWRLRELERELARLC-NH2 (SEQ ID NO: 22); Ac-WIGRLCTEILRLRNGN-NH2 (SEQ ID NO: 23); Ac-LAWRLRELERELARLC-NH2 (SEQ ID NO: 24); Ac-FI-GRLCTEILKLREGN-NH2 (SEQ ID NO: 25); FITC-Aβ3LAWRLRELERELARLC-NH2 (SEQ ID NO: 26); Ac-WIGRLCTEILRLRNGN-NH2 (SEQ ID NO: 27); FITC-AβLAWRLRELERELARLC-NH2 (SEQ ID NO: 28); Ac-AIGRLCTEILRLRNGA-NH2 (SEQ ID NO: 29); FITC-AβLAWRLRELERELARLC-NH2 (SEQ ID NO: 30); Ac-WIGRLCTEILRLRNGN-NH2 (SEQ ID NO: 31); FITC-AβLAWALRELERELARLC-NH2 (SEQ ID NO: 32); Ac-WIGRLCTEIR$^H$RLRNGN-NH2 (SEQ ID NO: 33); FITC-AβLAWRLRELERELARLC-NH2 (SEQ ID NO: 34); Ac-WIGRLCTEIRRLRNGN-NH2 (SEQ ID NO: 35); FITC-AβLAWRLRELERELARLC-NH2 (SEQ ID NO: 36); Ac-WIGRLCTEIR$^H$RLRNGN-NH2 (SEQ ID NO: 37); DZ-GLAWRLRELERELARLC-NH2 (SEQ ID NO: 38); Ac-WIGRLCTEIK(DZ)RLRNGN-NH2 (SEQ ID NO: 39); or Ac-LAWRLRELERELARLC-NH2 (SEQ ID NO: 40), wherein $R^H$ is L-homoarginine; Aβ is L-β-alanine; DZ is diazirine photocrosslinker; and FITC is 5-fluorescein isothiocyanate linked via thiourea bond to N-terminal amine. See Hong et al., PNAS May 4, 2021 118(18)e2101027118; doi:10.1073/pnas.2101027118, herein incorporated by reference in its entirety with specific mention of Table S2.

In one example embodiment, the target binding moiety is a KRAS binding molecule according to the formula:

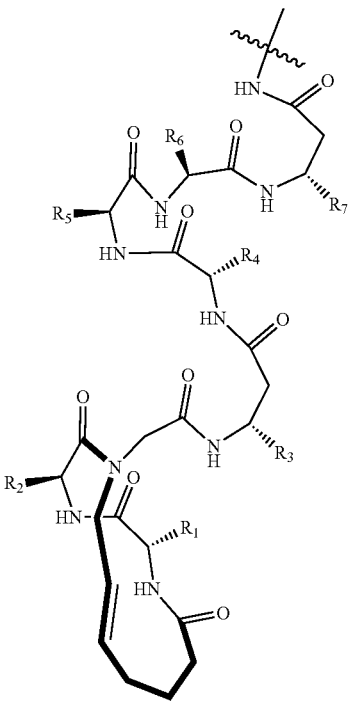

wherein the R groups may be any substituent known in the art. In one example embodiment, $R_4$ is an electrophilic group. In one example embodiment the $R_4$ is

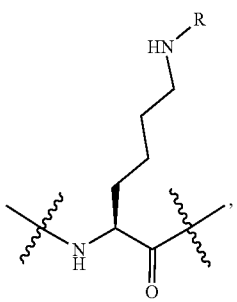

where R is H,

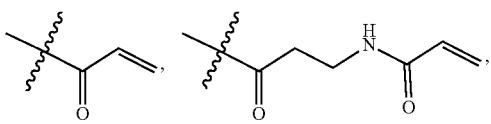

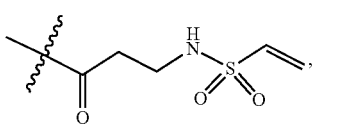

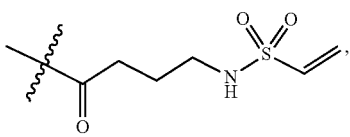

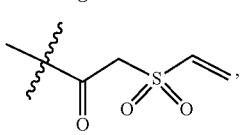

, or

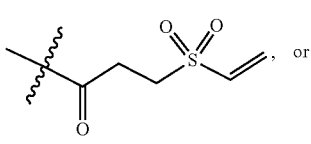

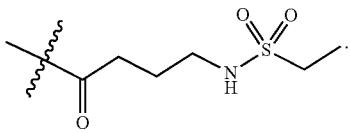

Yoo et al., ACS Chem. Biol. 2020, 15, 6, 1604-1612, incorporated herein by reference in their entirety.

FKBP12$^{F36V}$

In another example embodiment, the protein binding moiety can be designed to bind an FK506-binding protein (FKBP). The FKBP may be FKBP12, which binds to intracellular calcium release channels and TGF-β type I receptor. In one example embodiment, the FKBP protein binding moiety is an FKBP12$^{F36V}$ binding molecule. In another example embodiment, the binding molecule is selected from

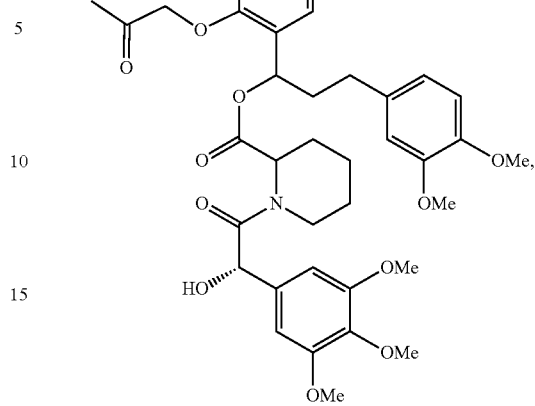

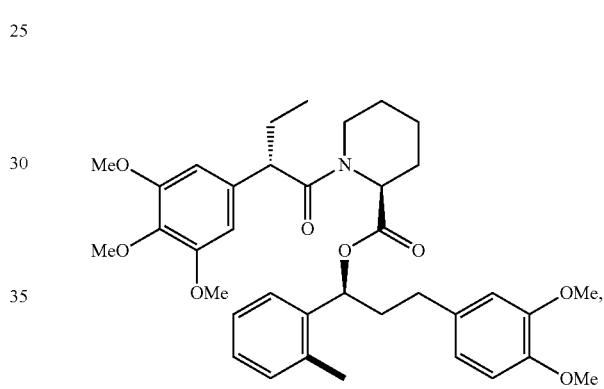

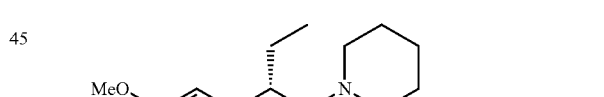

analog thereof.

Tyrosine phosphorylation on FGFR1 can trigger signaling cascade to induce PI3K/AKT/mTOR signaling and increased transcription of G-CSF, a blood growth factor. See, e.g. Turner et al, Nature Reviews Cancer 2010.

In one example embodiment, an ABL kinase is utilized to target the FKBP12$^{F36V}$ In an embodiment, the chimeric small molecule is selected from:

203  204
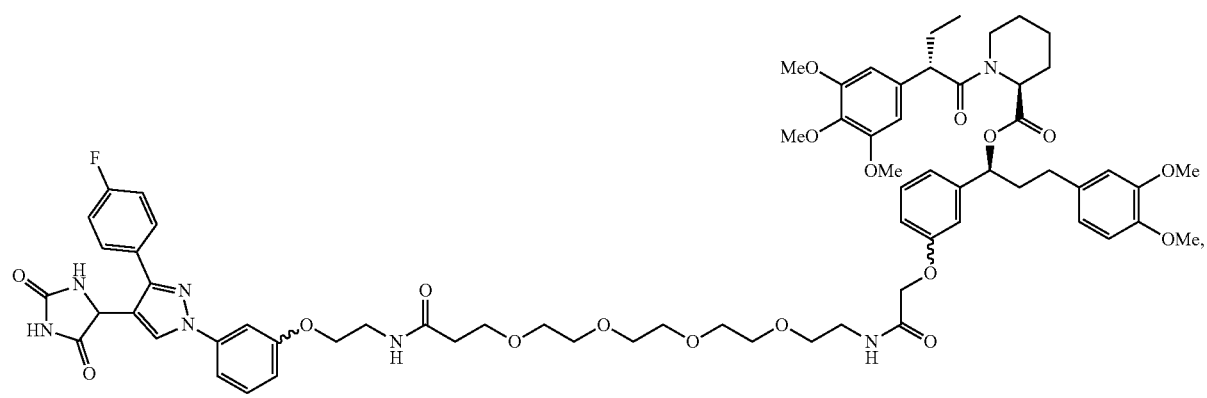
AD-181 (DPHm-F36Vm)
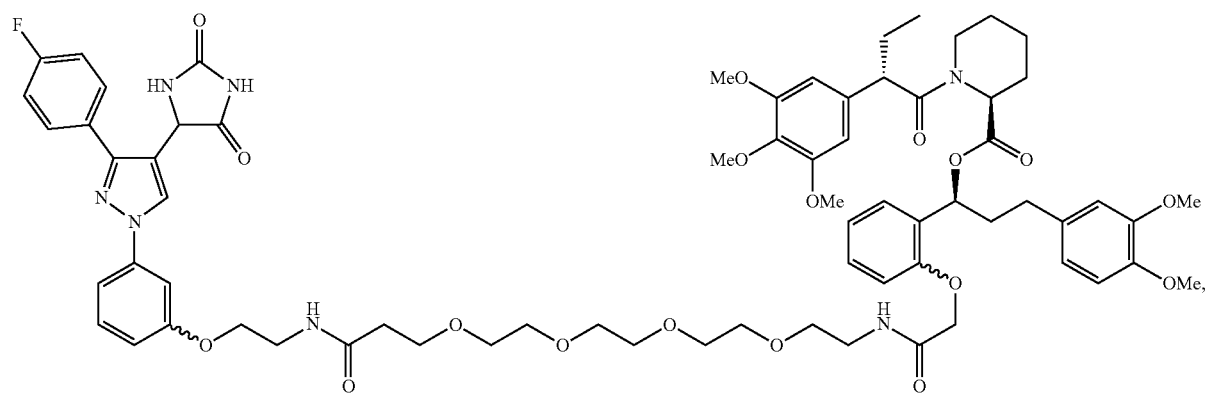
AD-194 (DPHm-F36Vo)
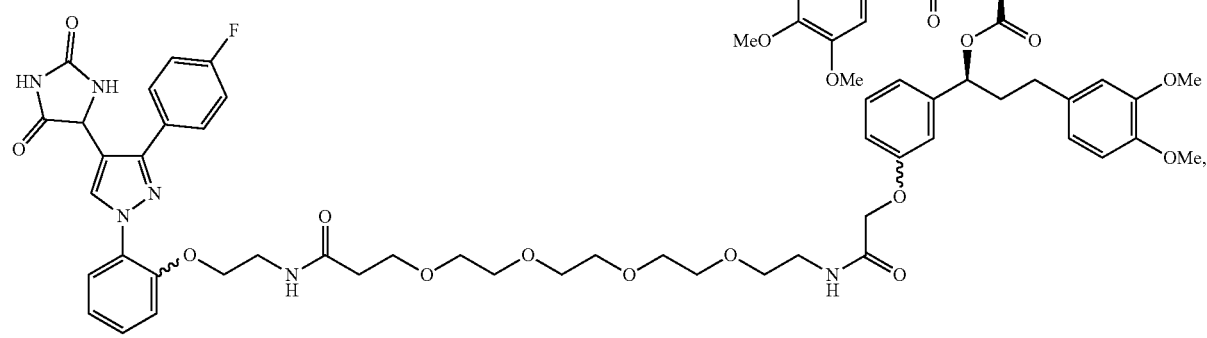
AD-220 (DPHo-F36Vm)

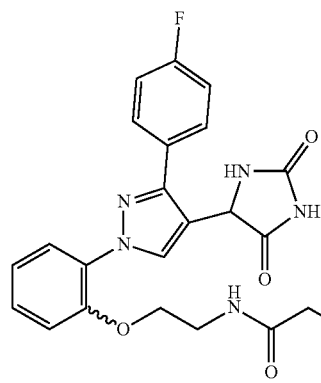
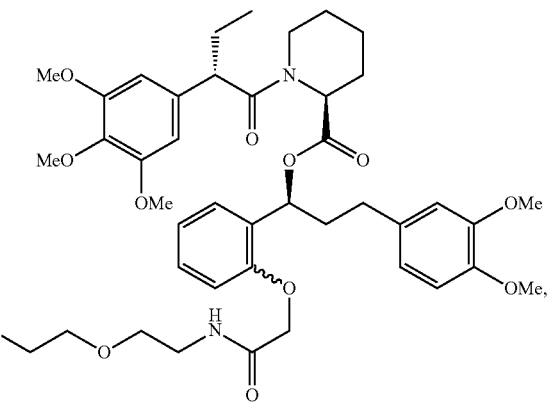
AD-221 (DPHo-F36Vo)
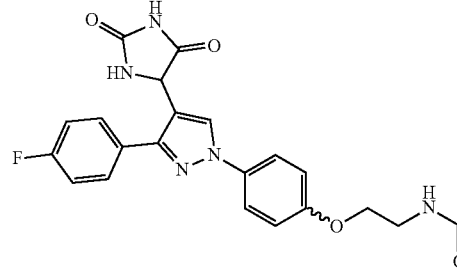
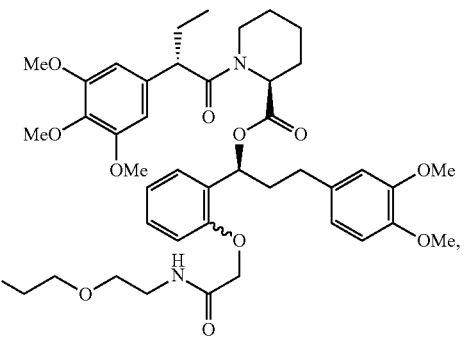
AD-217 (DPHp-F36Vo)
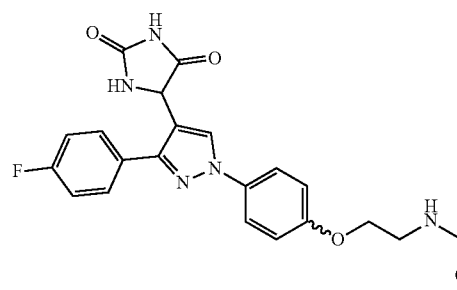
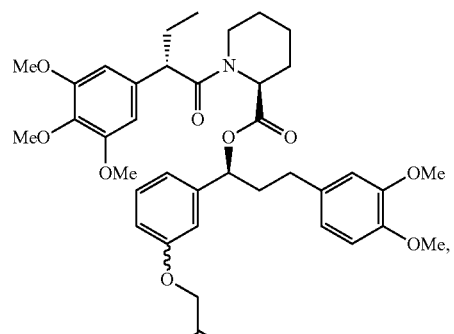
AD-202 (DPHp-F36Vm)

VS1043
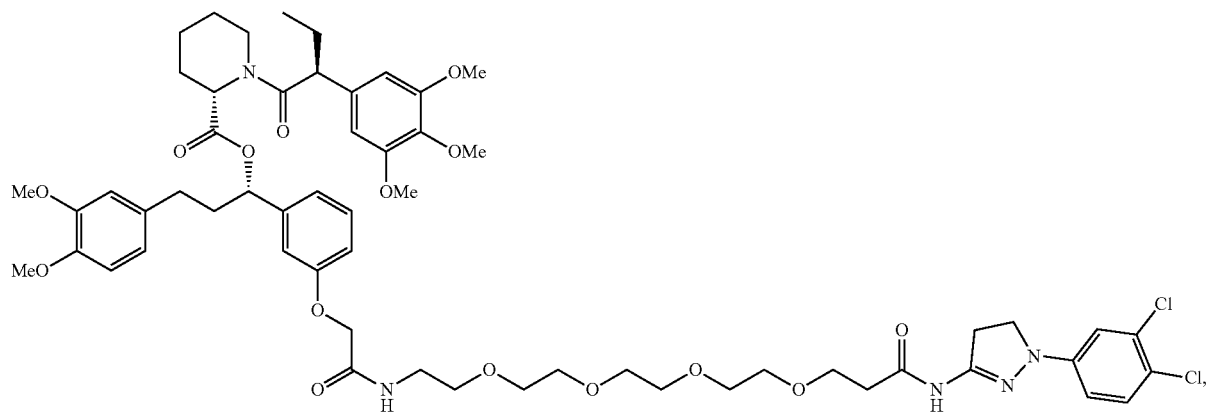
Exact Mass: 1151.4637
VS1074
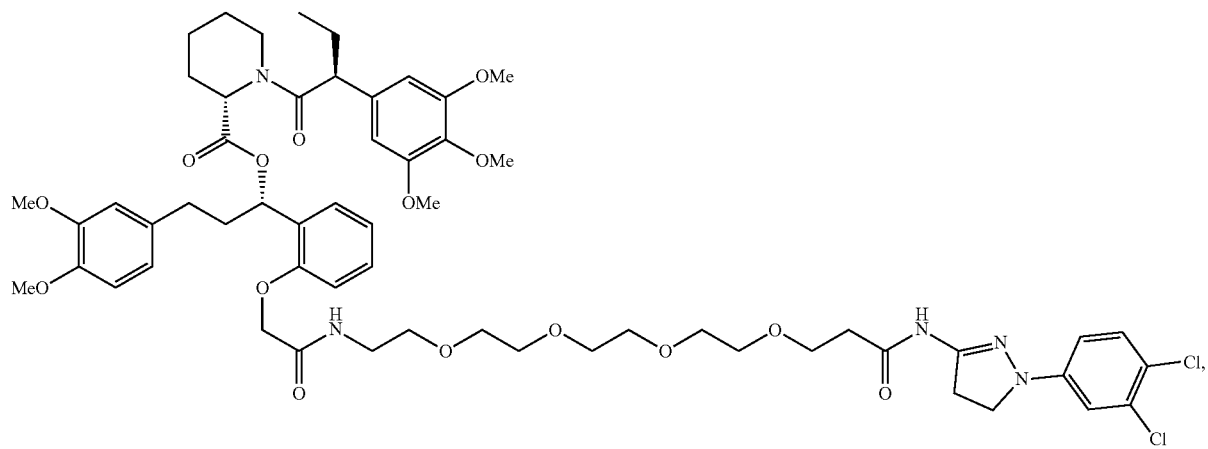
Exact Mass: 1151.4637
VS1100
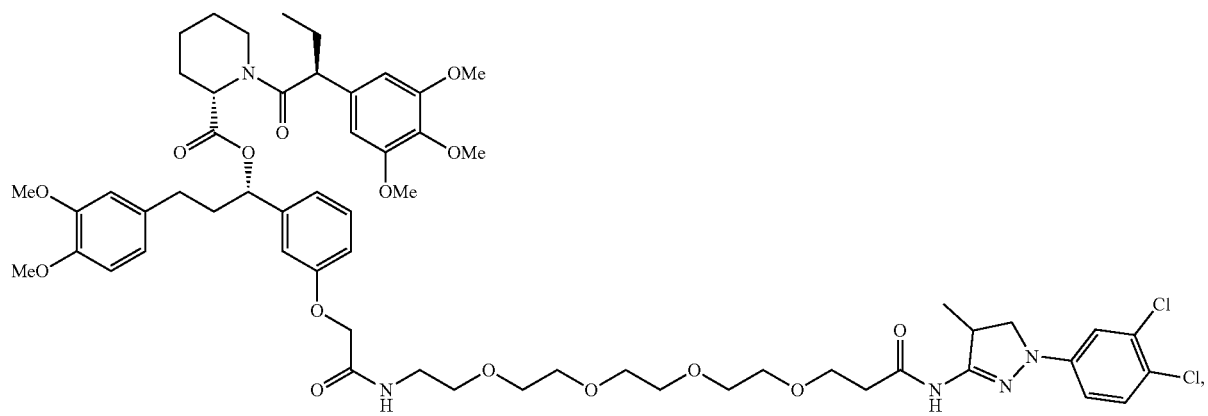

VS1101
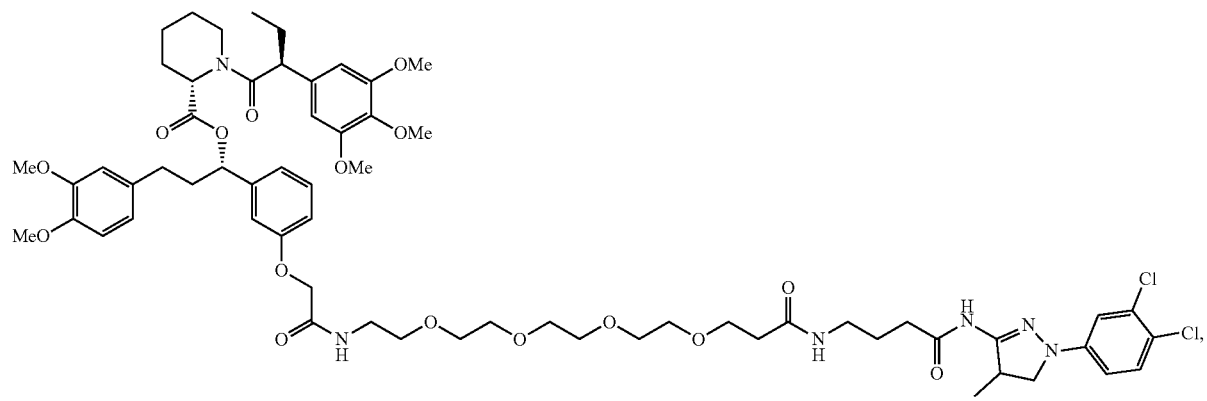
VS1107
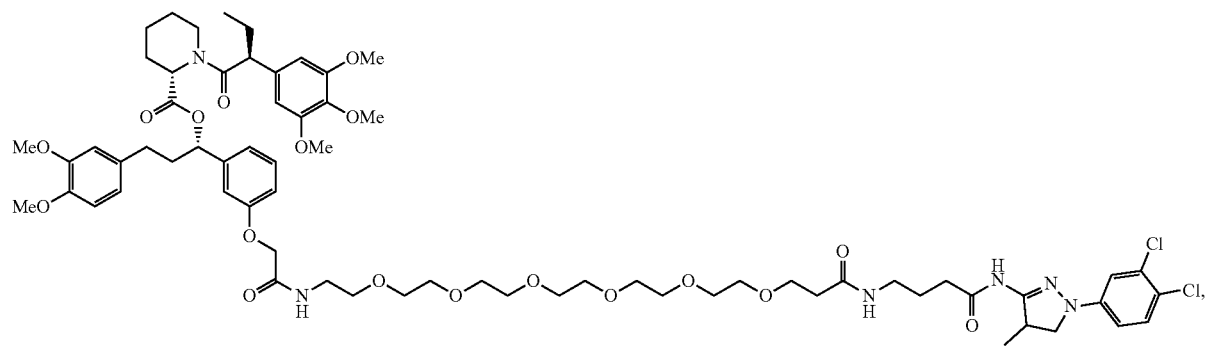
and
VS1106
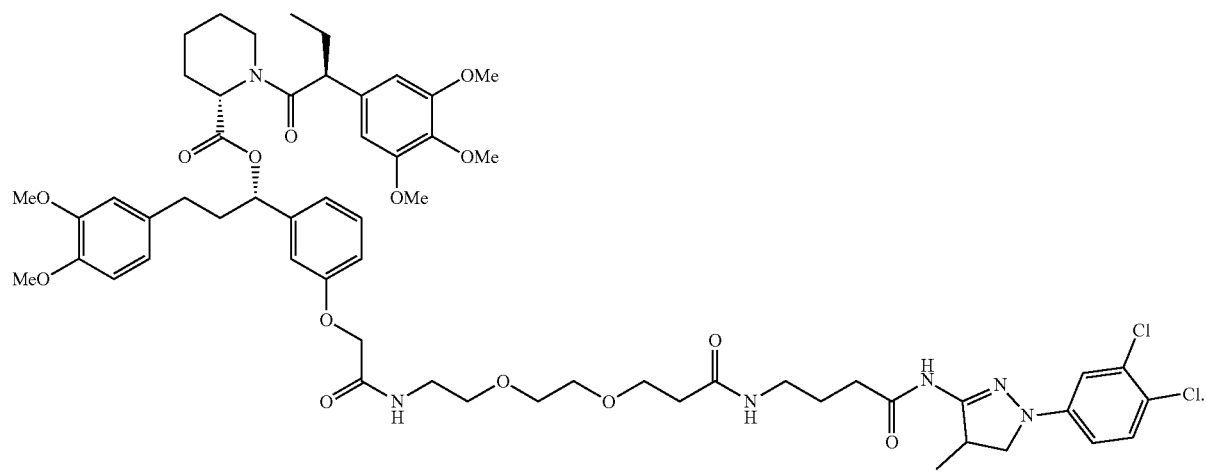

In one example embodiment, the chimeric small molecule is according to

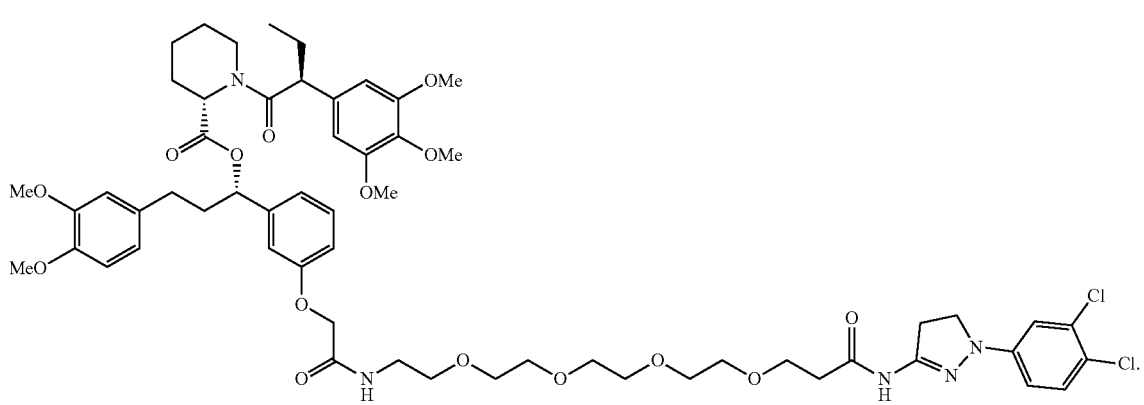

Exact Mass: 1151.4637

In one example embodiment, the molecule is capable of activating FGFR1/mTOR/G-CSF signaling in a dose-dependent manner.

EGFR

In one example embodiment, the protein binding moiety is an EGFR binding moiety. EGFR, is a tyrosine kinase receptor belonging to the ErbB family of receptors that mediates cell growth, differentiation and repair in cells, especially non-cancerous cells, but EGF is overexpressed in certain cells such as many solid tumors, including colorectal, non-small-cell lung cancer, squamous cell carcinoma of the ovary, kidney, head, pancreas, neck and prostate, and especially breast cancer.

In one embodiment, the protein binding molecule is an EGFR binding molecule of the formula,

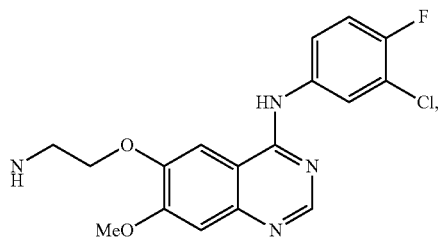 [SMILES: COc1cc2ncnc(Nc3ccc(F)c(Cl)c3)c2cc1OCCN]

or an analog thereof.

HSP90

Heat Shock Protein 90 (Hsp90) is an ATP dependent molecular chaperone that with its co-chaperones modulates proteins involved in cell cycle control and signal transduction. Like many ATP dependent proteins, the protein undergoes a functional cycle that is linked to its ATPase cycle.

In an embodiment, HSP90 binding molecule is

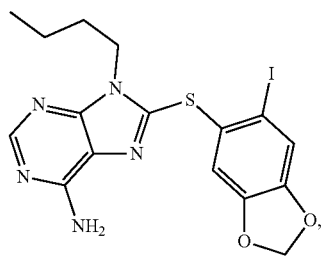 [SMILES: CCCCn1c(Sc2cc3c(cc2I)OCO3)nc2c(N)ncnc21]

or analog thereof.

Additional HSP90 binders include geldanamycin and derivatives thereof, including Tanespimycin (IC50 of 5 nM in cell free assay), according to the formula;

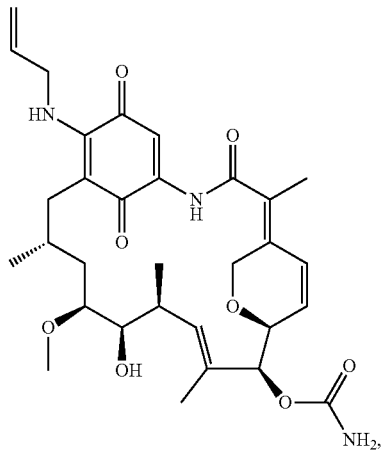 [SMILES: C=CCNC1=C2C[C@@H](C)C[C@H](OC)[C@H](O)[C@@H](C)/C=C(\C)[C@H](OC(N)=O)[C@@H]3C=C/C(=C(\C)C(=O)NC(=CC1=O)C2=O)CO3]

Alvespimycin (IC50 of 62 nM in cell-free assay), according to the formula;

213

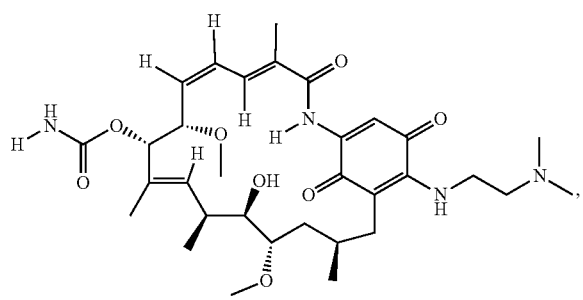 [SMILES: CO[C@H]1/C=C\C=C(/C)C(=O)NC2=CC(=O)C(NCCN(C)C)=C(C[C@@H](C)C[C@H](OC)[C@H](O)[C@@H](C)/C=C(\C)[C@@H]1OC(N)=O)C2=O]

EC141 according to the formula;

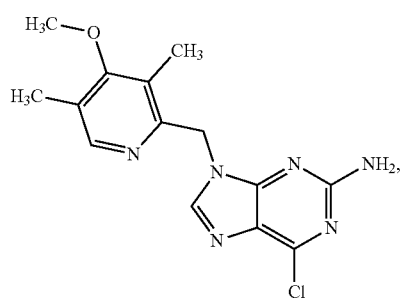 [SMILES: COc1c(C)cnc(Cn2cnc3c(Cl)nc(N)nc32)c1C]

Novobiocin according to the formula

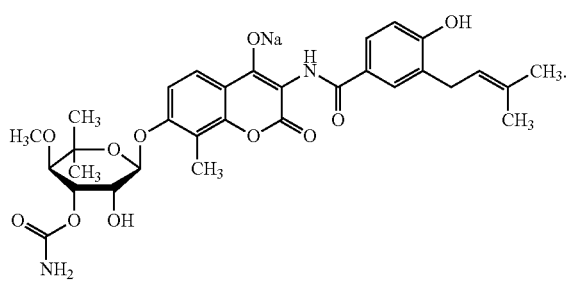

(IC50=700uM)

Novobiocin analogs can also be utilized and as described in Hall et al., J Med Chem. 2016 Feb. 11; 59(3): 925-933; doi: 10.1021/acs.jmedchem.5b01354, incorporated by reference, which can be used as a MAPK signaling disruptor.

BTK

Bruton's Tyrosine Kinase (BTK) is a protein involved in multiple signaling cascades and is widely expressed in B cells. First, BTK is a cytoplasmic protein and thus available for interactions with cytoplasmic kinases, such as AMPK.

In an embodiment, the BTK binding molecule selected from the group consisting of,

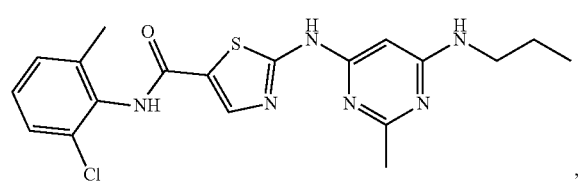

214

-continued

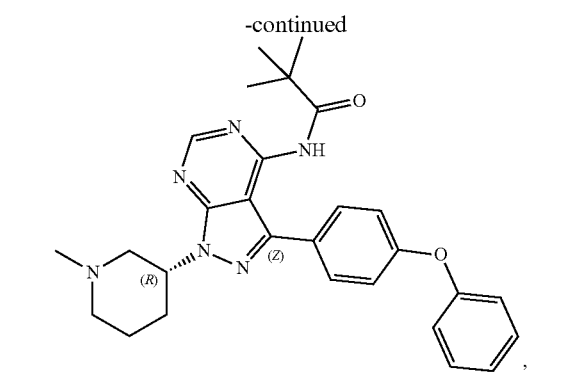

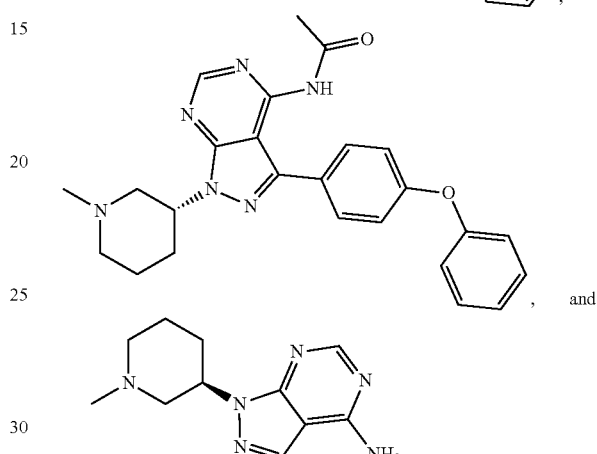

or an analog thereof.

MDM2

In an embodiment, the target protein binding moiety is an MDM2 binding moiety according to

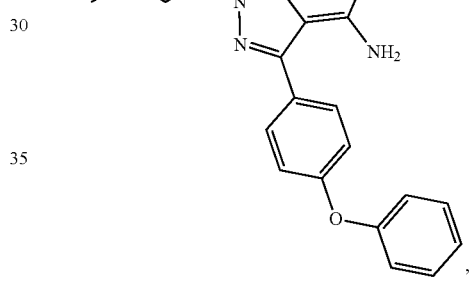

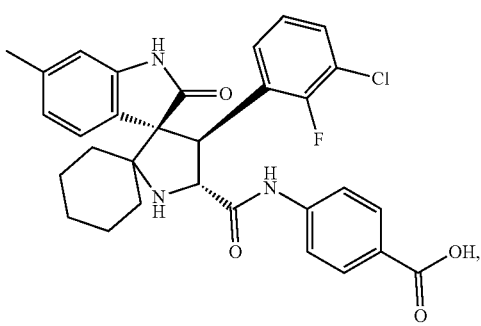 [SMILES: Cc1ccc2c(c1)NC(=O)[C@]21[C@@H](c2cccc(Cl)c2F)[C@H](C(=O)Nc2ccc(C(=O)O)cc2)NC12CCCCC2]

or a derivative or analog thereof.

BRD4

In an embodiment, the target protein binding moiety is a BRD4 binding moiety selected from the group consisting of

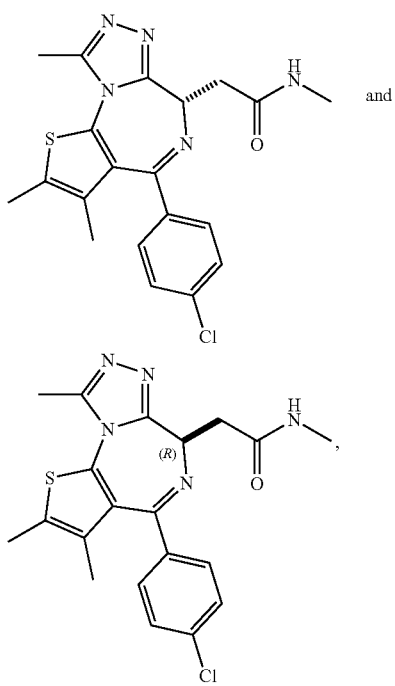 and , or an analog thereof.

FGFR1

In one example embodiment, the target protein binding moiety inhibits FGFR1 fusion proteins. In one example embodiment, the FGFR1 fusion protein inhibitor is Dovitinib, also known as TK1258, according to the formula

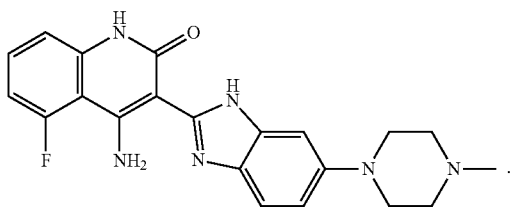 [SMILES: CN1CCN(c2ccc3nc(-c4c(N)c5c(F)cccc5[nH]c4=O)[nH]c3c2)CC1]

PtDA, PtPB

In one example embodiment, target protein binding moiety is a PtpA binding moiety is according to the formula

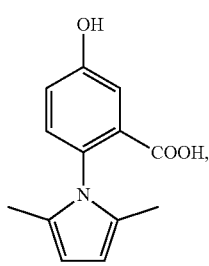

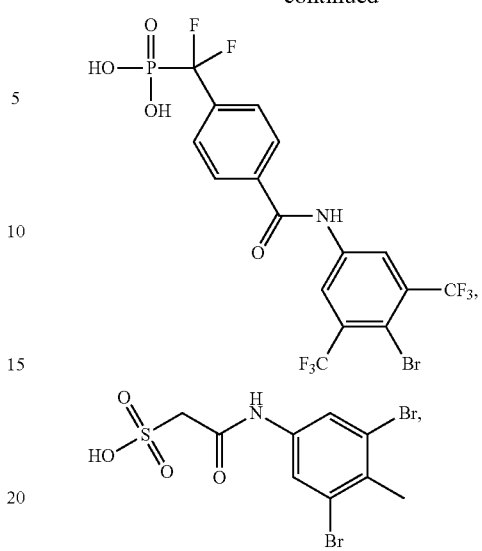

or any derivatives thereof.

In preferred embodiments, the PtpB binding moiety is according to the formula

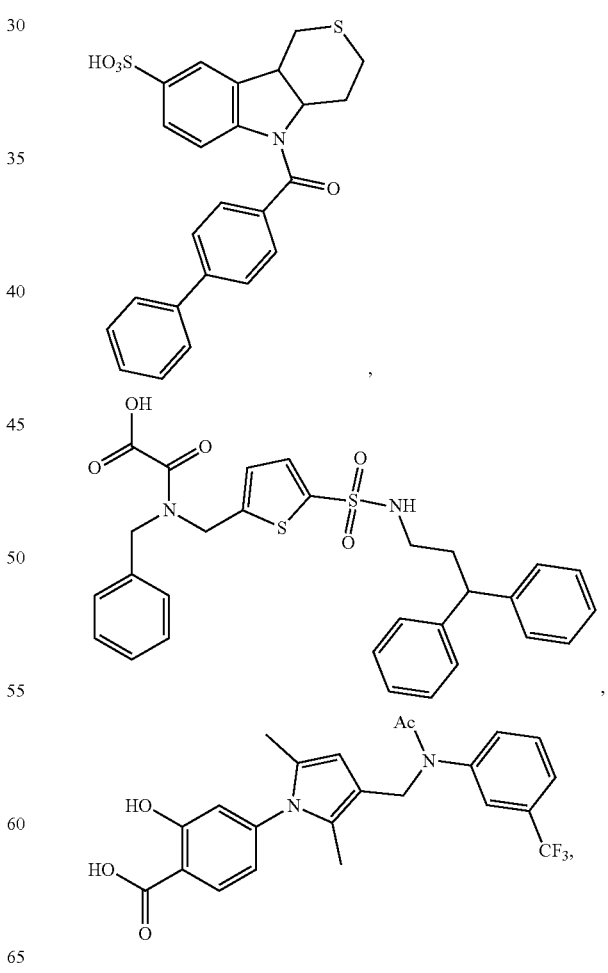

217
-continued
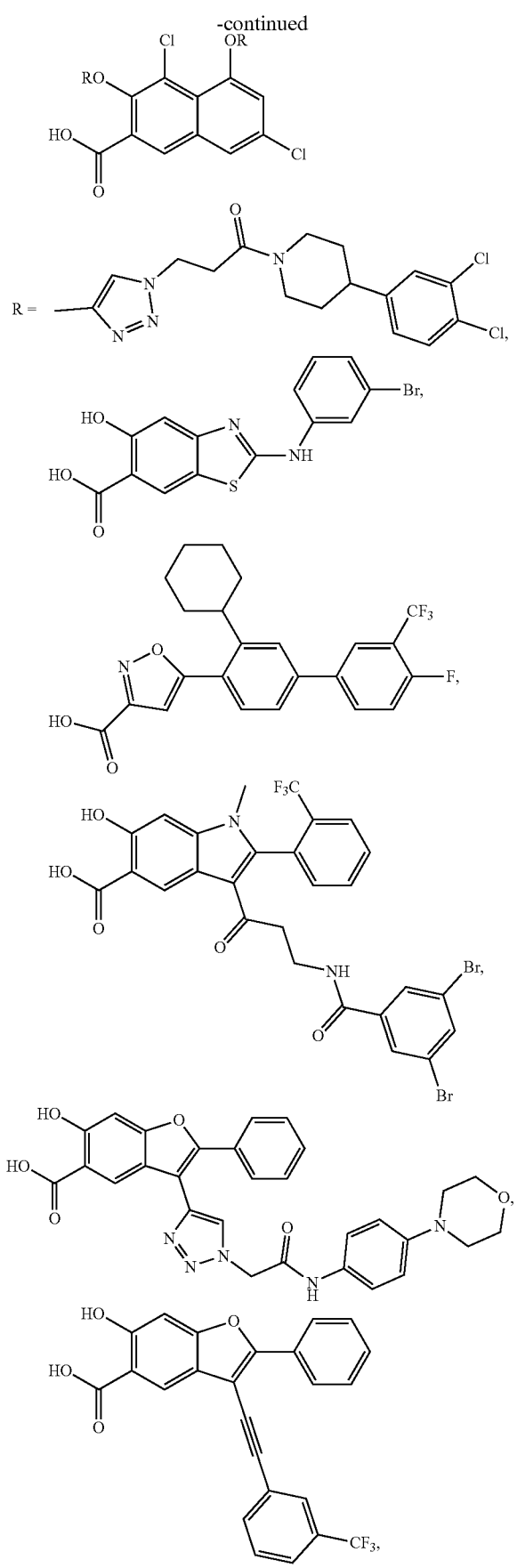
218
-continued
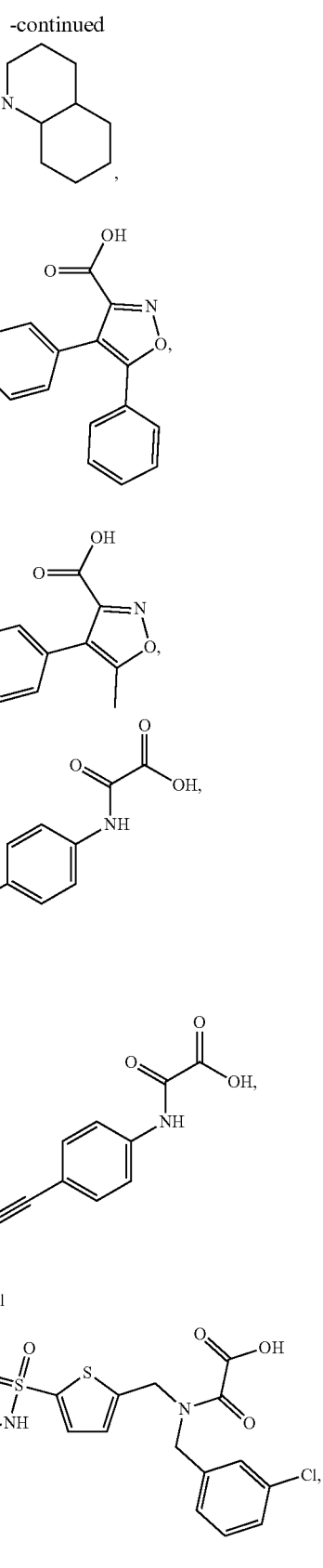
or any derivatives thereof.

SapM
In one example embodiment, the target protein binding moiety is a SapM binding moiety. In an example embodiment, the SapM binding moiety contains a trihydroxybenzene group. In an example embodiment, the SapM binding moiety comprises of a benzylidenemalononitrile scaffold. In one example embodiment, the SapM binding moiety has the formula:
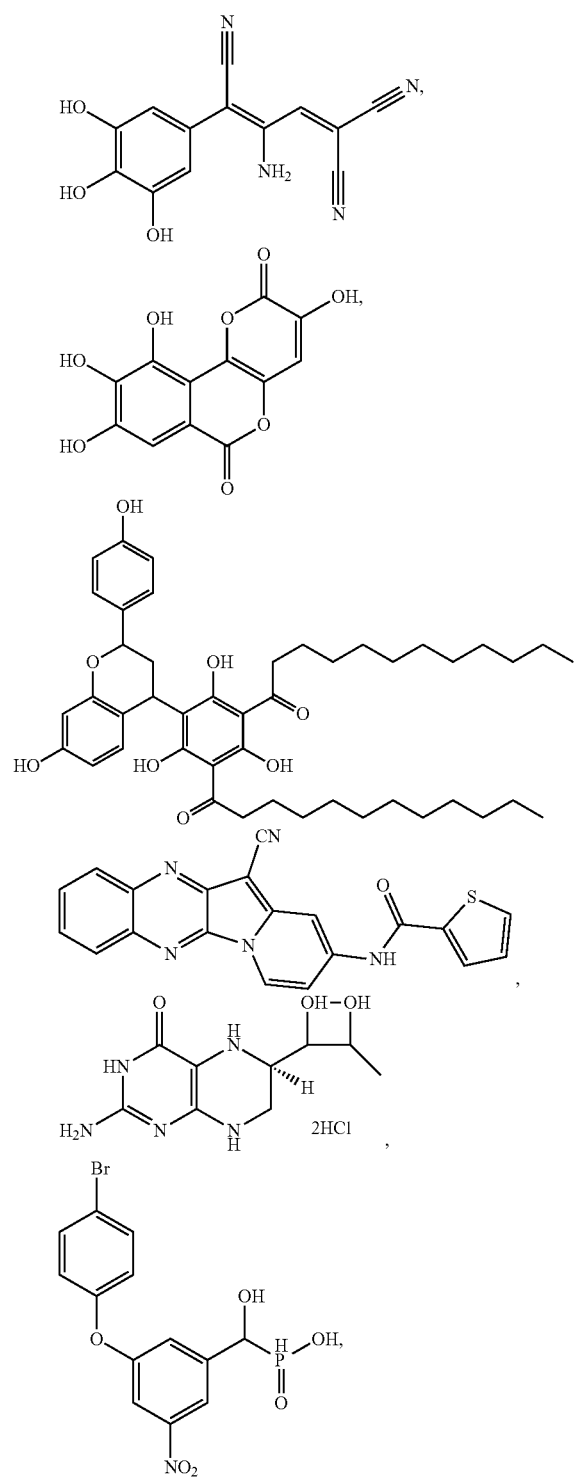
-continued
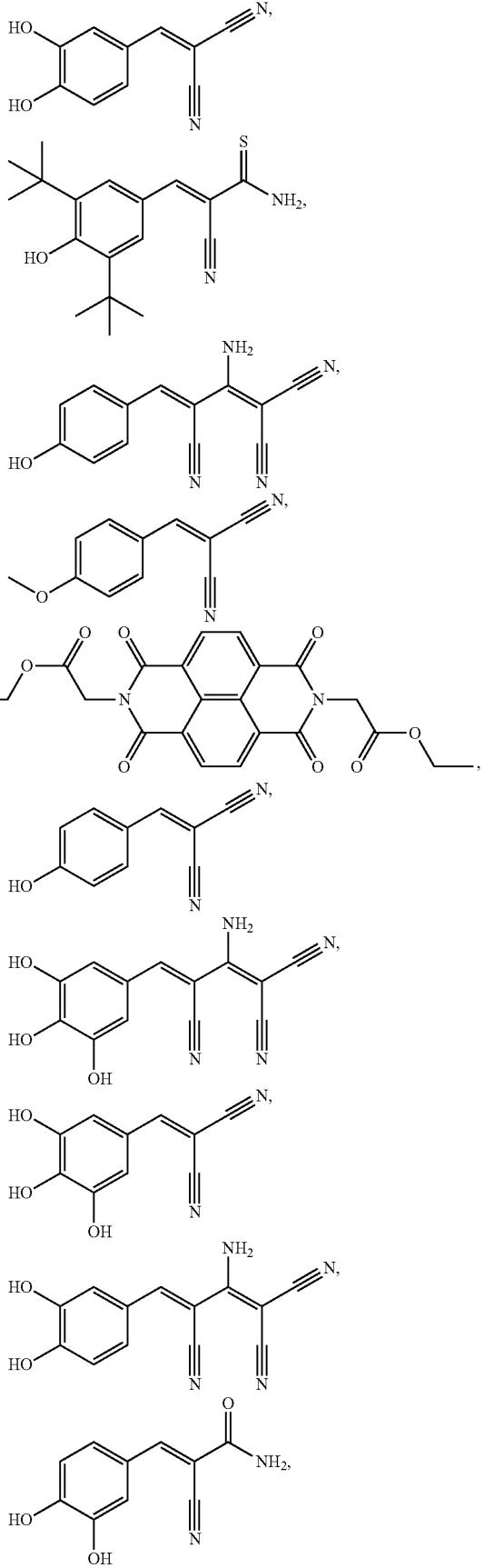

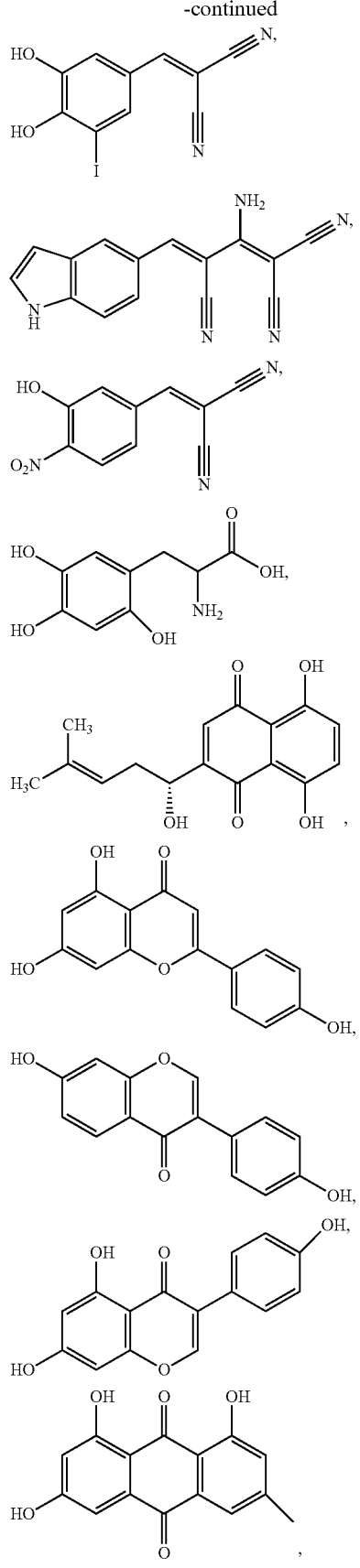
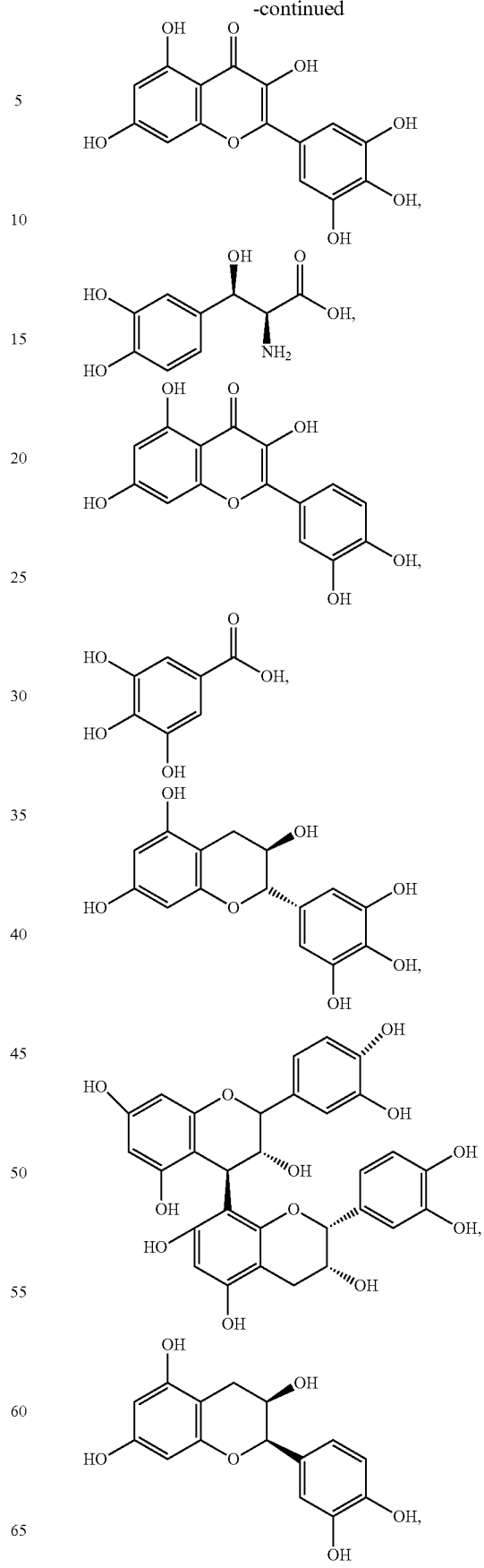

-continued

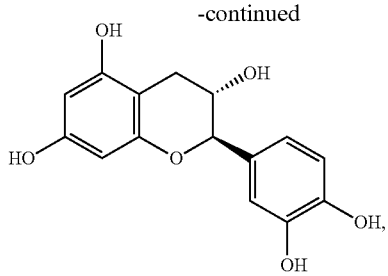

or any derivatives thereof. In one example embodiment the SapM binding moiety is L-ascorbic acid (L-AC) and 2-phospho-L-ascorbic acid (2P-AC).

UMPK

In one example embodiment the target binder is a M. tb kinase inhibitor. In an example embodiment, the M. tb kinase inhibitor is a UMPK inhibitor and any derivative thereof identified in US Patent Application US US20090209022, herein incorporated by reference.

Colistin

In preferred embodiments, the PsA associated target protein binding moiety is Colistin, which has the formula:

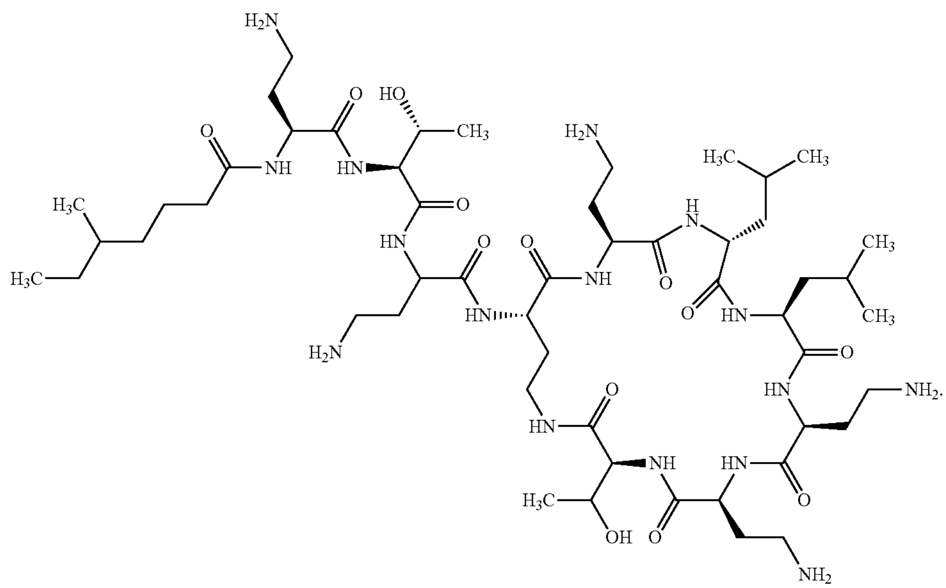 [SMILES: CCC(C)CCCC(=O)N[C@@H](CCN)C(=O)N[C@H](C(=O)NC(CCN)C(=O)N[C@H]1CCNC(=O)[C@H](C(C)O)NC(=O)[C@H](CCN)NC(=O)[C@H](CCN)NC(=O)[C@H](CC(C)C)NC(=O)[C@@H](CC(C)C)NC(=O)[C@H](CCN)NC1=O)[C@@H](C)O]

Electrophilic Reactive Group

In one example embodiment, the molecules or binding moieties as disclosed herein may be modified to include an electrophilic reactive group. In one embodiment, the electrophilic reactive group is located between the linker and target binding moiety. In an embodiment, the electrophilic reactive group is located between two linkers, a first linker attached to the kinase binder and a second linker attached to the target binding moiety. An electrophilic reactive group, as used herein, is typically a functional group that can form a reversible or irreversible bond with a nucleophilic functional group. The electrophilic reactive group allows for the target binding moiety to directly attach to the target kinase. Upon attaching to the electrophilic reactive group, the kinase is now tagged with the target binding moiety. In one example embodiment, the molecules or binding moieties may be modified at an electrophilic reactive group to reduce or lessen the strength of covalent binding capabilities of an electrophilic reactive group, or to increase the binding affinity or strength of binding of an electrophilic reactive group as desired according to the application. In an embodiment, a binding molecule may be chosen that would create irreversible covalent binding at a target. When used in a chimeric small molecule, such tight bonding may be less desirable. Thus, modification of such electrophilic reactive group would be desirable and can be modified to reduce the interaction, see, e.g. sciencedirect.com/science/article/pii/S0968089618320807. In particular, reactivity can be designed to allow for covalent binding at the target, with reversible or irreversible properties, depending on desired functionality. In an embodiment, the electrophilic reactive group is designed to react with an amino acid side chain reactive group. The amino acid side chain reactive group may be nucleophilic. The nucleophilic amino acid side chain reactive group may comprise arginine, lysine, histidine, cysteine, aspartic acid, glutamic acid and tyrosine. In one preferred embodiment, the electrophilic reactive group reacts with lysine. An exemplary database that can aid in identification for protein ligand interaction around the binding site is described in Du et al, Nucleic Acids Research, Volume 49, Issue D1, 8 Jan. 2021, Pages D1122-D1129, incorporated herein by reference, with the database, CovalentInDB accessible at cadd.zju.edu.cn/cidb/. The approach can be used with any design of the electrophilic reactive group for molecules as disclosed herein.

N-acyl-N-alkyl Sulfonimide (NASA)

NASA chemistry may be used to accomplish the design of the electrophilic reactive group by forming a reversible or irreversible bond with a nucleophilic functional group located on the kinase. NASA chemistry is generally described in *Nat Commun* 9, 1870 (2018), incorporated herein by reference. In preferred embodiments, the kinase binding moiety can be attached to a linker utilizing N-acyl N-alkyl sulfonamide (NASA) electrophilic reactive group further attached to a kinase binding moiety. The chimeric small molecule containing a NASA will, upon non-covalent binding to a target enzyme, covalently bond to the enzyme as the NASA chemically reacts with a proximal lysine or other amino acid as described herein. The NASA modified chimeric small molecule then disassociates from the kinase leaving behind the protein targeting binder covalently attached to the kinase. This modified kinase will then bind to the target protein through the newly attached binder and further modify the protein. In an example embodiment, NASA chemistry is used to label a kinase binding moiety. Accordingly, an embodiment comprises methods of making compositions disclosed herein using NASA chemistry, and as further described in the examples.

In an example embodiment, a NASA analogue has the formula:

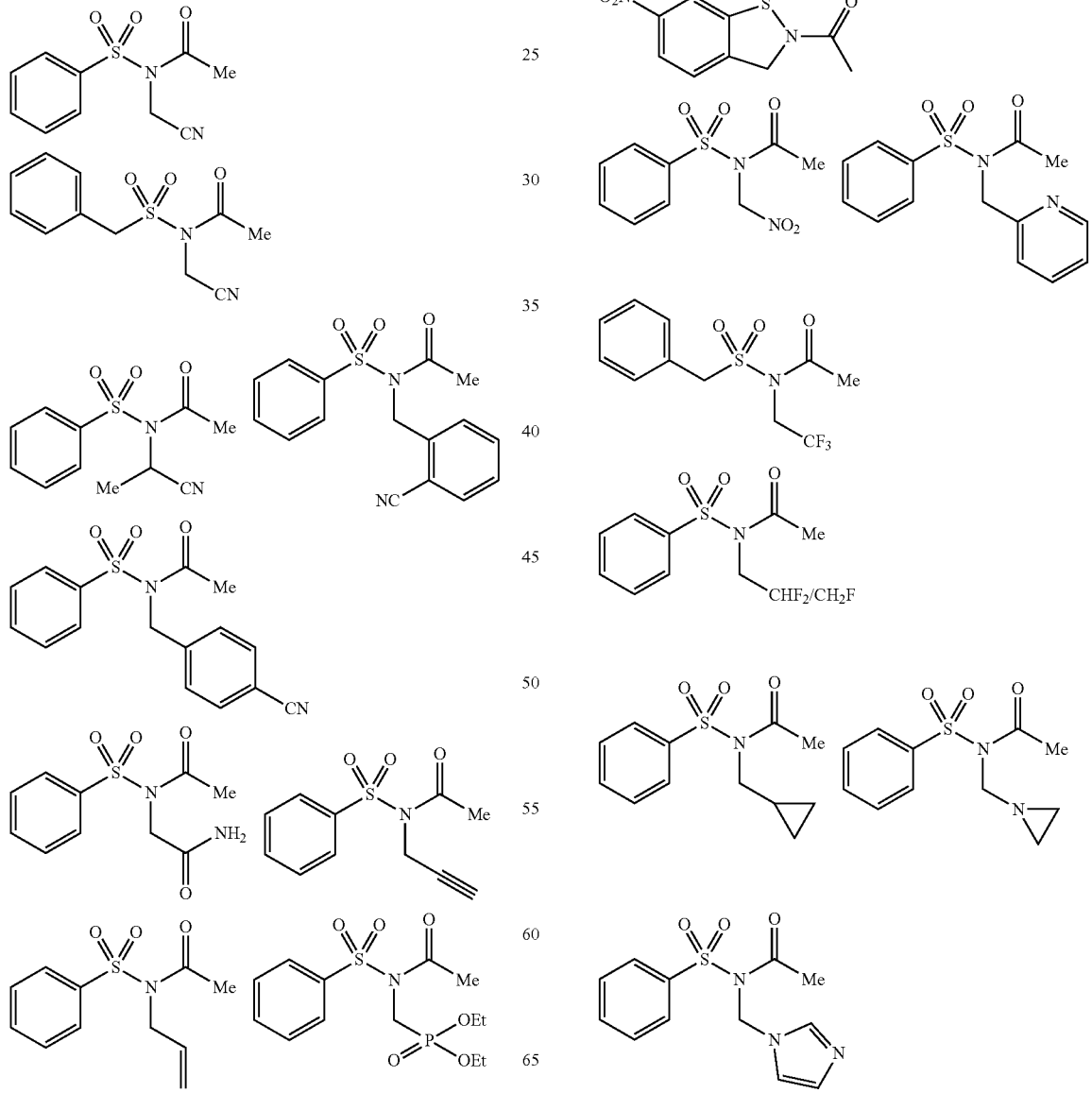

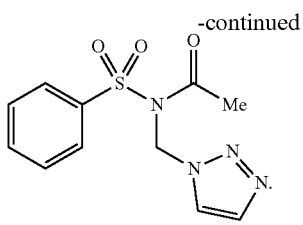

Dibromophenyl Benzoate

In preferred embodiments, the electrophilic reactive group is dibromophenyl benzoate (DB). DB can be used to functionalize a linker by reacting with a nucleophile located on a kinase. The dibromophenyl group acts as the leaving group facilitating the reaction while the benzoate stabilizes the now attached moiety. In a preferred embodiment, a linker connecting a kinase binding moiety and protein binding moiety is functionalized with DB to label a target kinase with the protein binding moiety. DB chemistry is generally described in Takaoka et al. *Chem. Sci.*, (2015), 6, 3217-3224, incorporated herein by reference.

N-sulfonyl Pyridone

In preferred embodiments, the electrophilic reactive group is N-sulfonyl pyridone (SP). SP can be used to functionalize a linker by undergoing sulfonylation with a nucleophile located on a kinase. In a preferred embodiment, a linker connecting an kinase binding moiety and protein binding moiety is functionalized with SP to label a target kinase with the protein binding moiety. SP chemistry is generally described in K. Matsuo et al. *Angew. Chem. Int. Ed.* 2018, 57, 659 incorporated herein by reference.

In one example embodiment, the electrophilic reactive group comprises one of

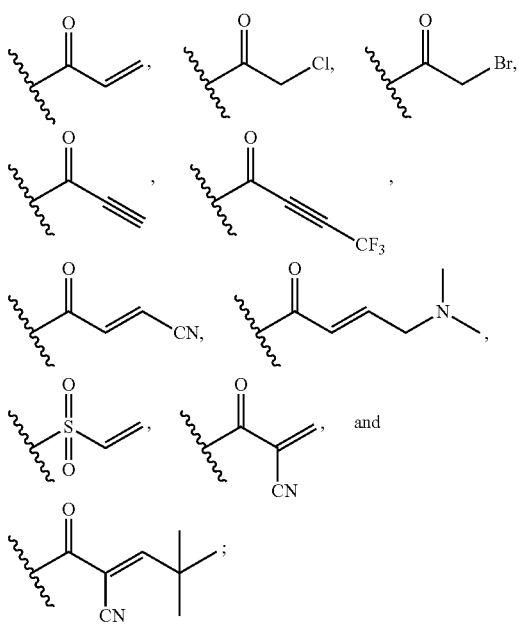

In an example embodiment, the electrophilic reactive group has the formula: wherein R1 is selected from C—O, SO2, Me-C—O, or Me-SO2, R2 is selected from H, alkane, alkene, alkyne, amine, nitrile, nitro, ether, alcohol, thiol, sulfone, sulfonate, halogen, carbonyl; acyl; ketone; carboxylate ester; amide; enone; anhydride; imide, cyclic hydrocarbon, an unsaturated cyclic hydrocarbon, a heterocycle, one or more fused rings thereof; an aliphatic halide such as —OCF2Cl or any combination thereof, and the benzene ring is optionally substituted at any position.

Photo-Reactive Group

In one example embodiment, the electrophilic reactive group is a photo-reactive group. In one embodiment, the photo-reactive group is a photoactivated cell-surface reactive group. In another embodiment, the photoactivated cell-surface reactive group is a benzophenone, azide, or diazirine, wherein the group is activated to become a carbon-centered radical, nitrene, or carbene, respectively. In another embodiment, the photo-reactive group is a thienyl-substituted alpha-ketoamide, see e.g. Ota, E., et al. "Thienyl-Substituted α-Ketoamide: A Less Hydrophobic Reactive Group for Photo-Affinity Labeling." *ACS Chem. Biol.* 2018, 13 (4), 876-880.

Linker

A linker or linking moiety is a bifunctional or multifunctional moiety that can be used to link one or more of target binding moiety, protein binding moiety. In some embodiments, the linker has a functionality capable of reacting with the moieties for covalent attachment. The linker moiety is preferably a chemical linker moiety and is represented in the formulas of the present invention as L. In an embodiment, the linker moiety may preferably comprise one or more repeats, e.g. 1, 2, 3, 4, 5, 6, 7, 8 or more repeats, which may be utilized to facilitate or improve spacing, conformation, and/or performance of the molecules. The linker described herein may refer to both L1 and L2 or L1 and L2 are different linkers described herein.

A linker or linking moiety can be used to link a kinase binding moiety to the target binding moiety, and/or the electrophilic reactive group to either the kinase binder, target binding moiety, or both. When more than one linker molecule is used in a molecule, the linkers may be the same or different from each other.

In one example embodiment, the linker may be represented with an exit vector. In one example embodiment, the exit vector may be represented independently of the linker. Exit vector parameters can be identified in part based on average orientation of a substituent attached to a variation point which can be generated using chemoinformatics software. An exit vector may comprise outgoing bonds from a chemical moiety. In an embodiment, the exit vector is provided as bonds on the linker or from the binding moiety, providing conformation of attachment between the linker and the activator moiety and/or the localizing moiety.

Exit Vectors

One or more exit vectors may be utilized with the molecules described herein. In certain embodiments, the linker or kinase binding moiety may be represented with an exit vector comprised in the linker or kinase binding moiety. In an embodiment, the exit vector may be represented independently of the linker or kinase binding moiety. Exit vector parameters can be identified in part based on average orientation of a substituent attached to a variation point which can be generated using chemoinformatics software. An exit vector may comprise outgoing bonds from a chemical moiety. In an embodiment, the exit vector is provided as bonds on the linker or from an Abl binding moiety, providing conformation of attachment between the linker and the Abl binding moiety and/or the second Abl binding moiety. The exit vector may also be represented independent of the linker of the formulas detailed herein. In an embodiment, the exit vector is comprised in W.

In an embodiment, the bond is chosen to be energetically favorable, preferably increasing binding affinity. The exit vector may be adjusted depending on the linker utilized in the molecules. In embodiments, the exit vector is a chemical moiety or bond that facilitates stereochemical protrusion that may further facilitate subsequent coupling, bonding and/or accessibility.

In one example embodiment, the kinase binding moiety has an adapter or reactive handle, both used herein interchangeably. The reactive handle comprises the group on the kinase binding moiety that attaches to the linker. In one example embodiment, the reactive handle can perform click chemistry, amide coupling chemistry, crosslinking chemistry, alkylation, or sulfonation chemistry. (See e.g. Nwe, K.; Brechbiel, M. W. Growing Applications of "Click Chemistry" for Bioconjugation in Contemporary Biomedical Research. Cancer Biotherapy and Radiopharmaceuticals, 2009, 24, 289-302.)

In one example embodiment, the bond is chosen to be energetically favorable, preferably increasing binding affinity. The exit vector may be adjusted depending on the linker utilized in the molecules. In one example embodiment, the exit vector is a chemical moiety or bond that facilitates stereochemical protrusion that may further facilitate subsequent coupling, bonding and/or accessibility.

In an embodiment, L is a rigid linker, which may be selected from the group consisting of:

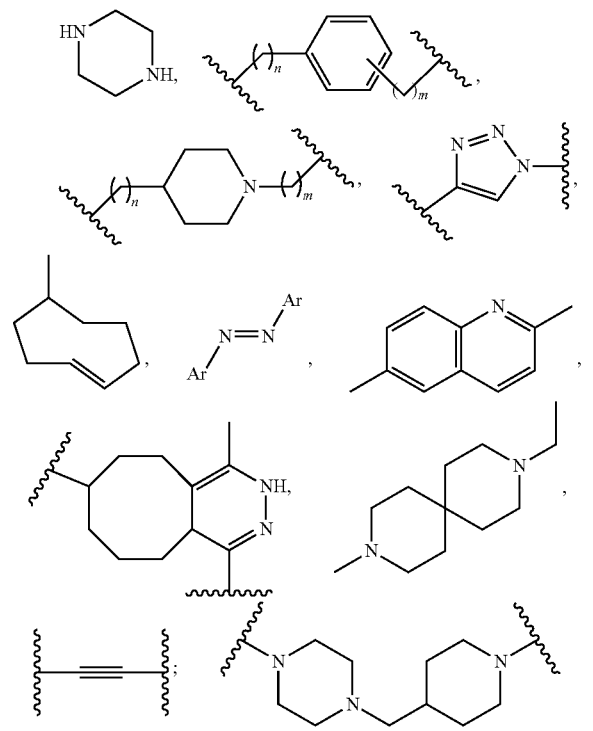

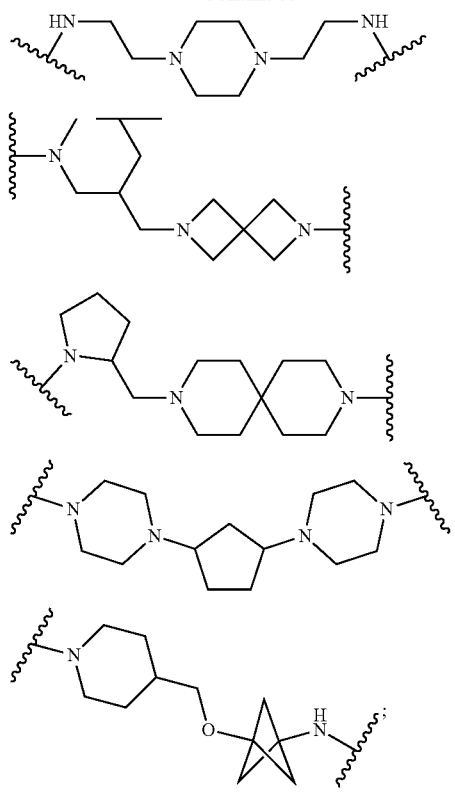

or any combination thereof; and wherein any atom in within a ring may substituted for C, N O, S; the linkers may bond to one or more PEG molecules before bonding to A and optionally B; and m and n may be independently selected from 0 to 6.

In preferred example embodiments, the linker L has one covalent attachment point to a kinase binding molecule and two covalent attachment points to the other kinase binding molecule. A covalent attachment point may be any single, double, triple, or quadruple bond between one component of the BFM/chimeric small molecule and another. In preferred example embodiments, the linker is attached to one kinase binding molecule, i.e. A, and the other, i.e. B, according to the formula

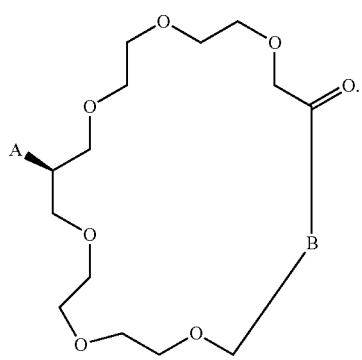

In one example embodiment, the PEG compounds in the previously mentioned linker can be substituted for any linker mentioned herein. In One example embodiment, the previously mentioned linker is optimized for physiochemical properties, such as solubility and/or permeability, and/or pharmacokinetic properties, such as microsomal stability or target binding.

In one example embodiment, the kinase binder has an adapter or reactive handle, both used herein interchangeably. The reactive handle comprises the group on the kinase binder that attaches to the linker. In one example embodiment, the reactive handle can perform click chemistry, amide coupling chemistry, crosslinking chemistry, alkylation, or sulfonation chemistry.

Bio-Orthogonal Group

The chimeric small molecules disclosed herein may further comprise a biorthogonal group. A chimeric small molecule may be configured to include a bio-orthogonal group as a device to remove the kinase binding moiety from the target kinase. This occurs when a coupling molecule, selected to react with the biorthogonal molecule, is introduced into the system containing the kinase bound chimeric small molecule and bonds to the bio-orthogonal group. As a result, the kinase binding molecule is no longer operable and cannot bind to the target kinase. In one example embodiment, the kinase binder comprises a bio-orthogonal group. In one example embodiment, the kinase binder is modified to contain a bio-orthogonal group. Bio-orthogonal chemistry comprises chemical reactions carried out in a biological environment without reacting with endogenous systems, such as functional groups. Bio-orthogonal groups comprise moieties capable of bio-orthogonal chemistry. Non-limiting examples of bio-orthogonal groups include tetrazines, triazines, cyclooctenes, cyclopropenes and diazo groups.

In one example embodiment, the bio-orthogonal group comprises one of

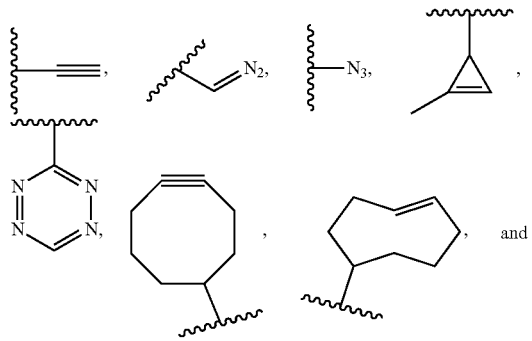

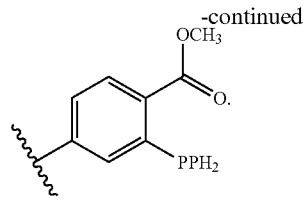

Example Chimeric Small Molecules

Chimeric small molecules may be assembled using any combination of the above kinase binding moieties, linkers, electrophilic activation groups, and target binding moieties. The following description provides, by way of reference only, certain chimeric small molecules that can be generated according to the design principles and examples moieties provided above.

In an example embodiment, the chimeric small molecule has the formula:

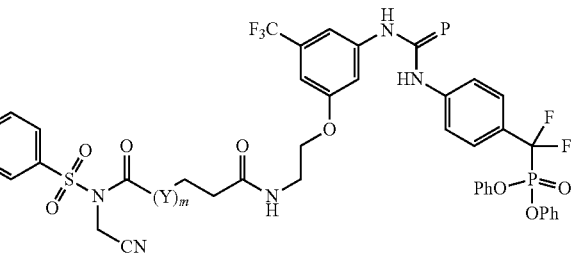

wherein X and Y are independently selected from $CH_2$ or $(CH_2)_2O$ and n and m are independently selected from 1, 2, 3, 4, 5, or 6.

Methods of Use

In another aspect, chimeric small molecules as described above may be used in methods to endow new functions to cellular kinases or to regulate the activity of cellular kinases. The chimeric small molecules find use for treatment in a variety of diseases and disorders. In an example embodiment, a target binding moiety can bind to a target of interest, preferably localizing in a region of a target of interest, allowing the protein to which the protein binding moiety is bound to modify a target. Exemplary applications include use in rewiring of cellular signaling. See, Lim et al., Nat Rev Mol Cell Biol 2010, 11(6), 393-403. For example, cell signaling can be addressed by appending phosphoryl groups to specific signaling protein of interest with dose and temporal control to allow rewiring of kinase signaling pathways in disease or health. The chimeric small molecule systems herein may enable targeted degradation of a target where phosphorylation sites are targets that recruit ubiquitin ligase and signal degradation. See, Toure et al., Angewandte Chemie (Inter'l ed. In English) 2016, 55(6), 1966-73. Similarly, preventing protein aggregation can aid in treatment in cancer treatment approaches. As described herein, addition of negatively charged phosphoryl groups using the chimeric small molecules on a protein prone to aggregation may increase solubility and reduce self-aggregation. Guo et al., FEBS Letters, 2005, 579 (17), 3574-3578; Zhang et al., Protein Expression and Purification 2004 36(2) 207-216. Exemplary

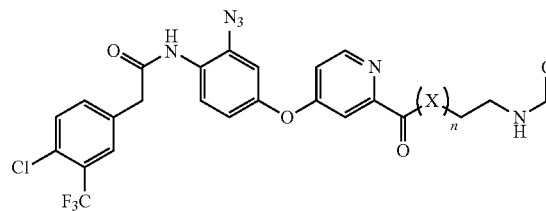

embodiments comprising methods of treatment of kinasopathies are also provided. Exemplary embodiments further include regulation of nucleotide binding proteins, which may include use with orthogonally tagged nucleases such as Cas, and phosphorylation of transcription factors to affect binding. In one example embodiment, the invention described herein relates to a method for therapy in which cells are modified ex vivo by the chimeric small molecules to modify at least one target substrate, with subsequent administration of the edited cells to a patient in need thereof.

Methods of Modifying Target Substrates

The chimeric small molecules disclosed herein can be utilized in methods of modifying a target substrate. Methods of modifying the target substrate can include generating a repurposed/reprogrammed cellular protein by delivering a chimeric small molecule, as described herein. In an example embodiment, the chimeric small molecules can be used to inhibit nucleotide binding proteins, inhibit oncogenic kinases, generate neo-antigens to evoke an immune response, as molecule prosthetics of kinasopathies, treatment of pathogens and induction of receptor tyrosine kinase signaling.

Methods of modifying a substrate are provided, which may be in a cell. In one example embodiment, a chimeric small molecule as described herein is introduced. In one example embodiment, the modifying comprises inducing post-translational modification of a target protein. In one example embodiment, the post-translational modification is phosphorylation. The method comprises administering to cell or cell population a chimeric small molecule. Methods of modifying the target substrate can include contacting the target substrate with a chimeric small molecule, e.g. bifunctional molecule, of the present invention. Contacting can allow for bonding to, or association with the target substrate, or to a molecule in proximity to a target substrate. Modification may be by inducing a conformational change via binding, changing structural stability, phosphorylation of a target, or via another mechanisms that affects the behavior of the target substrate. By way of example, activation or inactivation of the target substrate via the binding of the chimeric small molecule results in modification of the target substrate one or more new modification sites that would otherwise remain unmodified when the chimeric small molecule is not bound to the target substrate. In an aspect the methods comprise inducing phosphorylation of a target protein in the cell. The methods may comprise contacting a target substrate with the chimeric small molecule.

In an example embodiment, the chimeric small molecule can label the cellular protein with the target binding moiety for the target substrate via the electrophilic reactive group moiety. The electrophilic reactive group reacts with and bonds to a nucleophilic side chain on the cellular kinase. Labelling of the cellular kinase can allow for bonding to, or association with, the target substrate, or to a molecule in proximity to a target substrate facilitating modification of the target substrate. In one example embodiment, this approach allows utilization of protein inhibitor moieties, as well as activators and neutral binding molecules to induce target modification. Such kinase binding moieties tethered with an electrophilic reactive group, e.g. a chemoselective electrophilic warhead, exhibits site-specific labeling of a side chain nucleophilic residue, e.g. nucleophilic side chain amino acid, proximal to the inhibitor binding site. Generally, labeling proximal to the inhibitor binding site refers to a reactive group at, within, or at a distance to the binding moiety binding site that allows the electrophilic reactive group to react at or near the time and/or space of the binding site of the binding moiety. The tethering of the electrophilic warhead can comprise a linker, bond, and/or exit vector or adapter which may, in some instances, In one aspect, the target substrate is not a natural substrate of the protein, or wherein activation of the protein by the binding moiety results in modification of the target substrate by the protein at one or more new modification sites that would otherwise remain unmodified by the protein when not activated by binding to the activator moiety. Modification may be by inducing a conformational change via binding, changing structural stability, phosphorylation of a target, or via other mechanisms that affects the behavior of the target substrate, e.g. removal of groups such as phosphatases, methyltransferases. Modifying can include the post-translational modification as disclosed herein, including, for example, phosphorylation, hydroxylation, acetylation, methylation, glycosylation, prenylation, amidation, eliminylation, lipidation, acylation, lipoylation, deacetylation, formylation, S-nitrosylation, S-sulfenylation, sulfonylation, sulfinylation, succinylation, sulfation, carbonylation, or alkylation. In one aspect, the methods comprise inducing phosphorylation of a target protein in or on the cell. The methods may comprise contacting a target substrate with the chimeric small molecule. In one example embodiment, the target substrate is in proximity to a kinase specific to the protein binding moiety of the molecule. Chimeric small molecules that induce phosphorylation can be optionally provided with adenosine monophosphate (AMP) or another molecule providing an additional phosphate group. Without being bound by theory, the addition of the AMP or other phosphate providing molecule can enhance phosphorylation.

In an example embodiment, inhibition of nucleotide-binding proteins may comprise inhibition binding of a CRISPR-Cas protein to a nucleic acid or transcription factors binding to DNA. Thus, proteins that have been modified to comprise a binding domain that can be targeted by an orthogonal tag, e.g. Cas9 comprising a FKBP binding domain, can be inhibited by the use of small molecules comprising an orthogonal tag, such as a dTAG. Sequence specific modular adaptors consisting of a DNA-binding protein and a self-ligating protein tag can be utilized. See, e.g. Nguyen et al., Rational design of a DNA sequence-specific modular protein tag by tuning the alkylation kinetics, Chem Sci., 40 (2019) doi: 10.1039/C9SC02990G. Similarly, nucleotide binding may be modified via the modification of transcription factors with the chimeric small molecules. Because post-translation phosphorylation of transcription factors might be necessary for direct binding interactions or a conformational change in a transcription factor, thereby leading to, activating, or inhibiting gene transcription, methods of modification of transcription factors are provided. In an example embodiment, methods of use can comprise eliciting an immune reaction, creation of an autoantigen, and target deactivation. In an exemplary embodiment, hyperphosphorylation or neo-phosphorylation of a target protein may result in immune recruitment to a target, for example via trigger display of neo-epitopes and T-cell attack on cells displaying the epitopes. In one application, the small molecules disclosed herein are utilized in human leukocyte antigen (HLA) display and immune response. Neo-phosphorylation to elicit an immune response can find use in cancer immunotherapy approaches. In an exemplary approach, a kinase is selected for the phosphorylation of p53, for example, at Ser33, Ser315 and/or Thr82. This phosphorylation leads to subsequent binding and conformational changes which leads to activation as a transcription factor. See, e.g. Ryan and Vousden, Nature, 419 (2002). Thus design of a molecule comprising a binding moiety for an kinase that phosphorylates or dephosphorylates along with a target for p53 can allow control of nucleotide binding based on desired conformation of the transcription factor. See also, e.g. Mattiske T, Tan M H, Dearsley O, Cloosterman D, Hii C S, Gécz J, et al. (2018) Regulating transcriptional activity by phosphorylation: A new mechanism for the ARX homeodomain transcription factor. PLoS ONE 13(11): e0206914. Doi:10.1371/journal.pone.0206914.

Kinasopathies

Treatment of kinasopathies is also contemplated, see, generally, Lahiry et al., Nature Reviews Genetics, 2011, with Table 1 disclosure of inherited kinasopathies incorporated herein by reference. Accordingly, for kinasopathies that have a loss of function, a chimeric small molecule according to the invention can recruit a working kinase to provide the lost function. See, e.g. Lahiry et. al, Nature Reviews Genetics volume 11, pages 60-74 (2010) (discussing various germline disorders and cancers related to kinase dysfunction), incorporated herein by reference, in particular Supplementary Table 1 of inherited kinasopathies and Supplementary Table 2 of kinases associated with cancer. In an exemplary embodiment, Src family protein tyrosine kinases (SFKs) are stabilized in active conformation by phosphorylation of a conserved YA in the active A-loop conformation. By targeting an SFK for modification, e.g. phosphorylation at the A-loop, treatment of aberrant SFK can address kinasopathies associated with the SFK, e.g. ALL, CML. See, e.g. Mechanism of Drug-Resistance in Kinases, Expert Opin Investig Drugs. 2011 February; 20(2): 153-208; doi: 10.1517/13543784.2011.546344.

Methods of Use with Kinase Inhibitor Binding Moiety

In one example embodiment, the method comprises generating a reprogrammed cellular kinase by delivering a chimeric small molecule of the formula A-$L_1$-E-B or A-$L_1$-E-$L_2$-B, wherein A is an protein binding moiety specific for the cellular protein to be repurposed/reprogrammed; B is a target binding moiety specific for the target substrate to be modified; $L_1$ and $L_2$ is a linker; and E is an electrophilic reactive group whereby the chimeric small molecule labels the cellular protein with the target binding moiety for the target substrate; and modifying the target substrate by binding of the repurposed/reprogrammed protein to the target substrate via the target binding moiety, whereby the repurposed/reprogrammed cellular protein introduces one or more modifications to the target substrate. In one example embodiment, the protein binding moiety has a half-life about 2, 3, 4, 5, 6 or 7 times less than a half-life of the protein to be repurposed/reprogrammed. In one example embodiment, the protein to be reprogrammed is an oxidoreductase, transferase, hydrolase, lyase, isomerase, ligase, or translocase. In one example embodiment, an inhibitor is a protein binding moiety. In one example embodiment, the protein to be repurposed/reprogrammed is a kinase and the protein binding moiety is a kinase inhibitor. In one example embodiment, the kinase inhibitor is a 'promiscuous' kinase inhibitor. In one example embodiment, the method comprises administering a coupling molecule thereby quenching the inhibitory activity of the protein inhibitor. In one example embodiment, the coupling molecule is one or more of an aldehyde, alkene, alkyne, strained alkyne, cyclooctyne, trans-cyclooctene, cyclopropene, oxanorbornadiene, norbornene, phosphine, electron-rich dienophile, isonitrile, isocyanopropanoate, tetrazole, 2-acylboronic acid, or any derivative thereof. In one example embodiment, the cyclooctyne derivative comprises dibenzocyclooctyne, biarylazacyclooctynone, or dimethoxyazacyclooctyne. In one example embodiment, the method comprises a strained alkyne comprising a bicyclononyne or dioxabiaryldecyne.

In one example embodiment, the method comprises a chimeric small molecule wherein the protein binding moiety has a half-life about 2, 3, 4, 5, or 6 times less than a half-life of the protein to be reprogrammed. In an example embodiment, the protein to be reprogrammed is an oxidoreductase, transferase, hydrolase, lyase, isomerase, ligase, or translocase. In an example embodiment, the kinase binding moiety is an inhibitor. In an example embodiment, the protein to be reprogrammed is a kinase and the kinase binding moiety is a kinase inhibitor. In an example the kinases inhibitor is a promiscuous kinase inhibitor.

In one example embodiment, the method comprises a chimeric small molecule wherein the kinase binding moiety contains a bio-orthogonal group capable of reacting with and bonding to a coupling molecule. In an example embodiment, the method further comprises administering a coupling molecule. The coupling small molecule is administered to react with the bio-orthogonal group on the chimeric small molecule and, as a result, quench the kinase inhibitor from binding to the kinase. In an example embodiment, the coupling molecule is one or more of an aldehyde, alkene, alkyne, strained alkyne, cyclooctyne, trans-cyclooctene, cyclopropene, oxanorbornadiene, norbornene, phosphine, electron-rich dienophile, isonitrile, isocyanopropanoate, tetrazole, 2-acylboronic acid, or any derivative thereof. In an example embodiment, the cyclooctyne derivative comprises dibenzocyclooctyne, biarylazacyclooctynone, or dimethoxyazacyclooctyne. In one example embodiment, the strained alkyne comprises bicyclononyne or dioxabiaryldecyne.

In one example embodiment, the coupling molecule is co-administered with the chimeric small molecule. In an example embodiment, the coupling molecule is administered after the administration of the chimeric small molecule. In an example embodiment, the coupling molecule is administered within 24 hours, or within 12 hours, or within 11 hours, or within 10 hours, or within 9 hours, or within 8 hours, or within 7 hours, or within 6 hours, or within 5 hours, or within 4 hours, or within 3 hours, or within 2 hours, or within 1 hour, or within 30 minutes or less of administering the chimeric small molecule.

Delivery of Coupling Molecules

In one aspect, the method comprises an additional step of administering or delivering a coupling molecule. The coupling molecule, as previously described, reacts with a bio-orthogonal group on the protein targeting moiety. This reaction suppresses binding of the binding moiety to the protein. When utilized with a chimeric small molecule comprising an electrophilic reactive group, the protein binding moiety may be released from the chimeric small molecule, and the coupling molecule may bind to the biorthogonal group of the kinase binding moiety, thereby preventing the kinase binding moiety from further binding the kinase. In one example embodiment, the coupling molecule is utilized with a kinase binding moiety that is an inhibitor of the protein.

The coupling molecule may be administered in any pharmaceutical formulation, effective amount, and dosage form previously described. The coupling molecule may be delivered using any previously described method or administered with any co-therapies or combinations and as described herein. The chimeric small molecule and the coupling molecule may be delivered or administered concurrently or sequentially. The concurrent delivery of the coupling molecule and chimeric small molecule may occur within the same delivery method or with a separate delivery method. The concurrent but separate delivery of the coupling small molecule may be the same type of delivery method or a different type of delivery method previously described. Sequential delivery of the coupling molecule may occur with the same type of delivery method or different type of delivery method. Sequential delivery of the coupling molecule may occur within 24 hours, or within 12 hours, or within 11 hours, or within 10 hours, or within 9 hours, or within 8 hours, or within 7 hours, or within 6 hours, or within 5 hours, or within 4 hours, or within 3 hours, or within 2 hours, or within 1 hour, or within 30 minutes or less of administering the chimeric small molecule.

Coupling Molecules

In one preferred embodiment, a coupling molecule is introduced to a system containing the chimeric small molecule. As the coupling molecule comes into contact with the chimeric small molecule bound to the target protein, it quenches the binding between the protein binding moiety and target protein. In one example embodiment, the coupling molecule is a molecule capable of undergoing a reaction with a biorthogonal molecule, which is a substituent of the protein binding moiety. The reaction results in the coupling molecule attaching to the protein binding moiety and, as a result, the protein binding moiety no longer binds to the protein. In one example embodiment, the coupling molecule can react with the bio-orthogonal moiety through an aldehyde/ketone-nucleophile reaction, dipolar cycloaddition, phosphine ligation, Diels-Alder cycloaddition, [4+1] cycloaddition, nitrile imine-alkene reaction, or 2-acylboronic acid condensation, or any other bio-orthogonal reaction.

In one example embodiment, the coupling molecule and bio-orthogonal moiety couple through a aldehyde/ketone-nucleophile condensation. Classily, an aldehyde couples with an amine group such as alkoxyamine or hydrazine, for example. While intracellular metabolites contain aldehydes and ketones, this approach is effective on the cell surface. In one preferred embodiment, the coupling molecule is an aldehyde.

In one example embodiment, the coupling molecule and bio-orthogonal moiety couple through a dipolar cycloaddition. Dipolar cycloadditions typically occur between azides and alkynes and either in the presence or absence of copper. In the case of copper free dipolar cycloadditions, the alkyne is strained to facilitate the reaction. In most cases, the strained alkyne is cyclooctyne or any derivative thereof. Non-limiting examples of cyclooctynes include: dibenzocyclooctyne, biarylazacyclooctynone, and dimethoxyazacyclooctyne. In one example embodiment, the coupling molecule is an alkyne. In an example embodiment the coupling molecule is a strained alkyne. In one preferred embodiment, the coupling molecule is cyclooctyne. While it is understood any strained alkyne may be used other non-limiting examples include bicyclononyne, dioxabiaryldecyne, and any derivative thereof.

The dipolar cycloaddition may also comprise a reaction between oxanorbornadiene and an azide. In this case, after the cycloaddition between the oxanorbornadiene and azide, a spontaneous retro-Diels Alder reaction occurs generating a triazole and furan. In one example embodiment the coupling molecule is oxanorbornadiene or any derivative thereof.

The dipolar cycloaddition may also comprise the reaction between norbornene and a nitrile oxide. In one example embodiment, the coupling molecule is norbornene. The coupling molecule may also perform a dipolar cycloaddition with another dipolar molecule such as a nitrone, (imino) syndone, or 1,3-dithiolium-4-olate and would comprise of the counterpart unsaturated hydrocarbon.

In one example embodiment, the coupling molecule and bio-orthogonal moiety couple through a phosphine ligation, or interchangeably referred to as the Staudinger ligation. A phosphine ligation typically occurs between an azide and phosphine typically forming a phosphine oxide and a stable amide linkage or, when electron deficient aromatic azides are used, forming an iminophosphorane. In one example embodiment, the coupling molecule is a phosphine or any derivative thereof. Phosphine ligations may also comprise a cyclopropene in place of the azide. Non-limiting examples of cyclopropane include: cyclopropenones, cyclopropenethiones, cyclopropenium ions.

In one example embodiment, the coupling molecule and bio-orthogonal moiety couple through a Diels-Alder cycloaddition. The reaction is an inverse electron-demand Diels-Alder and classically occurs between an electron-poor diene and an electron-rich dienophile. In one example embodiment, the coupling molecule is an electron-rich dienophile. The Diels-Alder cycloaddition may comprise a tetrazine ligation wherein a strained unsaturated hydrocarbon and a tetrazine or triazene couple to form a pyridazine. In one example embodiment, the coupling molecule is a strained unsaturated hydrocarbon. The unsaturated hydrocarbon may also be cyclic. Non-limiting example of strained, cyclic unsaturated hydrocarbons include cyclooctynes, trans-cyclooctenes, norbornenes, cyclopropenes, and azetines. In preferred embodiments, the coupling molecule is a cyclooctyne, trans-cyclooctene, or a derivative thereof.

In one example embodiment, the coupling molecule and bio-orthogonal moiety couple through a [4+1] cycloaddition. The reaction involves the coupling of an isonitrile with, classically, a tetrazine followed by a spontaneous retro-Diels Alder elimination. The conjugate of the reaction is more stable if the isonitrile is tertiary. However, less stable conjugates are formed when the isonitrile is primary or secondary. In one preferred embodiment, the coupling molecule is an isonitrile or any derivative thereof. In one example embodiment, the isonitrile is tertiary. In one preferred embodiment, the coupling molecule is isocyanopropanoate or any derivative thereof.

In one example embodiment, the coupling molecule and bio-orthogonal moiety couple through a nitrile imine-alkene cycloaddition. Classically, tetrazole is photolyzed to generate nitrile imine which readily couple with unsaturated hydrocarbons. The wavelength necessary for photolysis is dependent on the substituents of tetrazine. However, photolysis is not required if hydrazonoyl chlorides are present, which, at neutral pH, spontaneously generate nitrile imines from tetrazole. In one preferred embodiment the coupling molecule is an unsaturated hydrocarbon and is optionally introduced with a hydrazonoyl chloride.

In one example embodiment, the coupling molecule and bio-orthogonal moiety couple through a 2-acylboronic acid condensation. In this reaction, the boronic acid couples with an amine to form a stable diazaborine. In one preferred embodiment, the coupling molecule is 2-acylboronic acid or any derivative thereof. See e.g., Shieh P, Bertozzi C R. Design strategies for bioorthogonal smart probes. *Org Biomol Chem.* 2014; 12(46):9307-9320. doi:10.1039/c4ob01632g and Mike L. W. J., et al., Recent developments in bioorthogonal chemistry and the orthogonality within, *Curr. Opin. Chem. Biol.*, 2021, 60, 79-88, herein incorporated by reference.

Oncogenic Applications

In one example embodiment, the disease is associated with cancer. In particular, the disease is oncogenic. Many oncogenic targets are known and can be regulated by post-translational modifications. See, e.g. Chen, L., Liu, S. & Tao, Y. Regulating tumor suppressor genes: post-translational modifications. *Sig Transduct Target Ther* 5, 90 (2020); doi:10.1038/s41392-020-0196-9. Exemplary post-translational modification types of proteins implicated in oncogenesis and their expression pattern are found in Table 1 of Sharma, et al., (2019). Post-Translational Modifications (PTMs), from a Cancer Perspective: An Overview. Oncogen 2(3): 12, specifically incorporated herein by reference.

The chimeric small molecules disclosed herein can be utilized in methods of treating cancer. Methods of treating cancer can include generating a repurposed/reprogrammed cellular protein by administering a chimeric small molecule, as described herein. The chimeric small molecule labels the cellular protein with an oncogenic target kinase binding moiety via the electrophilic reactive group moiety. The electrophilic reactive group reacts with and bonds to a nucleophilic side chain on the cellular protein. Labelling of the cellular protein can allow for bonding to, or association with, the oncogenic target protein, or to a molecule in proximity to the oncogenic protein facilitating modification of the target substrate. In one aspect, the methods comprise inducing phosphorylation of the oncogenic target protein in or on the cell. The methods may comprise contacting the oncogenic target protein with the chimeric small molecule. In one example embodiment, the oncogenic target protein is in proximity to a kinase specific to the protein binding moiety of the molecule. Chimeric small molecules that induce phosphorylation can be optionally provided with adenosine monophosphate (AMP) or another molecule providing an additional phosphate group. Without being bound by theory, the addition of the AMP or other phosphate providing molecule can enhance phosphorylation.

Methods of treating cancer are provided. The method of treating cancer comprises generating a reprogrammed cellular protein by administering to a subject in need thereof a chimeric small molecule of the formula: A-$L_1$-E-B or A-$L_1$-E-$L_2$-B, wherein A is an protein binding moiety; E is an electrophilic reactive group and B is an oncogenic target protein to be modified, whereby the chimeric small molecule labels the cellular protein with the target binding moiety for the target substrate; and modifying the oncogenic target protein by binding of the repurposed/reprogrammed protein to the target substrate via the target binding moiety, whereby the repurposed/reprogrammed cellular protein introduces one or more modifications to the target substrate. In one example embodiment, the target binding moiety is specific for KRAS, RAS, $FKPB^{12F36V}$, EGFR, HSP90, BTK, MDM2, BRD4, BCR-ABL, NF-κB, LDH-A, p53, GP73, MUC1, MUC16, CD44, GPCR, HMGB1, RIOK1, CHK1, UBE2F, HuR, PTEN, STAT-3, Osteopontin, EGFRs, AKT, DAPK1, Rho, Ubc9, FOXK2, HIC1, HER2, BRAF, BCL-2, CD117, (KIT), ALK, PI3K, Delta, DNMT1, or SMO. In one example embodiment, the cellular protein to be reprogrammed is a oxidoreductase, transferase, hydrolase, lyase, isomerase, ligase, translocase. In one example embodiment, the kinase binding moiety is a kinase inhibitor. In one example embodiment, the kinase inhibitor is specific for PK, PKC, AMPK, MAPK, EGFR, FGFR, NGFR, TrkA, ABL, BCKDK, CDK, PI3K, VEGFR, BRAF, MEK, AKT, ALK, BTK, FLT3, JAK2, AURKA, c-MET, DDR, FKBP, INSR, IKK, JNK, mTOR, PAK, PDK1, PDK2, PTK2/FAK, pyruvate kinases, RAC-α, RIPK, TYK2, SHP, aPKC, NOP, μ opioid receptor, δ opioid receptor, UMPK, SphK, or GSK-3. In one example embodiment, administering a coupling molecule thereby quenching the inhibitory activity of the kinase inhibitor.

Methods of treating a disease associated with aberrant KRAS signaling is provided, comprising administering a composition comprising a chimeric small molecule, the chimeric small molecule comprising the KRAS binding molecule and a kinase binding molecule of as described herein. In one example embodiment, the kinase binding molecule is a target for an kinase selected from the group consisting of: PK, PKC, AMPK, MAPK, EGFR, FGFR, NGFR, TrkA, ABL, BCKDK, CDK, PI3K, VEGFR, BRAF, MEK, AKT, ALK, BTK, FLT3, JAK2, AURKA, c-MET, DDR, FKBP, INSR, IKK, JNK, mTOR, PAK, PDK1, PDK2, PTK2/FAK, pyruvate kinases, RAC-α, RIPK, TYK2, SHP, aPKC, NOP, μ opioid receptor, δ opioid receptor, UMPK, SphK, or GSK-3. In an embodiment, the kinase binding molecule is an AMPK binding moiety. In one example embodiment, the KRAS is $KRAS^{G12C}$. In one example embodiment, the chimeric small molecule phosphorylates one or more residues on KRAS selected from the group consisting of Ser17, Ser39, Ser65, Ser106, Ser122, Ser136, Ser2, Thr2, Thr35, Thr50, Thr74, Thr87, Thr124, Thr127, Thr148.

In an example embodiment, a method of treating cancer in a cell is provided, comprising administering a chimeric small molecule of the present invention. In one example the small molecule comprises a PI3K kinase binder, a linker, an electrophilic reactive group, and a p53 target binding moiety, e.g. based on idasanutlin. In one example embodiment, the molecule comprises a binder of PI3K based on the inhibitor PIK108 that further optionally comprises bioorthogonal group, e.g. cyclopropenyl. The binding moiety PIK108 comprises a linker connected to the electrophilic reactive group, e.g. dibromophenyl benzoate. The electrophilic reactive group, in turn, is connected to the p53 protein target binding moiety, optionally via a linker. Upon binding to the PI3K kinase via PIK108, proximal lysines of the binding pocket of PI3K, and will react with the lysine-reactive group (e.g., dibromophenyl benzoate) and expel the kinase inhibitor, leaving the PI3K tagged with the p53 binder. The kinase which is covalently labeled with the target binding moiety can then hyper and/or neo-phosphorylate the p53. Administration of a tetrazine coupling molecule can quench the cyclopropenyl biorthogonal group when displayed on the PI3K binding molecule, and deactivate the expelled kinase binding moiety.

Exemplary oncogenic fusion proteins that can be treated by the binding of a multimeric kinase include fusions associated with the ABL proteins. ABL proteins are non-receptor tyrosine kinases that are normally under well-orchestrated regulation. However, chromosome translocations that join the ABL genes with genes coding for other proteins give rise to various oncogenic fusion proteins (BCR-ABL, TEL-ABL, NUP214-ABL, etc.) that are prone to dimerization (or oligomerization) and subsequent autophosphorylation. Consequently, ABL kinase becomes constitutively active and lead to diseases such has chronic myeloid leukemia (CML), acute lymphocytic leukemia (ALL) and other myeloproliferative disorders. An example oncogenic fusion is BCR-ABL. This may be particularly true for kinases such as Abl which must form complexes to become active.

In example embodiments, the cancer is characterized by an oncofusion of a kinase, e.g. ABL-kinase. Oncogenic ABL fusion proteins are known in the art and implicated in a variety of proliferative disorders. Chromosome translocations occur joining the genes of ABL with genes coding for other proteins, giving rise to various proteins that are prone to dimerization (or oligomerization) and autophosphorylation, making the ABL kinase constitutively active and leading to myeloproliferative disorders. In example embodiments, the oncofusion is TEL-ABL or NUP214-ABL.

Translocation events in cancer have been shown to be associated with fusions involving ALK, BRAF, EGFR, FGFR1, 2 and 3, NTRK1, 2 and 3, PDGFRA, PRKCA and B, RAF1, RET, ROS1, FGR, MET, PIK3CA, and PKN1. Chimeric small molecules designed as molecular glue for targeting of the fusions using the design considerations for the small molecules as described herein. In particular, druggable kinases that engage in fusions include AKT3, ALK, BRAF, BRD4, CD74, EGFR, EML4, ERBB4, ESR1, FGFR2, FGFR3, JAK2, MET, NOTCH1, NRG1, NTRK1, NTRK3, NUP214-ABL1, PDGFRA, PDGFRB, PML-RARA, RAF1, RET, ROS1, TMPRSS2, and TRIM33-RET have also been identified.

Additional fusions that can be targeted with the chimeric small molecules taught herein include, but are not limited to, ACSM2B-NOTCH2, ACTG2-ALK, ACVR2A-AKT3, AFF3-TMPRSS2, AGGF1-RAF1, AGK-BRAF, AKAP13-NRG1, AKAP13-NTRK3, AKAP13-RET, AKAP7-ESR1, AKT3-ADSS, AKT3-CDC14A, AKT3-HEATR1, AKT3-PPP2R2A, AKT3-PTPRR, ALK-GALNT14, ALK-SCEL, ALK-STK39, AP3B1-BRAF, ARHGEF25-NTRK1, ARID2-TMPRSS2, ATAD2-ERBB4, ATF7IP-TMPRSS2, ATG7-BRAF, ATP1A1-NOTCH2, ATP1B1-NRG1, ATP2B4-ERBB4, B4GALT1-RAF1, BACE2-TMPRSS2, BAIAP2L1-MET, BCL2L11-BRAF, BCR-ABL1, BRAF-AP3B1, BRAF-ATG7, BRAF-CUL1, BRAF-DENND2A, BRAF-FAM114A2, BRAF-HIBADH, BRAF-MACF1, BRAF-MED4, BRAF-SND1, BRAF-SUGC1, BRD4-AKAP8L, BRD4-CC2D1A, BRD4-CSE1L, BRD4-CSN2, BRD4-CYP4F22, BRD4-GNAT1, BRD4-MFSD12, BRD4-NOTCH3, BRD4-PGLYRP1, BRD4-PGLYRP2, BRD4-SLC1A6, BRD4-ZC3H15, C8orf34-MET, CBR4-ERBB4, CCAR2-FGFR2, CCDC6-RET, CD74-ROS1, CDC27-BRAF, CDK12-JAK2, CDK2-ALK, CEL-NTRK1, CEP170-AKT3, CEP85L-ROS1, CHIC2-PDGFRA, CLCN6-RAF1, CLOCK-PDGFRA, CLTC-ROS1, CMTM8-RAF1, CUX1-BRAF, DANCR-PDGFRA, DLG5-RET, DLG5-TMPRSS2, DNM1-FGFR2, DOCK8-JAK2, DSTYK-BRAF, EGFR-ACADM, EGFR-C7orf72, EGFR-CHODL, EGFR-DYM, EGFR-GRB10, EGFR-GYG1, EGFR-INSL4, EGFR-LYST, EGFR-RCL1, EGFR-SEPT14, EGFR-SEPT14P24, EGFR-TEAD3, EGFR-VSTM2A, EIF5-NOTCH2, EML4-ALK, EML4-NTRK3, EPHB2-NTRK1, EPS15L1-BRD4, ERBB4-RBM33, ERBB4-SDCCAG8, ERBB4-SLC25A10, ERC1-RET, ERG-TMPRSS2, ESR1-ASPH, ESR1-BNC2, ESR1-GNAS, ESR1-MYCT1, ESR1-, DE7B, ESR1-POLH, ESR1-POLR2E, ESR1-SIM1, ESR1-SYNE1, ESR1-TFB1M, ESR1-UTRN, ETV6-NTRK3, EZR-ROS1, FAM114A2-BRAF, FAM193A-FGFR3, FAT1-NTRK3, FBXL20-NOTCH2, FGFR2-AP1M1, FGFR2-B1CC1, FGFR2-CASP7, FGFR2-CCAR2, FGFR2-CCDC186, FGFR2-CCDC6, FGFR2-CTNNA3, FGFR2-EIF4A2, FGFR2-ENPP2, FGFR2-FRK, FGFR2-OFD1, FGFR2-SHTN1, FGFR2-SMN1, FGFR2-TACC2, FGFR2-USP10, FGFR3-AES, FGFR3-AMBRA1, FGFR3-ELAVL3, FGFR3-FBXO28, FGFR3-MLLT10, FGFR3-TACC3, FKBP15-RET, FOXO1-PDGFRB, FRMD3-BRD4, GPRC5A-NRG1, GTF2IRD1-ALK, HDLBP-TMPRSS2, HIBADH-BRAF, HMGN2P46-TMPRSS2, IGHGP-NOTCH1, IRF2BP2-NTRK1, JAK2-CSTF3, JAK2-DOCK8, JAK2-GLDC, JAK2-RCL1, KANSL1L-ERBB4, KCNQ5-ALK, KDM7A-BRAF, KIAA1211-PDGFRA, KIF5B-MET, KLHL7-BRAF, LMNA-NTRK1, LMNA-RAF1, LYN-NTRK3, MACF1-BRAF, MAGI3-NOTCH2, MALAT1-ALK, MAP3K7-PDGFRB, MAPK1-NOTCH1, MESDC2-TMPRSS2, MET-C8orf34, MET-CNTNAP5, MET-DYNC1I1, MET-ST7-AS2, MET-TFG, MET-WNT2, MGP-ESR1, MKRN1-BRAF, MPRIP-RAF1, NCOA4-RET, NDUFS4-TMPRSS2, NOTCH1-CHST9, NOTCH1-EXD3, NOTCH1-LCN15, NOTCH1-MAPK1, NOTCH1-SDCCAG3, NOTCH1-SPTAN1, NOTCH1-TMEM117, NOTCH2-ADAM30, NOTCH2-CWH43, NOTCH2-MNDA, NOTCH2-PSMA5, NOTCH2-REG4, NOTCH2-SEC22B, NOTCH2-SPAG17, NRG1-PMEPA1, NRG1-STMN2, NTRK1-DYNC2H1, NTRK3-ETV6, NTRK3-LOXL2, NTRK3-PEAK1, NTRK3-RBPMS, NUP214-ABL1, OXR1-MET, PAICS-PDGFRA, PAPD7-RAF1, PCM1-NRG1, PDE7A-NRG1, PDE9A-TMPRSS2, PDGFRA-FIP1L1, PDGFRA-GRID2, PDGFRA-SCFD2, PDGFRA-USP8, PKHD1-ESR1, PLGRKT-JAK2, PML-RARA, PPP4R3B-ALK, PTGFRN-NOTCH2, PTPRZ1-MET, RAB3IL1-NRG1, RAB5B-ALK, RAC1P2-EGFR, RAF1-AGGF1, RAF1-C9orf153, RAF1-EIF3L, RAF1-GXYLT2, RAF1-IQSEC1, RAF1-NXPH1, RAF1-PHC3, RAF1-RPL32, RAF1-SSUH2, RAF1-TRAK1, RBPMS-NTRK3, RET-CCDC6, RET-MRLN, RET-NCOA4, RHBDD2-EGFR, ROS1-CD74, ROS1-CLTC, ROS1-FBXO9, SCP2-TMPRSS2, SDC4-NRG1, SEC61G-EGFR, SIK3-TMPRSS2, SLC34A2-ROS1, SLC45A3-TMPRSS2, SMAD4-NRG1, SMARCA4-BRD4, SMN1-FGFR2, SND1-BRAF, SPECC1L-RET, SQSTM1-NTRK1, SSBP2-NTRK1, STRN-ALK, SYNE1-ESR1, TACC3-FGFR3, TAX1BP1-BRAF, TBL1XR1-RET, TCEA1-EGFR, TFG-MET, TFG-NTRK1, THAP7-NRG1, THBS1-NRG1, TMEFF2-TMPRSS2, TMEM165-PDGFRA, TMPRSS2-ATF7IP, TMPRSS2-BRAF, TMPRSS2-CALB1, TMPRSS2-DGKG, TMPRSS2-DIAPH1, TMPRSS2-EML4, TMPRSS2-ERG, TMPRSS2-ETV4, TMPRSS2-ETV5, TMPRSS2-GUCA2A, TMPRSS2-HDLBP, TMPRSS2-HSF2BP, TMPRSS2-INPP4B, TMPRSS2-IRS2, TMPRSS2-KLF4, TMPRSS2-MORC3, TMPRSS2-RPS6, TMPRSS2-MX1, TMPRSS2-PDE9A, TMPRSS2-PHF12, TMPRSS2-SARS, TMPRSS2-TMEFF2, TMPRSS2-TMEM109, TPM1-ALK, TPM3-NTRK1, TRAK1-RAF1, TRIM24-BRAF, TRIM27-RET, TTC13-JAK2, TULP4-ESR1, UBXN8-NRG1, USP28-TMPRSS2, USP46-PDGFRA, VCL-FGFR2, VPS18-NTRK3, WRN-NRG1, ZBTB7B-NTRK1, ZC3HAV1-BRAF, ZEB2-AKT3, and ZNF430-BRD4.

Example targetable fusions include ALK fusions, such as TFG-ALK. ALK fusions have been identified in multiple cancer types, for example lung adenocarcinoma, bladder, colorectal, breast, renal cell, renal medullary and thyroid cancers. In particular, EML4-ALK fusions were found in lung adenocarcinoma, STRN-ALK fusion in thyroid cancer and in papillary renal carcinoma, TPM1-ALK fusion in bladder cancer, SMEK2-ALK fusion in rectal adenocarcinoma and GTF2IRD1-ALK fusion in thyroid cancer. Another targetable fusion includes BRAF fusions, which are associated with prostate cancer, melanoma, radiation-induced thyroid cancer, and pediatric low-grade gliomas. In particular, TRIM-BRAF fusion has been found in rectal adenocarcinoma, ATG7-BRAF in melanoma, and ZC3HAV1-BRAF as well as FAM114A2-BRAF in thyroid cancer. Other example fusions include AGK-BRAF, SND1-BRAF, MACF1-BRAF, TAX1BP1-BRAF and CDC27-BRAF. It is known in the art BRAF dimers are not sensitive to RAF inhibitors and instead be treated to inhibition downstream through, for example, MEK inhibition.

Another targetable fusion includes FGFR fusions, which have been identified in glioblastoma multiforme, bladder urothelial carcinoma, lung squamous cell carcinoma, kidney papillary cell carcinoma, brain low-grade glioma, prostate adenocarcinoma, head and neck squamous cell carcinoma, breast invasive carcinoma, stomach adenocarcinoma tumor types. In particular, FGFR3-TACC3 fusion has been found in papillary renal carcinoma, FGFR3-ELAVL3 in low-grade glioma and FGFR3-BAIAP2L1 in bladder cancer. Another targetable fusion is WASF2-FGR fusions, which have been found in in lung squamous carcinoma, ovarian serous cystadenocarcinoma and skin cutaneous melanoma. Another targetable fusion includes MET fusions, which have been found in low-grade glioma, hepatocellular carcinoma, lung adenocarcinoma and thyroid carcinoma. In particular, BAIAP2L1-MET and C8orf34-MET have been found in papillary renal carcinoma, KIF5B-MET in lung adenocarcinoma, and TFG-MET in thyroid papillary carcinoma. Another notable fusion is TPR-MET.

Another targetable fusion includes NTRK fusions, which have been associated with congenital fibrosarcoma, human secretory breast carcinoma, and papillary thyroid cancer, including glioblastoma, cholangiocarcinoma and pediatric high-grade glioma. In particular, PAN3-NTRK2 have been found in head and neck squamous cell carcinoma, AFAP1-NTRK2 low-grade glioma, TRIM24-NTRK2 in lung adenocarcinoma, and TPM3-NTRK1 in sarcoma and thyroid cancer. Another targetable fusion includes PIK3CA fusions, which have been found in endometrial cancers, breast invasive carcinomas, and colorectal, head, and neck cancers. In particular, TBL1XR1-PIK3CA fusions have been found in breast cancer and prostate adenocarcinoma, FNDC3B-PIK3CA fusion in uterine corpus endometrial carcinoma, and TBL1XR1-PIK3CA fusions in invasive breast carcinoma and prostate cancer. Another targetable fusion is PKC fusions, which have been found in papillary glioneuronal tumors and benign fibrous histiocytoma. PRKCA fusions have been found in lung squamous cell carcinoma and PRKCB fusions have been found in lung squamous cell carcinoma, lung adenocarcinoma and low-grade glioma. Example fusions include PRKCA was fused with IGF2BP3. TANC2-PRKCA.

Another targetable fusion includes PKN1 fusions and have been found in squamous cell carcinoma of the lung and hepatocellular carcinoma. Example PKN1 fusions include ANXA4-PKN1 and TECR-PKN1. Another targetable fusion includes RAF1, also known as CRAF, fusions, which have been found in melanoma and prostate adenocarcinoma. In particular AGGF1-RAF1 has been found in papillary thyroid carcinoma and prostate cancer. Another targetable fusion includes RET fusions, which have been found in lung adenocarcinoma and thyroid cancer. In particular, CCDC6-RET fusions have been found in thyroid cancer and colon adenocarcinoma while ERC1-RET fusion has been found in breast cancer. Other example fusions include RET with AKAP13, FKBP15, SPECC1L, and TBL1XR1. Another targetable fusion is ROS1 fusions, such as CEP85L-ROS1 which has been found in glioblastoma and single angiosarcoma. Another notable ROS1 fusion is CD74-ROS1 while other fusions have been found in 8/513 lung adenocarcinomas.

Tyrosine kinase fusion genes are a notable class of oncogenes. Tyrosine kinase fusions have been found in leukemia and solid tumors. Like other fusions, they are created by translocations and other chromosomal rearrangements of a subset of tyrosine kinase genes. These fusions include ABL, PDGFRA, PDGFRB, FGFR1, SYK, RET, JAK2 and ALK. The kinase domain is activated by enforced oligomerization and inactivation of inhibitory domains. Activated tyrosine kinase fusions then signal via an array of transduction cascades. The fusion partner recruits proteins that contribute to signaling, protein stability, cellular localization and oligomerization.

See, e.g. Stransky, N., Cerami, E., Schalm, S. et al. The landscape of kinase fusions in cancer. Nat Commun 5, 4846 (2014). doi: 10.1038/ncomms5846 (including, in particular, FIG. 1, providing a landscape of recurrent kinase fusions in solid tumors, incorporated by reference); Medves et al., J Cell Mol Med. 2012 February; 16(2):237-48; doi: 10.1111/j.1582-4934.2011.01415.x. (including, in particular, TK fusions and their inhibitor molecules of Table 1, incorporated by reference); and Gao, Qingsong et al. "Driver Fusions and Their Implications in the Development and Treatment of Human Cancers." Cell reports vol. 23,1 (2018): 227-238.e3. doi:10.1016/j.celrep.2018.03.050, each of which is incorporated herein by reference in their entirety.

Gao et al. provides a table of potentially druggable fusion events and their targets in Table S5, specifically incorporated herein by reference for its teaching of fusions, targets and indications associated with the fusion events.

Exemplary cancers associated with such fusions include adrenocortical carcinoma, bladder urothelial carcinoma, brain lower grade glioma, breast invasive carcinoma, cervical squamous cell carcinoma and endocervical adenocarcinoma, cholangiocarcinoma, colon adenocarcinoma, esophageal carcinoma, glioblastoma multiforme, head and neck squamous cell carcinoma, kidney chromophobe, kidney renal clear cell carcinoma, kidney renal papillary cell carcinoma, acute myeloid leukemia, liver hepatocellular carcinoma, lung adenocarcinoma, lung squamous cell carcinoma, lymphoid neoplasm diffuse large B cell lymphoma, mesothelioma, ovarian serous cystadenocarcinoma, pancreatic adenocarcinoma, pheochromocytoma and paraganglioma, prostate adenocarcinoma, rectum adenocarcinoma, sarcoma, skin cutaneous melanoma, stomach adenocarcinoma, testicular germ cell tumors, thymoma, thyroid carcinoma, uterine carcinosarcoma, uterine corpus endometrial carcinoma, and uveal melanoma.

Isoforms of RAS have conserved amino acid sequences in the Swtich-I and Switch-II regions of Ras. The Switch regions of Ras are the binding interface for effector proteins and Ras regulators such as GTPase-activating proteins (GAPs) and guanine nucleotide exchange factors (GEFs). Several cancer mutations are located within Switch II, and the P-loop attached to Switch-I. Thus, phosphorylation of loop residues in the Swicth-I or Switch-II may address Ras activity, as post-translation modifications of loop residues are known generally to generate conformational changes.

KRAS is a key regulator of cell proliferation, differentiation and survival, and is the most frequently mutated oncogene in human cancers. An exemplary oncogenic driver mutation is KRAS$^{G12C}$ The active GTP-bound state of KRAS is a closed conformation, while the inactive, GDP-bound states is an open conformation. In KRAS G12C, and other oncogenic RAS mutations, a dysregulated excess of cellular GTP-bound RAS results, with the RAS function remaining in the open conformation active state that results in uncontrolled cell growth and proliferation, invasiveness and evasion of immune surveillance. Accordingly, inhibition of GTPases (e.g. Ras) is within the scope of the chimeric small molecules disclosed herein.

Without being bound by a particular scientific theory, it is proposed phosphorylation of KRAS, particularly KRAS$^{G12C}$ may facilitate generation of conformational change, perhaps by disrupting binding to GTPase-activating proteins, thereby decreasing Ras activity which is implicated in oncogenesis. For example, phosphorylation of T35 or S17 residues which coordinate to Mg$^{2+}$ ion that also coordinates to the gamma- and beta-phosphates of GTP can potentially disrupt the 4-way Mg2+ chelation. This tetra-chelated Mg2+ state is characteristic of the active GTP-bound state "closed conformation") while inactive GDP-bound state only has S17 and the gamma-phosphate of GDP involved in Mg$^{2+}$ binding. Further without being bound by theory, it may be that phosphorylation of any Switch-I or Switch-II or Switch-adjacent residues can disrupt protein-protein interactions between the Switch regions and Ras regulators, and the activating proteins, or that phosphorylation of loop residues in Switch-I or Switch II can cause conformation changes, as post-translational modifications of loop residues are often known to generate conformational changes. Accordingly, modulating KRAS signaling with a kinase utilizing the phosphorylation inducing chimeric small molecules described herein may be useful as an anti-cancer therapy by disrupting KRAS membrane localization or binding partners.

In one aspect, the method comprises treating cancer as a result of KRAS. In one example embodiment, the chimeric small molecule target binding moiety targets KRAS, NF-kB, LDH-A, p53, GP73, MUC1, MUC16, CD44, GPCR, HMGB1, RIOK1, CHK1, UBE2F, HuR, PTEN, STAT-3, Osteopontin, EGFRs, AKT, DAPK1, Rho, Ubc9, FOXK2, HIC1, HER2, BRAF, BCL-2, CD117, (KIT), ALK, PI3K, Delta, DNMT1, SMO.

In one example embodiment, the chimeric small molecule target binding moiety targets MYC, K-RAS, N-RAS, TP53, KDM6A, NPM1, H-RAS, FGFR3, MSH6, TP53, EGFR, PIK3CA, ABL1, CTNNB1, KIT, INF1A, JAK2, BRAF, IDHI, RET, PDGFRA, MET, APC, CDC27, CDK4, prostate-specific antigen, alpha fetoprotein, breast mucin, gpIOO, g250, p53, MART-I, MAGE, BAGE, GAGE, tyrosinase, Tyrosinase related protein 11, Tyrosinase related protein, or RAD50.

Additional cancer targets, indications and small molecules target binding moieties are provided in Table 2 of Sharma BS (2019). Post-Translational Modifications (PTMs), from a Cancer Perspective: An Overview. Oncogen 2(3): 12, specifically incorporated herein by reference.

Diseases/Disorders

In some embodiments, the disease is associated with aberrant protein expression, or expression of a tumor antigen, e.g., a proliferative disease, a precancerous condition, a cancer, or a non-cancer related indication associated with expression of the tumor antigen, which may in some embodiments comprise a target selected from B2M, CD247, CD3D, CD3E, CD3G, TRAC, TRBC1, TRBC2, HLA-A, HLA-B, HLA-C, DCK, CD52, FKBP1A, CIITA, NLRC5, RFXANK, RFX5, RFXAP, or NR3C1, HAVCR2, LAG3, PDCD1, PD-L2, CTLA4, CEACAM (CEACAM-1, CEACAM-3 and/or CEACAM-5), VISTA, BTLA, TIGIT, LAIR1, CD160, 2B4, CD80, CD86, B7-H3 (CD113), B7-H4 (VTCN1), HVEM (TNFRSF14 or CD107), KIR, A2aR, MHC class I, MHC class II, GAL9, adenosine, and TGF beta, or PTPN11 DCK, CD52, NR3C1, LILRB1, CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8) aNeu5Ac(2-3)bDGalp(1-4)bDGlcp(1-1)Cer); TNF receptor family member B cell maturation (BCMA); Tn antigen ((Tn Ag) or (GalNAca-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); n kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4)bDGlcp(1-1)Cer); transglutaminase 5 (TGS5); high molecular weight-melanoma-associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT- 2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1), CD19, BCMA, CD70, G6PC, Dystrophin, including modification of exon 51 by deletion or excision, DMPK, CFTR (cystic fibrosis transmembrane conductance regulator). In one example embodiment, the targets comprise CD70, or a Knock-in of CD33 and Knock-out of B2M. In one example embodiment, the targets comprise a knockout of TRAC and B2M, or TRAC B2M and PD1, with or without additional target genes. In one example embodiment, the disease is cystic fibrosis with targeting of the SCNN1A gene. In one example embodiment, the modification via the chimeric small molecules is used in multiple sclerosis, e.g. αB-crystallin, or in SLE with multiple targets (see, e.g. Doyle and Mamula, Curr Opin Immunol. 2012). Treating Intracellular Pathogens Additional Diseases and Disorders In one example embodiment, the treatment is for disease/disorder of an organ, including liver disease, eye disease, muscle disease, heart disease, blood disease, brain disease, kidney disease, or may comprise treatment for an autoimmune disease, central nervous system disease, cancer and other proliferative diseases, neurodegenerative disorders, inflammatory disease, metabolic disorder, musculoskeletal disorder and the like.

Particular diseases/disorders include chondroplasia, achromatopsia, acid maltase deficiency, adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemia, Gaucher's disease, generalized gangliosidoses (e.g., GM1), hemochromatosis, the hemoglobin C mutation in the 6th codon of beta-globin (HbC), hemophilia, Huntington's disease, Hurler Syndrome, hypophosphatasia, Klinefelter syndrome, Krabbes Disease, Langer-Giedion Syndrome, leukodystrophy, long QT syndrome, Marfan syndrome, Moebius syndrome, mucopolysaccharidosis (MPS), nail patella syndrome, nephrogenic diabetes insipidus, neurofibromatosis, Neimann-Pick disease, osteogenesis imperfecta, *porphyria*, Prader-Willi syndrome, progeria, *Proteus* syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, and Wiskott-Aldrich syndrome.

In one example embodiment, the disease is associated with expression of a tumor antigen, e.g., a proliferative disease, a precancerous condition, a cancer, or a non-cancer related indication associated with expression of the tumor antigen, which may in some embodiments comprise a target selected from B2M, CD247, CD3D, CD3E, CD3G, TRAC, TRBC1, TRBC2, HLA-A, HLA-B, HLA-C, DCK, CD52, FKBP1A, CIITA, NLRC5, RFXANK, RFX5, RFXAP, or NR3C1, HAVCR2, LAG3, PDCD1, PD-L2, CTLA4, CEACAM (CEACAM-1, CEACAM-3 and/or CEACAM-5), VISTA, BTLA, TIGIT, LAIR1, CD160, 2B4, CD80, CD86, B7-H3 (CD113), B7-H4 (VTCN1), HVEM (TNFRSF14 or CD107), KIR, A2aR, MHC class I, MHC class II, GAL9, adenosine, and TGF beta, or PTPN11 DCK, CD52, NR3C1, LILRB1, CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bD-Galp(1-4)bDGlcp(1-1)Cer); TNF receptor family member B cell maturation (BCMA); Tn antigen ((Tn Ag) or (GalNAca-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); n kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100);

oncogene fusion protein consisting of breakpoint cluster region (BCR) and Abelson murine leukemia viral oncogene homolog 1 (Abl) (ber-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4) bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRLS); and immunoglobulin lambda-like polypeptide 1 (IGLL1), CD19, BCMA, CD70, G6PC, Dystrophin, DMPK, CFTR (cystic fibrosis transmembrane conductance regulator).

In one example embodiment, the disease is Metachromatic Leukodystrophy, and the target is Arylsulfatase A, the disease is Wiskott-Aldrich Syndrome and the target is Wiskott-Aldrich Syndrome protein, the disease is Adreno leukodystrophy and the target is ATP-binding cassette DI, the disease is Human Immunodeficiency Virus and the target is receptor type 5-C—C chemokine or CXCR4 gene, the disease is Beta-thalassemia and the target is Hemoglobin beta subunit, the disease is X-linked Severe Combined ID receptor subunit gamma and the target is interleukin-2 receptor subunit gamma, the disease is Multisystemic Lysosomal Storage Disorder cystinosis and the target is cystinosin, the disease is Diamond-Blackfan anemia and the target is Ribosomal protein S19, the disease is Fanconi Anemia and the target is Fanconi anemia complementation groups (e.g. FNACA, FNACB, FANCC, FANCD1, FANCD2, FANCE, FANCF, RAD51C), the disease is Shwachman-Bodian-Diamond Bodian-Diamond syndrome and the target is Shwachman syndrome gene, the disease is Gaucher's disease and the target is Glucocerebrosidase, the disease is Hemophilia A and the target is Anti-hemophiliac factor OR Factor VIII, Christmas factor, Serine protease, Factor Hemophilia B IX, the disease is Adenosine deaminase deficiency (ADA-SCID) and the target is Adenosine deaminase, the disease is GM1 gangliosidoses and the target is beta-galactosidase, the disease is Glycogen storage disease type II, Pompe disease, the disease is acid maltase deficiency acid and the target is alpha-glucosidase, the disease is Niemann-Pick disease, SMPD1-associated (Types Sphingomyelin phosphodiesterase 1 OR A and B) acid and the target is sphingomyelinase, the disease is Krabbe disease, globoid cell leukodystrophy and the target is Galactosylceramidase or galactosylceramide lipidosis and the target is galactocerebrosidase, Human leukocyte antigens DR-15, DQ-6, the disease is Multiple Sclerosis (MS) DRB1, the disease is Herpes Simplex Virus 1 or 2. The disease can be Hepatitis B with a target of one or more of PreC, C, X, PreS1, PreS2, S, P and/or SP gene(s).

In one example embodiment, the immune disease is severe combined immunodeficiency (SCID), Omenn syndrome, and in one aspect the target is Recombination Activating Gene 1 (RAG1) or an interleukin-7 receptor (IL7R). In one example embodiment, the disease is Transthyretin Amyloidosis (ATTR), Familial amyloid cardiomyopathy, and in one aspect, the target is the TTR gene, including one or more mutations in the TTR gene. In one example embodiment, the disease is Alpha-1 Antitrypsin Deficiency (AATD) or another disease in which Alpha-1 Antitrypsin is implicated, for example GvHD, Organ transplant rejection, diabetes, liver disease, COPD, Emphysema and Cystic Fibrosis, in one example embodiment, the target is SERPINA1.

In one example embodiment, the disease is primary hyperoxaluria, which, in one example embodiment, the target comprises one or more of Lactate dehydrogenase A (LDHA) and hydroxy Acid Oxidase 1 (HAO 1). In one example embodiment, the disease is primary hyperoxaluria type 1 (ph1) and other alanine-glyoxylate aminotransferase (agxt) gene related conditions or disorders, such as Adenocarcinoma, Chronic Alcoholic Intoxication, Alzheimer's Disease, Cooley's anemia, Aneurysm, Anxiety Disorders, Asthma, Malignant neoplasm of breast, Malignant neoplasm of skin, Renal Cell Carcinoma, Cardiovascular Diseases, Malignant tumor of cervix, Coronary Arteriosclerosis, Coronary heart disease, Diabetes, Diabetes Mellitus, Diabetes Mellitus Non-Insulin-Dependent, Diabetic Nephropathy, Eclampsia, Eczema, Subacute Bacterial Endocarditis, Glioblastoma, Glycogen storage disease type 1I, Sensorineural Hearing Loss (disorder), Hepatitis, Hepatitis A, Hepatitis B, Homocystinuria, Hereditary Sensory Autonomic Neuropathy Type 1, Hyperaldosteronism, Hypercholesterolemia, Hyperoxaluria, Primary Hyperoxaluria, Hypertensive disease, Inflammatory Bowel Diseases, Kidney Calculi, Kidney Diseases, Chronic Kidney Failure, leiomyosarcoma, Metabolic Diseases, Inborn Errors of Metabolism, Mitral Valve Prolapse Syndrome, Myocardial Infarction, Neoplasm Metastasis, Nephrotic Syndrome, Obesity, Ovarian Diseases, Periodontitis, Polycystic Ovary Syndrome, Kidney Failure, Adult Respiratory Distress Syndrome, Retinal Diseases, Cerebrovascular accident, Turner Syndrome, Viral hepatitis, Tooth Loss, Premature Ovarian Failure, Essential Hypertension, Left Ventricular Hypertrophy, Migraine Disorders, Cutaneous Melanoma, Hypertensive heart disease, Chronic glomerulonephritis, Migraine with Aura, Secondary hypertension, Acute myocardial infarction, Atherosclerosis of aorta, Allergic asthma, pineoblastoma, Malignant neoplasm of lung, Primary hyperoxaluria type I, Primary hyperoxaluria type 2, Inflammatory Breast Carcinoma, Cervix carcinoma, Restenosis, Bleeding ulcer, Generalized glycogen storage disease of infants, Nephrolithiasis, Chronic rejection of renal transplant, Urolithiasis, pricking of skin, Metabolic Syndrome X, Maternal hypertension, Carotid Atherosclerosis, Carcinogenesis, Breast Carcinoma, Carcinoma of lung, Nephronophthisis, Microalbuminuria, Familial Retinoblastoma, Systolic Heart Failure Ischemic stroke, Left ventricular systolic dysfunction, Cauda Equina Paraganglioma, Hepatocarcinogenesis, Chronic Kidney Diseases, Glioblastoma Multiforme, Non-Neoplastic Disorder, Calcium Oxalate Nephrolithiasis, Ablepharon-Macrostomia Syndrome, Coronary Artery Disease, Liver carcinoma, Chronic kidney disease stage 5, Allergic rhinitis (disorder), Crigler Najjar syndrome type 2, and Ischemic Cerebrovascular Accident. In one example embodiment, treatment is targeted to the liver. In one example embodiment, the gene is AGXT, with a cytogenetic location of 2q37.3 and the genomic coordinate are on Chromosome 2 on the forward strand at position 240,868,479-240,880,502.

Treatment can also target collagen type vii alpha 1 chain (col7a1) gene related conditions or disorders, such as Malignant neoplasm of skin, Squamous cell carcinoma, Colorectal Neoplasms, Crohn Disease, Epidermolysis Bullosa, Indirect Inguinal Hernia, Pruritus, Schizophrenia, Dermatologic disorders, Genetic Skin Diseases, Teratoma, Cockayne-Touraine Disease, Epidermolysis Bullosa Acquisita, Epidermolysis Bullosa Dystrophica, Junctional Epidermolysis Bullosa, Hallopeau-Siemens Disease, Bullous Skin Diseases, Agenesis of corpus callosum, Dystrophia unguium, Vesicular Stomatitis, Epidermolysis Bullosa With Congenital Localized Absence Of Skin And Deformity Of Nails, Juvenile Myoclonic Epilepsy, Squamous cell carcinoma of esophagus, Poikiloderma of Kindler, pretibial Epidermolysis bullosa, Dominant dystrophic epidermolysis bullosa albopapuloid type (disorder), Localized recessive dystrophic epidermolysis bullosa, Generalized dystrophic epidermolysis bullosa, Squamous cell carcinoma of skin, Epidermolysis Bullosa Pruriginosa, Mammary Neoplasms, Epidermolysis Bullosa Simplex Superficialis, Isolated Toenail Dystrophy, Transient bullous dermolysis of the newborn, Autosomal Recessive Epidermolysis Bullosa Dystrophica Localisata Variant, and Autosomal Recessive Epidermolysis Bullosa Dystrophica Inversa.

In one example embodiment, the disease is acute myeloid leukemia (AML), targeting Wilms Tumor I (WTI) and HLA expressing cells. In one example embodiment, the therapy is T cell therapy, as described elsewhere herein, comprising engineered T cells with WTI specific TCRs. In one example embodiment, the target is CD157 in AML.

In one example embodiment, the disease is a blood disease. In one example embodiment, the disease is hemophilia, in one aspect the target is Factor XI. In other embodiments, the disease is a hemoglobinopathy, such as sickle cell disease, sickle cell trait, hemoglobin C disease, hemoglobin C trait, hemoglobin S/C disease, hemoglobin D disease, hemoglobin E disease, a thalassemia, a condition associated with hemoglobin with increased oxygen affinity, a condition associated with hemoglobin with decreased oxygen affinity, unstable hemoglobin disease, methemoglobinemia. Hemostasis and Factor X and XII deficiencies can also be treated. In one example embodiment, the target is BCL11A gene (e.g., a human BCL11a gene), a BCL11a enhancer (e.g., a human BCL11a enhancer), or a HFPH region (e.g., a human HPFH region), beta globulin, fetal hemoglobin, γ-globin genes (e.g., HBG1, HBG2, or HBG1 and HBG2), the erythroid specific enhancer of the BCL11LA gene (BCL11 Ae), or a combination thereof.

In one example embodiment, the target locus can be one or more of RAC, TRBC1, TRBC2, CD3E, CD3G, CD3D, B2M, CIITA, CD247, HLA-A, HLA-B, HLA-C, DCK, CD52, FKBP1A, NLRC5, RFXANK, RFX5, RFXAP, NR3C1, CD274, HAVCR2, LAG3, PDCD1, PD-L2, HCF2, PAI, TFPI, PLAT, PLAU, PLG, RPOZ, F7, F8, F9, F2, F5, F7, F10, F11, F12, F13A1, F13B, STAT1, FOXP3, IL2RG, DCLRE1C, ICOS, MHC2TA, GALNS, HGSNAT, ARSB, RFXAP, CD20, CD81, TNFRSF13B, SEC23B, PKLR, IFNG, SPTB, SPTA, SLC4A1, EPO, EPB42, CSF2 CSF3, VFW, SERPINCA1, CTLA4, CEACAM (e.g., CEACAM-1, CEACAM-3 and/or CEACAM-5), VISTA, BTLA, TIGIT, LAIR1, CD160, 2B4, CD80, CD86, B7-H3 (CD113), B7-H4 (VTCN1), HVEM (TNFRSF14 or CD107), KIR, A2aR, MHC class I, MHC class II, GAL9, adenosine, and TGF beta, PTPN11, and combinations thereof. In one example embodiment, the target sequence within the genomic nucleic acid sequence at Chr1 1:5,250,094-5,250,237, —strand, hg38; Chr1 1:5,255,022-5,255,164, —strand, hg38; nondeletional HFPH region; Chr1 1:5,249,833 to Chr1 1:5,250,237, —strand, hg38; Chr1 1:5,254,738 to Chr1 1:5,255, 164, —strand, hg38; Chr1 1:5,249,833-5,249,927, —strand, hg3; Chr1 1:5,254,738-5,254,851, —strand, hg38; Chr1 1:5,250, 139-5,250,237, —strand, hg38.

In one example embodiment, the disease is associated with high cholesterol, and regulation of cholesterol is provided, in some embodiments, regulation is effected by modification in the target PCSK9. Other diseases in which PCSK9 can be implicated, and thus would be a target for the systems and methods described herein include Abetalipoproteinemia, Adenoma, Arteriosclerosis, Atherosclerosis, Cardiovascular Diseases, Cholelithiasis, Coronary Arteriosclerosis, Coronary heart disease, Non-Insulin-Dependent Diabetes Mellitus, Hypercholesterolemia, Familial Hypercholesterolemia, Hyperinsulinism, Hyperlipidemia, Familial Combined Hyperlipidemia, Hypobetalipoproteinemias, Chronic Kidney Failure, Liver diseases, Liver neoplasms, melanoma, Myocardial Infarction, Narcolepsy, Neoplasm Metastasis, Nephroblastoma, Obesity, Peritonitis, Pseudoxanthoma Elasticum, Cerebrovascular accident, Vascular Diseases, Xanthomatosis, Peripheral Vascular Diseases, Myocardial Ischemia, Dyslipidemias, Impaired glucose tolerance, Xanthoma, Polygenic hypercholesterolemia, Secondary malignant neoplasm of liver, Dementia, Overweight, Hepatitis C, Chronic, Carotid Atherosclerosis, Hyperlipoproteinemia Type IIa, Intracranial Atherosclerosis, Ischemic stroke, Acute Coronary Syndrome, Aortic calcification, Cardiovascular morbidity, Hyperlipoproteinemia Type IIb, Peripheral Arterial Diseases, Familial Hyperaldosteronism Type II, Familial hypobetalipoproteinemia, Autosomal Recessive Hypercholesterolemia, Autosomal Dominant Hypercholesterolemia 3, Coronary Artery Disease, Liver carcinoma, Ischemic Cerebrovascular Accident, and Arteriosclerotic cardiovascular disease NOS. In one example embodiment, the treatment can be targeted to the liver, the primary location of activity of PCSK9.

In one example embodiment, the disease or disorder is Hyper IGM syndrome or a disorder characterized by defective CD40 signaling. In one example embodiment, the insertion of CD40L exons is used to restore proper CD40 signaling and B cell class switch recombination. In one example embodiment, the target is CD40 ligand (CD40L)-edited at one or more of exons 2-5 of the CD40L gene, in cells, e.g., T cells or hematopoietic stem cells (HSCs).

In one example embodiment, the disease is merosin-deficient congenital muscular dystrophy (mdcmd) and other laminin, alpha 2 (*lama*2) gene related conditions or disorders. The therapy can be targeted to the muscle, for example, skeletal muscle, smooth muscle, and/or cardiac muscle. In one example embodiment, the target is Laminin, Alpha 2 (*LAMA*2) which may also be referred to as Laminin-12 Subunit Alpha, Laminin-2 Subunit Alpha, Laminin-4 Subunit Alpha 3, Merosin Heavy Chain, Laminin M Chain, LAMM, Congenital Muscular Dystrophy and Merosin. *LAMA*2 has a cytogenetic location of 6q22.33 and the genomic coordinate are on Chromosome 6 on the forward strand at position 128,883, 141-129,516,563. In one example embodiment, the disease treated can be Merosin-Deficient Congenital Muscular Dystrophy (MDCMD), Amyotrophic Lateral Sclerosis, Bladder Neoplasm, Charcot-Marie-Tooth Disease, Colorectal Carcinoma, Contracture, Cyst, Duchenne Muscular Dystrophy, Fatigue, Hyperopia, Renovascular Hypertension, melanoma, Mental Retardation, Myopathy, Muscular Dystrophy, Myopia, Myositis, Neuromuscular Diseases, Peripheral Neuropathy, Refractive Errors, Schizophrenia, Severe mental retardation (I.Q. 20-34), Thyroid Neoplasm, Tobacco Use Disorder, Severe Combined Immunodeficiency, Synovial Cyst, Adenocarcinoma of lung (disorder), Tumor Progression, Strawberry nevus of skin, Muscle degeneration, *Microdontia* (disorder), Walker-Warburg congenital muscular dystrophy, Chronic Periodontitis, Leukoencephalopathies, Impaired cognition, Fukuyama Type Congenital Muscular Dystrophy, Scleroatonic muscular dystrophy, Eichsfeld type congenital muscular dystrophy, Neuropathy, Muscle eye brain disease, Limb-Muscular Dystrophies, Girdle, Congenital muscular dystrophy (disorder), Muscle fibrosis, cancer recurrence, Drug Resistant Epilepsy, Respiratory Failure, Myxoid cyst, Abnormal breathing, Muscular dystrophy congenital merosin negative, Colorectal Cancer, Congenital Muscular Dystrophy due to Partial *LAMA*2 Deficiency, and Autosomal Dominant Craniometaphyseal Dysplasia.

In one aspect, the target is superoxide dismutase 1, soluble (SOD1), which can aid in treatment of a disease or disorder associated with the gene. In one example embodiment, the disease or disorder is associated with SOD1, and can be, for example, Adenocarcinoma, Albuminuria, Chronic Alcoholic Intoxication, Alzheimer's Disease, Amnesia, Amyloidosis, Amyotrophic Lateral Sclerosis, Anemia, Autoimmune hemolytic anemia, Sickle Cell Anemia, Anoxia, Anxiety Disorders, Aortic Diseases, Arteriosclerosis, Rheumatoid Arthritis, Asphyxia Neonatorum, Asthma, Atherosclerosis, Autistic Disorder, Autoimmune Diseases, Barrett Esophagus, Behcet Syndrome, Malignant neoplasm of urinary bladder, Brain Neoplasms, Malignant neoplasm of breast, Oral candidiasis, Malignant tumor of colon, Bronchogenic Carcinoma, Non-Small Cell Lung Carcinoma, Squamous cell carcinoma, Transitional Cell Carcinoma, Cardiovascular Diseases, Carotid Artery Thrombosis, Neoplastic Cell Transformation, Cerebral Infarction, Brain Ischemia, Transient Ischemic Attack, Charcot-Marie-Tooth Disease, Cholera, Colitis, Colorectal Carcinoma, Coronary Arteriosclerosis, Coronary heart disease, Infection by *Cryptococcus neoformans*, Deafness, Cessation of life, Deglutition Disorders, Presenile dementia, Depressive disorder, Contact Dermatitis, Diabetes, Diabetes Mellitus, Experimental Diabetes Mellitus, Insulin-Dependent Diabetes Mellitus, Non-Insulin-Dependent Diabetes Mellitus, Diabetic Angiopathies, Diabetic Nephropathy, Diabetic Retinopathy, Down Syndrome, Dwarfism, Edema, Japanese Encephalitis, Toxic Epidermal Necrolysis, Temporal Lobe Epilepsy, Exanthema, Muscular fasciculation, Alcoholic Fatty Liver, Fetal Growth Retardation, Fibromyalgia, Fibrosarcoma, Fragile X Syndrome, Giardiasis, Glioblastoma, Glioma, Headache, Partial Hearing Loss, Cardiac Arrest, Heart failure, Atrial Septal Defects, Helminthiasis, Hemochromatosis, Hemolysis (disorder), Chronic Hepatitis, HIV Infections, Huntington Disease, Hypercholesterolemia, Hyperglycemia, Hyperplasia, Hypertensive disease, Hyperthyroidism, Hypopituitarism, Hypoproteinemia, Hypotension, natural Hypothermia, Hypothyroidism, Immunologic Deficiency Syndromes, Immune System Diseases, Inflammation, Inflammatory Bowel Diseases, Influenza, Intestinal Diseases, Ischemia, Kearns-Sayre syndrome, Keratoconus, Kidney Calculi, Kidney Diseases, Acute Kidney Failure, Chronic Kidney Failure, Polycystic Kidney Diseases, leukemia, Myeloid Leukemia, Acute Promyelocytic Leukemia, Liver Cirrhosis, Liver diseases, Liver neoplasms, Locked-In Syndrome, Chronic Obstructive Airway Disease, Lung Neoplasms, Systemic Lupus Erythematosus, Non-Hodgkin Lymphoma, Machado-Joseph Disease, Malaria, Malignant neoplasm of stomach, Animal Mammary Neoplasms, Marfan Syndrome, Meningomyelocele, Mental Retardation, Mitral Valve Stenosis, Acquired Dental Fluorosis, Movement Disorders, Multiple Sclerosis, Muscle Rigidity, Muscle Spasticity, Muscular Atrophy, Spinal Muscular Atrophy, Myopathy, Mycoses, Myocardial Infarction, Myocardial Reperfusion Injury, Necrosis, Nephrosis, Nephrotic Syndrome, Nerve Degeneration, nervous system disorder, Neuralgia, Neuroblastoma, Neuroma, Neuromuscular Diseases, Obesity, Occupational Diseases, Ocular Hypertension, Oligospermia, Degenerative polyarthritis, Osteoporosis, Ovarian Carcinoma, Pain, Pancreatitis, Papillon-Lefevre Disease, Paresis, Parkinson Disease, Phenylketonurias, Pituitary Diseases, Pre-Eclampsia, Prostatic Neoplasms, Protein Deficiency, Proteinuria, Psoriasis, Pulmonary Fibrosis, Renal Artery Obstruction, Reperfusion Injury, Retinal Degeneration, Retinal Diseases, Retinoblastoma, Schistosomiasis, Schistosomiasis *mansoni*, Schizophrenia, Scrapie, Seizures, Age-related cataract, Compression of spinal cord, Cerebrovascular accident, Subarachnoid Hemorrhage, Progressive supranuclear palsy, Tetanus, Trisomy, Turner Syndrome, Unipolar Depression, Urticaria, Vitiligo, Vocal Cord Paralysis, Intestinal *Volvulus*, Weight Gain, HMN (Hereditary Motor Neuropathy) Proximal Type I, Holoprosencephaly, Motor Neuron Disease, Neurofibrillary degeneration (morphologic abnormality), Burning sensation, Apathy, Mood swings, Synovial Cyst, Cataract, Migraine Disorders, Sciatic Neuropathy, Sensory neuropathy, Atrophic condition of skin, Muscle Weakness, Esophageal carcinoma, Lingual- Facial-Buccal Dyskinesia, Idiopathic pulmonary hypertension, Lateral Sclerosis, Migraine with Aura, Mixed Conductive-Sensorineural Hearing Loss, Iron deficiency anemia, Malnutrition, Prion Diseases, Mitochondrial Myopathies, MELAS Syndrome, Chronic progressive external ophthalmoplegia, General Paralysis, Premature aging syndrome, Fibrillation, Psychiatric symptom, Memory impairment, Muscle degeneration, Neurologic Symptoms, Gastric hemorrhage, Pancreatic carcinoma, Pick Disease of the Brain, Liver Fibrosis, Malignant neoplasm of lung, Age related macular degeneration, Parkinsonian Disorders, Disease Progression, Hypocupremia, Cytochrome-c Oxidase Deficiency, Essential Tremor, Familial Motor Neuron Disease, Lower Motor Neuron Disease, Degenerative myelopathy, Diabetic Polyneuropathies, Liver and Intrahepatic Biliary Tract Carcinoma, Persian Gulf Syndrome, Senile Plaques, Atrophic, Frontotemporal dementia, Semantic Dementia, Common Migraine, Impaired cognition, Malignant neoplasm of liver, Malignant neoplasm of pancreas, Malignant neoplasm of prostate, Pure Autonomic Failure, Motor symptoms, Spastic, Dementia, Neurodegenerative Disorders, Chronic Hepatitis C, Guam Form Amyotrophic Lateral Sclerosis, Stiff limbs, Multisystem disorder, Loss of scalp hair, Prostate carcinoma, Hepatopulmonary Syndrome, Hashimoto Disease, Progressive Neoplastic Disease, Breast Carcinoma, Terminal illness, Carcinoma of lung, Tardive Dyskinesia, Secondary malignant neoplasm of lymph node, Colon Carcinoma, Stomach Carcinoma, Central neuroblastoma, Dissecting aneurysm of the thoracic aorta, Diabetic macular edema, Microalbuminuria, Middle Cerebral Artery Occlusion, Middle Cerebral Artery Infarction, Upper motor neuron signs, Frontotemporal Lobar Degeneration, Memory Loss, Classical phenylketonuria, CADASIL Syndrome, Neurologic Gait Disorders, Spinocerebellar Ataxia Type 2, Spinal Cord Ischemia, Lewy Body Disease, Muscular Atrophy, Spinobulbar, Chromosome 21 monosomy, Thrombocytosis, Spots on skin, Drug-Induced Liver Injury, Hereditary Leber Optic Atrophy, Cerebral Ischemia, ovarian neoplasm, Tauopathies, Macroangiopathy, Persistent pulmonary hypertension, Malignant neoplasm of ovary, Myxoid cyst, Drusen, Sarcoma, Weight decreased, Major Depressive Disorder, Mild cognitive disorder, Degenerative disorder, Partial Trisomy, Cardiovascular morbidity, hearing impairment, Cognitive changes, Ureteral Calculi, Mammary Neoplasms, Colorectal Cancer, Chronic Kidney Diseases, Minimal Change Nephrotic Syndrome, Non-Neoplastic Disorder, X-Linked Bulbo-Spinal Atrophy, Mammographic Density, Normal Tension Glaucoma Susceptibility To Finding), Vitiligo-Associated Multiple Autoimmune Disease Susceptibility 1 (Finding), Amyotrophic Lateral Sclerosis And/Or Frontotemporal Dementia 1, Amyotrophic Lateral Sclerosis 1, Sporadic Amyotrophic Lateral Sclerosis, monomelic Amyotrophy, Coronary Artery Disease, Transformed migraine, Regurgitation, Urothelial Carcinoma, Motor disturbances, Liver carcinoma, Protein Misfolding Disorders, TDP-43 Proteinopathies, Promyelocytic leukemia, Weight Gain Adverse Event, Mitochondrial cytopathy, Idiopathic pulmonary arterial hypertension, Progressive cGVHD, Infection, GRN-related frontotemporal dementia, Mitochondrial pathology, and Hearing Loss.

In one example embodiment, the disease is associated with the gene ATXN1, ATXN2, or ATXN3, which may be targeted for treatment. In some embodiments, the CAG repeat region located in exon 8 of ATXN1, exon 1 of ATXN2, or exon 10 of the ATXN3 is targeted. In one example embodiment, the disease is spinocerebellar ataxia 3 (sca3), sca1, or sca2 and other related disorders, such as Congenital Abnormality, Alzheimer's Disease, Amyotrophic Lateral Sclerosis, Ataxia, Ataxia Telangiectasia, Cerebellar Ataxia, Cerebellar Diseases, Chorea, Cleft Palate, Cystic Fibrosis, Mental Depression, Depressive disorder, Dystonia, Esophageal Neoplasms, Exotropia, Cardiac Arrest, Huntington Disease, Machado-Joseph Disease, Movement Disorders, Muscular Dystrophy, Myotonic Dystrophy, Narcolepsy, Nerve Degeneration, Neuroblastoma, Parkinson Disease, Peripheral Neuropathy, Restless Legs Syndrome, Retinal Degeneration, Retinitis Pigmentosa, Schizophrenia, Shy-Drager Syndrome, Sleep disturbances, Hereditary Spastic Paraplegia, Thromboembolism, Stiff-Person Syndrome, Spinocerebellar Ataxia, Esophageal carcinoma, Polyneuropathy, Effects of heat, Muscle twitch, Extrapyramidal sign, Ataxic, Neurologic Symptoms, Cerebral atrophy, Parkinsonian Disorders, Protein S Deficiency, Cerebellar degeneration, Familial Amyloid Neuropathy Portuguese Type, Spastic syndrome, Vertical Nystagmus, Nystagmus End-Position, Antithrombin III Deficiency, Atrophic, Complicated hereditary spastic paraplegia, Multiple System Atrophy, Pallidoluysian degeneration, Dystonia Disorders, Pure Autonomic Failure, Thrombophilia, Protein C, Deficiency, Congenital Myotonic Dystrophy, Motor symptoms, Neuropathy, Neurodegenerative Disorders, Malignant neoplasm of esophagus, Visual disturbance, Activated Protein C Resistance, Terminal illness, Myokymia, Central neuroblastoma, Dyssomnias, Appendicular Ataxia, Narcolepsy-Cataplexy Syndrome, Machado-Joseph Disease Type I, Machado-Joseph Disease Type II, Machado-Joseph Disease Type III, Dentatorubral-Pallidoluysian Atrophy, Gait Ataxia, Spinocerebellar Ataxia Type 1, Spinocerebellar Ataxia Type 2, Spinocerebellar Ataxia Type 6 (disorder), Spinocerebellar Ataxia Type 7, Muscular Spinobulbar Atrophy, Genomic Instability, Episodic ataxia type 2 (disorder), Bulbo-Spinal Atrophy X-Linked, Fragile X Tremor/Ataxia Syndrome, Thrombophilia Due to Activated Protein C Resistance (Disorder), Amyotrophic Lateral Sclerosis 1, Neuronal Intranuclear Inclusion Disease, Hereditary Antithrombin Iii Deficiency, and Late-Onset Parkinson Disease.

In one example embodiment, the disease is associated with expression of a tumor antigen-cancer or non-cancer related indication, for example acute lymphoid leukemia, diffuse large B cell lymphoma, follicular lymphoma, chronic lymphocytic leukemia, Hodgkin lymphoma, non-Hodgkin lymphoma. In one example embodiment, the target can be TET2 intron, a TET2 intron-exon junction, a sequence within a genomic region of chr4.

In one example embodiment, neurodegenerative diseases can be treated. In one example embodiment, the target is Synuclein, Alpha (SNCA). In one example embodiment, the disorder treated is a pain related disorder, including congenital pain insensitivity, Compressive Neuropathies, Paroxysmal Extreme Pain Disorder, High grade atrioventricular block, Small Fiber Neuropathy, and Familial Episodic Pain Syndrome 2. In one example embodiment, the target is Sodium Channel, Voltage Gated, Type X Alpha Subunit (SCNIOA).

In one example embodiment, hematopoietic stem cells and progenitor stem cells are modified, including for treatment of lysosomal storage diseases, glycogen storage diseases, mucopolysaccharidosis, or any disease in which the secretion of a protein will ameliorate the disease. In one embodiment, the disease is sickle cell disease (SCD). In another embodiment, the disease is β-thalassemia.

Methods and systems can target Dystrophia Myotonica-Protein Kinase (DMPK). Disorders or diseases associated with DMPK include Atherosclerosis, Azoospermia, Hyper-trophic Cardiomyopathy, Celiac Disease, Congenital chromosomal disease, Diabetes Mellitus, Focal glomerulosclerosis, Huntington Disease, Hypogonadism, Muscular Atrophy, Myopathy, Muscular Dystrophy, Myotonia, Myotonic Dystrophy, Neuromuscular Diseases, Optic Atrophy, Paresis, Schizophrenia, Cataract, Spinocerebellar Ataxia, Muscle Weakness, Adrenoleukodystrophy, Centronuclear myopathy, Interstitial fibrosis, myotonic muscular dystrophy, Abnormal mental state, X-linked Charcot-Marie-Tooth disease 1, Congenital Myotonic Dystrophy, Bilateral cataracts (disorder), Congenital Fiber Type Disproportion, Myotonic Disorders, Multisystem disorder, 3-Methylglutaconic aciduria type 3, cardiac event, Cardiogenic Syncope, Congenital Structural Myopathy, Mental handicap, Adrenomyeloneuropathy, Dystrophia myotonica 2, and Intellectual Disability.

In one example embodiment, the disease is an inborn error of metabolism. The disease may be selected from Disorders of Carbohydrate Metabolism (glycogen storage disease, G6PD deficiency), Disorders of Amino Acid Metabolism (phenytketonuria, maple syrup urine disease, glutaric acidemia type 1), Urea Cycle Disorder or Urea Cycle Defects (carbamoyl phosphate synthetase I deficiency), Disorders of Organic Acid Metabolism (alkaptonuria, 2-hydroxyglutaric acidurias), Disorders of Fatty Acid Oxidation/Mitochondrial Metabolism (Medium-chain acyl-coenzyme A dehydrogenase deficiency), Disorders of Porphyrin metabolism (acute intermittent *porphyria*), Disorders of Purine/Pyrimidine Metabolism (Lesch-Nyhan syndrome), Disorders of Steroid Metabolism (lipoid congenital adrenal hyperplasia, congenital adrenal hyperplasia), Disorders of Mitochondrial Function (Kearns-Sayre syndrome), Disorders of Peroxisomal function (Zellweger syndrome), or Lysosomal Storage Disorders (Gaucher's disease, Niemann-Pick disease).

In one example embodiment, the target can comprise Recombination Activating Gene 1 (RAG1), BCL11 A, PCSK9, laminin, alpha 2 (*lama*2), ATXN3, alanine-glyoxylate aminotransferase (AGXT), collagen type vii alpha 1 chain (COL7a1), spinocerebellar ataxia type 1 protein (ATXN1), Angiopoietin-like 3 (ANGPTL3), Frataxin (FXN), Superoxidase Dismutase 1, soluble (SOD1), Synuclein, Alpha (SNCA), Sodium Channel, Voltage Gated, Type X Alpha Subunit (SCN10A), Spinocerebellar Ataxia Type 2 Protein (ATXN2), Dystrophia Myotonica-Protein Kinase (DMPK), beta globin locus on chromosome 11, acyl-coenzyme A dehydrogenase for medium chain fatty acids (ACADM), long-chain 3-hydroxyl-coenzyme A dehydrogenase for long chain fatty acids (HADHA), acyl-coenzyme A dehydrogenase for very long-chain fatty acids (ACADVL), Apolipoprotein C3 (APOCIII), Transthyretin (TTR), Angiopoietin-like 4 (ANGPTL4), Sodium Voltage-Gated Channel Alpha Subunit 9 (SCN9A), Interleukin-7 receptor (IL7R), glucose-6-phosphatase, catalytic (G6PC), haemochromatosis (HFE), SERPINA1, C90RF72, β-globin, dystrophin, γ-globin.

In one example embodiment, the disease or disorder is associated with Apolipoprotein C3 (APOCIII), which can be targeted for editing. In example embodiments, the disease or disorder may be Dyslipidemias, Hyperalphalipoproteinemia Type 2, Lupus Nephritis, Wilms Tumor 5, Morbid obesity and spermatogenic, Glaucoma, Diabetic Retinopathy, Arthrogryposis renal dysfunction cholestasis syndrome, Cognition Disorders, Altered response to myocardial infarction, Glucose Intolerance, Positive regulation of triglyceride biosynthetic process, Renal Insufficiency, Chronic, Hyperlipidemias, Chronic Kidney Failure, Apolipoprotein C-III Deficiency, Coronary Disease, Neonatal Diabetes Mellitus, Neonatal, with Congenital Hypothyroidism, Hypercholesterolemia Autosomal Dominant 3, Hyperlipoproteinemia Type III, Hyperthyroidism, Coronary Artery Disease, Renal Artery Obstruction, Metabolic Syndrome X, Hyperlipidemia, Familial Combined, Insulin Resistance, Transient infantile hypertriglyceridemia, Diabetic Nephropathies, Diabetes Mellitus (Type 1), Nephrotic Syndrome Type 5 with or without ocular abnormalities, and Hemorrhagic Fever with renal syndrome.

In one example embodiment, the target is Angiopoietin-like 4(ANGPTL4). Diseases or disorders associated with ANGPTL4 that can be treated include ANGPTL4 is associated with dyslipidemias, low plasma triglyceride levels, regulator of angiogenesis and modulate tumorigenesis, and severe diabetic retinopathy, both proliferative diabetic retinopathy and non-proliferative diabetic retinopathy.

In one example embodiment, the target binding moiety binds to the target protein of interest in order to induce phosphorylation from kinases, even if the target protein of interest, i.e. target substrate, is not a substrate for the kinase. One such protein is in the bromodomain family of proteins. Bromodomains are a family of (~110 amino acid) structurally and evolutionary conserved protein interaction modules that specifically recognize acetylated lysines present in substrate proteins, notably histones. Bromodomains exist as components of large multidomain nuclear proteins that are associated with chromatin remodeling, cell signaling and transcriptional control. Examples of bromodomain-containing proteins with known functions include: (i) histone acetyltransferases (HATs), including CREBBP, GCN5, PCAF and TAFII250; (ii) methyltransferases such as ASH1L and MLL; (iii) components of chromatin-remodeling complexes such as Swi2/Snf2; and (iv) a number of transcriptional regulators (Florence et al. Front. Biosci. 2001, 6, D1008-1018, hereby incorporated by reference in its entirety.).

Bromodomain mediated or BET-mediated such as BRD2-mediated, BRD3-mediated, BRD4-mediated, and/or BRDT-mediated disorders or conditions may be any disease or other deleterious condition in which one or more of the bromodomain-containing proteins, such as BET proteins including BRD2, BRD3, BRD4 and/or BRDT, or a mutant thereof, are known to play a role. Accordingly, another embodiment of the present disclosure relates to treating or lessening the severity of one or more diseases in which one or more of the bromodomain-containing proteins, such as BET proteins, such as BRD2, BRD3, BRD4, and/or BRDT, or a mutant thereof, are known to play a role. For example, a disease or condition in which the biological function of bromodomain affects the development and/or course of the disease or condition, and/or in which modulation of bromodomain alters the development, course, and/or symptoms. Bromodomain mediated disease or condition includes a disease or condition for which bromodomain inhibition provides a therapeutic benefit, e.g. wherein treatment with bromodomain inhibitors, including compounds described herein, provides a therapeutic benefit to the subject suffering from or at risk of the disease or condition. Compounds for inhibiting bromodomains or bromodomain inhibitors are typically compounds which inhibit the binding of a bromodomain with its cognate acetylated proteins, for example, the bromodomain inhibitor is a compound which inhibits the binding of a bromodomain to acetylated lysine residues.

Methods for modifying a protein of interest are also provided, the method comprising contacting the protein of interest with a compound disclosed herein in an environment comprising one or more activators. Methods for the treatment of a disease, disorder, or condition in a subject in need thereof can comprise administering a molecule disclosed herein to a subject.

Pathogenic Applications

The chimeric small molecules disclosed herein can be utilized in methods of treating infection by a pathogen. Methods of treating infection by a pathogen can include generating a repurposed/reprogrammed cellular protein by administering a chimeric small molecule, as described herein. The chimeric small molecule labels the cellular kinase with a pathogenic target binding moiety via the electrophilic reactive group moiety. The electrophilic reactive group reacts with and bonds to a nucleophilic side chain on the cellular kinase. Labelling of the cellular kinase can allow for bonding to, or association with, the pathogenic target protein via the target binding moiety, or to a molecule in proximity to the pathogenic target protein, thereby facilitating modification of the target substrate. In one aspect, the methods comprise inducing phosphorylation of the target substrate, i.e. pathogenic protein, in or on the cell. The methods may comprise contacting the pathogenic protein with the chimeric small molecule. In one example embodiment, the pathogenic protein is in proximity to a kinase specific to the kinase binding moiety of the molecule. Chimeric small molecules that induce phosphorylation can be optionally provided with adenosine monophosphate (AMP) or another molecule providing an additional phosphate group. Without being bound by theory, the addition of the AMP or other phosphate providing molecule can enhance phosphorylation.

Methods for treating infection by a pathogen are provided. The method comprises, generating a reprogrammed cellular protein by administering to a subject in need thereof a chimeric small molecule of the formula: A-$L_1$-E-B or A-$L_1$-E-$L_2$-B, wherein A is an protein binding moiety; $L_1$ and $L_2$ is a linker; E is an electrophilic reactive group and B is a pathogen protein to be modified, whereby the chimeric small molecule labels the cellular protein with the target binding moiety for the target substrate; and modifying the pathogen protein by binding of the repurposed/reprogrammed protein to the pathogen protein via the target binding moiety, whereby the repurposed/reprogrammed cellular protein introduces one or more modifications to the target substrate. In one example embodiment, the cellular protein to be reprogrammed is a oxidoreductase, transferase, hydrolase, lyase, isomerase, ligase, translocase. In one example embodiment, the pathogen is a viruses, bacteria, fungi, or protozoa. In one example embodiment, the bacteria is *Mycobacterium tuberculosis* (Mtb) or *Pseudomonas aeruginosa* (PsA). In one example embodiment, the pathogen is Mtb and the pathogen protein is one or more of PtpA, PtpB, SapM, ESAT-6, and Rv2966c. In one example embodiment, the pathogen is (PsA) and the target binding moiety is Colistin. In one example embodiment, the kinase binding moiety is a kinase inhibitor. In one example embodiment, the kinase inhibitor is a promiscuous inhibitor. In one example embodiment, a step of administering a coupling molecule thereby quenching the inhibitor activity of the kinase inhibitor is provided.

A pathogen may include viruses, bacteria, fungi, and protozoa. In one example embodiment, the pathogen is a pathogenic bacteria and may include: spirochetes; *spirilla*; vibrios; gram-negative aerobic rods and *cocci*; enterics; *pyogenic cocci*; and endospore-forming bacteria; actinomycetes and related bacteria; rickettsias and chlamydiae; mycoplasmas, which are groups defined by some bacteriological criteria. A pathogenic bacteria may include: *Escherichia coli, Salmonella enterica, Salmonella typhi, Shigella dysenteriae, Yersinia pestis, Pseudomonas aeruginosa, Vibrio cholerae, Bordetella pertussis, Haemophilus influenza, Helicobacter pylori, Campylobacter jejuni, Neisseria gonorrhoeae, Neisseria meningitidis, Brucella abortus, Bacteroides fragilis, Staphylococcus aureus, Streptococcus pyogenes, Streptococcus pneumoniae, Bacillus anthracis, Bacillus cereus, Clostridium tetani, Clostridium perfringens, Clostridium botulinum, Clostridium difficile, Corynebacterium diphtheriae, Listeria monocytogenes, Mycobacterium tuberculosis, Mycobacterium leprae, Chlamydia trachomatis, Chlamydia pneumoniae, Mycoplasma pneumoniae, Rickettsia, Treponema pallidum, Borrelia burgdorferi*, or a variant thereof. (Todar, K. Textbook of Bacteriology (2020) Online).

A target virus may belong to any morphological category including helical, envelope, or icosahedral. A target virus may comprise of DNA or RNA, may be single stranded or double stranded, and may be linear or circular. The genome of the virus may be one nucleic acid molecule or several nucleic acid segments. A target virus may belong to the family: Adenoviridae, Papovaviridae, Parvoviridae, Herpesviridae, Poxviridae, Anelloviridae, Pleolipoviridae, Reoviridae, Picornaviridae, Caliciviridae, Togaviridae, Arenaviridae, Flaviviridae, Orthomyxoviridae, Paramyxoviridae, Bunyaviridae, Rhabdoviridae, Filoviridae, Astroviridae, Bornaviridae, Arteriviridae, Hepeviridae, Retroviridae, Caulimoviridae, Hepadnaviridae, Coronaviridae. In one example embodiment, the virus is SARS-CoV-2. (Gelderblom HR. Structure and Classification of Viruses. In: Baron S, editor. Medical Microbiology. 4th edition. Galveston (TX): University of Texas Medical Branch at Galveston; 1996. Chapter 41).

In an exemplary embodiments, the pathogen is a pathogenic fungi and may include: *Aspergillus; Blastomyces; Candida; Coccidioides; Cryptococcus; Fusarium; Microsporum; Epidermophyton; Trichophyton; Histoplasma; Rhizopus; Mucor; Rhizomucor; Syncephalastrum; Cunninghamella; Apophysomyces; Lichtheimia* (formerly *Absidia*); Eumycetoma; *Pneumocystis; Trichophyton; Microsporum; Epidermophyton; Sporothrix; Paracoccidioides; Talaromyces* or a variant or species thereof. (CDC)

In an exemplary embodiment, the pathogen is a pathogenic protozoa belonging to the group: Sarcodina; *Mastigophora; Ciliophora*; or Sporozoa defined by their mode of movement. (CDC) In one example embodiment, the pathogenic protozoa may include: Entamoeba; Trichomonas; Leishmania; Chilomonas; *Giardia; Isopora; Sarcocystis; Nosema; Balantidium*; Eimeria; Histomonas; Trypanosoma; Plasmodium; Babesia; or Haemoproteus or a variant or species thereof.

In one aspect, the method comprises treating infection by a pathogen as a result of M. tb. In an example embodiment, the pathogenic target is *Mycobacterium tuberculosis* (M. tb). Successful infection of host macrophages by M. tb hinges on the weakening of the diverse microbicidal responses by the host cell. M. tb furthers infection by impeding the host cellular signaling machinery. Therefore, infection can be inhibited by phosphorylating proteins associated with M. tb, which promotes increased signaling to the immune system. In one example embodiment, the chimeric small molecule target binding moiety targets the pathogen is M.tb and the pathogen protein is one or more of PtpA, PtpB, SapM, ESAT-6, and Rv2966c.

In a preferred embodiment, the target protein is Mtb protein tyrosine phosphatases (Ptp). Ptps belong to a large family of signaling enzymes and are required for optimal bacillary survival. PTPs, with protein tyrosine kinases, regulate numerous cellular functions, such as cell growth, proliferation, differentiation, metabolism, and immune response. M.tb encodes PtpA and PtpB and secretes them into the cytoplasm of host macrophages. PtpA prevents phagolysosome acidification by dephosphorylation of its substrate, Human Vacuolar Protein Sorting 33B. This results in the exclusion of the macrophage vacuolar-H+-ATPase (V-ATPase) from the vesicle. Once inside the macrophage, mPTPB activates Akt signaling and simultaneously blocks ERK1/2 and p38 activation thereby preventing host macrophage apoptosis and cytokine production. Inhibition of PtpA and PtpB decreases Mtb survival. See e.g. Dutta N. K. et al. Mycobacterial Protein Tyrosine Phosphatases A and B Inhibitors Augment the Bactericidal Activity of the Standard Anti-tuberculosis Regimen. *ACS Infect Dis.* 2016; 2(3):231-239 and Ruddraraju, K. V. et al. Therapeutic Targeting of Protein Tyrosine Phosphatases from *Mycobacterium tuberculosis*. *Microorganisms* 2021, 9(1), 14 incorporated herein by reference.

In an example embodiment, a method of treating *Mycobacterium tuberculosis* in macrophages is provided, comprising administering chimeric small molecule of the present invention. In one example the small molecule comprises a MAPK kinase binder, a linker, an electrophilic reactive group, and a *Mycobacterium* target binding moiety. In one example embodiment, the molecule comprises a binder of MAPK p38a based on the inhibitor SB203580 that further comprises an azide bioorthogonal group. The binding moiety comprises a linker connected to the electrophilic reactive group N-acyl-N-alkyl sulfonamide. The electrophilic reactive group, in turn, is connected to the Mtb protein target binding moiety for PtpA via a linker. Upon binding to the MAPK kinase via SB203580, proximal lysines of the binding pocket of p38a MAPK, K15, K54, K66, K152, K165, will react with the lysine-reactive group (e.g., N-acyl-N-alkyl sulfonamide) and expel the kinase inhibitor, leaving the MAPK tagged with the PtpA binder. The kinase which is covalently labeled with the PtpA binder can then hyper and/or neo-phosphorylate the Mtb PtpA proteins, which can lead to HLA-display and generation of a strong immune response against the pathogen-specific phosphopeptides, allowing deactivation and elimination of infected macrophages by the immune system. Administration of a cyclooctyne coupling molecule can quench the azide biorthogonal group displayed on the kinase binding molecule, and deactivate the expelled kinase binding moiety.

In one preferred embodiment, the target protein is SapM. M. tb produces SapM, a alkaline phosphatase, for survival as it inhibits phagosome maturation in host macrophages. See e.g., Fernandez-Soto, P., et. al. Mechanism of catalysis and inhibition of *Mycobacterium tuberculosis* SapM, implications for the development of novel antivirulence drugs. *Sci Rep* 2019, 9, 10315 and Fernández-Soto, P., et al. Discovery of uncompetitive inhibitors of SapM that compromise intracellular survival of *Mycobacterium tuberculosis. Sci Rep* 2021, 11, 7667. incorporated herein by reference.

In one example embodiment, the target protein is ESAT-6. M tb. produces ESAT-6 to mediate regulation of host immune responses. ESAT-6 directly inhibits T cell IFN-γ production by activation of p38 MAPK and indirectly through reprogramming of antigen presenting cells to produce less IL-12p70, an essential IFN-γ stimulating cytokine. Jung, B G., et al. Early Secreted Antigenic Target of 6-kDa of *Mycobacterium tuberculosis* Stimulates IL-6 Production by Macrophages through Activation of STAT3. *Sci Rep* 2017, 7, 40984.

In one example embodiment, the target protein is Rv2966c. Rv2966c is a RsmD-like methyltransferase, which carries out the transferase function through its N-terminal domain. This protein has been identified as a potential therapeutic target for its role in the function of M. tb and a conserved subunit similar to that of ATP binding pocket of kinases. The highly conserved subunit is called S-adenosylmethionine (SAM). In one example embodiment, the Rv2966c binding moiety targets a SAM subunit. See e.g. Kumar A., et al. "Structural and Functional Characterization of Rv2966c Protein Reveals an RsmD-like Methyltransferase from *Mycobacterium tuberculosis* and the Role of Its N-terminal Domain in Target Recognition" *J Biol Chem.* 2011, 286(22): 19652-19661 and Copeland, R., et al. "Protein methyltransferases as a target class for drug discovery." *Nat Rev Drug Discov* 2009, 8, 724-732, incorporated herein by reference.

Uridine 5'-monophosphate kinase (UMPK) catalyzes the reversible transfer of the γ-phosphoryl group from ATP to UMP in the presence of a divalent cation, usually Mg2+. Sequence comparisons of bacterial UMPKs show they do not resemble UMPKs from other organisms. Furthermore, bacterial UMPKs are specific for UMP and exist in solution as stable homohexamers. See e.g. Rostirolla D. C., et al. "UMP Kinase from *Mycobacterium Tuberculosis*: Mode of Action and Allosteric Interactions, and Their Likely Role in Pyrimidine Metabolism Regulation." *Archives of Biochemistry and Biophysics* 2011, 505 (2), 202-212.

In one aspect, the method comprises treating infection by a pathogen as a result of PsA. PsA is a gram-negative, rod-shaped bacterium that commonly causes nosocomial pneumonia. In an example embodiment, the chimeric small molecule target binding moiety targets the pathogen PsA and is Colistin. Colistin, a polymyxin, is sulfomethylated and naturally ineffective antibiotic. Within the body at physiological temperature and pH, Colistin is hydrolyzed and becomes active. Colistin binds to phospholipids and disrupts the bacterial cell membrane. See e.g. Levin A. S., et al. Intravenous Colistin as Therapy for Nosocomial Infections Caused by Multidrug-Resistant *Pseudomonas aeruginosa* and *Acinetobacter baumannii, Clinical Infectious Diseases* 1999, 28, (5), 1008-1011. Colistin binds to lipopolysaccharide in the bacterial outer membrane, and also targets lipopolysaccharide in the cytoplasmic membrane. See, e.g. Sabnis et al., 2019, Colistin kills bacteria by targeting lipopolysaccharide in the cytoplasmic membrane, eLife doi: 10.7554/eLife.65836.

Pharmaceutical Formulations

Also described herein are pharmaceutical formulations that can contain an amount, effective amount, and/or least effective amount, and/or therapeutically effective amount of one or more compounds, molecules, compositions, vectors, vector systems, cells, or a combination thereof (which are also referred to as the primary active agent or ingredient elsewhere herein) described in greater detail elsewhere herein a pharmaceutically acceptable carrier or excipient. As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo. As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient. When present, the compound can optionally be present in the pharmaceutical formulation as a pharmaceutically acceptable salt. In some embodiments, the pharmaceutical formulation can include, such as an active ingredient, a CRISPR-Cas system or component thereof described in greater detail elsewhere herein. In some embodiments, the pharmaceutical formulation can include, such as an active ingredient, a CRISPR-Cas polynucleotide described in greater detail elsewhere herein. In some embodiments, the pharmaceutical formulation can include, such as an active ingredient one or more modified cells, such as one or more modified cells described in greater detail elsewhere herein.

In some embodiments, the active ingredient is present as a pharmaceutically acceptable salt of the active ingredient. As used herein, "pharmaceutically acceptable salt" refers to any acid or base addition salt whose counter-ions are non-toxic to the subject to which they are administered in pharmaceutical doses of the salts. Suitable salts include, hydrobromide, iodide, nitrate, bisulfate, phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, camphorsulfonate, naphthalenesulfonate, propionate, malonate, mandelate, malate, phthalate, and pamoate.

The pharmaceutical formulations described herein can be administered to a subject in need thereof via any suitable method or route to a subject in need thereof. Suitable administration routes can include, but are not limited to auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes, which typically depends on the disease to be treated and/or the active ingredient(s).

Where appropriate, compounds, molecules, compositions, vectors, vector systems, cells, or a combination thereof described in greater detail elsewhere herein can be provided to a subject in need thereof as an ingredient, such as an active ingredient or agent, in a pharmaceutical formulation. As such, also described are pharmaceutical formulations containing one or more of the compounds and salts thereof, or pharmaceutically acceptable salts thereof described herein. Suitable salts include, hydrobromide, iodide, nitrate, bisulfate, phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, camphorsulfonate, naphthalenesulfonate, propionate, malonate, mandelate, malate, phthalate, and pamoate.

In some embodiments, the subject in need thereof has or is suspected of having a cancer or a symptom thereof. In some embodiments, the subject in need thereof has or is suspected of having, a neurobiological disease or disorder, a psychiatric disease or disorder, a cancer, an autoimmune disease or disorder, a thrombosis disease, a heart disease, a kidney disease, a lung disease, or a blood vessel disease, or a combination thereof. As used herein, "agent" refers to any substance, compound, molecule, and the like, which can be biologically active or otherwise can induce a biological and/or physiological effect on a subject to which it is administered to. As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

Pharmaceutically Acceptable Carriers and Secondary Ingredients and Agents

The pharmaceutical formulation can include a pharmaceutically acceptable carrier. Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with agents, such as lubricants, preservatives, stabilizers, wetting agents, emulsifiers, salts for influencing osmotic pressure, buffers, coloring, flavoring and/or aromatic substances, and the like which do not deleteriously react with the active compound.

In some embodiments, the pharmaceutical formulation can also include an effective amount of secondary active agents, including but not limited to, biologic agents or molecules including, but not limited to, e.g. polynucleotides, amino acids, peptides, polypeptides, antibodies, aptamers, ribozymes, hormones, immunomodulators, antipyretics, anxiolytics, antipsychotics, analgesics, antispasmodics, anti-inflammatories, anti-histamines, anti-infectives, chemotherapeutics, and combinations thereof.

Effective Amounts

In some embodiments, the amount of the primary active agent and/or optional secondary agent can be an effective amount, least effective amount, and/or therapeutically effective amount. As used herein, "effective amount" refers to the amount of the primary and/or optional secondary agent included in the pharmaceutical formulation that achieve one or more therapeutic effects or desired effect. As used herein, "least effective" amount refers to the lowest amount of the primary and/or optional secondary agent that achieves the one or more therapeutic or other desired effects. As used herein, "therapeutically effective amount" refers to the amount of the primary and/or optional secondary agent included in the pharmaceutical formulation that achieves one or more therapeutic effects.

The effective amount, least effective amount, and/or therapeutically effective amount of the primary and optional secondary active agent described elsewhere herein contained in the pharmaceutical formulation can range from about 0 to 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 pg, ng, µg, mg, or g or be any numerical value with any of these ranges.

In some embodiments, the effective amount, least effective amount, and/or therapeutically effective amount can be an effective concentration, least effective concentration, and/or therapeutically effective concentration, which can each range from about 0 to 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 pM, nM, µM, mM, or M or be any numerical value with any of these ranges.

In other embodiments, the effective amount, least effective amount, and/or therapeutically effective amount of the primary and optional secondary active agent can range from about 0 to 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 IU or be any numerical value with any of these ranges.

In some embodiments, the primary and/or the optional secondary active agent present in the pharmaceutical formulation can range from about 0 to 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.9, to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% w/w, v/v, or w/v of the pharmaceutical formulation.

In some embodiments where a cell population is present in the pharmaceutical formulation (e.g., as a primary and/or or secondary active agent), the effective amount of cells can range from about 2 cells to $1\times10^1$/mL, $1\times10^{20}$/mL or more, such as about $1\times10^1$/mL, $1\times10^2$/mL, $1\times10^3$/mL, $1\times10^4$/mL, $1\times10^5$/mL, $1\times10^6$/mL, $1\times10^7$/mL, $1\times10^8$/mL, $1\times10^9$/mL, $1\times10^{10}$/mL, $1\times10^{11}$/mL, $1\times10^{12}$/mL, $1\times10^{13}$/mL, $1\times10^{14}$/mL, $1\times10^{15}$/mL, $1\times10^{16}$/mL, $1\times10^{17}$/mL, $1\times10^{18}$/mL, $1\times10^{19}$/mL, to/or about $1\times10^{20}$/mL.

In some embodiments, the amount or effective amount, particularly where an infective particle is being delivered (e.g. a virus particle having the primary or secondary agent as a cargo), the effective amount of virus particles can be expressed as a titer (plaque forming units per unit of volume) or as a MOI (multiplicity of infection). In some embodiments, the effective amount can be $1\times10^1$ particles per pL, nL, µL, mL, or L to $1\times10^{20}$/particles per pL, nL, µL, mL, or L or more, such as about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, $1\times10^{18}$, $1\times10^{19}$, to/or about $1\times10^{20}$ particles per pL, nL, µL, mL, or L. In some embodiments, the effective titer can be about $1\times10^1$ transforming units per pL, nL, µL, mL, or L to $1\times10^{20}$/transforming units per pL, nL, µL, mL, or L or more, such as about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, $1\times10^{18}$, $1\times10^{19}$, to/or about $1\times10^{20}$ transforming units per pL, nL, µL, mL, or L. In some embodiments, the MOI of the pharmaceutical formulation can range from about 0.1 to 10 or more, such as 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10 or more.

In some embodiments, the amount or effective amount of the one or more of the active agent(s) described herein contained in the pharmaceutical formulation can range from about 1 µg/kg to about 10 mg/kg based upon the bodyweight of the subject in need thereof or average bodyweight of the specific patient population to which the pharmaceutical formulation can be administered.

In one example embodiment where there is a secondary agent contained in the pharmaceutical formulation, the effective amount of the secondary active agent will vary depending on the secondary agent, the primary agent, the administration route, subject age, disease, stage of disease, among other things, which will be one of ordinary skill in the art.

When optionally present in the pharmaceutical formulation, the secondary active agent can be included in the pharmaceutical formulation or can exist as a stand-alone compound or pharmaceutical formulation that can be administered contemporaneously or sequentially with the compound, derivative thereof, or pharmaceutical formulation thereof.

In some embodiments, the effective amount of the secondary active agent can range from about 0 to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% w/w, v/v, or w/v of the total secondary active agent in the pharmaceutical formulation. In additional embodiments, the effective amount of the secondary active agent can range from about 0 to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% w/w, v/v, or w/v of the total pharmaceutical formulation.

Dosage Forms

In some embodiments, the pharmaceutical formulations described herein can be provided in a dosage form. The dosage form can be administered to a subject in need thereof. The dosage form can be effective generate specific concentration, such as an effective concentration, at a given site in the subject in need thereof. As used herein, "dose," "unit dose," or "dosage" can refer to physically discrete units suitable for use in a subject, each unit containing a predetermined quantity of the primary active agent, and optionally present secondary active ingredient, and/or a pharmaceutical formulation thereof calculated to produce the desired response or responses in association with its administration. In some embodiments, the given site is proximal to the administration site. In some embodiments, the given site is distal to the administration site. In some cases, the dosage form contains a greater amount of one or more of the active ingredients present in the pharmaceutical formulation than the final intended amount needed to reach a specific region or location within the subject to account for loss of the active components such as via first and second pass metabolism.

The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, parenteral, subcutaneous, intramuscular, intravenous, internasal, and intradermal. Other appropriate routes are described elsewhere herein. Such formulations can be prepared by any method known in the art.

Dosage forms adapted for oral administration can discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution. The oral dosage form can be administered to a subject in need thereof. Where appropriate, the dosage forms described herein can be microencapsulated.

The dosage form can also be prepared to prolong or sustain the release of any ingredient. In some embodiments, compounds, molecules, compositions, vectors, vector systems, cells, or a combination thereof described herein can be the ingredient whose release is delayed. In some embodiments the primary active agent is the ingredient whose release is delayed. In some embodiments, an optional secondary agent can be the ingredient whose release is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Weiterstadt, Germany), zein, shellac, and polysaccharides.

Coatings may be formed with a different ratio of water-soluble polymer, water insoluble polymers, and/or pH dependent polymers, with or without water insoluble/water soluble non-polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Where appropriate, the dosage forms described herein can be a liposome. In these embodiments, primary active ingredient(s), and/or optional secondary active ingredient(s), and/or pharmaceutically acceptable salt thereof where appropriate are incorporated into a liposome. In one example embodiment where the dosage form is a liposome, the pharmaceutical formulation is thus a liposomal formulation. The liposomal formulation can be administered to a subject in need thereof.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, a primary active ingredient, optional secondary active ingredient, and/or pharmaceutically acceptable salt thereof where appropriate can be formulated with a paraffinic or water-miscible ointment base. In other embodiments, the primary and/or secondary active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, a primary active ingredient, optional secondary active ingredient, and/or pharmaceutically acceptable salt thereof where appropriate can be in a dosage form adapted for inhalation is in a particle-size-reduced form that is obtained or obtainable by micronization. In some embodiments, the particle size of the size reduced (e.g. micronized) compound or salt or solvate thereof, is defined by a $D_{50}$ value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active (primary and/or secondary) ingredient, which may be generated by various types of metered dose pressurized aerosols, nebulizers, or insufflators. The nasal/inhalation formulations can be administered to a subject in need thereof.

In some embodiments, the dosage forms are aerosol formulations suitable for administration by inhalation. In some of these embodiments, the aerosol formulation contains a solution or fine suspension of a primary active ingredient, secondary active ingredient, and/or pharmaceutically acceptable salt thereof where appropriate and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a primary active ingredient, optional secondary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, 3 or more doses are delivered each time. The aerosol formulations can be administered to a subject in need thereof.

For some dosage forms suitable and/or adapted for inhaled administration, the pharmaceutical formulation is a dry powder inhalable-formulations. In addition to a primary active agent, optional secondary active ingredient, and/or pharmaceutically acceptable salt thereof where appropriate, such a dosage form can contain a powder base such as lactose, glucose, trehalose, mannitol, and/or starch. In some of these embodiments, a primary active agent, secondary active ingredient, and/or pharmaceutically acceptable salt thereof where appropriate is in a particle-size reduced form. In further embodiments, a performance modifier, such as L-leucine or another amino acid, cellobiose octaacetate, and/or metals salts of stearic acid, such as magnesium or calcium stearate. In some embodiments, the aerosol formulations are arranged so that each metered dose of aerosol contains a predetermined amount of an active ingredient, such as the one or more of the compositions, compounds, vector(s), molecules, cells, and combinations thereof described herein.

Dosage forms adapted for vaginal administration can be presented as pessaries, tampons, creams, gels, pastes, foams, or spray formulations. Dosage forms adapted for rectal administration include suppositories or enemas. The vaginal formulations can be administered to a subject in need thereof.

Dosage forms adapted for parenteral administration and/or adapted for injection can include aqueous and/or non-aqueous sterile injection solutions, which can contain antioxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and re-suspended in a sterile carrier to reconstitute the dose prior to administration. Extemporaneous injection solutions and suspensions can be prepared in some embodiments, from sterile powders, granules, and tablets. The parenteral formulations can be administered to a subject in need thereof.

For some embodiments, the dosage form contains a predetermined amount of a primary active agent, secondary active ingredient, and/or pharmaceutically acceptable salt thereof where appropriate per unit dose. In an embodiment, the predetermined amount of primary active agent, secondary active ingredient, and/or pharmaceutically acceptable salt thereof where appropriate can be an effective amount, a least effect amount, and/or a therapeutically effective amount. In other embodiments, the predetermined amount of a primary active agent, secondary active agent, and/or pharmaceutically acceptable salt thereof where appropriate, can be an appropriate fraction of the effective amount of the active ingredient.

Co-Therapies and Combination Therapies

In some embodiments, the pharmaceutical formulation(s) described herein can be part of a combination treatment or combination therapy. The combination treatment can include the pharmaceutical formulation described herein and an additional treatment modality. The additional treatment modality can be a chemotherapeutic, a biological therapeutic, surgery, radiation, diet modulation, environmental modulation, a physical activity modulation, and combinations thereof.

In some embodiments, the co-therapy or combination therapy can additionally include but not limited to, polynucleotides, amino acids, peptides, polypeptides, antibodies, aptamers, ribozymes, hormones, immunomodulators, antipyretics, anxiolytics, antipsychotics, analgesics, antispasmodics, anti-inflammatories, anti-histamines, anti-infectives, chemotherapeutics, and combinations thereof.

Administration of the Pharmaceutical Formulations

The pharmaceutical formulations or dosage forms thereof described herein can be administered one or more times hourly, daily, monthly, or yearly (e.g. 1, 2, 3, 4, 5, 6, 7, 8, 9, 10, 11, 12, 13, 14, 15, 16, 17, 18, 19, 20, or more times hourly, daily, monthly, or yearly). In some embodiments, the pharmaceutical formulations or dosage forms thereof described herein can be administered continuously over a period of time ranging from minutes to hours to days. Devices and dosages forms are known in the art and described herein that are effective to provide continuous administration of the pharmaceutical formulations described herein. In some embodiments, the first one or a few initial amount(s) administered can be a higher dose than subsequent doses. This is typically referred to in the art as a loading dose or doses and a maintenance dose, respectively. In some embodiments, the pharmaceutical formulations can be administered such that the doses over time are tapered (increased or decreased) overtime so as to wean a subject gradually off of a pharmaceutical formulation or gradually introduce a subject to the pharmaceutical formulation.

As previously discussed, the pharmaceutical formulation can contain a predetermined amount of a primary active agent, secondary active agent, and/or pharmaceutically acceptable salt thereof where appropriate. In some of these embodiments, the predetermined amount can be an appropriate fraction of the effective amount of the active ingredient. Such unit doses may therefore be administered once or more than once a day, month, or year (e.g. 1, 2, 3, 4, 5, 6, or more times per day, month, or year). Such pharmaceutical formulations may be prepared by any of the methods well known in the art.

Where co-therapies or multiple pharmaceutical formulations are to be delivered to a subject, the different therapies or formulations can be administered sequentially or simultaneously. Sequential administration is administration where an appreciable amount of time occurs between administrations, such as more than about 15, 20, 30, 45, 60 minutes or more. The time between administrations in sequential administration can be on the order of hours, days, months, or even years, depending on the active agent present in each administration. Simultaneous administration refers to administration of two or more formulations at the same time or substantially at the same time (e.g. within seconds or just a few minutes apart), where the intent is that the formulations be administered together at the same time.

Delivery and Administration

Methods for modifying a target of interest comprises administering or delivering or otherwise contacting a cell via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the composition is introduced into an embryo by microinjection. The compositions may be microinjected into the nucleus or the cytoplasm of the embryo.

An actively targeting lipid particle or nanoparticle or liposome or lipid bilayer delivery system (generally as to embodiments of the invention, "lipid entity of the invention" delivery systems) are prepared by conjugating targeting moieties, including small molecule ligands, peptides and monoclonal antibodies, on the lipid or liposomal surface; for example, certain receptors, such as folate and transferrin (Tf) receptors (TfR), are overexpressed on many cancer cells and have been used to make liposomes tumor cell specific. Liposomes that accumulate in the tumor microenvironment can be subsequently endocytosed into the cells by interacting with specific cell surface receptors. To efficiently target liposomes to cells, such as cancer cells, it is useful that the targeting moiety have an affinity for a cell surface receptor and to link the targeting moiety in sufficient quantities to have optimum affinity for the cell surface receptors; and determining these aspects are within the ambit of the skilled artisan. In the field of active targeting, there are a number of cell-, e.g., tumor-, specific targeting ligands.

Also as to active targeting, with regard to targeting cell surface receptors such as cancer cell surface receptors, targeting ligands on liposomes can provide attachment of liposomes to cells, e.g., vascular cells, via a noninternalizing epitope; and, this can increase the extracellular concentration of that which is being delivered, thereby increasing the amount delivered to the target cells. A strategy to target cell surface receptors, such as cell surface receptors on cancer cells, such as overexpressed cell surface receptors on cancer cells, is to use receptor-specific ligands or antibodies. Many cancer cell types display upregulation of tumor-specific receptors. For example, TfRs and folate receptors (FRs) are greatly overexpressed by many tumor cell types in response to their increased metabolic demand. Folic acid can be used as a targeting ligand for specialized delivery owing to its ease of conjugation to nanocarriers, its high affinity for FRs and the relatively low frequency of FRs, in normal tissues as compared with their overexpression in activated macrophages and cancer cells, e.g., certain ovarian, breast, lung, colon, kidney and brain tumors. Overexpression of FR on macrophages is an indication of inflammatory diseases, such as psoriasis, Crohn's disease, rheumatoid arthritis and atherosclerosis; accordingly, folate-mediated targeting of the invention can also be used for studying, addressing or treating inflammatory disorders, as well as cancers. Folate-linked lipid particles or nanoparticles or liposomes or lipid bilayers of the invention ("lipid entity of the invention") deliver their cargo intracellularly through receptor-mediated endocytosis. Intracellular trafficking can be directed to acidic compartments that facilitate cargo release, and, most importantly, release of the cargo can be altered or delayed until it reaches the cytoplasm or vicinity of target organelles. Delivery of cargo using a lipid entity of the invention having a targeting moiety, such as a folate-linked lipid entity of the invention, can be superior to nontargeted lipid entity of the invention. The attachment of folate directly to the lipid head groups may not be favorable for intracellular delivery of folate-conjugated lipid entity of the invention, since they may not bind as efficiently to cells as folate attached to the lipid entity of the invention surface by a spacer, which may can enter cancer cells more efficiently. A lipid entity of the invention coupled to folate can be used for the delivery of complexes of lipid, e.g., liposome, e.g., anionic liposome and virus or capsid or envelope or virus outer protein, such as those herein discussed such as adenovirus or AAV. Tf is a monomeric serum glycoprotein of approximately 80 KDa involved in the transport of iron throughout the body. Tf binds to the TfR and translocates into cells via receptor-mediated endocytosis. The expression of TfR can be higher in certain cells, such as tumor cells (as compared with normal cells and is associated with the increased iron demand in rapidly proliferating cancer cells. Accordingly, the invention comprehends a TfR-targeted lipid entity of the invention, e.g., as to liver cells, liver cancer, breast cells such as breast cancer cells, colon such as colon cancer cells, ovarian cells such as ovarian cancer cells, head, neck and lung cells, such as head, neck and non-small-cell lung cancer cells, cells of the mouth such as oral tumor cells.

Also as to active targeting, a lipid entity of the invention can be multifunctional, i.e., employ more than one targeting moiety such as CPP, along with Tf; a chimeric small system; e.g., a combination of Tf and poly-L-arginine which can provide transport across the endothelium of the blood-brain barrier. EGFR is a tyrosine kinase receptor belonging to the ErbB family of receptors that mediates cell growth, differentiation and repair in cells, especially non-cancerous cells, but EGF is overexpressed in certain cells such as many solid tumors, including colorectal, non-small-cell lung cancer, squamous cell carcinoma of the ovary, kidney, head, pancreas, neck and prostate, and especially breast cancer. The invention comprehends EGFR-targeted monoclonal antibody(ies) linked to a lipid entity of the invention. HER-2 is often overexpressed in patients with breast cancer, and is also associated with lung, bladder, prostate, brain and stomach cancers. HER-2, encoded by the ERBB2 gene. The invention comprehends a HER-2-targeting lipid entity of the invention, e.g., an anti-HER-2-antibody (or binding fragment thereof)-lipid entity of the invention, a HER-2-targeting-PEGylated lipid entity of the invention (e.g., having an anti-HER-2-antibody or binding fragment thereof), a HER-2-targeting-maleimide-PEG polymer-lipid entity of the invention (e.g., having an anti-HER-2-antibody or binding fragment thereof). Upon cellular association, the receptor-antibody complex can be internalized by formation of an endosome for delivery to the cytoplasm. With respect to receptor-mediated targeting, the skilled artisan takes into consideration ligand/target affinity and the quantity of receptors on the cell surface, and that PEGylation can act as a barrier against interaction with receptors. The use of antibody-lipid entity of the invention targeting can be advantageous. Multivalent presentation of targeting moieties can also increase the uptake and signaling properties of antibody fragments. In practice of the invention, the skilled person takes into account ligand density (e.g., high ligand densities on a lipid entity of the invention may be advantageous for increased binding to target cells). Preventing early by macrophages can be addressed with a sterically stabilized lipid entity of the invention and linking ligands to the terminus of molecules such as PEG, which is anchored in the lipid entity of the invention (e.g., lipid particle or nanoparticle or liposome or lipid bilayer). The microenvironment of a cell mass such as a tumor microenvironment can be targeted; for instance, it may be advantageous to target cell mass vasculature, such as the tumor vasculature microenvironment. Thus, the invention comprehends targeting VEGF. VEGF and its receptors are well-known proangiogenic molecules and are well-characterized targets for antiangiogenic therapy. Many small-molecule inhibitors of receptor tyrosine kinases, such as VEGFRs or basic FGFRs, have been developed as anticancer agents and the invention comprehends coupling any one or more of these peptides to a lipid entity of the invention, e.g., phage IVO peptide(s) (e.g., via or with a PEG terminus), tumor-homing peptide APRPG such as APRPG-PEG-modified. VCAM, the vascular endothelium plays a key role in the pathogenesis of inflammation, thrombosis and atherosclerosis. CAMs are involved in inflammatory disorders, including cancer, and are a logical target, E- and P-selectins, VCAM-1 and ICAMs. Can be used to target a lipid entity of the invention, e.g., with PEGylation. Matrix metalloproteases (MMPs) belong to the family of zinc-dependent endopeptidases. They are involved in tissue remodeling, tumor invasiveness, resistance to apoptosis and metastasis. There are four MMP inhibitors called TIMP1-4, which determine the balance between tumor growth inhibition and metastasis; a protein involved in the angiogenesis of tumor vessels is MT1-MMP, expressed on newly formed vessels and tumor tissues. The proteolytic activity of MT1-MMP cleaves proteins, such as fibronectin, elastin, collagen and laminin, at the plasma membrane and activates soluble MMPs, such as MMP-2, which degrades the matrix. An antibody or fragment thereof such as a Fab' fragment can be used in the practice of the invention such as for an antihuman MT1-MMP monoclonal antibody linked to a lipid entity of the invention, e.g., via a spacer such as a PEG spacer. α β-integrins or integrins are a group of transmembrane glycoprotein receptors that mediate attachment between a cell and its surrounding tissues or extracellular matrix. Integrins contain two distinct chains (heterodimers) called α- and β-subunits. The tumor tissue-specific expression of integrin receptors can be utilized for targeted delivery in the invention, e.g., whereby the targeting moiety can be an RGD peptide such as a cyclic RGD. Aptamers are ssDNA or RNA oligonucleotides that impart high affinity and specific recognition of the target molecules by electrostatic interactions, hydrogen bonding and hydrophobic interactions as opposed to the Watson-Crick base pairing, which is typical for the bonding interactions of oligonucleotides. Aptamers as a targeting moiety can have advantages over antibodies: aptamers can demonstrate higher target antigen recognition as compared with antibodies; aptamers can be more stable and smaller in size as compared with antibodies; aptamers can be easily synthesized and chemically modified for molecular conjugation; and aptamers can be changed in sequence for improved selectivity and can be developed to recognize poorly immunogenic targets. Such moieties as a sgc8 aptamer can be used as a targeting moiety (e.g., via covalent linking to the lipid entity of the invention, e.g., via a spacer, such as a PEG spacer). The targeting moiety can be stimuli-sensitive, e.g., sensitive to an externally applied stimuli, such as magnetic fields, ultrasound or light; and pH-triggering can also be used, e.g., a labile linkage can be used between a hydrophilic moiety such as PEG and a hydrophobic moiety such as a lipid entity of the invention, which is cleaved only upon exposure to the relatively acidic conditions characteristic of the particular environment or microenvironment such as an endocytic vacuole or the acidotic tumor mass. pH-sensitive copolymers can also be incorporated in example embodiments of the invention can provide shielding; diortho esters, vinyl esters, cysteine-cleavable lipopolymers, double esters and hydrazones are a few examples of pH-sensitive bonds that are quite stable at pH 7.5, but are hydrolyzed relatively rapidly at pH 6 and below, e.g., a terminally alkylated copolymer of N-isopropylacrylamide and methacrylic acid that copolymer facilitates destabilization of a lipid entity of the invention and release in compartments with decreased pH value; or, the invention comprehends ionic polymers for generation of a pH-responsive lipid entity of the invention (e.g., poly(methacrylic acid), poly(diethylaminoethyl methacrylate), poly(acrylamide) and poly(acrylic acid)). Temperature-triggered delivery is also within the ambit of the invention. Many pathological areas, such as inflamed tissues and tumors, show a distinctive hyperthermia compared with normal tissues. Utilizing this hyperthermia is an attractive strategy in cancer therapy since hyperthermia is associated with increased tumor permeability and enhanced uptake. This technique involves local heating of the site to increase microvascular pore size and blood flow, which, in turn, can result in an increased extravasation of embodiments of the invention. Temperature-sensitive lipid entity of the invention can be prepared from thermosensitive lipids or polymers with a low critical solution temperature. Above the low critical solution temperature (e.g., at site such as tumor site or inflamed tissue site), the polymer precipitates, disrupting the liposomes to release. Lipids with a specific gel-to-liquid phase transition temperature are used to prepare these lipid entities of the invention; and a lipid for a thermosensitive embodiment can be dipalmitoylphosphatidylcholine. Thermosensitive polymers can also facilitate destabilization followed by release, and a useful thermosensitive polymer is poly (N-isopropylacrylamide). Another temperature triggered system can employ lysolipid temperature-sensitive liposomes. The invention also comprehends redox-triggered delivery: The difference in redox potential between normal and inflamed or tumor tissues, and between the intra- and extra-cellular environments has been exploited for delivery; e.g., GSH is a reducing agent abundant in cells, especially in the cytosol, mitochondria and nucleus. The GSH concentrations in blood and extracellular matrix are just one out of 100 to one out of 1000 of the intracellular concentration, respectively. This high redox potential difference caused by GSH, cysteine and other reducing agents can break the reducible bonds, destabilize a lipid entity of the invention and result in release of payload. The disulfide bond can be used as the cleavable/reversible linker in a lipid entity of the invention, because it causes sensitivity to redox owing to the disulfide to-thiol reduction reaction; a lipid entity of the invention can be made reduction sensitive by using two (e.g., two forms of a disulfide-conjugated multifunctional lipid as cleavage of the disulfide bond (e.g., via tris(2-carboxyethyl)phosphine, dithiothreitol, L-cysteine or GSH), can cause removal of the hydrophilic head group of the conjugate and alter the membrane organization leading to release of payload. Calcein release from reduction-sensitive lipid entity of the invention containing a disulfide conjugate can be more useful than a reduction-insensitive embodiment. Enzymes can also be used as a trigger to release payload. Enzymes, including MMPs (e.g. MMP2), phospholipase A2, alkaline phosphatase, transglutaminase or phosphatidylinositol-specific phospholipase C, have been found to be overexpressed in certain tissues, e.g., tumor tissues. In the presence of these enzymes, specially engineered enzyme-sensitive lipid entity of the invention can be disrupted and release the payload. an MMP2-cleavable octapeptide (Gly-Pro-Leu-Gly-Ile-Ala-Gly-Gln) (SEQ ID NO: 1) can be incorporated into a linker, and can have antibody targeting, e.g., antibody 2C5. The invention also comprehends light- or energy-triggered delivery, e.g., the lipid entity of the invention can be light-sensitive, such that light or energy can facilitate structural and conformational changes, which lead to direct interaction of the lipid entity of the invention with the target cells via membrane fusion, photo-isomerism, photofragmentation or photopolymerization; such a moiety therefor can be benzoporphyrin photosensitizer. Ultrasound can be a form of energy to trigger delivery; a lipid entity of the invention with a small quantity of particular gas, including air or perfluorinated hydrocarbon can be triggered to release with ultrasound, e.g., low-frequency ultrasound (LFUS). Magnetic delivery: A lipid entity of the invention can be magnetized by incorporation of magnetites, such as $Fe_3O_4$ or $\gamma$-Fe2O3, e.g., those that are less than 10 nm in size. Targeted delivery can be then by exposure to a magnetic field.

Also as to active targeting, the invention also comprehends intracellular delivery. Since liposomes follow the endocytic pathway, they are entrapped in the endosomes (pH 6.5-6) and subsequently fuse with lysosomes (pH<5), where they undergo degradation that results in a lower therapeutic potential. The low endosomal pH can be taken advantage of to escape degradation. Fusogenic lipids or peptides, which destabilize the endosomal membrane after the conformational transition/activation at a lowered pH. Amines are protonated at an acidic pH and cause endosomal swelling and rupture by a buffer effect Unsaturated dioleoylphosphatidylethanolamine (DOPE) readily adopts an inverted hexagonal shape at a low pH, which causes fusion of liposomes to the endosomal membrane. This process destabilizes a lipid entity containing DOPE and releases the cargo into the cytoplasm; fusogenic lipid GALA (SEQ ID NO: 41), cholesteryl-GALA (SEQ ID NO: 41) and PEG-GALA (SEQ ID NO: 41) may show a highly efficient endosomal release; a pore-forming protein listeriolysin 0 may provide an endosomal escape mechanism; and, histidine-rich peptides have the ability to fuse with the endosomal membrane, resulting in pore formation, and can buffer the proton pump causing membrane lysis.

Also as to active targeting, cell-penetrating peptides (CPPs) facilitate uptake of macromolecules through cellular membranes and, thus, enhance the delivery of CPP-modified molecules inside the cell. CPPs can be split into two classes: amphipathic helical peptides, such as transportan and MAP, where lysine residues are major contributors to the positive charge; and Arg-rich peptides, such as TATp, Antennapedia or penetratin. TATp is a transcription-activating factor with 86 amino acids that contains a highly basic (two Lys and six Arg among nine residues) protein transduction domain, which brings about nuclear localization and RNA binding. Other CPPs that have been used for the modification of liposomes include the following: the minimal protein transduction domain of Antennapedia, a *Drosophila* homeoprotein, called penetratin, which is a 16-mer peptide (residues 43-58) present in the third helix of the homeodomain; a 27-amino acid-long chimeric CPP, containing the peptide sequence from the amino terminus of the neuropeptide galanin bound via the Lys residue, multipara, a wasp venom peptide; VP22, a major structural component of HSV-1 facilitating intracellular transport and transportan (18-mer) amphipathic model peptide that translocates plasma membranes of mast cells and endothelial cells by both energy-dependent and -independent mechanisms. The invention comprehends a lipid entity of the invention modified with CPP(s), for intracellular delivery that may proceed via energy dependent micropinocytosis followed by endosomal escape. The invention further comprehends organelle-specific targeting. A lipid entity of the invention surface-functionalized with the triphenyl phosphonium (TPP) moiety or a lipid entity of the invention with a lipophilic cation, rhodamine 123 can be effective in delivery of cargo to mitochondria. DOPE/sphingomyelin/stearyl-octa-arginine can delivers cargos to the mitochondrial interior via membrane fusion. A lipid entity of the invention surface modified with a lysosomotropic ligand, octadecyl rhodamine B can deliver cargo to lysosomes. Ceramides are useful in inducing lysosomal membrane permeabilization; the invention comprehends intracellular delivery of a lipid entity of the invention having a ceramide. The invention further comprehends a lipid entity of the invention targeting the nucleus, e.g., via a DNA-intercalating moiety. The invention also comprehends multifunctional liposomes for targeting, i.e., attaching more than one functional group to the surface of the lipid entity of the invention, for instance to enhances accumulation in a desired site and/or promotes organelle-specific delivery and/or target a particular type of cell and/or respond to the local stimuli such as temperature (e.g., elevated), pH (e.g., decreased), respond to externally applied stimuli such as a magnetic field, light, energy, heat or ultrasound and/or promote intracellular delivery of the cargo. All of these are considered actively targeting moieties.

An embodiment of the system may comprise an actively targeting lipid particle or nanoparticle or liposome or lipid bilayer delivery system; or a lipid particle or nanoparticle or liposome or lipid bilayer comprising a targeting moiety whereby there is active targeting or wherein the targeting moiety is an actively targeting moiety. A targeting moiety can be one or more targeting moieties, and a targeting moiety can be for any desired type of targeting such as, e.g., to target a cell such as any herein-mentioned; or to target an organelle such as any herein-mentioned; or for targeting a response such as to a physical condition such as heat, energy, ultrasound, light, pH, chemical such as enzymatic, or magnetic stimuli; or to target to achieve a particular outcome such as delivery of payload to a particular location, such as by cell penetration.

It should be understood that as to each possible targeting or active targeting moiety herein-discussed, there is one example embodiment of the invention wherein the delivery system comprises such a targeting or active targeting moiety.

Further embodiments are illustrated in the following Examples which are given for illustrative purposes only and are not intended to limit the scope of the invention.

Methods of Screening

Methods of screening for the combination of the protein binding moieties to be provided in the chimeric small molecule are provided herein. In one embodiment, the methods of screening identify binders of a protein target substrate. In one embodiment, the kinase binding moiety is a kinase inhibitor of an oncogenic fusion of a kinase target substrate. By way of example, reference in the screening embodiment described screening Abl kinase binders for BCR-ABL; however, the screening method described is applicable to identification of kinase binders of other target substrates utilized in chimeric small molecules detailed herein. In example methods of screening, binders, for example inhibitors of BCR-ABL are identified based on the binding location on Abl.

The methods of nucleic acid analysis can be utilized for screening of chemical libraries, and to identify additional binders for use within the context of the embodiments disclosed herein.

In some embodiments, the disclosed methods can be used to screen chemical libraries for agents that bind kinase and modulate activation or inactivation of the same. By exposing cells, or fractions thereof, tissues, or even whole animals, to different members of the chemical libraries, and performing the methods described herein, different members of a chemical library can be screened for their effect on kinase binding and activation state.

In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

Screening for Chimeric Small Molecules

A further aspect of the invention relates to a method for identifying a chimeric small molecule capable of modulating one or more phenotypic aspects of a cell or cell population as disclosed herein, comprising: a) applying a candidate chimeric small agent to the cell or cell population; b) detecting modulation of one or more phenotypic aspects of the cell or cell population by the candidate agent, thereby identifying the agent. The phenotypic aspects of the cell or cell population that is modulated may be a gene signature or biological program specific to a cell type or cell phenotype or phenotype specific to a population of cells (e.g., an inflammatory phenotype or suppressive immune phenotype). In one example embodiment, steps can include administering candidate modulating agents to cells, detecting identified cell (sub)populations for changes in signatures, or identifying relative changes in cell (sub) populations which may comprise detecting relative abundance of particular gene signatures.

The term "modulate" broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to statistically significant increase or decrease in the measured variable. By means of example, modulation may encompass an increase in the value of the measured variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without said modulation; or modulation may encompass a decrease or reduction in the value of the measured variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said modulation. Preferably, modulation may be specific or selective, hence, one or more desired phenotypic aspects of an immune cell or immune cell population may be modulated without substantially altering other (unintended, undesired) phenotypic aspect(s).

After the chimeric small molecule is applied, a representative cell sample can be subjected to analysis, for example at various time points, and compared to a control, such as a sample from an organism or cell, for example a cell from an organism, or a standard value. By exposing cells, or fractions thereof, tissues, or even whole animals, to different members of the chemical libraries, and performing the methods described herein, different members of a chemical library can be screened for their effect on immune phenotypes thereof simultaneously in a relatively short amount of time, for example using a high throughput method.

In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

Further embodiments are illustrated in the following Examples which are given for illustrative purposes only and are not intended to limit the scope of the invention.

EXAMPLES

Example 1—Chimeric Small Molecules

Harnessing Enzyme Inhibitors to Build Chimeras

Exemplary chimeric small molecules are formed by joining a kinase binder with a binder of a target protein-of-interest. Here, Applicants used the inhibitor-directed site-selective fast labeling of the kinase with the target binding moiety. Inhibitors tethered with a chemoselective electrophilic reactive group exhibit site-specific labeling of a side chain nucleophilic residue proximal to the inhibitor binding site, this approach has worked for several inhibitors. To neutralize the inhibitor following labeling, Applicants used bio-orthogonal handles (e.g., using cyclopropyl or azide) that do not perturb the binding of the inhibitor to the kinase. Upon completion of the proximity-induced labeling reaction, the cells will be treated with a large reactive group (e.g., tetrazine, cyclooctyne) whose conjugation will prevent the inhibitor from binding to the kinase, thereby deactivating the inhibitor. Applicants leveraged readily available inhibitors with low residence time (high $k_{off}$) to allow rapid labeling and quenching.

Development and Application of Kinase-Binder Platform

In this work, Applicants developed and applied the novel kinase binder platform to find binders to label the kinases via proximity-induced labeling. Here, Applicants turned kinase inhibitors into labelers with the trifunctional molecule (kinase inhibitor-lysine reactive group-M.tb protein targeting group). The molecules bind to kinases via the kinase inhibitor, proximal lysines react with the lysine-reactive group (e.g., N-acyl-N-alkyl sulfonamide or NASA), and expel the kinase inhibitor, leaving the kinase tagged with an M.tb binder. The kinases, then covalently labeled with an M.tb binder, will hyper- and/or neo-phosphorylate the M.tb proteins, leading to HLA-display and an immune response. The kinase inhibitor contains a small bio-orthogonal group (e.g., cyclopropenyl, azide, tetrazine) that does not perturb the binding of the inhibitor to the kinase, and the inhibitor is quenched (e.g., with cyclooctyne), so the bulky group prevents the inhibitor from binding to the kinase. Applicants optimized NASA (covalent labeling) chemistry (see below) and optimized quenching the inhibitor (see below). Applicants focused on the NASA electrophilic reactive group since it is one of the most rapid cell-compatible proximity-induced labeling reagents, which was successfully used for labeling of PKC kinase by Applicants.

Design and Optimization of NASA Chemistry for 5 Kinase Inhibitors

Applicants selected five kinases to optimize the NASA chemistry to label kinases with an inhibitor: MAPK, EGFR, ABL, CDK8, and P13K (FIG. 18). These kinases and inhibitors were chosen based on the following criteria (1) high kinase abundance in macrophages, (2) well-established binders with nanomolar activity, available crystal structure, and low residence time to ensure efficiency of the deactivation step, (3) binder should accommodate a small biorthogonal handle without affecting its binding potency/residence time (4) high density of lysines on the kinase close to the binding pocket, (5) labeling of kinase should not interfere with its enzymatic activity. For example, to design a probe for labeling of p38α MAPK, Applicants have chosen the following three binders: SB203580, Skepinone-B and Sorafenib with residence times 5, 150 and 88 seconds respectively (FIG. 18). The crystal structure of SB203580 (PDB: 3GCP) shows that linker attachment at the sulfoxide should not affect binding, and lysines (K15, K54, K66, K152, K165) are in close proximity to the binding pocket. Docking studies show that attachment of azide in ortho position to the fluoro group does not interfere with binding; however, the product of click reaction does not bind to p38α. Similar analysis of crystal structures for Skepinone (PDB: 3QUE) and Sorafenib (PDB: 3HEG) were performed. Gefitinib, Imatinib, Idelasilib and compound 5 were selected as binders of EGFR, ABL, PI3K and CDK8, respectively, due to their relatively low residence time (7s-17 min) and high availability of lysines in the close proximity to binding pockets (6 Lys for EGFR, 10 Lys for ABL, 6 Lys for CDK8, and 10 Lys for PI3K). For all of the inhibitors shown in FIG. 16, Applicants optimized labeling by creating trifunctional probes with: kinase binder-NASA group-coumarin and measure labeling via in-gel fluorescence of cell lysate after treatment with probes. Representative examples of fluorescent probe and mechanism of labeling are shown in FIG. 17A. As an alternative to NASA, dibromophenyl benzoate and N-sulfonyl pyridone electrophilic reactive groups will be considered. Applicants chose binders with 3 linkers per kinase (5 kinases total) to synthesize coumarin probes with and without the orthogonal binding group (15 compounds×2 variations=30 compounds), prioritizing the best 3 kinase-inhibitor pairs.

Design and Optimize Bioorthogonal Chemistry for 5 Kinase Inhibitors

Applicants focused on click reaction between azide (substituent on kinase inhibitor) and cyclooctyne (quenching reagent) as a deactivating step. Mechanism of inhibitor deactivation is illustrated in FIGS. 17 and 19 where click renders the kinase inactive. Alternatively, inverse Diels-Alder reaction between tetrazine (bioisostere of phenyl) and trans-cyclooctene or cyclopropene will be considered. To optimize biorthogonal chemistry, various quenching reagents will be added to cells pretreated with optimized probes. Reaction conditions for the quenching step will be varied (concentration of coupling molecule, incubation time) and the activity of labeled kinases towards their natural substrates will be evaluated. Applicants measured if the kinase is quenched by looking at the kinase-substrate phosphorylation. If the kinase inhibitor is quenched, then the kinase phosphorylation of its substrate will be returned to basal levels.

Target Selection: Immune Evasion is a Hallmark of PsA and M.Tb

The gram-negative pathogen PsA remains a serious human health threat with increasing instances of antibiotic-resistance and immune-system evasion. The outer-membrane of PsA acts as a physical barrier for antibiotics and hinders recognition by the immune system. Upon initial infection, the bacterium secretes alkaline protease and elastase, which degrade the complement protein C3b. Moreover, lipopolysaccharide (LPS) variants can interfere with C3b deposition. During the late stages of infection, PsA forms biofilms that protect the bacteria from complement-mediated phagocytosis. The forced recruitment of complement proteins, antibodies, or macrophages to PsA at high, local concentrations using chimeras empowers the immune system to deactivate these pathogens.

M.tb. also evades the host immune system through multiple mechanisms. The bacteria enter macrophages by conjugating to the complement proteins and subsequently uses their ESX-1 apparatus to secrete proteins that block endosome acidification and the immune system. For example, M.tb. attenuates antigen processing and MHC-II expression, secretes ESAT-6 to aid in phagosomal escape and intracellular survival and secretes protein tyrosine phosphatase A (PtpA) and mammalian cell entry protein 3E (Mce3E) to suppress the innate immune responses. PtpA, PtpB and SapM (secreted acid phosphatase) act on $H^+$-V-ATPase and phosphatidylinositol, respectively, to prevent the phagosome acidification and maturation. M.tb limits the autophagy initiation by secreting enhanced intracellular survival protein, which rapidly acetylates host dual proteins phosphatase (DUSP16) and mitogen-activated protein kinase phosphatase-7 (MKP-7).

Recently, Applicants demonstrated the ability of phosphorylation-inducing chimeric small molecules (PHICS) to hyper-phosphorylate a non-native substrate of the kinase. Protein hyperphosphorylation not only deactivates the protein, but it also appends neo-epitopes on the target, which can potentially be recognized by the immune system (via HLA display) to evoke a robust immune response. Since M.tb secretes its several key proteins (e.g., PtpA, PtpB, SapM, ESAT-6, Rv2966c) in macrophages, Applicants will develop PHICS against these targets and demonstrate clearance of the infected macrophages by T cells.

PHosphorylation-Inducing Chimeric Small Molecules (PHICS)

Neo-phosphorylations (unobserved in the native cellular environment) can also alter protein structure and function, and evoke immune response. PHICS-mediated neo-phosphorylation on M.tb proteins may evoke a strong immune response against the pathogen-specific phosphopeptides, allowing deactivation and elimination of infected macrophages by the immune system. Several phosphorylation sites recruit ubiquitin ligase and signal degradation. As such, PHICS may enable the deactivation and degradation of targeted proteins. Finally, the proposal to incorporate kinase inhibitors using proximity-induced labeling chemistries will allow engagement of kinases that are highly abundant in macrophages, thereby increasing opportunities to induce a desired therapeutic outcome.

Applicants note that PHICS will complement PROTACs in multiple ways. For example, PHICS can have several target sites (Ser, Thr, Tyr, and His) while PROTACs target only lysine. The efficiency of PROTAC depends on the efficiency of ubiquitination, which is a complex process compared to phosphorylation. Ubiquitination is a multistep modification involving the appendage of a protein and often yields a heterogeneous mixture of poly-ubiquitinated species in substoichiometric amounts. Phosphorylation is relatively simple, involving the appendage of a small phosphoryl group, which does not concatenate to form chains. Finally, ubiquitination involves large complexes compared to those of kinases. Additionally, PHICS target M. tb secretory proteins and kinases abundant in macrophages. Therefore, immune-response induced by neo-phosphorylations will be more selective towards infected cells. Because of its catalytic nature, PHICS may produce more prolonged effects until the clearance of the infected cells. PROTAC may inhibit the activity of a M.tb protein by degradation, but it is envisioned that PHICS-induced immune response would destroy the infected cell, preventing a subsequent infection of surrounding cells.

TABLE 2

Relative stability and reactivity of NASA analogs and alternatives

| Compound | Hydrolysis[a] | Hydrolysis[b] | Reactivity with Lysine | Reactivity with peptide |
|---|---|---|---|---|
| VS1356 | 44% | 96% | 0% | 0% |
| VS1358 | 70% | 86% | 10% from NHS Ester | 11% from NHS Ester |
| VS1377 | — | — | 8% from NHS Ester | 0% |
| VS1364 | 81% | 89% | 0% | 0% |
| VS1366 | 100% | 100% | 87% from NHS Ester | 80% from NHS Ester |
| VS1387 | 100% | 100% | 85% from NHS Ester | NA |
| UD37 | 100% | 100% | Reactivity observed | Reactivity observed |
| UD38 | 50% | 91% | 62% from NHS Ester | 60% from NHS Ester |
| UD46 | | 100% | 48% NHS Ester | 53% from NHS Ester |
| UD51 | | 100% | 15% from NHS Ester | 12% from NHS Ester |
| UD60 | | 88% | 33% from NHS Ester | 49% from NHS Ester |
| UD69 | | 100% | 4% from NHS Ester | 7% from NHS Ester |

4 uL of 10 mM compound, 32 uL 50 mM HEPES + 4 uL 50 mM lysine or tripeptide. Incubated for 16 h.

[b]For Stability: 4 uL of 10 mM compound, 32 uL 50 mM HEPES + 4 uL DMSO. Incubated for 16 h.

[a]Incubated for 12 h.

In Table 2, Applicants validated the relative stability of NASA analogs and alternatives by monitoring the hydrolysis of the molecules in the presence of Lysine and model peptide. The reactivity of the NASA analogs/alternatives was then identified.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

```
                             SEQUENCE LISTING

Sequence total quantity: 41
SEQ ID NO: 1              moltype = AA   length = 12
FEATURE                   Location/Qualifiers
source                    1..12
                          mol_type = protein
                          organism = synthetic construct
SEQUENCE: 1
RYYRWKKKKK KK                                                                 12

SEQ ID NO: 2              moltype = AA   length = 17
FEATURE                   Location/Qualifiers
source                    1..17
                          mol_type = protein
                          organism = synthetic construct
SEQUENCE: 2
FGGFTGARKS ARKLANQ                                                            17

SEQ ID NO: 3              moltype = AA   length = 23
FEATURE                   Location/Qualifiers
source                    1..23
                          mol_type = protein
                          organism = synthetic construct
SEQUENCE: 3
REPRILSEEE QEMFRDFDYI ADW                                                     23

SEQ ID NO: 4              moltype = AA   length = 17
FEATURE                   Location/Qualifiers
source                    1..17
                          mol_type = protein
                          organism = synthetic construct
MOD_RES                   1
                          note = X is a 4-pentenoic acid residue
MOD_RES                   4
                          note = X is N-allylglycine
SEQUENCE: 4
XFEXIYRTDI LRTEEGN                                                            17

SEQ ID NO: 5              moltype = AA   length = 17
FEATURE                   Location/Qualifiers
source                    1..17
                          mol_type = protein
                          organism = synthetic construct
MOD_RES                   1
                          note = X is a 4-pentenoic acid
MOD_RES                   4
                          note = X is N-allylglycine
SEQUENCE: 5
XFEXIYRTEL LKAEEAN                                                            17

SEQ ID NO: 6              moltype = AA   length = 17
FEATURE                   Location/Qualifiers
source                    1..17
                          mol_type = protein
                          organism = synthetic construct
MOD_RES                   1
                          note = X is a 4-pentenoic acid
MOD_RES                   4
                          note = X is N-allylglycine
SEQUENCE: 6
XFEXIYRLEL LKAEEAN                                                            17

SEQ ID NO: 7              moltype = AA   length = 12
```

```
FEATURE                 Location/Qualifiers
source                  1..12
                        mol_type = protein
                        organism = synthetic construct
MOD_RES                 1
                        note = X is 4-pentenoic acid residue
MOD_RES                 4
                        note = X is N-allyglycine
SEQUENCE: 7
XFEXIYRLEL LK                                                               12

SEQ ID NO: 8            moltype = AA  length = 17
FEATURE                 Location/Qualifiers
source                  1..17
                        mol_type = protein
                        organism = synthetic construct
MOD_RES                 1
                        note = X is a 4-pentenoic acid
MOD_RES                 4
                        note = X is N-allylalanine
SEQUENCE: 8
XFEXIYRLEL LKAEEAN                                                          17

SEQ ID NO: 9            moltype = AA  length = 21
FEATURE                 Location/Qualifiers
source                  1..21
                        mol_type = protein
                        organism = synthetic construct
MOD_RES                 1
                        note = X is a 4-pentenoic acid
MOD_RES                 4
                        note = X is N-allylglycine
SEQUENCE: 9
XFEXIYRLEL LKAIBEEAIB N                                                     21

SEQ ID NO: 10           moltype = AA  length = 17
FEATURE                 Location/Qualifiers
source                  1..17
                        mol_type = protein
                        organism = synthetic construct
MOD_RES                 1
                        note = X is a 4-pentenoic acid
MOD_RES                 4
                        note = X is N-allyglycine
SEQUENCE: 10
XAEXIYRLEL LKAEAAA                                                          17

SEQ ID NO: 11           moltype = AA  length = 16
FEATURE                 Location/Qualifiers
source                  1..16
                        mol_type = protein
                        organism = synthetic construct
SEQUENCE: 11
FIGRLCTEIL KLREGN                                                           16

SEQ ID NO: 12           moltype = AA  length = 16
FEATURE                 Location/Qualifiers
source                  1..16
                        mol_type = protein
                        organism = synthetic construct
SEQUENCE: 12
LAWRLRELER ELARLC                                                           16

SEQ ID NO: 13           moltype = AA  length = 16
FEATURE                 Location/Qualifiers
source                  1..16
                        mol_type = protein
                        organism = synthetic construct
SEQUENCE: 13
WIGRLCTEIL RLRNGN                                                           16

SEQ ID NO: 14           moltype = AA  length = 16
FEATURE                 Location/Qualifiers
source                  1..16
                        mol_type = protein
                        organism = synthetic construct
SEQUENCE: 14
LAWRLRELER ELARLC                                                           16
```

```
SEQ ID NO: 15           moltype = AA  length = 16
FEATURE                 Location/Qualifiers
source                  1..16
                        mol_type = protein
                        organism = synthetic construct
SEQUENCE: 15
AIGRLCTEIL RLRNGA                                                            16

SEQ ID NO: 16           moltype = AA  length = 16
FEATURE                 Location/Qualifiers
source                  1..16
                        mol_type = protein
                        organism = synthetic construct
SEQUENCE: 16
LAWRLRELER ELARLC                                                            16

SEQ ID NO: 17           moltype = AA  length = 16
FEATURE                 Location/Qualifiers
source                  1..16
                        mol_type = protein
                        organism = synthetic construct
SEQUENCE: 17
WIGRLCTEIL RLRNGN                                                            16

SEQ ID NO: 18           moltype = AA  length = 16
FEATURE                 Location/Qualifiers
source                  1..16
                        mol_type = protein
                        organism = synthetic construct
SEQUENCE: 18
LAWALRELER ELARLC                                                            16

SEQ ID NO: 19           moltype = AA  length = 16
FEATURE                 Location/Qualifiers
source                  1..16
                        mol_type = protein
                        organism = synthetic construct
MOD_RES                 10
                        note = X is L-homoarginine
SEQUENCE: 19
WIGRLCTEIX RLRNGN                                                            16

SEQ ID NO: 20           moltype = AA  length = 16
FEATURE                 Location/Qualifiers
source                  1..16
                        mol_type = protein
                        organism = synthetic construct
SEQUENCE: 20
LAWRLRELER ELARLC                                                            16

SEQ ID NO: 21           moltype = AA  length = 16
FEATURE                 Location/Qualifiers
source                  1..16
                        mol_type = protein
                        organism = synthetic construct
SEQUENCE: 21
WIGRLCTEIR RLRNGN                                                            16

SEQ ID NO: 22           moltype = AA  length = 16
FEATURE                 Location/Qualifiers
source                  1..16
                        mol_type = protein
                        organism = synthetic construct
SEQUENCE: 22
LAWRLRELER ELARLC                                                            16

SEQ ID NO: 23           moltype = AA  length = 16
FEATURE                 Location/Qualifiers
source                  1..16
                        mol_type = protein
                        organism = synthetic construct
SEQUENCE: 23
WIGRLCTEIL RLRNGN                                                            16

SEQ ID NO: 24           moltype = AA  length = 16
FEATURE                 Location/Qualifiers
source                  1..16
                        mol_type = protein
                        organism = synthetic construct
```

```
SEQUENCE: 24
LAWRLRELER ELARLC                                                               16

SEQ ID NO: 25           moltype = AA  length = 16
FEATURE                 Location/Qualifiers
source                  1..16
                        mol_type = protein
                        organism = synthetic construct
SEQUENCE: 25
FIGRLCTEIL KLREGN                                                               16

SEQ ID NO: 26           moltype = AA  length = 17
FEATURE                 Location/Qualifiers
source                  1..17
                        mol_type = protein
                        organism = synthetic construct
MOD_RES                 1
                        note = X is L-Beta-alanine
SEQUENCE: 26
XLAWRLRELE RELARLC                                                              17

SEQ ID NO: 27           moltype = AA  length = 16
FEATURE                 Location/Qualifiers
source                  1..16
                        mol_type = protein
                        organism = synthetic construct
SEQUENCE: 27
WIGRLCTEIL RLRNGN                                                               16

SEQ ID NO: 28           moltype = AA  length = 17
FEATURE                 Location/Qualifiers
source                  1..17
                        mol_type = protein
                        organism = synthetic construct
MOD_RES                 1
                        note = X is L-Beta-alanine
SEQUENCE: 28
XLAWRLRELE RELARLC                                                              17

SEQ ID NO: 29           moltype = AA  length = 16
FEATURE                 Location/Qualifiers
source                  1..16
                        mol_type = protein
                        organism = synthetic construct
SEQUENCE: 29
AIGRLCTEIL RLRNGA                                                               16

SEQ ID NO: 30           moltype = AA  length = 17
FEATURE                 Location/Qualifiers
source                  1..17
                        mol_type = protein
                        organism = synthetic construct
MOD_RES                 1
                        note = X is L-Beta-alanine
SEQUENCE: 30
XLAWRLRELE RELARLC                                                              17

SEQ ID NO: 31           moltype = AA  length = 16
FEATURE                 Location/Qualifiers
source                  1..16
                        mol_type = protein
                        organism = synthetic construct
SEQUENCE: 31
WIGRLCTEIL RLRNGN                                                               16

SEQ ID NO: 32           moltype = AA  length = 17
FEATURE                 Location/Qualifiers
source                  1..17
                        mol_type = protein
                        organism = synthetic construct
MOD_RES                 1
                        note = X is L-Beta-alanine
SEQUENCE: 32
XLAWALRELE RELARLC                                                              17

SEQ ID NO: 33           moltype = AA  length = 16
FEATURE                 Location/Qualifiers
source                  1..16
                        mol_type = protein
```

```
                              organism = synthetic construct
MOD_RES                       10
                              note = X is L-homoarginine
SEQUENCE: 33
WIGRLCTEIX RLRNGN                                                        16

SEQ ID NO: 34                 moltype = AA   length = 17
FEATURE                       Location/Qualifiers
source                        1..17
                              mol_type = protein
                              organism = synthetic construct
MOD_RES                       1
                              note = X is L-Beta-alanine
SEQUENCE: 34
XLAWRLRELE RELARLC                                                       17

SEQ ID NO: 35                 moltype = AA   length = 16
FEATURE                       Location/Qualifiers
source                        1..16
                              mol_type = protein
                              organism = synthetic construct
SEQUENCE: 35
WIGRLCTEIR RLRNGN                                                        16

SEQ ID NO: 36                 moltype = AA   length = 17
FEATURE                       Location/Qualifiers
source                        1..17
                              mol_type = protein
                              organism = synthetic construct
MOD_RES                       1
                              note = X is L-Beta-alanine
SEQUENCE: 36
XLAWRLRELE RELARLC                                                       17

SEQ ID NO: 37                 moltype = AA   length = 16
FEATURE                       Location/Qualifiers
source                        1..16
                              mol_type = protein
                              organism = synthetic construct
MOD_RES                       10
                              note = X is L-homoarginine
SEQUENCE: 37
WIGRLCTEIX RLRNGN                                                        16

SEQ ID NO: 38                 moltype = AA   length = 17
FEATURE                       Location/Qualifiers
source                        1..17
                              mol_type = protein
                              organism = synthetic construct
SEQUENCE: 38
GLAWRLRELE RELARLC                                                       17

SEQ ID NO: 39                 moltype = AA   length = 16
FEATURE                       Location/Qualifiers
source                        1..16
                              mol_type = protein
                              organism = synthetic construct
SITE                          10..11
                              note = diazirine photocrosslinker
SEQUENCE: 39
WIGRLCTEIK RLRNGN                                                        16

SEQ ID NO: 40                 moltype = AA   length = 16
FEATURE                       Location/Qualifiers
source                        1..16
                              mol_type = protein
                              organism = synthetic construct
SEQUENCE: 40
LAWRLRELER ELARLC                                                        16

SEQ ID NO: 41                 moltype = AA   length = 4
FEATURE                       Location/Qualifiers
source                        1..4
                              mol_type = protein
                              organism = synthetic construct
SEQUENCE: 41
GALA                                                                     4
```

What is claimed is:

1. A chimeric small molecule according to the formula A-L1-E-B or A-L1-E-L2-B, wherein A is a kinase protein binding moiety selected from the group consisting of FKBP, PKC, AMPK, ABL, PK, IRTK, MAPK, p38a MAPK, EGFR, FGFR, NGFR, TrkA, ABL, CDK, PI3K, VEGFR, BRAF, MEK, AKT, ALK, BTK, BCKDK, FLT3, JAK2, AURKA, c-MET, DDR, INSR, JNK, IkB, IKK, Lyn, mTOR, PAK, PDK, PTK2/FAK, pyruvate kinases, RAC-a, RIPK, TYK2, SHP, aPKC, NOP, GPC family, μ opioid receptor, δ opioid receptor, UMPK, SphK, PDGFR, and GSK-3 binding moiety;

B is a target oncogenic protein binding moiety selected from the group consisting of KRAS, RAS, $FKPB^{12F36V}$, EGFR, HSP90, BTK, MDM2, BRD4, BCR-ABL, NF-kB, LDH-A, p53, GP73, MUC1, MUC16, CD44, GPCR, HMGB1, RIOK1, CHK1, UBE2F, HuR, PTEN, STAT-3, Osteopontin, AKT, DAPK1, Rho, Ubc9, FOXK2, HIC1, HER2, BRAF, BCL-2, CD117, c-KIT, ALK, PI3K, Delta, DNMT1, and SMO;

L1 and L2 are each a linker; and

E is an electrophilic reactive group and is selected from the group consisting of:

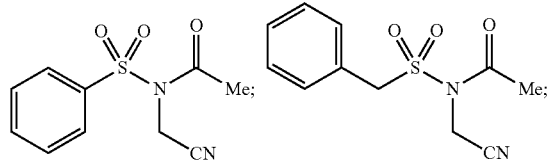
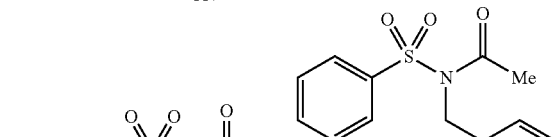
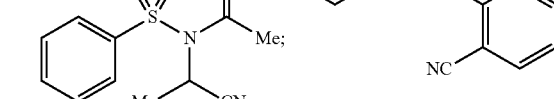
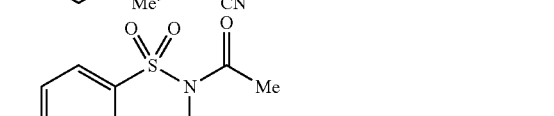
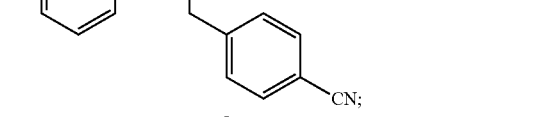
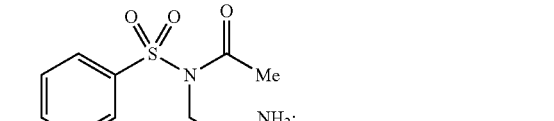
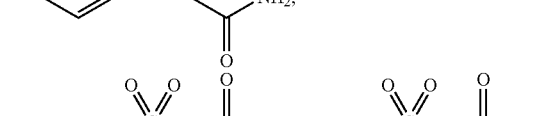
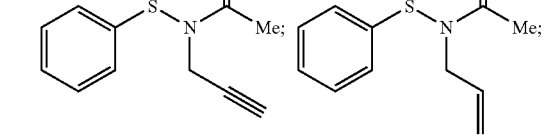

-continued

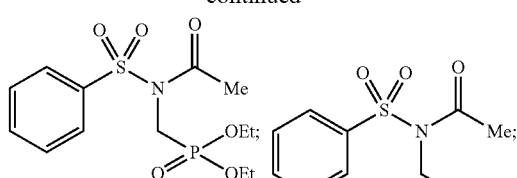
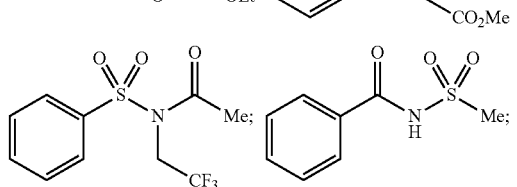
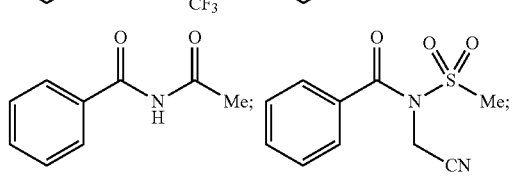
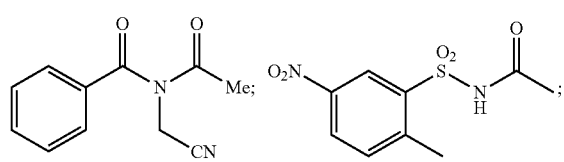
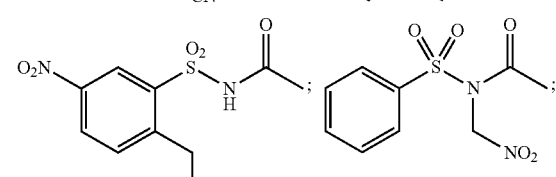
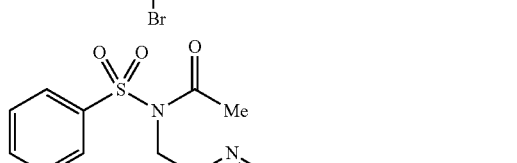
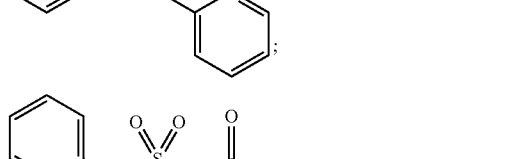
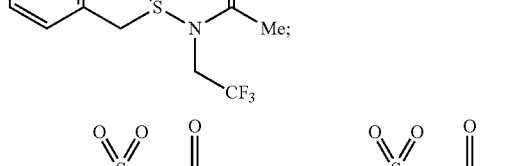
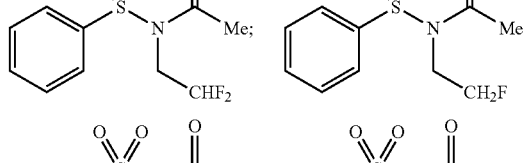
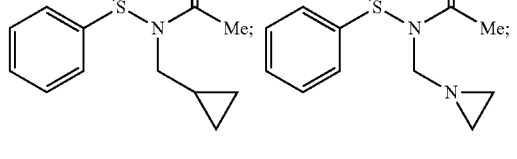

-continued

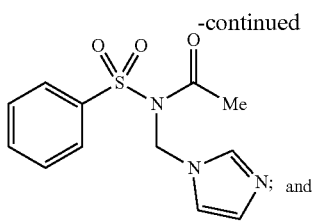

2. The chimeric small molecule of claim 1, wherein the kinase binding moiety has a half-life shorter than the half-life of the kinase.

3. The chimeric small molecule of claim 1, wherein the kinase binding moiety is a kinase inhibitor or kinase activator.

4. The chimeric small molecule of claim 3, wherein the kinase inhibitor is a promiscuous kinase inhibitor.

5. The chimeric small molecule of claim 1, wherein L selected from: alkane; alkene; alkyne; amine; ether; thiol; sulfone; carbonyl; acyl; ketone; carboxylate ester; amide; enone; anhydride; imide; PEG, or any combination thereof.

6. The chimeric small molecule of claim 1, wherein L1 and L2 are the same or are different molecules selected from alkane; alkene; alkyne; amine; ether; thiol; sulfone; carbonyl; acyl; ketone; carboxylate ester; amide; enone; anhydride; imide; PEG, or any combination thereof.

7. The chimeric small molecule of claim 1, wherein the kinase binding moiety further comprises a bio-orthogonal group.

8. The chimeric small molecule of claim 7, wherein the bio-orthogonal group is selected from tetrazines, triazines, cyclooctenes, cyclopropenes and diazo.

9. The chimeric small molecule of claim 7, wherein the bio-orthogonal group is selected from the group consisting of:

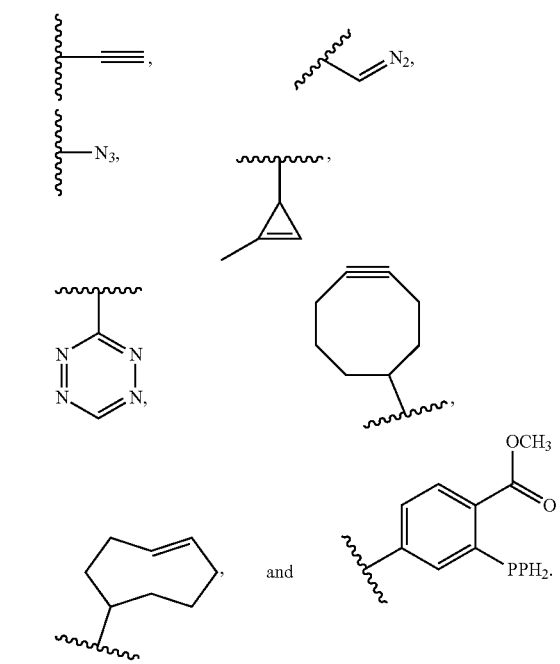

10. The chimeric small molecule of claim 1, wherein the target is a protein.

11. The chimeric small molecule of claim 1, wherein the chimeric small molecule is capable of covalently labeling a kinase with the kinase binding moiety.

12. The chimeric small molecule of claim 1 with the formula:

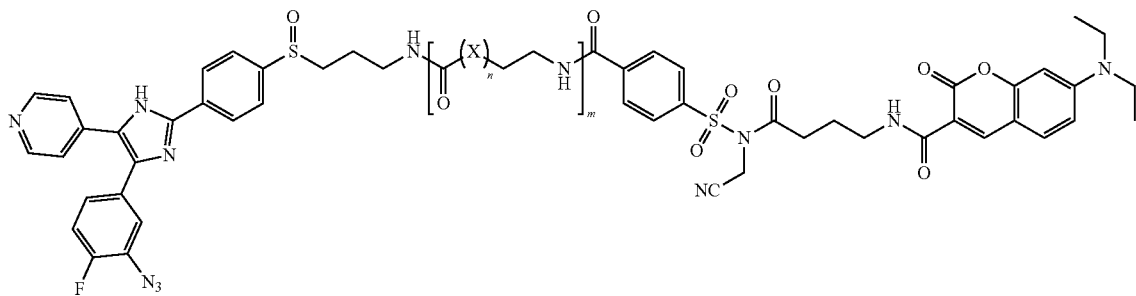

wherein m=0 or 1; n=1, 2, 3, 4 or 5; and X=CH2 or (CH2)2O.

13. The chimeric small molecule of claim 1 with the formula:

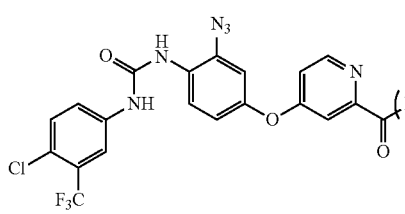

wherein X and Y are independently selected from CH2 or (CH2)2O and n and m are independently selected from 1, 2, 3, 4, 5, or 6.

14. A method of inducing modification of a target substrate comprising administering to a cell or cell population a chimeric small molecule of claim 1.

15. A method of modifying a substrate comprising introducing a molecule of claim 1 to a cell.

16. The chimeric small molecule of claim 2, wherein the kinase binding moiety half-life is at least 2, 3, 4, 5 times shorter than the half-life of the kinase.

17. The chimeric small molecule of claim 3, wherein the kinase inhibitor is sorafenib, SB2035890 or Skepinone B, or an analog or derivative thereof.

18. The chimeric small molecule of claim 3, wherein the kinase inhibitor is Gefitinib, or an analog or derivative thereof.

19. The chimeric small molecule of claim 3, wherein the kinase inhibitor is Imatinib, or an analog or derivative thereof.

20. The chimeric small molecule of claim 3, wherein the kinase inhibitor is Idelasilib, or an analog or derivative thereof.

21. The chimeric small molecule of claim 10, wherein the target protein is from a pathogen.

22. The chimeric small molecule of claim 21, wherein the pathogen is a virus, bacteria, fungi, or protozoa.

23. The chimeric small molecule of claim 3, wherein the target protein is in an intracellular or extracellular pathogen protein.

24. The chimeric small molecule of claim 23, wherein the intracellular pathogen is Mycobacterium tuberculosis or the extracellular pathogen is Pseudomonas aeruginosa.

25. The chimeric small molecule of claim 3, wherein the kinase binding moiety is a phosphatase A (PtpA) binding moiety or a phosphatase B (PtpB) binding moiety.

26. The chimeric small molecule of claim 11, wherein the labeling is of a nucleophile disposed on the kinase.

27. The method of claim 15, wherein the electrophilic reactive group reacts with a nucleophilic group of one of Cysteine, Serine, Threonine, Tyrosine, Glutamic Acid, Aspartic Acid, Lysine, Arginine, and Histidine.

* * * * *